(12) United States Patent
Cohnen et al.

(10) Patent No.: US 11,578,323 B2
(45) Date of Patent: Feb. 14, 2023

(54) RNA-PROGRAMMABLE ENDONUCLEASE SYSTEMS AND THEIR USE IN GENOME EDITING AND OTHER APPLICATIONS

(71) Applicants: CRISPR THERAPEUTICS AG, Zug (CH); BAYER HEALTHCARE LLC, Whippany, NJ (US)

(72) Inventors: Andre Cohnen, Titz-Hasselsweiler (DE); Moritz Schmidt, Cologne (DE); Wayne Coco, Pulheim (DE); Ashish Gupta, Leverkusen (DE); Jan Tebbe, Leverkusen (DE); Cindy Schulenburg, Leverkusen (DE); Christian Pitzler, Leverkusen (DE); Michael Biag Gamalinda, Leverkusen (DE); Sabine Jach, Leverkusen (DE); Florian Richter, Leverkusen (DE); Anup Arumughan, Leverkusen (DE); Corinna Saalwächter, Leverkusen (DE)

(73) Assignees: BAYER HEALTHCARE LLC, Whippany, NJ (US); CRISPR THERAPEUTICS AG, Zug (CH)

( * ) Notice: Subject to any disclaimer, the term of this patent is extended or adjusted under 35 U.S.C. 154(b) by 75 days.

(21) Appl. No.: 16/772,082

(22) PCT Filed: Dec. 14, 2018

(86) PCT No.: PCT/US2018/065863
§ 371 (c)(1),
(2) Date: Jun. 11, 2020

(87) PCT Pub. No.: WO2019/118935
PCT Pub. Date: Jun. 20, 2019

(65) Prior Publication Data
US 2020/0385720 A1    Dec. 10, 2020

(30) Foreign Application Priority Data
Dec. 14, 2017 (EP) .................................... 17207294

(51) Int. Cl.
*C12N 9/22* (2006.01)
*C12N 15/113* (2010.01)

(52) U.S. Cl.
CPC .............. *C12N 15/113* (2013.01); *C12N 9/22* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2016/0130608 A1* 5/2016 Doudna ............... C12N 15/907
435/462

FOREIGN PATENT DOCUMENTS

| WO | 2013/176772 A1 | 11/2013 |
| WO | 2017083852 A1 | 5/2017 |
| WO | 2017096041 A1 | 6/2017 |
| WO | 2019/118935 A1 | 6/2019 |

OTHER PUBLICATIONS

Uniprot Accession AOA133QCR3, Jun. 2016.*
Ngo et al. in The Protein Folding Problem and Tertiary Structure Prediction, 1994, Merz et al. (ed.), Birkhauser, Boston, MA, pp. 433 and 492-495.*
Genbank Accession No. LS483312.1, Jun. 17, 2018.*
Hou, Z., et al., "Efficient genome engineering in human pluripotent stem cells using Cas9 from Neisseria meningitidis," PNAS, vol. 110(39):15644-15649 (2013).
International Preliminary Report on Patentability, PCT/US2018/065863, dated Jun. 16, 2020, 7 pages.
International Search Report and Written Opinion, PCT/US2018/065863, dated Apr. 10, 2019, 12 pages.
Kaminski, R. et al., "Excision of HIV-1 DNA by gene editing: a proof-of-concept in vivo study," Gene Therapy,vol. 23 (8-9):690-695 (2016).
Mali, P. et al., "RNA Guided Human Genome Engineering via Cas9," Science, vol. 339 (6121):823-826 (2013).
Muller, M. et al., "*Streptococcus thermophilus* CRISPR-Cas9 Systems Enable Specific Editing of the Human Genome," Molecular Therapy,vol. 24 (3):636-644 (2016).

* cited by examiner

*Primary Examiner* — Richard G Hutson
(74) *Attorney, Agent, or Firm* — Marshall, Gerstein & Borun LLP

(57) ABSTRACT

Aspects of this invention inter alia relate to novel systems for targeting, editing or manipulating DNA in a cell, comprising one or more heterologous vector(s) encoding a SluCas9 nuclease from *Staphylococcus lugdunensis* or variants thereof, and one or more guide RNAs (gRNAs), or a SluCas9 nuclease or variant thereof and one or more gRNAs.

5 Claims, 10 Drawing Sheets
Specification includes a Sequence Listing.

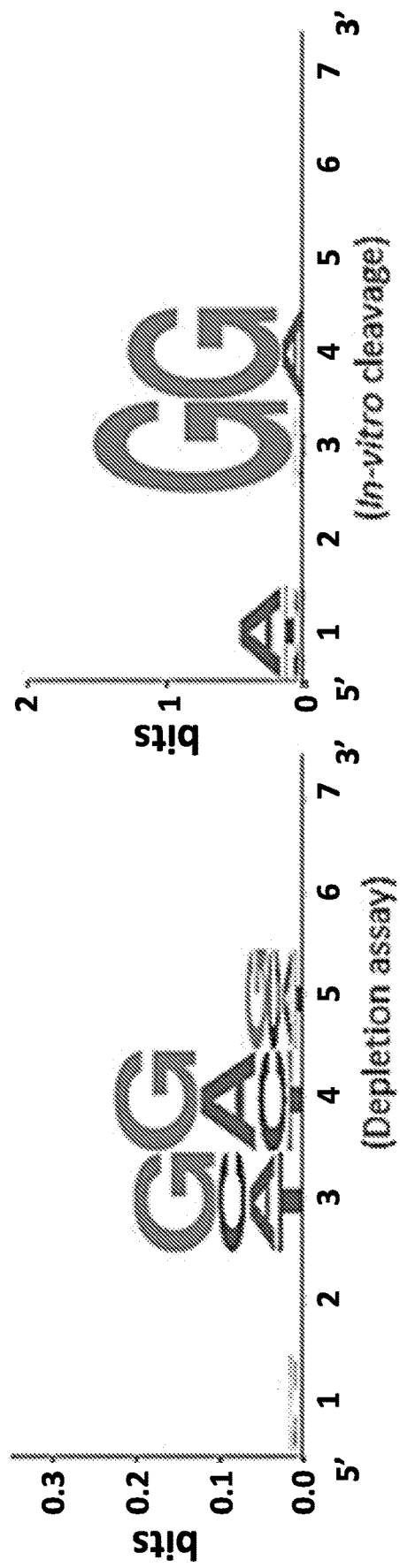

FIG. 4A

```
atggtgagcaagggcgaggagctgttcaccggggtggtgcccatcctggtcgagctggacggcgacgtaaacggccacaagttcagcgtgtccggcga
agggcgatgccacctacggcaagctgaccctgaagttcatctgcaccaccggcaagctgcccgtgccctggcccaccctcgtgaccaccctgacccatgcgt
gcagtgcttcagccgctaccccgaccacatgaagcagcacgacttcttcaagtccgccatgcccgaaggctacgtccaggagcgcaccatcttcttcaaggacga
cggcaactacaagacccgcgccgaggtgaagttcgagggcgacaccctggtgaaccgcatcgagctgaagggcatcgacttcaaggaggacggcaacatcct
ggggcacaagctggagtacaactacaacagccacaacgtctatatcatggccgacaagcagaagaacggcatcaaggtgaacttcaagatccgccacaacatcg
aggacggcagcgtgcagctcgccgaccactaccagcagaacacccccatcggcgacggccccgtgctgctgcccgacaaccactacctgagcacccagtccaa
gctgagcaaagaccccaacgagaagcgcgatcacatggtcctgctggagttcgtgaccgccgccgggatcactctcggcatggacgagctgtacaagtaa
```

FIG. 4B

| BFP20nt_1 | gggtcagggtggtcacgagg | gtggcc |
| BFP20nt_2 | ccctcgaacttcacctcggc | gcgggtc |
| BFP22nt_2 | cgccctcgaacttcacctcggc | gcgggtc |

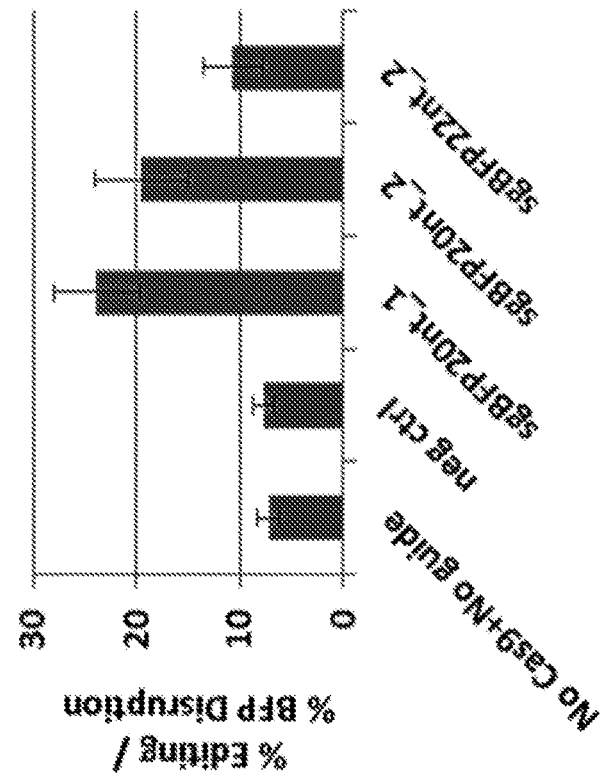

FIG. 4C

FIG. 5A HBB20nt_1 ggtgaacgtggatgaagttg gtggtga

RNA-PROGRAMMABLE ENDONUCLEASE SYSTEMS AND THEIR USE IN GENOME EDITING AND OTHER APPLICATIONS

CROSS-REFERENCE TO RELATED APPLICATIONS

This application is a 35 U.S.C. § 371 national stage filing of International Application No. PCT/US2018/065863 filed on Dec. 14, 2018, which claims priority to European Application No. 17207294.4, filed on Dec. 14, 2017. The entire contents of these applications are incorporated herein by reference in their entirety.

INCORPORATION BY REFERENCE OF SEQUENCE LISTING

The instant application contains a Sequence Listing which has been submitted electronically in ASCII format via EFS-Web, and is hereby incorporated by reference in its entirety. Said ASCII copy, created on Jun. 11, 2020, is named CBTN_014US_Sequence_Listing.txt and is 103341 bytes in size.

FIELD

The present disclosure generally relates to the field of molecular biology, including compositions and methods relating to novel systems including RNA-programmable endonucleases, associated guide RNAs and/or target sequences, and methods for producing and using the same in various applications, including methods for modulating transcription, as well as methods for targeting, editing, and/or manipulating DNA in a cell.

BACKGROUND

Endonucleases such as Zinc-finger endonucleases (ZFNs), Transcription-activator like effector nucleases (TALENs) and ribonucleases have been harnessed as site-specific nucleases for genome targeting, genome editing, gene silencing, transcription modulation, promoting recombination and other molecular biological techniques. CRISPR-Cas systems provide a source of novel nucleases and endonucleases, including CRISPR-Cas9.

Editing genomes using the RNA-guided DNA targeting principle of CRISPR (Clustered Regularly Interspaced Short Palindromic Repeats)-Cas ((CRISPR associated proteins), as described in WO2013/176722, has been exploited widely over the past few years. Three types of CRISPR-Cas systems (type I, type II and IIb, and type III) have previously been described, and a fourth was more recently identified (type V). Most uses of CRISPR-Cas for genome editing have been with the type II system. The main advantage provided by the bacterial type II CRISPR-Cas system lies in the minimal requirement for programmable DNA interference: an endonuclease, Cas9, guided by a customizable dual-RNA structure. As initially demonstrated in the original type II system of *Streptococcus pyogenes*, trans-activating CRISPR RNA (tracrRNA) binds to the invariable repeats of precursor CRISPR RNA (pre-crRNA) forming a dual-RNA that is essential for both RNA co-maturation by RNase III in the presence of Cas9, and invading DNA cleavage by Cas9. As demonstrated in *Streptococcus pyogenes*, Cas9 guided by the duplex formed between mature activating tracr RNA and targeting crRNA introduces site-specific double-stranded DNA (dsDNA) breaks in the invading cognate DNA. Cas9 is a multi-domain enzyme that uses an HNH nuclease domain to cleave the target strand (defined as complementary to the spacer sequence of crRNA) and a RuvC-like domain to cleave the non-target strand, enabling the conversion of the dsDNA cleaving Cas9 into a nickase by selective motif inactivation. DNA cleavage specificity is determined by two parameters: the variable, spacer-derived sequence of crRNA targeting the protospacer sequence (a protospacer is defined as the sequence on the DNA target that is non-complementary to the spacer of crRNA) and a short sequence, the Protospacer Adjacent Motif (PAM), located immediately 3' (downstream) of the protospacer on the non-target DNA strand.

Studies have demonstrated that RNA-guided Cas9 can be employed as a genome editing tool in human cells, mice, zebrafish, *drosophila*, worms, plants, yeast and bacteria, as well as various other species. The system is versatile, enabling multiplex genome engineering by programming Cas9 to edit several sites in a genome simultaneously by using multiple guide RNAs. The conversion of Cas9 into a nickase was shown to facilitate homology-directed repair in mammalian genomes with reduced mutagenic activity. In addition, the DNA-binding activity of a Cas9 catalytic inactive mutant has, for example, been exploited to engineer RNA-programmable transcriptional silencing and activating devices or epigenetic modifiers.

The present invention provides a novel CRISPR-Cas endonuclease of the CRISPR-Cas9 family from *Staphylococcus lugdunensis* (SluCas9) and variants thereof having different and advantageous characteristics and functionalities from known CRISPR-Cas endonucleases and thus provides further opportunities for genome editing that previously did not exist. The present invention further provides suitable PAM sequences and suitable guide RNAs (gRNAs), such as single-guide-RNAs (sgRNAs), for use in prokaryotic, eukaryotic, and in vitro environments.

Existing CRISPR-Cas 9 systems have one or more of the following disadvantages:
 a) Their size is too large to be carried inside the genome of established therapeutically-suitable viral transfection systems such as adeno associated viruses (AAVs).
 b) Their activity in non-host environments is generally too low for use in these environments, for example, too low for efficient use in eukaryotic, and in particular in mammalian environments.
 c) Their nuclease action lacks fidelity, leading to unwanted off target effects that would for example make them unsuitable for gene therapeutic uses or other applications requiring high precision.
 d) They may trigger an immune response that can limit their use for in vivo applications in mammals.
 e) They require complex and/or long PAMs that restrict target selection for the DNA-targeting segment s.

The novel SluCas9 CRISPR-Cas system provided herein exhibits advantageous characteristics over the already existing CRISPR-Cas systems. In some embodiments, the SluCas9 CRISPR-Cas system exhibits a higher activity in prokaryotic, eukaryotic, and/or in vitro environments, and/or greater expression of the Cas endonuclease from a nucleic acid in eukaryotic environments, such as, e.g., a human host cell.

SUMMARY

This section provides a general summary of the disclosure, and is not comprehensive of its full scope or all of its features.

In some embodiments, provided herein are compositions and methods relating to novel systems including RNA-programmable endonucleases, associated guide RNAs and/or target sequences, and methods for producing and using the same in various applications, including methods for modulating transcription, as well as methods for targeting, editing, and/or manipulating DNA using such nucleic acids and/or polypeptides. Some embodiments of the disclosure also relate to recombinant cells and kits comprising one or more of the system elements disclosed herein.

In one aspect, provided herein is a composition comprising (a) a SluCas9 polypeptide according to SEQ ID NO: 2 or the following variants thereof: (I) variants of at least 75%, at least 80%, at least 85%, at least 90%, at least 95%, at least 99%, or 100% amino acid identity to the sequence according to SEQ ID NO: 2 over its entire length or from position 789 to position 1053 of SEQ ID NO: 2; (II) variants according to (I) that contain additional components, such as e.g. nuclear localization signals, to obtain activity of a SluCas9 CRISPR system comprising the SluCas9 polypeptide in a cell-free reaction or in a prokaryotic cell and in eukaryotic cellular environments, e.g., in a viable plant or animal, for example the polynucleotide sequence according to SEQ ID NO: 3; (III) a codon optimized variant of a corresponding polynucleotide sequence encoding a SluCas9 and the variants according to (I) and (II), for example the polynucleotide sequence from position 61 to 3225 of SEQ ID NO: 3 and the polynucleotide sequences according to SEQ ID NO: 44 and 45; or (IV) variants according to any of (I) to (III) further comprising i. one or more modification(s) or mutation(s) that result in a SluCas9 with a significantly reduced nuclease activity as compared to the corresponding SluCas9 without the one or more modification(s) or mutation(s) (e.g., SluCas9 comprising the amino acid sequence of SEQ ID NO: 2) or non-detectable nuclease activity, e.g., one or more amino acid substitution(s) (e.g., alanine substitution), wherein substitution is, with respect to SEQ ID NO: 2, at position 10 (e.g., D10A), position 559 (e.g., H559A), and/or position 582 (e.g., N582A); and/or ii. C- or N-terminally attached polypeptide with a nucleobase editing activity or deaminase activity, e.g., attached via a linker peptide sequence; and (b) one or more single heterologous guide RNA(s) (sgRNA(s)) or nucleic acid (e.g., DNA) encoding the one or more sgRNA(s), each sgRNA comprising: (I) a DNA-targeting segment comprised of RNA and capable of hybridizing to a target sequence in a polynucleotide locus, (II) a tracr mate sequence comprised of RNA, and (III) a tracr RNA sequence comprised of RNA, wherein the tracr mate sequence is capable of hybridizing to the tracr sequence, and wherein (I), (II), and (III) are arranged in a 5' to 3' orientation.

In some embodiments, the SluCas9 polypeptide of (a) comprises a contiguous sequence of amino acids (e.g., a contiguous sequence of 265 amino acids) having at least 75% amino acid identity to the amino acid sequence from position 789 to position 1053, inclusive, of SEQ ID NO: 2.

In some embodiments, the SluCas9 polypeptide of (a) comprises a contiguous sequence of amino acids (e.g., a contiguous sequence of 265 amino acids) having at least 90% amino acid identity to the amino acid sequence from position 789 to position 1053, inclusive, of SEQ ID NO: 2.

In some embodiments, the DNA-targeting segment has a length from 18 nucleotides to 22 nucleotides, and a protospacer sequence in the polynucleotide locus complementary to the target sequence is directly adjacent to a suitable PAM sequence for the SluCas9 polypeptide of (a) on its 3' end or such PAM sequence is part of the 3' portion of the DNA-targeting segment.

In some embodiments, a protospacer sequence in the polynucleotide locus complementary to the target sequence is directly adjacent to the PAM sequence "NNGG" on its 3' end or such PAM sequence is part of the 3' portion of the DNA-targeting segment.

In another aspect, provided herein is a method of targeting, editing, modifying, or manipulating a target DNA at one or more locations in a cell (e.g., in vitro or in vivo) or in a cell-free system, comprising: (a) introducing a heterologous SluCas9 polypeptide or a polypeptide that exhibits an identity of at least 75% to SEQ ID NO: 2 or a nucleic acid encoding the same into the cell or cell-free system; and (b) introducing one or more single heterologous guide RNA(s) (sgRNA(s)) or nucleic acid (e.g., DNA) encoding the one or more sgRNA(s), each sgRNA comprising: (I) a DNA-targeting segment comprised of RNA and capable of hybridizing to a target sequence in a polynucleotide locus, (II) a tracr mate sequence comprised of RNA, and (III) a tracr RNA sequence comprised of RNA, wherein the tracr mate sequence is capable of hybridizing to the tracr sequence, and wherein (I), (II), and (III) are arranged in a 5' to 3' orientation; and (c) creating one or more nicks or cuts or base edits in the target DNA, wherein the SluCas9 polypeptide is directed to the target DNA by the sgRNA in its processed or unprocessed form.

In another aspect, provided herein is the use of a composition comprising (a) a SluCas9 polypeptide or a polypeptide that exhibits an identity of at least 75% to SEQ ID NO: 2, or a nucleic acid encoding the same; and/or (b) one or more single heterologous guide RNA(s) (sgRNA(s)) or nucleic acid (e.g., DNA) encoding the one or more sgRNA(s), each sgRNA comprising: (1) a DNA-targeting segment comprised of RNA and capable of hybridizing to a target sequence in a polynucleotide locus, (II) a tracr mate sequence comprised of RNA, and (III) a tracr RNA sequence comprised of RNA, wherein the tracr mate sequence is capable of hybridizing to the tracr sequence, and wherein (I), (II), and (III) are arranged in a 5' to 3' orientation; for targeting, editing, modifying, or manipulating a target DNA at one or more locations in a cell (e.g., in vitro or in vivo) or in a cell-free system.

In another aspect, provided herein is a cell comprising (a) a SluCas9 polypeptide or a polypeptide that exhibits an identity of at least 75% to SEQ ID NO: 2, or a nucleic acid encoding the same; and (b) one or more single heterologous guide RNA(s) (sgRNA(s)) or nucleic acid (e.g., DNA) encoding the one or more sgRNA(s), each sgRNA comprising: (1) a DNA-targeting segment comprised of RNA and capable of hybridizing to a target sequence in a polynucleotide locus, (II) a tracr mate sequence comprised of RNA, and (III) a tracr RNA sequence comprised of RNA, wherein the tracr mate sequence is capable of hybridizing to the tracr sequence, and wherein (I), (II), and (II) are arranged in a 5' to 3' orientation.

In another aspect, provided herein is a kit comprising (a) a nucleic acid sequence encoding SluCas9 or a polypeptide that exhibits an identity of at least 75% to SEQ ID NO: 2, wherein the nucleic acid sequence encoding such SluCas9 is operably linked to a promoter; (b) one or more single heterologous guide RNA(s) (sgRNA(s)) or nucleic acid (e.g., DNA) encoding the one or more sgRNA(s), each sgRNA comprising: (1) a DNA-targeting segment comprised of RNA and capable of hybridizing to a target sequence in a polynucleotide locus, (II) a tracr mate sequence comprised of RNA, and (III) a tracr RNA sequence comprised of RNA, wherein the tracr mate sequence is capable of hybridizing to the tracr sequence, and wherein (I), (II), and (II) are arranged in a 5' to 3' orientation.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1A shows a schematic of the N7-PAM library.

FIG. 1B shows results for cleavage of the N7-PAM library by SluCas9 as assessed by a depletion assay with BL21DE3 cells transformed with the N7-PAM library (pML2070) or control BL21DE3 cells. The size of the character for a particular base refers to the activity at such position.

FIG. 1C shows results for in vitro cleavage of the N7-PAM library by SluCas9, as assessed by next generation sequencing of the cleaved fragments. The size of the character for a particular base refers to the activity at such position.

FIG. 3A shows a schematic for a "live-dead" assay in a plate format. FIG. 3B shows a schematic for a "live-dead" assay in a liquid culture format. FIG. 3C shows results for a "live-dead" assay carried out in the liquid culture format.

FIGS. 4A-4C show SluCas9 activity in mammalian cells as assessed by BFP disruption. FIG. 4A shows the forward strand sequence of BFP in HEK293T cells. PAM regions for 2 different BFP guides are depicted in light grey. FIG. 4B shows sequences for 2 different guides targeting BFP (20 nt each) and a longer version of the $2^{nd}$ guide, followed by the 7 nucleotides long PAM sequences for these. FIG. 4C shows quantification of FACS analysis showing guide-dependent loss of BFP signal. Guide not targeting BFP (targeting HBB gene, sequence below) was used for negative Control.

FIGS. 5A-5C show detection of SluCas9 activity in mammalian cells by ddPCR and T7E1 assay. FIG. 5A shows the DNA-targeting segment targeting the HBB gene in HEK cells. FIG. 5B shows quantification of ddPCR analysis of the HBB locus showing guide-dependent editing. FIG. 5C shows agarose gel analysis for indel-dependent DNA cleavage using T7E1 endonuclease. Cleaved products are indicated by arrows on the right.

FIG. 7A shows the percent of GFP and RFP expressing cells 2 days following co-transfection. FIG. 7B shows SluCas9 expression 2 days following co-transfection. Beta-actin expression was used as an internal control, and the ratio of SluCas9 signal to beta-actin signal is shown for each condition (Cas9/β-actin). FIG. 7C shows the percent of BFP− cells 5 days following co-transfection.

DETAILED DESCRIPTION OF THE INVENTION

Figure 2A:
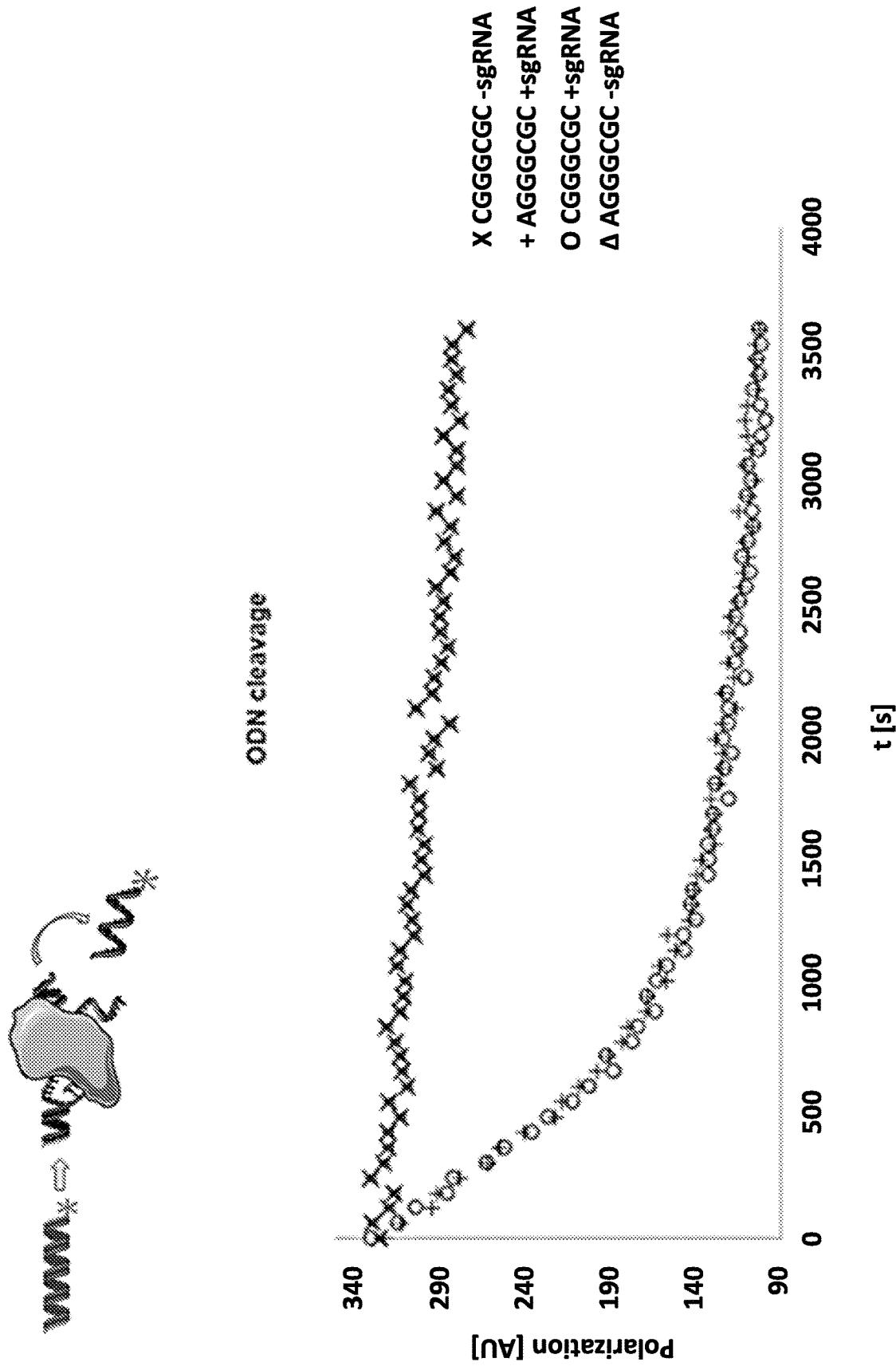
FIG. 2A shows a schematic for the cleavage of fluorescently labeled oligonucleotides (ODNs) including a SluCas9 PAM by SluCas9 (top panel), and results for the cleavage kinetics of an ODN including the SluCas9 PAM as identified by the cleavage assays and an ODN including the SluCas9 PAM with the A at position 1 substituted with C (bottom panel).

Most existing type II CRISPR Cas systems are based on the enzyme from *Streptococcus pyogenes*, which has the particular disadvantage of being too large for packaging into viral vectors as AAV (1638 amino acids). There is an alternative type II CRISPR Cas system based on the nuclease from *Staphylococcus aureus* (EP 2 898 075) which is significantly smaller in size. However, this nuclease requires a rather complex PAM which greatly restricts is usability for gene editing applications.

Provided is a novel system for targeting, editing or manipulating DNA in a cell, comprising one or more heterologous vector(s) encoding a type II CRISPR-Cas nuclease from *Staphylococcus lugdunensis* (SluCas9), variants of this nuclease, and one or more guide RNAs (gRNAs), e.g., one or more single guide RNAs (sgRNAs), or a SluCas9 nuclease and one or more gRNAs.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Unless otherwise defined, all terms of art, notations and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The SluCas9 gene editing system disclosed herein includes a small (e.g., 1053 amino acid), highly active nuclease that requires only a "simple" PAM sequence.

From the sequencing of the whole genome of *Staphylococcus lugdunensis* there is an annotation for an open reading frame that might encode a CRISPR Cas nuclease: gi|488391463|ref|WP_002460848.1| hypothetical protein [*Staphylococcus lugdunensis*]; A0A133QCR3; A0A133QCR3_STALU (SEQ ID NO: 1, encoding the amino acid sequence of SEQ ID NO: 35).

However, no evidence exists on whether this open reading frame is expressed, or if expressed, whether the encoded protein might be a functional nuclease. Further, Applicant is unaware of any teaching on the additional (and essential) components (e.g., PAM and gRNA) necessary to convert this into a functional CRISPR-Cas gene editing tool.

Besides a novel variant of the SluCas9 enzyme according to SEQ ID NO: 2 (having a threonine at position 737 as compared to the serine at this position in SEQ ID NO: 35), nucleic acids comprising codon optimized polynucleotide sequences encoding SluCas9 (SEQ ID NO: 2) are particularly disclosed herein.

Provided are polynucleotide (SEQ ID NO: 1) and amino acid sequences (SEQ ID NO: 2 or 35) of SluCas9 polypeptides as well as the following variants thereof:
(I) variants of at least 75%, at least 80%, at least 85%, at least 90%, at least 95%, at least 99%, or 100% amino acid identity to the sequence according to SEQ ID NO: 2 over its entire length or from position 789 to position 1053 of SEQ ID NO: 2;
(II) variants according to (I) that contain additional components, such as e.g. nuclear localization signals, to obtain activity of a SluCas9 CRISPR system comprising the SluCas9 polypeptide in a cell-free reaction or in a prokaryotic cell and in eukaryotic cellular environments, e.g., in a viable plant or animal, for example the polynucleotide sequence according to SEQ ID NO: 3;
(III) codon optimized variants of the corresponding polynucleotide sequences encoding SluCas9 and the variants according to (I) and (II), for example the polynucleotide sequence from position 61 to 3225 of SEQ ID NO: 3 and the polynucleotide sequences according to SEQ ID NO: 44 and 45; and
(IV) variants according to any of (I) to (III) that further comprise
  (a) one or more modification(s) or mutation(s) that result in a SluCas9 with a significantly reduced nuclease activity as compared to the corresponding SluCas9 without the one or more modification(s) or mutation(s) (e.g., SluCas9 comprising the amino acid sequence of SEQ ID NO: 2) or non-detectable nuclease activity, e.g., one or more amino acid substitution(s) (e.g., alanine substitution), wherein substitution is, with respect to SEQ ID NO: 2, at position 10 (e.g., D10A), position 559 (e.g., H559A), and/or position 582 (e.g., N582A); and/or
  (b) a C- or N-terminally attached polypeptide with a nucleobase editing activity or deaminase activity, e.g., attached via a linker peptide sequence.

Suitable polypeptides under (IV) (a) and their attachment to the C-terminal domain of a SluCas9 under (I), (II), (III) are described for example in WO2017/070632, Gaudelli et al., Nature 551(23 Nov. 2017), 464-471; Komor et al., Sci. Adv. 2017; 3eaao4774; Kim et al., Nature Biotechnol. 2017 April; 35(4) 371-376; Komor et al., Nature 533(7603); 420-424.

Instead of introducing double strand breaks into the target DNA sequence, SluCas9 Variants under (IV) could allow the conversion of any base pair into any possible other base pair. Non-limiting examples include a deaminase activity that could act upon cytosine, guanine or adenine bases and their subsequent repair within the cell to yield guanine, thymine, and guanine respectively.

If not otherwise specified, the term SluCas9 comprises the protein sequence according to SEQ ID NO: 2, 4, or 35, as well as all of the variants specified under (I), (II), (III), and (IV).

"Significantly reduced" for example used in the context of an enzymatic activity means that such enzymatic activity is lower than 10% of the activity of the reference protein (e.g. SEQ ID NO: 2), such as lower than 5%, lower than 2%, lower than 1%, or lower than 0.1% of such reference enzymatic activity.

Provided are SluCas9 polypeptides that exhibit at least 75% amino acid identity, at least 80% amino acid identity, at least 85% amino acid identity, at least 90% amino acid identity, at least 95% amino acid identity, at least 99% amino acid identity, or 100% amino acid identity to SEQ ID NO: 2.

Also provided are SluCas9 polypeptides comprising a contiguous sequence of amino acids (e.g., a contiguous sequence of 265 amino acids) having at least 75% amino acid identity, at least 80% amino acid identity, at least 85% amino acid identity, at least 90% amino acid identity, at least 95% amino acid identity, at least 99% amino acid identity, or 100% amino acid identity to the amino acid sequence from position 789 to position 1053, inclusive, of SEQ ID NO: 2.

Further, provided are SluCas9 polypeptides that exhibit at least 90%, 91%, 92%, 93%, 94%, 95%, 96%, 97%, 98%, 99%, 99.5%, or 99.9% sequence identity to SEQ ID NO: 2 or on nucleic acid level to a nucleic acid sequence encoding the same.

Also, further provided are SluCas9 polypeptides comprising a contiguous sequence of amino acids (e.g., a contiguous sequence of 265 amino acids) having at least 90%, 91%, 92%, 93%, 94%, 95%, 96%, 97%, 98%, 99%, 99.5%, or 99.9% sequence identity to the amino acid sequence from position 789 to position 1053, inclusive, of SEQ ID NO: 2 or on a nucleic acid level to a nucleic acid sequence encoding the same.

Provided are SluCas9 polypeptides comprising the amino acid sequence according to any one of SEQ ID NOs: 2, 4, and 35, and any DNA sequence encoding the same.

Also provided is a SluCas9 polypeptide comprising the amino acid sequence according to SEQ ID NO: 2, and corresponding DNA sequences including the polynucleotide sequence from position 61 to 3225 of SEQ ID NO: 3 and the polynucleotide sequences according to SEQ ID NO: 44 and 45.

CRISPR-Cas System Based on SluCas9

One embodiment according to the invention represents compositions comprising:
  (a) a SluCas9 polypeptide or a polynucleotide encoding such SluCas9;
  (b) a single heterologous guide RNA (sgRNA) or a nucleic acid (e.g., DNA) that allows the generation of such sgRNA in situ (e.g., nucleic acid encoding the sgRNA), wherein the sgRNA comprises:

i. a DNA-targeting segment comprised of RNA and capable of hybridizing to a target sequence in a polynucleotide locus,
ii. a tracr mate sequence comprised of RNA, and
iii. a tracr RNA sequence comprised of RNA, wherein the tracr mate sequence is capable of hybridizing to the tracr sequence, and wherein (i), (ii), and (iii) are arranged in a 5' to 3' orientation.

Within a sgRNA a tracr mate sequence and a tracr sequence is generally connected by a suitable loop sequence and form a stem-loop structure.

Further, in some embodiments the polynucleotide encoding SluCas9 and the sgRNAs contain a suitable promoter for the expression in a cellular or in vitro environment and/or a suitable nuclear localization signal.

Another embodiment according to the invention represents methods of targeting, editing, modifying, or manipulating a target DNA at one or more locations in a cell or in vitro, comprising:
(a) Introducing a heterologous SluCas9 polypeptide or a nucleic acid encoding same protein into a cell or into an in vitro environment; and
(b) Introducing a single heterologous guide RNA (sgRNA) or a nucleic acid (e.g., DNA) suitable for the generation of such sgRNA in situ (e.g., nucleic acid encoding the sgRNA), wherein the sgRNA comprises:
  i. a DNA-targeting segment comprised of RNA and capable of hybridizing to a target sequence in a polynucleotide locus,
  ii. a tracr mate sequence comprised of RNA, and
  iii. a tracr RNA sequence comprised of RNA, wherein the tracr mate sequence is capable of hybridizing to the tracr sequence, and wherein (i), (ii), and (iii) are arranged in a 5' to 3' orientation;
(c) creating one or more cuts, nicks or edits in the target DNA, wherein the SluCas9 polypeptide is directed to the target DNA by the gRNA in its processed or unprocessed form.

Another embodiment according to the invention is the use of a compositions comprising
(a) a SluCas9 polypeptide or a polynucleotide encoding such SluCas9;
(b) single heterologous guide RNA (sgRNA) or a nucleic acid (e.g., DNA) suitable for the generation of such sgRNA in situ (e.g., nucleic acid encoding the sgRNA), wherein the sgRNA comprises:
  i. a DNA-targeting segment comprised of RNA and capable of hybridizing to such target sequence in a polynucleotide locus,
  ii. a tracr mate sequence comprised of RNA, and
  iii. a tracr RNA sequence comprised of RNA, wherein the tracr mate sequence is capable of hybridizing to the tracr sequence, and wherein (i), (ii), and (iii) are arranged in a 5' to 3' orientation;
for targeting, editing, modifying, or manipulating a target DNA at one or more locations in a cell (e.g., in vitro or in vivo) or in a cell-free system.

Another embodiment according to the invention is a cell ex vivo or in vitro comprising:
(a) a heterologous SluCas9 polypeptide or a nucleic acid encoding the same
(b) a single heterologous guide RNA (sgRNA) or a nucleic acid (e.g., DNA) suitable for the generation of such sgRNA in situ (e.g., nucleic acid encoding the sgRNA), wherein the sgRNA comprises:
  i. a DNA-targeting segment comprised of RNA and capable of hybridizing to such target sequence in a polynucleotide locus,
  ii. a tracr mate sequence comprised of RNA, and
  iii. a tracr RNA sequence comprised of RNA, wherein the tracr mate sequence is capable of hybridizing to the tracr sequence, and wherein (i), (ii), and (iii) are arranged in a 5' to 3' orientation;
  or such cell whose genome has been targeting, editing, modifying, or manipulating using the above (a) and (b).

Additional embodiments according to the invention are Kits comprising:
(a) a nucleic acid sequence encoding SluCas9, wherein the nucleic acid sequence encoding SluCas9 is operably linked to a promoter or a ribosome binding site;
(b) single heterologous guide RNA (sgRNA) or a nucleic acid (e.g., DNA) suitable for the generation of such sgRNA in situ (e.g., nucleic acid encoding the sgRNA), wherein the sgRNA comprises:
  i. a DNA-targeting segment comprised of RNA and capable of hybridizing to such target sequence in a polynucleotide locus,
  ii. a tracr mate sequence comprised of RNA, and
  iii. a tracr RNA sequence comprised of RNA, wherein the tracr mate sequence is capable of hybridizing to the tracr sequence, and wherein (i), (ii), and (iii) are arranged in a 5' to 3' orientation.
or
(a) SluCas9 protein;
(b) one or more single heterologous guide RNAs (sgRNAs) each of which comprise(s):
  iv. a DNA-targeting segment comprised of RNA and capable of hybridizing to such target sequence in a polynucleotide locus,
  v. a tracr mate sequence comprised of RNA, and
  vi. a tracr RNA sequence comprised of RNA, wherein the tracr mate sequence is capable of hybridizing to the tracr sequence, and wherein (iv), (v), and (vi) are arranged in a 5' to 3' orientation.

Yet another embodiment according to the invention comprises compositions and methods for targeting, editing, modifying, or manipulating one or more target DNA(s) at one or more locations in a cell (e.g., in vitro or in vivo) or in a cell-free system, comprising:
(a) SluCas9
(b) guide RNA (gRNA) or a nucleic acid (e.g., DNA) suitable for the generation of such gRNA in situ (e.g., nucleic acid encoding the gRNA), wherein the gRNA comprises:
  i. a DNA-targeting segment comprised of RNA and capable of hybridizing to such target sequence in a polynucleotide locus,
  ii. a tracr RNA sequence comprised of RNA;
wherein (i) and (ii) are one a single RNA molecule and (iii) is on a separate RNA molecule.

Mutants

In some embodiments, the SluCas9 polypeptide is a mutant polypeptide with altered SluCas9 endoribonuclease activity or associated half-life of pre-crRNA, intermediate crRNA, or mature crRNA. In some embodiments, the SluCas9 polypeptide is a mutant polypeptide with altered or abrogated DNA endonuclease activity without substantially diminished or enhanced endoribonuclease activity or binding affinity to DNA. Such modification can allow for the sequence-specific DNA targeting of SluCas9 for the purpose of transcriptional modulation, activation, or repression; epigenetic modification or chromatin modification by methylation, demethylation, acetylation or deacetylation, or any other modifications of DNA binding and/or DNA-modifying proteins known in the art.

In some embodiments, the SluCas9 polypeptide is a mutant polypeptide with no DNA endonuclease activity.

In some embodiments, the cell is a bacterial cell, a fungal cell, an archaeal cell, a protist, a plant cell, or an animal cell.

In some embodiments, the SluCas9 polypeptide and the one or more guide RNAs (gRNAs), such as single heterologous guide RNA(s) (sgRNA(s)), are introduced into the cell by the same or different recombinant vectors encoding the polypeptide and the nucleic acid.

In some embodiments, the nucleic acid encoding the polypeptide, nucleic acid, or both the polypeptide and nucleic acid is modified.

In some embodiments, the method or system further comprises adding a donor DNA sequence, and wherein the target DNA sequence is edited by homology directed repair. In some embodiments, the polynucleotide donor template is physically linked to a crRNA or guide RNA In another aspect, provided herein is a method for modifying or editing double stranded DNA or single stranded target DNA, without having activity against single stranded RNA (ssRNA), double stranded RNA (dsRNA), or heteroduplexes of RNA and DNA.

Multiplexing

In another aspect, provided herein is a method for editing or modifying DNA at multiple locations in a cell consisting essentially of: i) introducing a SluCas9 polypeptide or a nucleic acid encoding a SluCas9 polypeptide into the cell; and ii) introducing a single heterologous nucleic acid comprising two or more pre-CRISPR RNAs (pre-crRNAs) either as RNA or encoded as DNA and under the control of one promoter into the cell, each pre-crRNA comprising a repeat-spacer array or repeat-spacer, wherein the spacer comprises a nucleic acid sequence that is complementary to a target sequence in the DNA and the repeat comprises a stem-loop structure, wherein the SluCas9 polypeptide cleaves the two or more pre-crRNAs upstream of the stem-loop structure to generate two or more intermediate crRNAs, wherein the two or more intermediate crRNAs are processed into two or more mature crRNAs, and wherein each two or more mature crRNAs guides the SluCas9 polypeptide to effect two or more double-strand breaks (DSBs) into the DNA. For example, one advantage of SluCas9 is that it is possible to introduce only one pre-crRNA which comprises several repeat-spacer units, which upon introduction, is processed by SluCas9 it into active repeat-spacer units targeting several different sequences on the DNA.

In some embodiments the pre-crRNA sequences in the single heterologous nucleic acid are joined together in specific locations, orientations, sequences or with specific chemicallinkages to direct or differentially modulate the endonuclease activity of SluCas9 at each of the sites specified by the different crRNA sequences.

In another aspect, provided herein is an example of a general method for editing or modifying the structure or function of DNA at multiple locations in a cell consisting essentially of: i) introducing an RNA-guided endonuclease, such as SluCas9, as a polypeptide or a nucleic acid encoding the RNA-guided endonuclease into the cell; and ii) introducing a single heterologous nucleic acid comprising or encoding two or more guide RNAs, either as RNA or encoded as DNA and under the control of one or more promoters, wherein the activity or function of the RNA-guided endonuclease is directed by the guide RNA sequences in the single heterologous nucleic acid.

Codon Optimized DNA Sequences for SluCas9

In some embodiments of the method, the nucleic acid sequence encoding the SluCas9 polypeptide is a modified nucleic acid, for example, codon optimized. In some embodiments of the method, the single heterologous nucleic acid is a modified nucleic acid. In some embodiments of the method, the method further comprises introducing into the cell a polynucleotide donor template. In some embodiments, the polynucleotide donor template is physically linked to a crRNA or guide RNA. In some embodiments of the method, the DNA is repaired at DSBs by either homology directed repair, non-homologous end joining, or microhomology-mediated end joining.

In some embodiments of the method, the SluCas9 polypeptide is more readily complexed with a mature crRNA in the local milieu, and thus more readily available for directing DNA endonuclease activity as a consequence of the crRNA being processed by the same SluCas9 polypeptide from the pre-crRNA in the local milieu.

In some embodiments of the method, the SluCas9 polypeptide is used to cleave, isolate or purify one or more mature crRNA sequences from a modified pre-crRNA oligonucleotide sequence in which heterologous sequences are incorporated 5' or 3' to one or more crRNA sequences within RNA oligonucleotide or DNA expression construct. The heterologous sequences can be incorporated to modify the stability, half-life, expression level or timing, interaction with the SluCas9 polypeptide or target DNA sequence, or any other physical or biochemical characteristics known in the art.

In some embodiments of the method, the pre-crRNA sequence is modified to provide for differential regulation of two or more mature crRNA sequences within the pre-crRNA sequence, to differentially modify the stability, half-life, expression level or timing, interaction with the SluCas9 polypeptide or target DNA sequence, or any other physical or biochemical characteristics known in the art.

In some embodiments, the SluCas9 polypeptide (or nucleic acid encoded variants thereof) is modified to improve desired characteristics such as function, activity, kinetics, half-life or the like. One such non-limiting example of such a modification is to replace a 'cleavage domain' of SluCas9 with a homologous or heterologous cleavage domain from a different nuclease, such as the RuvC or HNH domain from the Type II CRISPR-associated nuclease Cas9.

In one aspect, provided herein is a method for targeting, editing or manipulating DNA in a cell comprising linking an intact or partially or fully deficient SluCas9 polypeptide or pre-crRNA or crRNA moiety, to a dimeric FOK1 nuclease to direct endonuclease cleavage, as directed to one or more specific DNA target sites by one or more crRNA molecules. In another embodiment, the FOK1 nuclease system is a nickase or temperature sensitive mutant or any other variant known in the art.

In some embodiments, the SluCas9 polypeptide linked with a dimeric FOK1 nuclease is introduced into the cell together with a single heterologous nucleic acid comprising two or more pre-CRISPR RNAs (pre-crRNAs) either as RNA or encoded as DNA and under the control of one promoter into the cell, each pre-crRNA comprising a repeat-spacer array, wherein the spacer comprises a nucleic acid sequence that is complementary to a target sequence in the DNA and the repeat comprises a stem-loop structure, wherein the SluCas9 polypeptide cleaves the two or more pre-crRNAs upstream of the stem-loop structure to generate two or more intermediate crRNAs.

In one aspect, provided herein is a method for targeting, editing or manipulating DNA in a cell comprising linking an intact or partially or fully deficient SluCas9 polypeptide or pre-crRNA, intermediate crRNA, mature crRNA moiety, or gRNA (collectively referred to as crRNA), to a donor single or double strand DNA donor template to facilitate homologous recombination of exogenous DNA sequences, as directed to one or more specific DNA target sites by one or more guide RNA or crRNA molecules.

In yet another aspect, provided herein is a method for directing a DNA template, for homologous recombination or homology-directed repair, to the specific site of gene editing. In this regard, a single stranded or double stranded DNA template is linked chemically or by other means known in the art to a crRNA or guide RNA. In some embodiments the DNA template remains linked to the crRNA or guide RNA; in yet other examples, SluCas9 cleaves the crRNA or guide RNA, liberating the DNA template to enable or facilitate homologous recombination.

In yet another aspect, provided herein is a method for targeting, editing or manipulating DNA in a cell comprising linking an intact or partially or fully deficient SluCas9 polypeptide or pre-crRNA or crRNA moiety, to a transcriptional activator or repressor, or epigenetic modifier such as a methylase, demethylase, acetylase, or deacetylase, or signaling or detection, all aspects of which have been previously described for Cas9 systems, as directed to one or more specific DNA target sites by one or more crRNA molecules.

In another aspect, provided herein is a composition comprising a polynucleotide donor template linked to a crRNA or a guide RNA. A method for targeting, editing or manipulating DNA in a cell comprising linking a pre-crRNA or crRNA or guide RNA to a donor single or double strand polynucleotide donor template such that the donor template is cleaved from the pre-crRNA or crRNA or guide RNA by a SluCas9 polypeptide, thus facilitating homology directed repair by the donor template, as directed to one or more specific DNA target sites by one or more guide RNA or crRNA molecules.

SluCas9 can also be used to form a chimeric binding protein in which other domains and activities are introduced. By way of illustration, a FokI domain can be fused to a SluCas9 protein, which can contain a catalytically active endonuclease domain, or a FokI domain can be fused to a SluCas9 protein, which has been modified to render the SluCas9 endonuclease domain inactive. Other domains that can be fused to make chimeric proteins with SluCas9 including transcriptional modulators, epigenetic modifiers, tags and other labels or imaging agents, histones, and/or other modalities known in the art that modulate or modify the structure or activity of gene sequences.

Based on the sequence, and with reference to the structural specificity of binding of SluCas9 to the hairpin structures of crRNA forms, SluCas9 orthologues can be identified and characterized based on sequence similarities to the present system, as has been described with type I systems for example. For example, orthologs of SluCas9 [*Staphylococcus hyicus, Staphylococcus microti, Staphylococcus pasteuri*]

Nucleic Acid and/or Amino Acid Modifications

In some embodiments, polynucleotides introduced into cells comprise one or more modifications which can be used, for example, to enhance activity, stability or specificity, alter delivery, reduce innate immune responses in host cells, further reduce the protein size, or for other enhancements, as further described herein and known in the art. In some embodiments, such modifications will result in SluCas9 polypeptides which comprises an amino acid sequence having at least 75%, at least 80%, at least 85%, at least 90%, at least 95%, at least 99%, or 100%, amino acid sequence identity to the sequence of SEQ ID NO: 2 or the amino acid sequences of SEQ ID NO: 4.

In certain embodiments, modified polynucleotides are used in the CRISPR-Cas system, in which case the guide RNAs and/or a DNA or an RNA encoding a Cas endonuclease introduced into a cell can be modified, as described and illustrated below. Such modified polynucleotides can be used in the CRISPR-Cas system to edit any one or more genomic loci.

Components of CRISPR-Cas Systems

A. Guide RNAs/sgRNAs

In aspects of the invention the terms "chimeric RNA", "chimeric guide RNA", "guide RNA", "single guide RNA" and "synthetic guide RNA" are used interchangeably and refer to the polynucleotide sequence comprising the DNA-targeting segment, the tracr sequence and the tracr mate sequence. The term "guide sequence" or "DNA-targeting sequence" refers to the about 20 bp sequence within the guide RNA that specifies the target site and may be used interchangeably with the terms "guide" or 'spacer'. The term "tracr mate sequence" may also be used interchangeably with the term "direct repeat(s)".

In some aspects, a single guide RNA (sgRNA) according to the invention comprises:
i. a DNA-targeting segment or DNA-targeting sequence comprised of RNA and capable of hybridizing to a target sequence in a polynucleotide locus,
ii. a tracr mate sequence comprised of RNA, and
iii. a tracr RNA sequence comprised of RNA,
wherein the tracr mate sequence is capable of hybridizing to the tracr sequence, and wherein (i), (ii), and (iii) are arranged in a 5' to 3' orientation. In some embodiments, components (i), (ii), and (iii) are on a single chimeric RNA.

Within a sgRNA, a tracr mate sequence and a tracr sequence can connected by a suitable loop sequence and form a stem-loop structure.

In general, a tracr mate sequence includes any sequence that has sufficient complementarity with a tracr sequence to promote one or more of: (1) excision of a DNA-targeting segment flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm and may further account for secondary structures, such as self-complementarity within either the tracr sequence or tracr mate sequence. In some embodiments, the degree of complementarity between the tracr sequence and tracr mate sequence along the 30 nucleotides length of the shorter of the two when optimally aligned is about or more than 25%, 30%, 40%, 50%, 60%, 70%, 80%, 90%, 95%, 97.5%, 99%, or higher. In some embodiments, the tracr sequence is about or more than 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins.

In some embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a DNA-targeting segment, a tracr mate sequence, and a tracr sequence are as follows (listed 5' to 3'), where "N" represents a base of a DNA-targeting segment, the first block of lower case letters represent the tracr mate sequence, and the second block of lower case letters represent the tracr sequence, and the final poly-T sequence represents the transcription terminator:

The DNA-targeting segment of a guide RNA comprises a nucleotide sequence that is complementary to a sequence in a target DNA. In other words, the DNA-targeting segment of a guide RNA interacts with a target DNA in a sequence-specific manner via hybridization (i.e., base pairing). As such, the nucleotide sequence of the DNA-targeting segment may vary and determines the location within the target DNA that the guide RNA and the target DNA will interact. The DNA-targeting segment of a guide RNA can be modified (e.g. by genetic engineering) to hybridize to any desired sequence within a target DNA.

The DNA-targeting segment can have a length of from 10 nucleotides to 30 nucleotides.

In some embodiments, the DNA-targeting segment has a length of from 13 nucleotides to 25 nucleotides.

In some embodiments, the DNA-targeting segment has a length of from 15 nucleotides to 23 nucleotides.

In some embodiments, the DNA-targeting segment has a length of from 18 nucleotides to 22 nucleotides, such as from 20 to 22 nucleotides.

The percent complementarity between the DNA-targeting sequence of the DNA-targeting segment and the target sequence of the target DNA can be at least 60% (e.g. at least 65%, at least 70%, at least 75%, at least 80%, at least 85%, at least 90%, at least 95%, at least 97%, at least 98%, at least 99%, or 100%) over the 20-22 nucleotides.

A protospacer sequence complementary to the target sequence in the target DNA can be adjacent to a suitable PAM sequence for SluCas9 at its 3' end, or such PAM sequence can be part of the 3' portion of the DNA-targeting segment.

Using the CRISPR-Cas system for purposes of non-limiting illustrations of such uses, modifications of guide RNAs can be used to enhance the formation or stability of the CRISPR-Cas genome editing complex comprising guide RNAs and a Cas endonuclease such as SluCas9. Modifications of guide RNAs can also or alternatively be used to enhance the initiation, stability or kinetics of interactions between the genome editing complex with the target sequence in the genome, which can be used for example to enhance on-target activity. Modifications of guide RNAs can also or alternatively be used to enhance specificity, e.g. the relative rates of genome editing at the on-target site as compared to effects at other (off-target) sites.

Modifications can also or alternatively used to increase the stability of a guide RNA, e.g. by increasing its resistance to degradation by ribonucleases (RNases) present in a cell, thereby causing its half-life in the cell to be increased. Modifications enhancing guide RNA half-life can be particularly useful in embodiments in which a Cas endonuclease such as a SluCas9 is introduced into the cell to be edited via an RNA that needs to be translated in order to generate SluCas9 endonuclease, since increasing the half life of guide RNAs introduced at the same time as the RNA encoding the endonuclease can be used to increase the time that the guide RNAs and the encoded Cas endonuclease co-exist in the cell.

B. Protospacer-Adjacent Motif (PAM or PAM Sequence)

Suitable PAM sequences for SluCas9 include "ANGG" and "NNGG."

As illustrated in Examples 1, 2 and 3, a suitable Protospacer adjacent motif (PAM) for the SluCas9 system according to the invention is "NNGG".

The site of cleavage generally occurs within one to three base pairs upstream of the PAM sequence, such as within either one or three base pairs upstream of the PAM sequence, within three base pairs of the PAM sequence, or within three base pairs upstream of the PAM sequence "NNGG".

C. Use in Eukaryotic Cells

In one embodiment according to the invention the SluCas9 system herein described can be used in eukaryotic cells, such as mammalian cells. Such activity is exemplified in Example 4 and FIGS. 4A-4C and 5A-5C.

Other Features of the Invention

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease such as SluCas9 that are introduced into a cell, including, without limitation, modifications that enhance the stability of the RNA (such as by decreasing its degradation by RNases present in the cell), modifications that enhance translation of the resulting product (i.e., the endonuclease), and/or modifications that decrease the likelihood or degree to which the RNAs introduced into cells elicit innate immune responses. Combinations of modifications, such as the foregoing and others, can likewise be used. In the case of CRISPR-Cas, for example, one or more types of modifications can be made to guide RNAs (including those exemplified above), and/or one or more types of modifications can be made to RNAs encoding CAS endonuclease (including those exemplified above).

By way of illustration, guide RNAs used in the CRISPR-Cas system or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding a SluCas9 endonuclease, are more readily generated enzymatically. While fewer types of modifications are generally available for use in enzymatically produced RNAs, there are still modifications that can be used to, e.g. enhance stability, reduced the likelihood or degree of innate immune response, and/or enhance other attributes, as described further below and in the art; and new types of modifications are regularly being developed. By way of illustration of various types of modifications, especially those used frequently with smaller chemically synthesized RNAs, modifications can comprise one or more nucleotides modified at the 2' position of the sugar, in some embodiments a 2'-O-alkyl, 2'-O-alkyl-O-alkyl or 2'-fluoro-modified nucleotide. In some embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxy oligonucleotides against a given target.

A number of nucleotide and nucleoside modifications have been shown to make the oligonucleotide into which they are incorporated more resistant to nuclease digestion than the native oligonucleotide; these modified oligonucleotides survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, —N($CH_3$)—$CH_2$ (known as a methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones; amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177, 196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243:209-214 (2002); Nasevicius et al., Nat. Genet., 26:216-220 (2000); Lacenra et al., Proc. Natl. Acad. Sci., 97: 9591-9596 (2000); and U.S. Pat. No. 5,034,506, issued Jul. 23, 1991. Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g. one of the following at the 2' position: OH, SH, $SCH_3$, F, OCN, $OCH_3$, $OCH_3O(CH_2)n$ $CH_3$, $O(CH_2)n$ $NH_2$ or $O(CH_2)n$ $CH_3$ where n is from 1 to 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl: $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some embodiments, a modification includes 2'-methoxyethoxy (2'-O—CH2CH2OCH3, also known as 2'-O-(2-methoxyethyl)) (Martin et al, Helv. Chim. Acta, 1995, 78, 486). Other modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group. In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262. Further teaching of PNA compounds can be found in Nielsen et at, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g. hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g. 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2.6-diaminopurine. Kornberg, A, DNA Replication, W. H. Freeman & Co., San Francisco, pp 75-77 (1980); Gebeyehu et al., Nucl. Acids Res. 15:4513 (1997). A "universal" base known in the art, e.g. inosine, can also be induded. 5-Me-C substitutions have been shown to increase nucleic acid duplex stability by 0.6-1.2 degrees C. (Sanghvi, Y. S., in Crooke, S. T. and Lebleu, B., eds., Antisense Research and Applications, CRC Press, Boca Raton, 1993, pp. 276-278) and are embodiments of base substitutions.

Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other a-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandte Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and —O-6 substituted purines, comprising 2-aminopropyladenine, 5-propynyluracil and 5-propynylcytosine. 5-methylcytosine substitutions have been shown to increase nucleic acid duplex stability by 0.6-1.2 oc (Sanghvi, Y. S., Crooke, S. T. and Lebleu, B., eds, 'Antisense Research and Applications', CRC Press, Boca Raton, 1993, pp. 276-278) and are embodiments of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,681,941; 5,750, 692; 5,763,588; 5,830,653; 6,005,096; and US Patent Application Publication 20030158403.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, the guide RNAs and/or mRNA (or DNA) encoding an endonuclease such as SluCas9 are chemically linked to one or more moieties or conjugates that enhance the activity, cellular distribution, or cellular uptake of the oligonucleotide. Such moieties comprise but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g. hexyi-S-tritylthiol [Manoharan et al, Ann. N. Y Acad. Sci., 660: 306-309 (1992) and Manoharan et al., Bioorg. Med. Chem. Let., 3.-2765-2770 (1993)); a thiocholesterol [Oberhauser et al., Nucl. Acids Res., 20: 533-538 (1992)]; an aliphatic chain, e.g. dodecandiol or undecyl residues [Kabanov et al., FEBS Lett., 259: 327-330 (1990) and Svinarchuk et al., Biochimie, 75: 49-54 (1993)]; a phospholipid, e.g. di-hexadecyl-rac-glycerol or triethylammonium 1,2-di-O-hexadecyl-rac-glycero-3-H-phosphonate [Manoharan et al., Tetrahedron Lett., 36:3651-3654 (1995) and Shea et al., Nucl. Acids Res., 18: 3777-3783 (1990)]; a polyamine or a polyethylene glycol chain [Mancharan et al., Nucfeosides & Nucleotides, 14: 969-973 (1995)]; adamantane acetic acid [Manoharan et at., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacal. Exp. Ther., 277: 923-937 (1996)]. See also U.S. Pat. Nos. 4,828, 979; 4,948,882; 5,218,105; 5,525,465; 5,541,313; 5,545, 730; 5,552, 538; 5,578,717; 5,580,731; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762, 779; 4,789,737; 4,824,941; 4,835, 263; 4,876,335; 4,904,582; 4,958,013; 5,082, 830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241, 5,391, 723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599, 928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g. Hu, et al., Protein Pept Lett. 21(1 0):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g. hexyl-5-tritylthiol, a thiocholesterol, an aliphatic chain, e.g. dodecandiol or undecyl residues, a phospholipid, e.g. di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g. U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are generally produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding SluCas9 is approximately 4 kb in length and can be synthesized by in vitro transcription. Modifications to the mRNA can be applied to, e.g. increase its translation or stability (such as by increasing its resistance to degradation with a cell), or to reduce the tendency of the RNA to elicit an innate immune response that is often observed in cells following introduction of exogenous RNAs, particularly longer RNAs such as that encoding SluCas9.

Numerous such modifications have been described in the art, such as polyA tails, 5' cap analogs (e.g. Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates.

These and other modifications are known in the art, and new modifications of RNAs are regularly being developed.

There are numerous commercial suppliers of modified RNAs, including for example, Trilink Biotech, Axolabs, Bio-Synthesis Inc. Dharmacon and many others. As described by Trilink, for example, 5-Methyl-CTP can be used to impart desirable characteristics such as increased nuclease stability, increased translation or reduced interaction of innate immune receptors with in vitro transcribed RNA. 5'-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation as illustrated in publications by Konmann et al. and Warren et al. referred to below.

It has been shown that chemically modified mRNA delivered in vivo can be used to achieve improved therapeutic effects; see, e.g. Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found substituting just one quarter of the uridine and cytidine residues with 2-Thio-U and 5-Methyl-C respectively, resulted in a significant decrease in toll-like receptor (TLR) mediated recognition of the mRNA in mice. By reducing the activation of the innate immune system, these modifications can therefore be used to effectively increase the stability and longevity of the mRNA in vivo; see, e.g. Konmann et al., supra.

It has also been shown that repeated administration of synthetic messenger RNAs incorporating modifications designed to bypass innate anti-viral responses can reprogram differentiated human cells to pluripotency. See, e.g. Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs). and it was found that enzymatically synthesized RNA incorporating 5-Methyl-CTP, Pseudo-UTP and an Anti Reverse Cap Analog (ARCA) could be used to effectively evade the cell's antiviral response; see, e.g. Warren et al., supra. Other modifications of polynucleotides described in the art include, for example, the use of polyA tails, the addition of 5' cap analogs (such as m7G(5') ppp(5')G (mCAP)), modifications of 5' or 3' untranslated regions (UTRs), or treatment with phosphatase to remove 5' terminal phosphates- and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-1), that can mediate cellular responses to dsRNA, as well as Toll-like receptors (such as TLR3, TLR7 and TLR8) that can trigger the induction of cytokines in response to such molecules; see, e.g. the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and Maclachlan, Hum Gene Ther 19(2):111-24 (2008); and references cited therein.

A large variety of modifications have been developed and applied to enhance RNA stability, reduce innate immune responses, and/or achieve other benefits that can be useful in connection with the introduction of polynucleotides into human cells as described herein; see, e.g. the reviews by Whitehead K A et al., Annual Review of Chemical and Biomolecular Engineering, 2:77-96 (2011); Gaglione and Messere, Mini Rev Med Chern, 10(7):578-95 (2010); Chernolovskaya et al, Curr Opin Mol Ther., 12(2):158-67 (2010); Deleavey et al, Curr Protoc Nucleic Acid Chern Chapter 16:Unit 16.3 (2009); Behlke, Oligonucleotides 18(4):305-19 (2008): Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kale, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) has been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g. Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g. Kariko, K. et al., Immunity 23:165-175 (2005).

As is also known in the art, and commercially available, a number of conjugates can be applied to polynucleotides such as RNAs for use herein that can enhance their delivery and/or uptake by cells, including for example, cholesterol, tocopherol and folic acid, lipids, peptides, polymers, linkers and aptamers; see, e.g. the review by Winkler, Ther. Deliv. 4:791-809 (2013), and references cited therein.

Mimetics

A nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units, which gives PNA an amide containing backbone. The heterocyclic base moieties are bound directly or indirectly to aza nitrogen atoms of the amide portion of the backbone. Representative US patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are nonionic mimics of oligonucleotides, which are less likely to form undesired interactions with cellular proteins (Dwaine A. Braasch and David R. Corey, Biochemistry, 2002, 41(14), 45034510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (GeNA). The furanose ring normally present in a DNA/RNA molecule is replaced with a cydohexenyl ring. GeNA DMT protected phosphoramidite monomers have been prepared and used for oligomeric compound synthesis following classical phosphoramidite chemistry. Fully modified GeNA oligomeric compounds and oligonucleotides having specific positions modified with GeNA have been prepared and studied (see Wang et al., J. Am. Chem. Soc., 2000, 122, 85958602). In general the incorporation of GeNA monomers into a DNA chain increases its stability of a DNA/RNA hybrid. GeNA oligoadenylates formed complexes with RNA and DNA complements with similar stability to the native complexes. The study of incorporating GeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CHz-), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA ($T_m$=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A, 2000, 97, 5633-5638).

The synthesis and preparation of the LNA monomers adenine, cytosine, guanine, 5-methyl-cytosine. thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A nucleic acid can also include one or more substituted sugar moieties. Suitable polynucleotides comprise a sugar substituent group selected from: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)nO)$ $mCH_3$, $O(CHz)nOCH3$, $O(CHz)nNH_2$, $O(CH_2)CH_3$, $O(CH_2)nONH_2$, and $O(CH_2)nON((CH_2)nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, ONO, $NO_2$, $N_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy 2'-O—CH2 CHzOCH3, also known as -2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a O(CHz)zON(CH3)z group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O-CHz-O-CHz-N(CH3)z.

Other suitable sugar substituent groups include methoxy (—O—CH3), aminopropooxy (—O—CH$_z$CH$_z$CH$_z$NH$_z$), allyl (—CH$_z$—CH═CH$_z$), —O-allyl (—O—CH$_z$—CH═CH$_z$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. 1., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2 oc. (Sanghvi et al., eds., Antisense Research and Applications, CRC Press, Boca Raton, 1993, pp. 276-278) and are suitable base substitutions, e.g. when combined with 2'-O-methoxyethyl sugar modifications.

"Complementary" refers to the capacity for pairing, through base stacking and specific hydrogen bonding, between two sequences comprising naturally or non-naturally occurring (e.g. modified as described above) bases (nucleosides) or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g. Wobble base pairing and Hoogsteen base pairing).

It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santalucia, Nucl. Acids Research, 2005; 33 (19): 6258-6267.

Conjugates

Another possible modification of a nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a nucleic acid.

Conjugatemoieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994,4, 1053-1060), a thioether, e.g. hexyi-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g. dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g. di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 36513654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacal. Exp. Ther., 1996, 277, 923-937).

A conjugate may include a "Protein Transduction Domain" or PTD (also known as a CPP– cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of an exogenous polypeptide (e.g. a SluCas9 polypeptide). In some embodiments, a PTD is covalently linked to the C-terminus or the N-terminus of an exogenous polypeptide (e.g. a SluCas9 polypeptide). In some embodiments, a PTD is covalently linked to a nucleic acid (e.g. a guide RNA, a polynucleotide encoding a guide RNA, a polynucleotide encoding a SluCas9 polypeptide, etc.). Exemplary PTDs include but are not limited to a minimal undecapeptide protein transduction domain (for example corresponding to residues 47-57 of HIV-1 TAT comprising the YGRKKRRQRRR motif (for identifying but not for purposes of disclosure within this application); a polyarginine sequence comprising a number of arginines sufficient to direct entry into a cell (e.g. 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA97:13003-13008); In some embodiments, the PTD is an activatable CPP (ACPP) (Aguilera et al. (2009) Integr Bioi (Camb) June; 1(5-6): 371-381). ACPPs comprise a polycationic CPP (e.g. Arg9 or "R9") connected via a cleavable linker to a matching polyanion (e.g. Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane. In some embodiments the PTD is chemically modified in order to increase the bioavailability of the PTD. Exemplary modifications are disclosed in Expert Opin Drug Deliv. 2009 November; 6(11):1195-205.

Nucleic Acids Encoding a Guide RNA and/or a SluCas9 Polypeptide

The present disclosure provides a nucleic acid comprising a nucleotide sequence encoding a guide RNA and/or a SluCas9 polypeptide. In some embodiments, a guide RNA-encoding nucleic acid is an expression vector, e.g. a recombinant expression vector.

In some embodiments, a method involves contacting a target DNA or introducing into a cell (or a population of cells) one or more nucleic acids comprising nucleotide sequences encoding a guide RNA and/or a SluCas9 polypeptide. In some embodiments a cell comprising a target DNA is in vitro. In some embodiments a cell comprising a target DNA is in vivo. Suitable nucleic acids comprising nucleotide sequences encoding a guide RNA and/or a SluCas9 polypeptide include expression vectors, where an expression vector comprising a nucleotide sequence encoding a guide RNA and/or a SluCas9 polypeptide is a "recombinant expression vector."

In some embodiments, the recombinant expression vector is a viral construct, e.g. a recombinant adeno-associated virus construct (see, e.g. U.S. Pat. No. 7,078,387), a recombinant adenoviral construct, a recombinant lentiviral construct, a recombinant retroviral construct, etc. [00248] Suitable expression vectors include, but are not limited to, viral vectors (e.g. viral vectors based on vaccinia virus; poliovirus; adenovirus (see, e.g. Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g. Ali et al., Hum Gene Ther 9:8186, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166:154-165; and Flotte et al., PNAS (1993) 90:10613-10617); SV40; herpes simplex virus; human immunodeficiency virus (see, e.g. Miyoshi et al., PNAS 94:10319 23, 1997; Takahashi et al., J Viral 73:7812 7816, 1999); a retroviral vector (e.g. Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSGS (Stratagene), pSVK3, pBPV, pMSG, and pSVLSV40 (Phanmacia). However, any other vector may be used so long as it is compatible with the host cell. Depending on the host/vector system utilized, any of a number of suitable transcription and translation control elements, including constitutive and inducible promoters, transcription enhancer elements, transcription terminators, etc. may be used in the expression vector (see e.g. Bitter et al. (1987) Methods in Enzymology, 153:516-544).

In some embodiments, a nucleotide sequence encoding a guide RNA and/or a SluCas9 polypeptide is operably linked to a control element, e.g. a transcriptional control element, such as a promoter. The transcriptional control element may be functional in either a eukaryotic cell, e.g. a mammalian cell; or a prokaryotic cell (e.g. bacterial or archaeal cell). In some embodiments, a nucleotide sequence encoding a guide RNA and/or a SluCas9 polypeptide is operably linked to multiple control elements that allow expression of the nucleotide sequence encoding a guide RNA and/or a SluCas9 polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-1. Selection of the appropriate vector and promoter is well within the level of ordinary skill in the art.

The expression vector may also contain a ribosome binding site for translation initiation and a transcription terminator. The expression vector may also include appropriate sequences for amplifying expression. The expression vector may also include nucleotide sequences encoding protein tags (e.g. 6×His tag, hemagglutinin tag, green fluorescent protein, etc.) that are fused to the SluCas9 polypeptide, thus resulting in a chimeric polypeptide.

In some embodiments, a nucleotide sequence encoding a guide RNA and/or a SluCas9 polypeptide is operably linked to an inducible promoter. In some embodiments, a nucleotide sequence encoding a guide RNA and/or a SluCas9 polypeptide is operably linked to a constitutive promoter.

Methods of introducing a nucleic acid into a host cell are known in the art, and any known method can be used to introduce a nucleic acid (e.g. an expression construct) into a cell. Suitable methods include, e.g. viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g. Panyam et al., Adv Drug Deliv Rev. 2012 Sep. 13. pii: 50169-409X(12)00283-9.doi: 10.1016/j.addr. 2012.09.023), and the like.

Chimeric Polypeptides

The present disclosure provides a chimeric site-directed modifying polypeptide comprising a sequence derived from a SluCas9 polypeptide. A chimeric site-directed modifying polypeptide interacts with (e.g. binds to) a guide RNA (described above). The guide RNA guides the chimeric site-directed modifying polypeptide to a target sequence within target DNA (e.g. a chromosomal sequence or an extrachromosomal sequence, e.g. an episomal sequence, a minicircle sequence, a mitochondrial sequence, a chloroplast sequence, cell-free polynucleotide, etc.). A chimeric site-directed modifying polypeptide modifies target DNA (e.g. cleavage or methylation of target DNA) and/or a polypeptide associated with target DNA (e.g. methylation or acetylation of a histone tail). A chimeric site-directed modifying polypeptide is also referred to herein as a "chimeric site-directed polypeptide" or a "chimeric RNA binding site-directed modifying polypeptide."

A chimeric site-directed modifying polypeptide comprises two portions, an RNA-binding portion and an activity portion. A chimeric site-directed modifying polypeptide comprises amino acid sequences that are derived from at least two different polypeptides. A chimeric site-directed modifying polypeptide can comprise modified and/or naturally occurring polypeptide sequences (e.g. a first amino acid sequence from a modified or unmodified SluCas9 protein; and a second amino acid sequence other than the SluCas9 protein).

RNA-Binding Portion

In some cases, the RNA-binding portion of a chimeric site-directed modifying polypeptide is a naturally occurring polypeptide. In other cases, the RNA-binding portion of a chimeric site-directed modifying polypeptide is not a naturally occurring molecule (modified, e.g. mutation, deletion, insertion). Naturally occurring RNA-binding portions of interest are derived from site-directed modifying polypeptides known in the art. For example SEQ ID NO: 2 is a naturally occurring SluCas9 endonuclease that can be used as a site-directed modifying polypeptide. In some cases, the RNA-binding portion of a chimeric site-directed modifying polypeptide comprises an amino acid sequence having at least 75%, at least 80%, at least 85%, at least 90%, at least 95%, at least 98%, at least 99%, or 100%, amino acid sequence identity to the RNA-binding portion of a polypeptide set forth in SEQ ID NO: 2

Activity Portion

In addition to the RNA-binding portion, the chimeric site-directed modifying polypeptide comprises an "activity portion." In some embodiments, the activity portion of a chimeric site-directed modifying polypeptide comprises the naturally-occurring activity portion of a site-directed modifying polypeptide (e.g. SluCas9 endonuclease). In other embodiments, the activity portion of a subject chimeric site-directed modifying polypeptide comprises a modified amino acid sequence (e.g. substitution, deletion, insertion) of a naturally-occurring activity portion of a site-directed modifying polypeptide. Naturally-occurring activity portions of interest are derived from site-directed modifying polypeptides known in the art. For example, the sequence disclosed in SEQ ID NO: 2 is a naturally occurring SluCas9 endonucleases that can be used as a site-directed modifying polypeptide. The activity portion of a chimeric site-directed modifying polypeptide is variable and may comprise any heterologous polypeptide sequence that may be useful in the methods disclosed herein. In some embodiments, the activity portion of a site-directed modifying polypeptide comprises a portion of a SluCas9 ortholog that is at least 90% identical to activity portion amino acids of SEQ ID NO: 2. In some embodiments, a chimeric site-directed modifying polypeptide comprises: (i) an RNA-binding portion that interacts with a guide RNA, wherein the guide RNA comprises a nucleotide sequence that is complementary to a sequence in a target DNA; (ii) an activity portion that exhibits site-directed enzymatic activity (e.g. activity for RNA cleavage), wherein the site of enzymatic activity is determined by the palindromic hairpin structures formed by the repeats of pre-crRNA and cleaves the pre-crRNA 4 nt upstream of the hairpins generating intermediate forms of crRNAs composed of repeat spacer (5'-3'); and (iii) an activity portion that exhibits site-directed enzymatic activity (e.g. activity for DNA cleavage), wherein the site of enzymatic activity is determined by the guide RNA.

Exemplary Chimeric Site-Directed Modifying Polypeptides

In some embodiments, the activity portion of the chimeric site-directed modifying polypeptide comprises a modified form of the SluCas9 protein, including modified forms of any of the SluCas9 orthologs. In some instances, the modified form of the SluCas9 protein comprises an amino acid change (e.g. deletion, insertion, or substitution) that reduces or increases the naturally occurring nuclease activity of the SluCas9 protein. For example, in some instances, the modified form of the SluCas9 protein has less than 50%, less than 40%, less than 30%, less than 20%, less than 10%, less than 5%, or less than 1% of the nuclease activity of the corresponding wild-type SluCas9 polypeptide. In some cases, the modified form of the SluCas9 polypeptide has no substantial nuclease activity. In other cases, it may have 50%, 2-fold, 4-fold or up to an over 10-fold more nuclease activity.

In some cases, the chimeric site-directed modifying polypeptide comprises an amino acid sequence having at least 75%, at least 80%, at least 85%, at least 90%, at least 95%, at least 99% or 100% amino acid sequence identity to SEQ ID NO: 2. In some embodiments, the activity portion of the site-directed modifying polypeptide comprises a heterologous polypeptide that has DNA-modifying activity and/or transcription factor activity and/or DNA-associated polypeptide-modifying activity. In some cases, a heterologous polypeptide replaces a portion of the SluCas9 polypeptide that provides nuclease activity. In other embodiments, a site-directed modifying polypeptide comprises both a portion of the SluCas9 polypeptide that normally provides nuclease activity (and that portion can be fully active or can instead be modified to have less than 100% of the corresponding wild-type activity) and a heterologous polypeptide. In other words, in some cases, a chimeric site-directed modifying polypeptide is a fusion polypeptide comprising both the portion of the SluCas9 polypeptide that normally provides nuclease activity and the heterologous polypeptide. In other cases, a chimeric site-directed modifying polypeptide is a fusion polypeptide comprising a modified variant of the activity portion of the SluCas9 polypeptide (e.g. amino acid change, deletion, insertion) and a heterologous polypeptide. In yet other cases, a chimeric site-directed modifying polypeptide is a fusion polypeptide comprising a heterologous polypeptide and the RNA-binding portion of a naturally occurring or a modified site-directed modifying polypeptide.

For example, in a chimeric SluCas9 protein, a naturally occurring (or modified, e.g. mutation, deletion, insertion) SluCas9 polypeptide may be fused to a heterologous polypeptide sequence (i.e., a polypeptide sequence from a protein other than SluCas9 or a polypeptide sequence from another organism). The heterologous polypeptide sequence may exhibit an activity (e.g. enzymatic activity) that will also be exhibited by the chimeric SluCas9 protein (e.g. methyltransferase activity, acetyltransferase activity, kinase activity, ubiquitinating activity, etc.). A heterologous nucleic acid sequence may be linked to another nucleic acid sequence (e.g. by genetic engineering) to generate a chimeric nucleotide sequence encoding a chimeric polypeptide. In some embodiments, a chimeric SluCas9 polypeptide is generated by fusing a SluCas9 polypeptide (e.g. wild type SluCas9 or a SluCas9 variant, e.g. a SluCas9 with reduced or inactivated nuclease activity) with a heterologous sequence that provides for subcellular localization (e.g. a nuclear localization signal (NLS) for targeting to the nucleus; a mitochondrial localization signal for targeting to the mitochondria; a chloroplast localization signal for targeting to a chloroplast: an ER retention signal; and the like). In some embodiments, the heterologous sequence can provide a tag for ease of tracking or purification (e.g. a fluorescent protein, e.g. green fluorescent protein (GFP); YFP, RFP, CFP, mCherry, tdTomato, and the like; a HIS tag, e.g. a 6×His tag; a hemagglutinin (HA) tag; a FLAG tag; a Myc tag; and the like. In some embodiments, the heterologous sequence can provide for increased or decreased stability. In some embodiments, the heterologous sequence can provide a binding domain (e.g. to provide the ability of a chimeric SluCas9 polypeptide to bind to another protein of interest, e.g. a DNA or histone modifying protein, a transcription factor or transcription repressor, a recruiting protein, etc.) or to a nucleotide of interest (e.g., an aptamer or target site of a nucleotide binding protein).

Nucleic Acid Encoding a Chimeric Site-Directed Modifying Polypeptide

The present disclosure provides a nucleic acid comprising a nucleotide sequence encoding a chimeric site-directed modifying polypeptide. In some embodiments, the nucleic acid comprising a nucleotide sequence encoding a chimeric site-directed modifying polypeptide is an expression vector, e.g. a recombinant expression vector.

In some embodiments, a method involves contacting a target DNA or introducing into a cell (or a population of cells) one or more nucleic acids comprising a chimeric site-directed modifying polypeptide. Suitable nucleic acids comprising nucleotide sequences encoding a chimeric site-directed modifying polypeptide include expression vectors, where an expression vector comprising a nucleotide sequence encoding a chimeric site-directed modifying polypeptide is a "recombinant expression vector."

In some embodiments, the recombinant expression vector is a viral construct, e.g. a recombinant adeno-associated virus construct (see, e.g. U.S. Pat. No. 7,078,387), a recombinant adenoviral construct, a recombinant lentiviral construct, etc. Suitable expression vectors include, but are not limited to, viral vectors (e.g. viral vectors based on vaccinia virus; poliovirus; adenovirus (see, e.g. Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769: WO 93/19191; WO 94/28938; WO 95/11984 and WO 95/00655); adeno-associated virus (see, e.g. Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641648, 1999; Ali et al., Hum Mol Genet 5:591594, 1996; Srivastava in WO 93/09239, Samulski et al., J. Vir. (1989) 63:3822-3828; Mendelson et al., Viral. (1988) 166: 154-165; and Flotte et al., PNAS (1993) 90:10613-10617); SV40; herpes simplex virus; human immunodeficiency virus (see, e.g. Miyoshi et al., PNAS 94:10319 23, 1997; Takahashi et al., J Virol 73:7812 7816, 1999); a retroviral vector (e.g. Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSGS (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g. Bitter et al. (1987) Methods in Enzymology, 153:516-544).

In some embodiments, a nucleotide sequence encoding a chimeric site-directed modifying polypeptide is operably linked to a control element, e.g. a transcriptional control element, such as a promoter. The transcriptional control element may be functional in either a eukaryotic cell, e.g. a mammalian cell; or a prokaryotic cell (e.g. bacterial or archaeal cell). In some embodiments, a nucleotide sequence encoding a chimeric site-directed modifying polypeptide is operably linked to multiple control elements that allow expression of the nucleotide sequence encoding a chimeric site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-1. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g. 6×His tag, hemagglutinin (HA) tag, a fluorescent protein (e.g. a green fluorescent protein; a yellow fluorescent protein, etc.), etc.) that are fused to the chimeric site-directed modifying polypeptide.

In some embodiments, a nucleotide sequence encoding a chimeric site-directed modifying polypeptide is operably linked to an inducible promoter (e.g. heat shock promoter, Tetracycline-regulated promoter, Steroid-regulated promoter, Metal-regulated promoter, estrogen receptor-regulated promoter, etc.). In some embodiments, a nucleotide sequence encoding a chimeric site-directed modifying polypeptide is operably linked to a spatially restricted and/or temporally restricted promoter (e.g. a tissue specific promoter, a cell type specific promoter, etc.). In some embodiments, a nucleotide sequence encoding a chimeric site-directed modifying polypeptide is operably linked to a constitutive promoter.

Methods of introducing a nucleic acid into a host cell are known in the art, and any known method can be used to introduce a nucleic acid (e.g. an expression construct) into a stem cell or progenitor cell. Suitable methods include e.g. viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g. Panyam et., al Adv Drug Deliv Rev. 2012 Sep. 13. pp: 50169-409X (12)00283-9. doi: 10.1016/j.addr.2012.09.023), and the like.

Methods

The present disclosure provides methods for modifying a target DNA and/or a target DNA-associated polypeptide. Generally, a method involves contacting a target DNA with a complex (a "targeting complex"), which complex comprises a guide RNA and a SluCas9 polypeptide.

As discussed above, a gRNA or sgRNA and a SluCas9 polypeptide form a complex. The guide RNA provides target specificity to the complex by comprising a nucleotide sequence that is complementary to a sequence of a target DNA. The SluCas9 polypeptide of the complex provides the site-specific activity. In some embodiments, a complex modifies a target DNA, leading to, for example, DNA cleavage, DNA methylation, DNA damage, DNA repair, etc. In other embodiments, a complex modifies a target polypeptide associated with target DNA (e.g. a histone, a DNA-binding protein, etc.), leading to, for example, histone methylation, histone acetylation, histone ubiquitination, and the like. The target DNA may be, for example, naked (i.e. unbound by DNA associated proteins) DNA in vitro, chromosomal DNA in cells in vitro, chromosomal DNA in cells in vivo, etc.

SluCas9 proteins from various species may require different PAM sequences in the target DNA. Thus, for a particular SluCas9 protein of choice, the PAM sequence requirement may be different than the PAM sequence described above.

Exemplary methods are provided that take advantage of characteristics of SluCas9 orthologs include the following.

The nuclease activity cleaves target DNA to produce double strand breaks. These breaks are then repaired by the cell in one of two ways: non-homologous end joining, and homology-directed repair. In non-homologous end joining (NHEJ), the double-strand breaks are repaired by direct ligation of the break ends to one another. In the process a few base pairs can be inserted or deleted at the cleavage site. In homology-directed repair, a donor polynucleotide with homology to the cleaved target DNA sequence is used as a template for repair of the cleaved target DNA sequence, resulting in the transfer of genetic information from the donor polynucleotide to the target DNA As such, new nucleic acid material may be inserted/copied into the site. In some cases, a target DNA is contacted with a donor polynucleotide. In some cases, a donor polynucleotide is introduced into a cell. The modifications of the target DNA due to NHEJ and/or homology-directed repair lead to, for example, gene correction, gene replacement, gene tagging, transgene insertion, nucleotide deletion, nucleotide insertion, gene disruption, gene mutation, sequence replacement, etc. Accordingly, cleavage of DNA by a SluCas9 polypeptide may be used to delete nucleic acid material from a target DNA sequence (e.g. to disrupt a gene that makes cells susceptible to infection (e.g. the CCR5 or CXCR4 gene, which makes T cells susceptible to HIV infection, to remove disease-causing trinucleotide repeat sequences in neurons, to create gene knockouts and mutations as disease models in research, etc.) by cleaving the target DNA sequence and allowing the cell to repair the sequence in the absence of an exogenously provided donor polynucleotide. Thus, the methods can be used to knock out a gene (resulting in complete lack of transcription or altered transcription) or to knock in genetic material into a locus of choice in the target DNA Alternatively, if a guide RNA and a SluCas9 polypeptide are co-administered to cells with a donor polynucleotide sequence that includes at least a segment with homology to the target DNA sequence, the subject methods may be used to add, i.e., insert or replace, nucleic acid material to a target DNA sequence (e.g. to "knock in" a nucleic acid that encodes for a protein, an siRNA, an miRNA, etc.), to add a tag (e.g. 6×His, a fluorescent protein (e.g. a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g. introduce a mutation), and the like. As such, a complex comprising a guide RNA and a SluCas9 polypeptide is useful in any in vitro or in vivo application in which it is desirable to modify DNA in a site-specific, i.e., "targeted", way, for example gene knock-out, gene knock-in, gene editing, gene tagging, sequence replacement, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of PS cells, biological research, the targeting of genes of pathogens for deletion or replacement, etc.

In some embodiments, the SluCas9 polypeptide comprises a modified form of the SluCas9 protein. In some instances, the modified form of the SluCas9 protein comprises an amino acid change (e.g. deletion, insertion, or substitution) that reduces the naturally occurring nuclease activity of the SluCas9 protein. For example, in some instances, the modified form of the SluCas9 protein has less than 50%, less than 40%, less than 30%, less than 20%, less than 10%, less than 5%, or less than 1% of the nuclease activity of the corresponding wild-type SluCas9 polypeptide. In some cases, the modified form of the SluCas9 polypeptide has no substantial nuclease activity. When a SluCas9 polypeptide is a modified form of the SluCas9 protein that has no substantial nuclease activity, it can be referred to as "dSluCas9."

In some embodiments, the SluCas9 polypeptide comprises a heterologous sequence (e.g. a fusion). In some embodiments, a heterologous sequence can provide for subcellular localization of the SluCas9 polypeptide (e.g. a nuclear localization signal (NLS) for targeting to the nucleus; a mitochondrial localization signal for targeting to the mitochondria; a chloroplast localization signal for targeting to a chloroplast; an ER retention signal; and the like). In some embodiments, a heterologous sequence can provide a tag for ease of tracking or purification (e.g. a fluorescent protein, e.g. green fluorescent protein (GFP), YFP, RFP, CFP, mCherry, tdTomato, and the like; a his tag, e.g. a 6×His tag; a hemagglutinin (HA) tag; a FLAG tag; a Myc tag; and the like). In some embodiments, the heterologous sequence can provide for increased or decreased stability.

In some embodiments, a SluCas9 polypeptide can be codon-optimized. This type of optimization is known in the art and entails the mutation of foreign-derived DNA to mimic the codon preferences of the intended host organism or cell while encoding the same protein. Thus, the codons are changed, but the encoded protein remains unchanged. For example, if the intended target cell were a human cell, a human codon-optimized SluCas9 (or variant, e.g. enzymatically inactive variant) would be suitable. Any suitable SluCas9 polypeptide (e.g. any SluCas9 such as the sequence set forth in SEQ ID NO: 2) can be codon optimized. As another non-limiting example, if the intended host cell were a mouse cell, than a mouse codon-optimized SluCas9 (or variant, e.g. enzymatically inactive variant) would be suitable. While codon optimization is not required, it is acceptable and may be preferable in certain cases.

In one aspect, provided herein is a nucleic acid comprising a codon-optimized polynucleotide sequence encoding a SluCas9 polypeptide (e.g., a polypeptide comprising the amino acid sequence of SEQ ID NO: 2) or a variant thereof having at least about 90% (such as at least about any of 91%, 92%, 93%, 94%, 95%, 96%, 97%, 98%, 99%, or more) sequence identity to SEQ ID NO: 2. Such a codon-optimized polynucleotide encoding SluCas9 or a variant thereof is also referred to herein as a "codon-optimized SluCas9 polynucleotide" or a "codon-optimized SluCas9." In some embodiments, the codon-optimized SluCas9 encodes the SluCas9 polypeptide of SEQ ID NO: 2 or 35. In some embodiments, the codon-optimized SluCas9 is codon-optimized for expression in prokaryotic cells, such as bacterial cells. In some embodiments, the codon-optimized SluCas9 is codon-optimized for expression in eukaryotic cells, such as insect or mammalian cells. In some embodiments, the codon-optimized SluCas9 is codon-optimized for expression in human cells. In some embodiments, the codon optimization is performed according to GeneGPS® optimization (ATUM). In some embodiments, the codon optimization is performed according to a GeneOptimizer process (ThermoFisher Scientific). In some embodiments, the codon-optimized SluCas9 has at least about 90% (such as at least about any of 91%, 92%, 93%, 94%, 95%, 96%, 97%, 98%, 99%, or more) sequence identity to SEQ ID NO: 44 or 45. In some embodiments, the codon-optimized SluCas9 comprises (or consists of) the sequence of SEQ ID NO: 44 or 45.

In some embodiments, according to any of the nucleic acids described herein comprising a codon-optimized polynucleotide sequence encoding a SluCas9 polypeptide or a variant thereof, the nucleic acid further includes a nucleotide sequence encoding a gRNA. In some embodiments, the nucleic acid is an expression vector, e.g. a recombinant expression vector. In some embodiments, the nucleotide sequence encoding a SluCas9 polypeptide or a variant thereof comprises the codon-optimized polynucleotide sequence of SEQ ID NO: 44 or 45 or a variant thereof having at least 90% sequence identity to the codon-optimized polynucleotide sequence of SEQ ID NO: 44 or 45.

In some embodiments, provided herein is a nucleic acid comprising a polynucleotide sequence having at least 90%, 91%, 92%, 93%, 94%, 95%, 96%, 97%, 98%, or 99% sequence identity to SEQ ID NO: 44 or 45, wherein the polynucleotide sequence encodes a SluCas9 polypeptide or variant thereof as described herein. In some embodiments, the polynucleotide sequence comprises (or consists of) the codon-optimized polynucleotide sequence of SEQ ID NO: 44 or 45.

In some embodiments, provided herein is a nucleic acid comprising a polynucleotide sequence having at least 90%, 91%, 92%, 93%, 94%, 95%, 96%, 97%, 98% or 99% sequence identity to a subsequence of SEQ ID NO: 44 or 45, wherein the polynucleotide sequence encodes one or more SluCas9 domains. In some embodiments, the polynucleotide sequence comprises (or consists of) a subsequence of SEQ ID NO: 44 or 45. In some embodiments, the one or more SluCas9 domains include a nuclease domain (e.g., an HNH or RuvC domain). In some embodiments, the one or more SluCas9 domains include an RNA-binding domain (e.g., a Rec I domain). In some embodiments, the one or more SluCas9 domains include a PAM-interacting domain.

In some embodiments, according to any of the nucleic acids described herein comprising a codon-optimized polynucleotide sequence, the expression in a host cell of a SluCas9 polypeptide or variant thereof from the nucleic acid is increased as compared to the expression in the host cell of the SluCas9 polypeptide or variant thereof from a corresponding nucleic acid comprising a reference polynucleotide sequence from which the codon-optimized polynucleotide sequence is derived. In some embodiments, the codon-optimized polynucleotide sequence comprises the codon-optimized polynucleotide sequence of SEQ ID NO: 44 or 45, or a variant thereof having at least 90% sequence identity to the codon-optimized polynucleotide sequence of SEQ ID NO: 44 or 45. In some embodiments, the reference polynucleotide sequence comprises the SluCas9-encoding polynucleotide sequence from SEQ ID NO: 3, or a variant thereof having at least 90% sequence identity to the SluCas9-encoding polynucleotide sequence from SEQ ID NO: 3. In some embodiments, the expression of the SluCas9 polypeptide or variant thereof from the codon-optimized polynucleotide sequence in a host cell is increased by at least about 10% (such as by at least about any of 15%, 20%, 25%, 30%, 35%, 40%, 45%, 50%, 55%, 60%, 65%, 70%, 75%, 80%, 85%, 90%, 95%, 100%, or more) as compared to the expression in the host cell of the SluCas9 polypeptide or variant thereof from the reference polynucleotide sequence.

In some embodiments, a guide RNA and a SluCas9 polypeptide are used as an inducible system for shutting off gene expression in bacterial cells. In some cases, nucleic acids encoding an appropriate guide RNA and/or an appropriate SluCas9 polypeptide are incorporated into the chromosome of a target cell and are under control of an inducible promoter. When the guide RNA and/or the SluCas9 polypeptide are induced, the target DNA is cleaved (or otherwise modified) at the location of interest (e.g. a target gene on a separate plasmid), when both the guide RNA and the SluCas9 polypeptide are present and form a complex. As such, in some cases, bacterial expression strains are engineered to include nucleic acid sequences encoding an appropriate SluCas9 polypeptide in the bacterial genome and/or an appropriate guide RNA on a plasmid (e.g. under control of an inducible promoter), allowing experiments in which the expression of any targeted gene (expressed from a separate plasmid introduced into the strain) could be controlled by inducing expression of the guide RNA and the SluCas9 polypeptide. In some cases, the SluCas9 polypeptide has enzymatic activity that modifies target DNA in ways other than introducing double strand breaks. Enzymatic activity of interest that may be used to modify target DNA (e.g. by fusing a heterologous polypeptide with enzymatic activity to a SluCas9 polypeptide, thereby generating a chimeric SluCas9 polypeptide) includes, but is not limited methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). Methylation and demethylation is recognized in the art as an important mode of epigenetic gene regulation while DNA damage and repair activity is essential for cell survival and for proper genome maintenance in response to environmental stresses. As such, the methods herein find use in the epigenetic modification of target DNA and may be employed to control epigenetic modification of target DNA at any location in a target DNA by genetically engineering the desired complementary nucleic acid sequence into the DNA-targeting segment of a guide RNA. The methods herein also find use in the intentional and controlled damage of DNA at any desired location within the target DNA. The methods herein also find use in the sequence-specific and controlled repair of DNA at any desired location within the target DNA. Methods to target DNA-modifying enzymatic activities to specific locations in target DNA find use in both research and clinical applications.

In some cases, the SluCas9 polypeptide has activity that modulates the transcription of target DNA (e.g. in the case of a chimeric SluCas9 polypeptide, etc.). In some cases, a chimeric SluCas9 polypeptides comprising a heterologous polypeptide that exhibits the ability to increase or decrease transcription (e.g. transcriptional activator or transcription repressor polypeptides) is used to increase or decrease the transcription of target DNA at a specific location in a target DNA, which is guided by the DNA-targeting segment of the guide RNA. Examples of source polypeptides for providing a chimeric SluCas9 polypeptide with transcription modulatory activity include, but are not limited to light-inducible transcription regulators, small molecule/drug-responsive transcription regulators, transcription factors, transcription repressors, etc. In some cases, the method is used to control the expression of a targeted coding-RNA (protein-encoding gene) and/or a targeted non-coding RNA (e.g. tRNA, rRNA, snoRNA, siRNA, miRNA, long ncRNA. etc.). In some cases, the SluCas9 polypeptide has enzymatic activity that modifies a polypeptide associated with DNA (e.g. histone). In some embodiments, the enzymatic activity is methyltransferase activity, demethylase activity, acetyltransferase activity, deacetylase activity, kinase activity, phosphatase activity, ubiquitin ligase activity (i.e., ubiquitination activity), deubiquitinating activity, adenylation activity, deadenylation activity, SUMOylating activity, deSUMOylating activity, ribosylation activity, deribosylation activity, myristoylation activity, demyristoylation activity glycosylation activity (e.g. from GlcNAc transferase) or deglycosylation activity. The enzymatic activities listed herein catalyze covalent modifications to proteins. Such modifications are known in the art to alter the stability or activity of the target protein (e.g. phosphorylation due to kinase activity can stimulate or silence protein activity depending on the target protein). Of particular interest as protein targets are histones. Histone proteins are known in the art to bind DNA and form complexes known as nucleosomes. Histones can be modified (e.g. by methylation, acetylation, ubiquitination, phosphorylation) to elicit structural changes in the surrounding DNA, thus controlling the accessibility of potentially large portions of DNA to interacting factors such as transcription factors, polymerases and the like. A single histone can be modified in many different ways and in many different combinations (e.g. trimethylation of lysine 27 of histone 3, H3K27, is associated with DNA regions of repressed transcription while trimethylation of lysine 4 of histone 3, H3K4, is associated with DNA regions of active transcription). Thus, a site-directed modifying polypeptide with histone-modifying activity finds use in the site specific control of DNA structure and can be used to alter the histone modification pattern in a selected region of target DNA. Such methods find use in both research and clinical applications.

In some embodiments, multiple guide RNAs are used simultaneously to simultaneously modify different locations on the same target DNA or on different target DNAs. In some embodiments, two or more guide RNAs target the same gene or transcript or locus. In some embodiments, two or more guide RNAs target different unrelated loci. In some embodiments, two or more guide RNAs target different, but related loci.

In some cases, the SluCas9 polypeptide is provided directly as a protein. As one non-limiting example, fungi (e.g. yeast) can be transformed with exogenous protein and/or nucleic acid using spheroplast transformation (see Kawai et al., Bioeng Bugs. 2010 November-December; 1(6):395-403: 'Transformation of *Saccharomyces cerevisiae* and other fungi: methods and possible underlying mechanism"; and Tanka et al., Nature. 2004 Mar. 18; 428(6980): 323-8: "Conformational variations in an infectious protein determine prion strain differences"; both of which are herein incorporated by reference in their entirety). Thus, a SluCas9 polypeptide can be incorporated into a spheroplast (with or without nucleic acid encoding a guide RNA and with or without a donor polynucleotide) and the spheroplast can be used to introduce the content into a yeast cell. A SluCas9 polypeptide can be introduced into a cell (provided to the cell) by any convenient method; such methods are known to those of ordinary skill in the art. As another non-limiting example, a SluCas9 polypeptide can be injected directly into a cell (e.g. with or without nucleic acid encoding a guide RNA and with or without a donor polynucleotide), e.g. a cell of a zebrafish embryo, the pronucleus of a fertilized mouse oocyte, etc.

Target Cells of Interest

In some of the above applications, the methods may be employed to induce DNA cleavage, DNA modification, and/or transcriptional modulation in mitotic or post-mitotic cells in vivo and/or ex vivo and/or in vitro (e.g. to produce genetically modified cells that can be reintroduced into an individual). Because the guide RNA provide specificity by hybridizing to target DNA, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g. *Botryococcus braunii, Chlamydomonas reinhardtii, Nannochloropsis gaditana, Chlorella pyrenoidosa, Sargassum patens* C. Agardh, and the like, a fungal cell (e.g. a yeast cell), an animal cell, a cell from an invertebrate animal (e.g. fruit fly, cnidarian, echinoderm, nematode, etc.), a cell from a vertebrate animal (e.g. fish, amphibian, reptile, bird, mammal), a cell from a mammal, a cell from a rodent, a cell from a primate, a cellfrom a human, etc.).

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g. a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from an organism and allowed to grow in vitro for a limited number of passages, i.e., splittings, of the culture. For example, primary cultures are cultures that may have been passaged 0 times, 1 time, 2 times, 4 times, 5 times, 10 times, or 15 times, but not enough times go through the crisis stage. Generally, the primary cell lines of the present invention are maintained for fewer than 10 passages in vitro. Target cells are in many embodiments unicellular organisms, or are grown in culture.

If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

Nucleic Acids Encoding a Guide RNA and/or a SluCas9 Polypeptide

In some embodiments, a method involves contacting a target DNA or introducing into a cell (or a population of cells) one or more nucleic acids comprising nucleotide sequences encoding a guide RNA and/or a SluCas9 polypeptide and/or a donor polynucleotide. Suitable nucleic acids comprising nucleotide sequences encoding a guide RNA and/or a SluCas9 polypeptide include expression vectors, where an expression vector comprising a nucleotide sequence encoding a guide RNA and/or a SluCas9 polypeptide is a "recombinant expression vector."

In some embodiments, the recombinant expression vector is a viral construct, e.g. a recombinant adeno-associated virus construct (see, e.g. U.S. Pat. No. 7,078,387), a recombinant adenoviral construct, a recombinant lentiviral construct, etc.

Suitable expression vectors include, but are not limited to, viral vectors (e.g. viral vectors based on vaccinia virus; poliovirus; adenovirus (see, e.g. Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94112649, WO 93/03769; WO 93/19191; WO 94/28938; WO 95/11984 and WO 95/00655); adeno-associated virus (see, e.g. Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166: 154-165; and Flotte et al., PNAS (1993) 90:10613-10617); SV40; herpes simplex virus; human immunodeficiency virus (see, e.g. Miyoshi et al., PNAS 94:10319 23, 1997; Takahashi et al., J Virol 73:7812 7816, 1999); a retroviral vector (e.g. Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

In some embodiments, a nucleotide sequence encoding a guide RNA and/or a SluCas9 polypeptide is operably linked to a control element, e.g. a transcriptional control element, such as a promoter. The transcriptional control element may be functional in either a eukaryotic cell, e.g. a mammalian cell, or a prokaryotic cell (e.g. bacterial or archaeal cell). In some embodiments, a nucleotide sequence encoding a guide RNA and/or a SluCas9 polypeptide is operably linked to multiple control elements that allow expression of the nucleotide sequence encoding a guide RNA and/or a SluCas9 polypeptide in both prokaryotic and eukaryotic cells.

Depending on the host/vector system utilized, any of a number of suitable transcription and translation control elements, including constitutive and inducible promoters, transcription enhancer elements, transcription terminators, etc. may be used in the expression vector (e.g. U6 promoter, H1 promoter, etc.; see above) (see e.g. Bitter et al. (1987) Methods in Enzymology, 153:516-544).

In some embodiments, a guide RNA and/or a SluCas9 polypeptide can be provided as RNA. In such cases, the guide RNA and/or the RNA encoding the SluCas9 polypeptide can be produced by direct chemical synthesis or may be transcribed in vitro from a DNA encoding the guide RNA. Methods of synthesizing RNA from a DNA template are well known in the art. In some cases, the guide RNA and/or the RNA encoding the SluCas9 polypeptide will be synthesized in vitro using an RNA polymerase enzyme (e.g. T7 polymerase, T3 polymerase, SP6 polymerase, etc.). Once synthesized, the RNA may directly contact a target DNA or may be introduced into a cell by any of the well-known techniques for introducing nucleic acids into cells (e.g. microinjection, electroporation, transfection, etc.).

Nucleotides encoding a guide RNA (introduced either as DNA or RNA) and/or a SluCas9 polypeptide (introduced as DNA or RNA) and/or a donor polynucleotide may be provided to the cells using well-developed transfection techniques; see, e.g. Angel and Yanik (2010) PLoS ONE 5(7): e 11756, and the commercially available TransMessenger® reagents from Qiagen, Stemfect™ RNA Transfection Kit from Stemgent, and TransiT®-mRNA Transfection Kit from Mims Bio. See also Beumer et al. (2008) Efficient gene targeting in *Drosophila* by direct embryo injection with zinc-finger nucleases. PNAS 105(50):19821-19826. Alternatively, nucleic acids encoding a guide RNA and/or a SluCas9 polypeptide and/or a chimeric SluCas9 polypeptide and/or a donor polynucleotide may be provided on DNA vectors. Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

Vectors may be provided directly to the cells. In other words, the cells are contacted with vectors comprising the nucleic acid encoding guide RNA and/or a SluCas9 polypeptide and/or a chimeric SluCas9 polypeptide and/or a donor polynucleotide such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid encoding a guide RNA and/or a SluCas9 polypeptide and/or a chimeric SluCas9 polypeptide and/or a donor polynucleotide. Retroviruses, for example, lentiviruses, are particularly suitable to the method of the invention. Commonly used retroviral vectors are "defective", i.e., unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cel line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also be introduced by direct micro-injection (e.g. injection of RNA into a zebrafish embryo).

Vectors used for providing the nucleic acids encoding guide RNA and/or a SluCas9 polypeptide and/or a chimeric SluCas9 polypeptide and/or a donor polynucleotide to the cells will generally comprise suitable promoters for driving the expression, that is, transcriptional activation, of the nucleic acid of interest. In other words, the nucleic acid of interest will be operably linked to a promoter. This may include ubiquitously acting promoters, for example, the CMV-13-actin promoter, or inducible promoters, such as promoters that are active in particular cell populations or that respond to the presence of drugs such as tetracycline. By transcriptional activation, it is intended that transcription will be increased above basal levels in the target cell by at least 10 fold, by at least 100 fold, more usually by at least 1000 fold. In addition, vectors used for providing a guide RNA and/or a SluCas9 polypeptide and/or a chimeric SluCas9 polypeptide and/or a donor polynucleotide to the cells may include nucleic acid sequences that encode for selectable markers in the target cells, so as to identify cells that have taken up the guide RNA and/or a SluCas9 polypeptide and/or a chimeric SluCas9 polypeptide and/or a donor polynucleotide.

A guide RNA and/or a SluCas9 polypeptide and/or a chimeric SluCas9 polypeptide may instead be used to contact DNA or introduced into cells as RNA. Methods of introducing RNA into cells are known in the art and may include, for example, direct injection, transfection, or any other method used for the introduction of DNA. A SluCas9 polypeptide may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the SluCas9 polypeptide may be fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK motif (for identifying but not for purposes of disclosure within this application) also disclosed in J. Biol. Chem., 271 (1996), pp. 18188-18193. As another example, the permeant peptide comprises the HIV-1 tat basic region amino acid sequence, which may include, for example, amino acids 49-57 of naturally occurring tat protein.

Other permeant domains include poly-arginine motifs, for example, the region of amino acids 34-56 of HIV-1 rev protein, nona-arginine, acta-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A. 2000 Nov. 21; 97(24):13003-8; published US Patent Application Publications Nos. 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation. In some embodiments the polypeptide permeant domain is chemically modified in order to increase the bioavailability of the PTD. Exemplary modifications are disclosed in Expert Opin Drug Deliv. 2009 November; 6(11):1195-205.

A SluCas9 polypeptide may be produced in vitro or by eukaryotic cells, by prokaryotic cells, or by in vitro transcription and translation (IVTT) and it may be further processed by unfolding, e.g. heat denaturation, DTT reduction, etc. and may be further refolded, using methods known in the art.

Modifications of interest that do not alter primary sequence include chemical derivatization of polypeptides, e.g. acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the invention are guide RNAs and SluCas9 polypeptides that have been modified using ordinary molecular biological techniques and synthetic chemistry so as to improve their resistance to proteolytic degradation, to change the target sequence specificity, to optimize solubility properties, to alter protein activity (e.g. transcription modulatory activity, enzymatic activity, etc.) or to render them more suitable as a therapeutic agent. Analogs of such polypeptides include those containing residues other than naturally occurring L-amino acids, e.g. 0-amino acids or non-naturally occurring synthetic amino acids. D-amino acids may be substituted for some or all of the amino acid residues. The SluCas9 polypeptides may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The SluCas9 polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, such as at least about 75% by weight or at least about 95% by weight, and for therapeutic purposes, at least 99.5% by weight, in relation to contaminants related to the method of preparation of the product and its purification. Usually, the percentages will be based upon total protein. To induce DNA cleavage and recombination, or any desired modification to a target DNA, or any desired modification to a polypeptide associated with target DNA, the guide RNA and/or the SluCas9 polypeptide and/or the donor polynucleotide, whether they be introduced as nucleic acids or polypeptides, are provided to the cells for about 30 minutes to about 24 hours, e.g. 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g. every 1.5 days, every 2 days, every 3 days, or any other frequency from about every day to about every four days. The agent(s) may be provided to the cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. In cases in which two or more different targeting complexes are provided to the cell (e.g. two different guide RNAs that are complementary to different sequences within the same or different target DNA), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

Generally, an effective amount of the guide RNA and/or SluCas9 polypeptide and/or donor polynucleotide is provided to the target DNA or cells to induce target modification. An effective amount of the guide RNA and/or SluCas9 polypeptide and/or donor polynucleotide is the amount to induce a 2-fold increase or more in the amount of target modification observed between two homologous sequences relative to a negative control, e.g. a cell contacted with an empty vector or irrelevant polypeptide. That is to say, an effective amount or dose of the guide RNA and/or SluCas9 polypeptide and/or donor polynucleotide will induce a 2-fold increase, a 3-fold increase, a 4-fold increase or more in the amount of target modification observed at a target DNA region, in some instances a 5-fold increase, a 6-fold increase or more, sometimes a 7-fold or 8-fold increase or more in the amount of recombination observed, e.g. an increase of 10-fold, 50-fold, or 100-fold or more, in some instances, an increase of 200-fold, 500-fold, 700-fold, or 1000-fold or more, e.g. a 5000-fold, or 10,000-fold increase in the amount of recombination observed. The amount of target modification may be measured by any convenient method. For example, a silent reporter construct comprising complementary sequence to the targeting segment (targeting sequence) of the guide RNA flanked by repeat sequences that, when recombined, will reconstitute a nucleic acid encoding an active reporter may be co-transfected into the cells, and the amount of reporter protein assessed after contact with the guide RNA and/or SluCas9 polypeptide and/or donor polynucleotide, e.g. 2 hours, 4 hours, 8 hours, 12 hours, 24 hours, 36 hours, 48 hours, 72 hours or more after contact with the guide RNA and/or SluCas9 polypeptide and/or donor polynucleotide. As another, more sensitivity assay, for example, the extent of recombination at a genomic DNA region of interest comprising target DNA sequences may be assessed by PCR or Southern hybridization of the region after contact with a guide RNA and/or SluCas9 polypeptide and/or donor polynucleotide, e.g. 2 hours, 4 hours, 8 hours, 12 hours, 24 hours, 36 hours, 48 hours, 72 hours or more after contact with the guide RNA and/or SluCas9 polypeptide and/or donor polynucleotide.

Contacting the cells with a guide RNA and/or SluCas9 polypeptide and/or donor polynucleotide may occur in any culture media and under any culture conditions that promote the survival of the cells. For example, cells may be suspended in any appropriate nutrient medium that is convenient, such as Iscove's modified DMEM or RPMI1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are generally permissive of nonhomologous end joining and homology-directed repair. In applications in which it is desirable to insert a polynucleotide sequence into a target DNA sequence, a polynucleotide comprising a donor sequence to be inserted is also provided to the cell. By a "donor sequence" or "donor polynucleotide" it is meant a nucleic acid sequence to be inserted at the cleavage site induced by a SluCas9 polypeptide. The donor polynucleotide will contain sufficient homology to a genomic sequence at the cleavage site, e.g. 70%, 80%, 85%, 90%, 95%, or 100% homology with the nucleotide sequences flanking the cleavage site, e.g. within about 50 bases or less of the cleavage site, e.g. within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is generally not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide. The donor sequence may comprise certain sequence differences as compared to the genomic sequence, e.g. restriction sites, nucleotide polymorphisms, selectable markers (e.g. drug resistance genes, fluorescent proteins, enzymes etc.), etc., which may be used to assess for successful insertion of the donor sequence at the cleavage site or in some cases may be used for other purposes (e.g. to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, oxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g. from exonucleolytic degradation) by methods known to those of skill in the art. For example, one or more dideoxy-nucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and 0-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked (i.e. unmodified) nucleic acid, as nucleic acid complexed with an agent such as a liposome or poloxamer, or can be delivered by viruses (e.g. adenovirus, AAV), as described above for nucleic acids encoding a guide RNA and/or SluCas9 polypeptide and/or donor polynucleotide.

Following the methods described above, a DNA region of interest may be cleaved and modified, i.e., "genetically modified", ex vivo. In some embodiments, as when a selectable marker has been inserted into the DNA region of interest, the population of cells may be enriched for those comprising the genetic modification by separating the genetically modified cells from the remaining population. Prior to enriching, the "genetically modified" cells may make up only about 1% or more (e.g. 2% or more, 3% or more, 4% or more, 5% or more, 6% or more, 7% or more, 8% or more, 9% or more, 10% or more, 15% or more, or 20% or more) of the cellular population. Separation of "genetically modified" cells may be achieved by any convenient separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication. Such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the genetically modified cells. Cell compositions that are highly enriched for cells comprising modified DNA are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

Genetically modified cells produced by the methods described herein may be used immediately. Alternatively, the cells may be frozen at liquid nitrogen temperatures and stored for long periods of time, being thawed and capable of being reused. In such cases, the cells will usually be frozen in 10% dimethylsulfoxide (DMSO), 50% serum, 40% buffered medium, or some other such solution as is commonly used in the art to preserve cells at such freezing temperatures, and thawed in a manner as commonly known in the art for thawing frozen cultured cells.

The genetically modified cells may be cultured in vitro under various culture conditions. The cells may be expanded in culture, i.e., grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the respective cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Cells that have been genetically modified in this way may be transplanted to a subject for purposes such as gene therapy, e.g. to treat a disease or as an antiviral, antipathogenic, or anticancer therapeutic, for the production of genetically modified organisms in agriculture, or for biological research. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mouse, rat, guinea pig, hamster, lagomorpha (e.g. rabbit), etc.) may be used for experimental investigations.

Cells may be provided to the subject alone or with a suitable substrate or matrix, e.g. to support their growth and/or organization in the tissue to which they are being transplanted. Usually, at least $1\times10^3$ cells will be administered, for example $5\times10^3$ cells, $1\times10^4$ cells, $5\times10^4$ cells, $1\times10^5$ cells, $1\times10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g., US Application No. 20070254842, incorporated herein by reference); or by implanting a device upon which the cells have been reversibly affixed (see e.g. US Application Nos. 20080081064 and 20090196903, incorporated herein by reference). Cells may also be introduced into an embryo (e.g. a blastocyst) for the purpose of generating a transgenic animal (e.g. a transgenic mouse).

Delivery of SluCas9 Systems

Guide RNA polynucleotides (RNA or DNA) and/or SluCas9 polynucleotides (RNA or DNA) can be delivered by viral or non-viral delivery vehicles known in the art.

Polynucleotides may be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

A recombinant adeno-associated virus (AAV) vector may be used for delivery. Techniques to produce rAAV particles, in which an AAV genome to be packaged that includes the polynucleotide to be delivered, rep and cap genes, and helper virus functions are provided to a cell are standard in the art.

Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692. AAV Serotype

| | Genbank Accession No. |
|---|---|
| AAV-1 | NC_002077.1 |
| AAV-2 | NC_001401.2 |
| AAV-3 | NC_001729.1 |
| AAV-38 | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | 00813647.1 |
| AAV-13 | EU285562.1 |

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types transduced by the indicated AAV serotypes among others.

| Tissue/Cell Type | Serotype |
| --- | --- |
| Liver | AAV8, AAV9 |
| Skeletal muscle | AAV1, AAV7, AAV6, AAV8, AAV9 |
| Central nervous system | AAV5, AAV1, AAV4 |
| RPE | AAV5, AAV4 |
| Photoreceptor cells | AAV5 |
| Lung | AAV9 |
| Heart | AAV8 |
| Pancreas | AAV8 |
| Kidney | AAV2 |

The number of administrations of treatment to a subject may vary. Introducing the genetically modified cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

In other aspects of the disclosure, the guide RNA and/or SluCas9 polypeptide and/or donor polynucleotide are employed to modify cellular DNA in vivo, again for purposes such as gene therapy, e.g. to treat a disease or as an antiviral, antipathogenic, or anticancer therapeutic, for the production of genetically modified organisms in agriculture, or for biological research. In these in vivo embodiments, a guide RNA and/or SluCas9 polypeptide and/or donor polynucleotide are administered directly to the individual. A guide RNA and/or SluCas9 polypeptide and/or donor polynucleotide may be administered by any of a number of well-known methods in the art for the administration of peptides, small molecules and nucleic acids to a subject. A guide RNA and/or SluCas9 polypeptide and/or donor polynucleotide can be incorporated into a variety of formulations. More particularly, a guide RNA and/or SluCas9 polypeptide and/or donor polynucleotide of the present invention can be formulated into pharmaceutical compositions by combination with appropriate pharmaceutically acceptable carriers or diluents.

Pharmaceutical preparations are compositions that include one or more a guide RNA and/or SluCas9 polypeptide and/or donor polynucleotide present in a pharmaceutically acceptable vehicle. "Pharmaceutically acceptable vehicles" may be vehicles approved by a regulatory agency of the Federal or a state government or listed in the US Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semisolid, liquid or gaseous forms, such as tablets, capsules, powders, granules, ointments, solutions, suppositories, injections, inhalants, gels, microspheres, and aerosols. As such, administration of the a guide RNA and/or SluCas9 polypeptide and/or donor polynucleotide can be achieved in various ways, including oral, buccal, rectal, parenteral, intraperitoneal, intradermal, transdermal, intra-tracheal, intraocular, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (888). One strategy for drug delivery through the 888 entails disruption of the 888, either by osmotic means such as mannitol or leukotrienes, or biochemically by the use of vasoactive substances such as bradykinin. The potential for using 888 opening to target specific agents to brain tumors is also an option. A 888 disrupting agent can be co-administered with the therapeutic compositions of the invention when the compositions are administered by intravascular injection. Other strategies to go through the 888 may entail the use of endogenous transport systems, including Caveolin-1 mediated transcytosis, carrier-mediated transporters such as glucose and amino acid carriers, receptor-mediated transcytosis for insulin or transferrin, and active efflux transporters such aspglycoprotein. Active transport moieties may also be conjugated to the therapeutic compounds for use in the invention to facilitate transport across the endothelial wall of the blood vessel. Alternatively, drug delivery of therapeutics agents behind the 888 may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversibly affixed (see e.g. US Application Nos. 20080081064 and 20090196903, incorporated herein by reference).

Generally, an effective amount of a guide RNA and/or SluCas9 polypeptide and/or donor polynucleotide are provided. As discussed above with regard to ex vivo methods, an effective amount or effective dose of a guide RNA and/or SluCas9 polypeptide and/or donor polynucleotide in vivo is the amount to induce a 2 fold increase or more in the amount of recombination observed between two homologous sequences relative to a negative control, e.g. a cell contacted with an empty vector or irrelevant polypeptide. The amount of recombination may be measured by any convenient method, e.g. as described above and known in the art. The calculation of the effective amount or effective dose of a guide RNA and/or SluCas9 polypeptide and/or donor polynucleotide to be administered is within the skill of one of ordinary skill in the art, and will be routine to those persons skilled in the art. The final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally-administered dose, given the greater body of fluid into which the therapeutic composition is being administered. Similarly, compositions, which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, a guide RNA and/or SluCas9 polypeptide and/or donor polynucleotide may be obtained from a suitable commercial source. As a general proposition, the total pharmaceutically effective amount of a guide RNA and/or SluCas9 polypeptide and/or donor polynucleotide administered parenterally per dose will be in a range that can be measured by a dose response curve.

Therapies based on a guide RNA and/or SluCas9 polypeptide and/or donor polynucleotides, i.e., preparations of a guide RNA and/or SluCas9 polypeptide and/or donor polynucleotide to be used for therapeutic administration, must be sterile. Sterility is readily accomplished by filtration through sterile filtration membranes (e.g. 0.2 1-1m membranes). Therapeutic compositions generally are placed into a container having a sterile access port, for example, an intravenous solution bag or vial having a stopper pierceable by a hypodermic injection needle. The therapies based on a guide RNA and/or SluCas9 polypeptide and/or donor polynucleotide may be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g. increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g. sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices may be preferred.

The data obtained from cell culture and/or animal studies can be used in formulating a range of dosages for humans. The dosage of the active ingredient generally lies within a range of circulating concentrations that include the ED50 with low toxicity. The dosage can vary within this range depending upon the dosage form employed and the route of administration utilized. The components used to formulate the pharmaceutical compositions are in some embodiments of high purity and substantially free of potentially harmful contaminants (e.g. at least National Food (NF) grade, generally at least analytical grade, including at least pharmaceutical grade). Moreover, compositions intended for in vivo use are usually sterile. To the extent that a given compound must be synthesized prior to use, the resulting product is generally substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions that are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Genetically Modified Host Cells

The present disclosure provides genetically modified host cells, including isolated genetically modified host cells, where a genetically modified host cell comprises (has been genetically modified with:

1) an exogenous guide RNA; 2) an exogenous nucleic acid comprising a nucleotide sequence encoding a guide RNA; 3) an exogenous SluCas9 polypeptide (e.g. a naturally occurring SluCas9; a modified, i.e., mutated or variant, SluCas9; a chimeric SluCas9; etc.); 4) an exogenous nucleic acid comprising a nucleotide sequence encoding a SluCas9 polypeptide; or 5) any combination of the above. A genetically modified cell is generated by genetically modifying a host cell with, for example: 1) an exogenous guide RNA; 2) an exogenous nucleic acid comprising a nucleotide sequence encoding a guide RNA; 3) an exogenous SluCas9 polypeptide; 4) an exogenous nucleic acid comprising a nucleotide sequence encoding a SluCas9 polypeptide; or 5) any combination of the above.).

All cells suitable to be a target cell are also suitable to be a genetically modified host cell. For example, a genetically modified host cells of interest can be a cell from any organism (e.g. a bacterial cell, an archaeal cell, a cell of a single-cell eukaryotic organism, a plant cell, an algal cell, e.g. *Botryococcus braunii, Chlamydomonas reinhardtii, Nannochloropsis gaditana, Chlorella pyrenoidosa, Sargassum patens* C. Agardh, and the like, a fungal cell (e.g. a yeast cell), an animal cell, a cell from an invertebrate animal (e.g. fruit fly, cnidarian, echinoderm, nematode, etc.), a cell from a vertebrate animal (e.g. fish, amphibian, reptile, bird, mammal), a cell from a mammal (e.g. a pig, a cow, a goat, a sheep, a rodent. a rat, a mouse, a non-human primate, a human, etc.), etc.

In some embodiments, a genetically modified host cell has been genetically modified with an exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.). The DNA of a genetically modified host cell can be targeted for modification by introducing into the cell a guide RNA (or a DNA encoding a guide RNA, which determines the genomic location/sequence to be modified) and optionally a donor nucleic acid. In some embodiments, the nucleotide sequence encoding a SluCas9 polypeptide is operably linked to an inducible promoter (e.g. heat shock promoter, Tetracycline-regulated promoter, Steroid-regulated promoter, Metal-regulated promoter, estrogen receptor-regulated promoter, etc.). In some embodiments, the nucleotide sequence encoding a SluCas9 polypeptide is operably linked to a spatially restricted and/or temporally restricted promoter (e.g. a tissue specific promoter, a cell type specific promoter, a cell cycle specific promoter). In some embodiments, the nucleotide sequence encoding a SluCas9 polypeptide is operably linked to a constitutive promoter.

In some embodiments, a genetically modified host cell is in vitro. In some embodiments, a genetically modified host cell is in vivo. In some embodiments, a genetically modified host cell is a prokaryotic cell or is derived from a prokaryotic cell. In some embodiments, a genetically modified host cell is a bacterial cell or is derived from a bacterial cell. In some embodiments, a genetically modified host cell is an archaeal cell or is derived from an archaeal cell. In some embodiments, a genetically modified host cell is a eukaryotic cell or is derived from a eukaryotic cell. In some embodiments, a genetically modified host cell is a plant cell or is derived from a plant cell. In some embodiments, a genetically modified host cell is an animal cell or is derived from an animal cell. In some embodiments, a genetically modified host cell is an invertebrate cell or is derived from an invertebrate cell. In some embodiments, a genetically modified host cell is a vertebrate cell or is derived from a vertebrate cell. In some embodiments, a genetically modified host cell is a mammalian cell or is derived from a mammalian cell. In some embodiments, a genetically modified host cell is a rodent cell or is derived from a rodent cell. In some embodiments, a genetically modified host cell is a human cell or is derived from a human cell.

The present disclosure further provides progeny of a genetically modified cell, where the progeny can comprise the same exogenous nucleic acid or polypeptide as the genetically modified cell from which it was derived. The present disclosure further provides a composition comprising a genetically modified host cell.

Genetically Modified Stem Cells and Genetically Modified Progenitor Cells

In some embodiments, a genetically modified host cell is a genetically modified stem cell or progenitor cell. Suitable host cells include, e.g. stem cells (adult stem cells, embryonic stem cells, iPS cells, etc.) and progenitor cells (e.g. cardiac progenitor cells, neural progenitor cells, etc.). Suitable host cells include mammalian stem cells and progenitor cells, including, e.g. rodent stem cells, rodent progenitor cells, human stem cells, human progenitor cells, etc. Suitable host cells include in vitro host cells, e.g. isolated host cells.

In some embodiments, a genetically modified host cell comprises an exogenous guide RNA nucleic acid. In some embodiments, a genetically modified host cell comprises an exogenous nucleic acid comprising a nucleotide sequence encoding a guide RNA. In some embodiments, a genetically modified host cell comprises an exogenous SluCas9 polypeptide (e.g. a naturally occurring SluCas9; a modified, i.e., mutated or variant, SluCas9; a chimeric SluCas9; etc.). In some embodiments, a genetically modified host cell comprises an exogenous nucleic acid comprising a nucleotide sequence encoding a SluCas9 polypeptide. In some embodiments, a genetically modified host cell comprises exogenous nucleic acid comprising a nucleotide sequence encoding 1) a guide RNA and 2) a SluCas9 polypeptide.

In some cases, the SluCas9 polypeptide comprises an amino acid sequence having at least 75%, at least 80%, at least 85%, at least 90%, at least 95%, at least 99%, or 100% amino acid sequence identity to any of the sequences in SEQ ID NO: 2, or an active portion thereof which is at least 100, 150, 200, 300, 350, 400, or 500 amino acids long. In some embodiments, the active portion are the RNase domains. In other embodiments, the active portions are the DNase domains.

Compositions

The present disclosure provides a composition comprising a guide RNA and/or a site-directed modifying polypeptide. In some cases, the SluCas9 polypeptide is a chimeric polypeptide. A composition is useful for carrying out a method of the present disclosure, e.g. a method for site-specific modification of a target DNA; a method for site-specific modification of a polypeptide associated with a target DNA; etc.

Compositions Comprising a Guide RNA

The present disclosure provides a composition comprising a guide RNA. The composition can comprise, in addition to the guide RNA, one or more of: a salt, e.g. NaCl, MgCb, KCl, MgSO4, etc.; a buffering agent, e.g. a Tris buffer, N-(2-Hydroxyethyl)piperazine-N'-(2-ethanesulfonic acid) (HEPES), 2-(N-Morpholino)ethanesulfonic acid (MES), MES sodium salt, 3-(N-Morpholino)propanesulfonic acid (MOPS), N-tris[Hydroxymethyl]methyl-3-aminopropanesulfonic acid (TAPS), etc.; a solubilizing agent; a detergent, e.g. a non-ionic detergent such as TWEEN™-20, etc.; a nuclease inhibitor; and the like. For example, in some cases, a composition comprises a guide RNA and a buffer for stabilizing nucleic acids.

In some embodiments, a guide RNA present in a composition is pure, e.g. at least 75%, at least 80%, at least 85%, at least 90%, at least 95%, at least 98%, at least 99%, or more than 99% pure, where "% purity" means that guide RNA is the recited percent free from other macromolecules, or contaminants that may be present during the production of the guide RNA.

Compositions Comprising a Chimeric Polypeptide

The present disclosure provides a composition of a chimeric polypeptide. The composition can comprise, in addition to the guide RNA, one or more of: a salt, e.g. NaCl, MgCiz, KCl, MgSO4, etc.; a buffering agent, e.g. a Tris buffer, HEPES, MES, MES sodium salt, MOPS, TAPS, etc.; a solubilizing agent; a detergent, e.g. a non-ionic detergent such as TWEEN™-20, etc.; a protease inhibitor; a reducing agent (e.g. dithiothreitol); and the like.

In some embodiments, a chimeric polypeptide present in a composition is pure, e.g. at least 75%, at least 80%, at least 85%, at least 90%, at least 95%, at least 98%, at least 99%, or more than 99% pure, where "% purity" means that the site-directed modifying polypeptide is the recited percent free from other proteins, other macromolecules, or contaminants that may be present during the production of the chimeric polypeptide.

Compositions Comprising a Guide RNA and a SluCas9 Polypeptide

The present disclosure provides a composition comprising: (i) a guide RNA or a DNA polynucleotide encoding the same; and ii) a SluCas9 polypeptide, or a polynucleotide encoding the same. In some cases, the SluCas9 polypeptide is a chimeric SluCas9 polypeptide. In other cases, the SluCas9 polypeptide is a naturally occurring SluCas9 polypeptide. In some instances, the SluCas9 polypeptide exhibits enzymatic activity that modifies a target DNA. In other cases, the SluCas9 polypeptide exhibits enzymatic activity that modifies a polypeptide that is associated with a target DNA. In still other cases, the SluCas9 polypeptide modulates transcription of the target DNA.

The present disclosure provides a composition comprising: (i) a guide RNA, as described above, or a DNA polynucleotide encoding the same, the guide RNA comprising: (a) a first segment comprising a nucleotide sequence that is complementary to a sequence in a target DNA; and (b) a second segment that interacts with a SluCas9 polypeptide; and (ii) the SluCas9 polypeptide, or a polynucleotide encoding the same, the SluCas9 polypeptide comprising: (a) an RNA-binding portion that interacts with the guide RNA; and (b) an activity portion that exhibits site-directed enzymatic activity, wherein the site of enzymatic activity is determined by the guide RNA.

In some instances, a composition comprises: (i) a guide RNA, the guide RNA comprising: (a) a first segment comprising a nucleotide sequence that is complementary to a sequence in a target DNA; and (b) a second segment that interacts with a SluCas9 polypeptide; and (ii) the SluCas9 polypeptide, the SluCas9 polypeptide comprising: (a) an RNA-binding portion that interacts with the guide RNA; and (b) an activity portion that exhibits site-directed enzymatic activity, wherein the site of enzymatic activity is determined by the guide RNA.

In other embodiments, a composition comprises: (i) a polynucleotide encoding a guide RNA, the guide RNA comprising: (a) a first segment comprising a nucleotide sequence that is complementary to a sequence in a target DNA; and (b) a second segment that interacts with a site-directed modifying polypeptide; and (ii) a polynucleotide encoding the SluCas9 polypeptide, the SluCas9 polypeptide comprising: (a) an RNA-binding portion that interacts with the guide RNA; and (b) an activity portion that exhibits site-directed enzymatic activity, wherein the site of enzymatic activity is determined by the guide RNA.

The present disclosure provides a composition comprising: (i) a guide RNA, or a DNA polynucleotide encoding the same, the guide RNA comprising: (a) a first segment comprising a nucleotide sequence that is complementary to a sequence in a target DNA; and (b) a second segment that interacts with a SluCas9 polypeptide; and (ii) the SluCas9 polypeptide, or a polynucleotide encoding the same, the SluCas9 polypeptide comprising: (a) an RNA-binding portion that interacts with the guide RNA; and (b) an activity portion that modulates transcription within the target DNA, wherein the site of modulated transcription within the target DNA is determined by the guide RNA.

For example, in some cases, a composition comprises: (i) a guide RNA the guide RNA comprising: (a) a first segment comprising a nucleotide sequence that is complementary to a sequence in a target DNA; and (b) a second segment that interacts with a SluCas9 polypeptide; and (ii) the SluCas9 polypeptide, the SluCas9 polypeptide comprising: (a) an RNA-binding portion that interacts with the guide RNA; and (b) an activity portion that modulates transcription within the target DNA, wherein the site of modulated transcription within the target DNA is determined by the guide RNA.

As another example, in some cases, a composition comprises: (i) a DNA polynucleotide encoding a guide RNA, the guide RNA comprising: (a) a first segment comprising a nucleotide sequence that is complementary to a sequence in a target DNA; and (b) a second segment that interacts with a SluCas9 polypeptide; and (ii) a polynucleotide encoding the site-directed modifying polypeptide, the SluCas9 polypeptide comprising: (a) an RNA-binding portion that interacts with the guide RNA; and (b) an activity portion that modulates transcription within the target DNA, wherein the site of modulated transcription within the target DNA is determined by the guide RNA. A composition can comprise, in addition to i) a guide RNA, or a DNA polynucleotide encoding the same; and ii) a SluCas9 polypeptide, or a polynucleotide encoding the same, one or more of: a salt, e.g. NaCl, MgCiz, KCl, MgSO4, etc.; a buffering agent, e.g. a Tris buffer, HEPES, MES, MES sodium salt, MOPS, TAPS, etc.; a solubilizing agent a detergent, e.g. a non-ionic detergent such as TWEEN™-20, etc.; a protease inhibitor; a reducing agent (e.g. dithiothreitol); and the like.

In some cases, the components of the composition are individually pure, e.g. each of the components is at least 75%, at least 80%, at least 90%, at least 95%, at least 98%, at least 99%, or at least 99%, pure. In some cases, the individual components of a composition are pure before being added to the composition.

For example, in some embodiments, a SluCas9 polypeptide present in a composition is pure, e.g. at least 75%, at least 80%, at least 85%, at least 90%, at least 95%, at least 98%, at least 99%, or more than 99% pure, where "% purity" means that the SluCas9 polypeptide is the recited percent free from other proteins (e.g. proteins other than the SluCas9 polypeptide), other macromolecules, or contaminants that may be present during the production of the SluCas9 polypeptide.

Kits

The present disclosure provides kits for carrying out a method. A kit can include one or more of: a SluCas9 polypeptide; a nucleic acid comprising a nucleotide encoding a site-directed modifying polypeptide; a guide RNA; a nucleic acid comprising a nucleotide sequence encoding a guide RNA. A kit may comprise a complex that comprises two or more of: a SluCas9 polypeptide; a nucleic acid comprising a nucleotide encoding a SluCas9 polypeptide; a guide RNA; a nucleic acid comprising a nucleotide sequence encoding a guide RNA. In some embodiments, a kit comprises a SluCas9 polypeptide, or a polynucleotide encoding the same. In some embodiments, the SluCas9 polypeptide comprises: (a) an RNA-binding portion that interacts with the guide RNA; and (b) an activity portion that modulates transcription within the target DNA, wherein the guide RNA determines the site of modulated transcription within the target DNA. In some cases, the activity portion of the SluCas9 polypeptide exhibits reduced or inactivated nuclease activity. In some cases, the SluCas9 polypeptide is a chimeric SluCas9 polypeptide.

In some embodiments, a kit comprises: a SluCas9 polypeptide, or a polynucleotide encoding the same, and a reagent for reconstituting and/or diluting the SluCas9 polypeptide. In other embodiments, a kit comprises a nucleic acid (e.g. DNA, RNA) comprising a nucleotide encoding a SluCas9 polypeptide. In some embodiments, a kit comprises: a nucleic acid (e.g. DNA, RNA) comprising a nucleotide encoding a SluCas9 polypeptide; and a reagent for reconstituting and/or diluting the SluCas9 polypeptide.

A kit comprising a SluCas9 polypeptide, or a polynucleotide encoding the same, can further include one or more additional reagents, where such additional reagents can be selected from: a buffer for introducing the SluCas9 polypeptide into a cell; a wash buffer; a control reagent; a control expression vector or RNA polynucleotide; a reagent for in vitro production of the SluCas9 polypeptide from DNA, and the like. In some cases, the site-directed modifying polypeptide included in a kit is a chimeric SluCas9 polypeptide, as described above.

In some embodiments, a kit comprises a guide RNA, or a DNA polynucleotide encoding the same, the guide RNA comprising: (a) a first segment comprising a nucleotide sequence that is complementary to a sequence in a target DNA; and (b) a second segment that interacts with a site-directed modifying polypeptide. In some embodiments, a kit comprises: (i) a guide RNA, or a DNA polynucleotide encoding the same, the guide RNA comprising: (a) a first segment comprising a nucleotide sequence that is complementary to a sequence in a target DNA; and (b) a second segment that interacts with a SluCas9 polypeptide; and (ii) a SluCas9 polypeptide, or a polynucleotide encoding the same, the SluCas9 polypeptide comprising: (a) an RNA-binding portion that interacts with the guide RNA; and (b) an activity portion that exhibits site-directed enzymatic activity, wherein the site of enzymatic activity is determined by the guide RNA. In some embodiments, the activity portion of the SluCas9 polypeptide does not exhibit enzymatic activity (comprises an inactivated nuclease, e.g. via mutation). In some cases, the kit comprises a guide RNA and a SluCas9 polypeptide. In other cases, the kit comprises: (i) a nucleic acid comprising a nucleotide sequence encoding a guide RNA; and (ii) a nucleic acid comprising a nucleotide sequence encoding SluCas9 polypeptide. As another example, a kit can include: (i) a guide RNA, or a DNA polynucleotide encoding the same, comprising:

(a) a first segment comprising a nucleotide sequence that is complementary to a sequence in a target DNA; and (b) a second segment that interacts with a SluCas9 polypeptide; and (ii) the SluCas9 polypeptide, or a polynucleotide encoding the same, comprising: (a) an RNA-binding portion that interacts with the guide RNA; and (b) an activity portion that that modulates transcription within the target DNA, wherein the site of modulated transcription within the target DNA is determined by the guide RNA In some cases, the kit comprises: (i) a guide RNA; and a SluCas9 polypeptide. In other cases, the kit comprises: (i) a nucleic acid comprising a nucleotide sequence encoding a guide RNA; and (ii) a nucleic acid comprising a nucleotide sequence encoding SluCas9 polypeptide. The present disclosure provides a kit comprising: (1) a recombinant expression vector comprising (i) a nucleotide sequence encoding a guide RNA, wherein the guide RNA comprises: (a) a first segment comprising a nucleotide sequence that is complementary to a sequence in a target DNA; and (b) a second segment that interacts with a SluCas9 polypeptide; and (ii) a nucleotide sequence encoding the SluCas9 polypeptide, wherein the SluCas9 polypeptide comprises: (a) an RNA-binding portion that interacts with the guide RNA; and (b) an activity portion that exhibits site-directed enzymatic activity, wherein the site of enzymatic activity is determined by the guide RNA; and (2) a reagent for reconstitution and/or dilution of the expression vector.

The present disclosure provides a kit comprising: (1) a recombinant expression vector comprising: (i) a nucleotide sequence encoding a guide RNA, wherein the guide RNA comprises: (a) a first segment comprising a nucleotide sequence that is complementary to a sequence in a target DNA; and (b) a second segment that interacts with a SluCas9 polypeptide; and (ii) a nucleotide sequence encoding the SluCas9 polypeptide, wherein the SluCas9 polypeptide comprises: (a) an RNA-binding portion that interacts with the guide RNA; and (b) an activity portion that modulates transcription within the target DNA, wherein the site of modulated transcription within the target DNA is determined by the guide RNA; and (2) a reagent for reconstitution and/or dilution of the recombinant expression vector.

The present disclosure provides a kit comprising: (1) a recombinant expression vector comprising a nucleic acid comprising a nucleotide sequence that encodes a DNA targeting RNA comprising: (i) a first segment comprising a nucleotide sequence that is complementary to a sequence in a target DNA; and (ii) a second segment that interacts with a SluCas9 polypeptide; and (2) a reagent for reconstitution and/or dilution of the recombinant expression vector. In some embodiments of this kit, the kit comprises: a recombinant expression vector comprising a nucleotide sequence that encodes a SluCas9 polypeptide, wherein the SluCas9 polypeptide comprises: (a) an RNA-binding portion that interacts with the guide RNA; and (b) an activity portion that exhibits site-directed enzymatic activity, wherein the site of enzymatic activity is determined by the guide RNA. In other embodiments of this kit, the kit comprises: a recombinant expression vector comprising a nucleotide sequence that encodes a SluCas9 polypeptide, wherein the SluCas9 polypeptide comprises: (a) an RNA-binding portion that interacts with the guide RNA; and (b) an activity portion that modulates transcription within the target DNA, wherein the site of modulated transcription within the target DNA is determined by the guide RNA.

In some embodiments of any of the above kits, the kit comprises a single-molecule guide RNA. In some embodiments of any of the above kits, the kit comprises two or more single-molecule guide RNAs. In some embodiments of any of the above kits, a guide RNA (e.g. including two or more guide RNAs) can be provided as an array (e.g. an array of RNA molecules, an array of DNA molecules encoding the guide RNA(s), etc.). Such kits can be useful, for example, for use in conjunction with the above described genetically modified host cells that comprise a SluCas9 polypeptide. In some embodiments of any of the above kits, the kit further comprises a donor polynucleotide to effect the desired genetic modification. Components of a kit can be in separate containers; or can be combined in a single container.

In some cases, a kit further comprises one or more variant SluCas9 site-directed polypeptides that exhibit reduced endodeoxyribonuclease activity relative to wild-type SluCas9.

In some cases, a kit further comprises one or more nucleic acids comprising a nucleotide sequence encoding a variant SluCas9 site-directed polypeptide that exhibits reduced endodeoxyribonuclease activity relative to wild-type SluCas9.

Any of the above-described kits can further include one or more additional reagents, where such additional reagents can be selected from: a dilution buffer; a reconstitution solution; a wash buffer; a control reagent; a control expression vector or RNA polynucleotide; a reagent for in vitro production of the SluCas9 polypeptide from DNA, and the like.

In addition to above-mentioned components, a kit can further include instructions for using the components of the kit to practice the methods. The instructions for practicing the methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Non-Human Genetically Modified Organisms

In some embodiments, a genetically modified host cell has been genetically modified with an exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.). If such a cell is a eukaryotic single-cell organism, then the modified cell can be considered a genetically modified organism. In some embodiments, the non-human genetically modified organism is a SluCas9 transgenic multicellular organism.

In some embodiments, a genetically modified non-human host cell (e.g. a cell that has been genetically modified with an exogenous nucleic acid comprising a nucleotide sequence encoding a site-directed modifying polypeptide, e.g. a naturally occurring SluCas9; a modified, i.e., mutated or variant, SluCas9; a chimeric SluCas9; etc.) can generate a genetically modified nonhuman organism (e.g. a mouse, a fish, a frog, a fly, a worm, etc.). For example, if the genetically modified host cell is a pluripotent stem cell (i.e., PSC) or a germ cell (e.g. sperm, oocyte, etc.), an entire genetically modified organism can be derived from the genetically modified host cell. In some embodiments, the genetically modified host cell is a pluripotent stem cell (e.g. ESC, iPSC, pluripotent plant stem cell, etc.) or a germ cell (e.g. sperm cell, oocyte, etc.), either in vivo or in vitro that can give rise to a genetically modified organism. In some embodiments the genetically modified host cell is a vertebrate PSC (e.g. ESC, iPSC, etc.) and is used to generate a genetically modified organism (e.g. by injecting a PSC into a blastocyst to produce a chimeric/mosaic animal, which could then be mated to generate non-chimeric/non-mosaic genetically modified organisms; grafting in the case of plants; etc.). Any convenient method/protocol for producing a genetically modified organism, including the methods described herein, is suitable for producing a genetically modified host cell comprising an exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.). Methods of producing genetically modified organisms are known in the art. For example, see Cho et al., Curr Protoc Cell Biol. 2009 March; Chapter 19:Unit 19.11: Generation of transgenic mice; Gama et al., Brain Struct Funct. 2010 March; 214(2-3):91-109. Epub 2009 Nov. 25: Animal transgenesis: an overview; Husaini et al., GM Crops. 2011 June-December; 2(3):150-62. Epub 2011 Jun. 1: Approaches for gene targeting and targeted gene expression in plants.

In some embodiments, a genetically modified organism comprises a target cell for methods of the invention, and thus can be considered a source for target cells. For example, if a genetically modified cell comprising an exogenous nucleic acid comprising a nucleotide sequence encoding a site-directed modifying polypeptide (e.g. a naturally occurring SluCas9; a modified, i.e., mutated or variant, SluCas9; a chimeric SluCas9; etc.) is used to generate a genetically modified organism, then the cells of the genetically modified organism comprise the exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.). In some such embodiments, the DNA of a cell or cells of the genetically modified organism can be targeted for modification by introducing into the cell or cells a guide RNA (or a DNA encoding a guide RNA) and optionally a donor nucleic acid. For example, the introduction of a guide RNA (or a DNA encoding a guide RNA) into a subset of cells (e.g. brain cells, intestinal cells, kidney cells, lung cells, blood cells, etc.) of the genetically modified organism can target the DNA of such cells for modification, the genomic location of which will depend on the DNA-targeting sequence of the introduced guide RNA.

In some embodiments, a genetically modified organism is a source of target cells for methods of the invention. For example, a genetically modified organism comprising cells that are genetically modified with an exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.) can provide a source of genetically modified cells, for example PSCs (e.g. ESCs, iPSCs, sperm, oocytes, etc.), neurons, progenitor cells, cardiomyocytes, etc.

In some embodiments, a genetically modified cell is a PSC comprising an exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.). As such, the PSC can be a target cell such that the DNA of the PSC can be targeted for modification by introducing into the PSC a guide RNA (or a DNA encoding a guide RNA) and optionally a donor nucleic acid, and the genomic location of the modification will depend on the DNA-targeting sequence of the introduced guide RNA. Thus, in some embodiments, the methods described herein can be used to modify the DNA (e.g. delete and/or replace any desired genomic location) of PSCs derived from a genetically modified organism. Such modified PSCs can then be used to generate organisms having both (i) an exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.) and (ii) a DNA modification that was introduced into the PSC.

An exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.) can be under the control of (i.e., operably linked to) an unknown promoter (e.g. when the nucleic acid randomly integrates into a host cell genome) or can be under the control of (i.e., operably linked to) a known promoter. Suitable known promoters can be any known promoter and include constitutively active promoters (e.g. CMV promoter), inducible promoters (e.g. heat shock promoter, Tetracycline-regulated promoter, Steroid-regulated promoter, Metal-regulated promoter, estrogen receptor-regulated promoter, etc.), spatially restricted and/or temporally restricted promoters (e.g. a tissue specific promoter, a cell type specific promoter, etc.), etc.

A genetically modified organism (e.g. an organism whose cells comprise a nucleotide sequence encoding a SluCas9 polypeptide, e.g. a naturally occurring SluCas9; a modified, i.e., mutated or variant, SluCas9; a chimeric SluCas9; etc.) can be any organism including for example, a plant; algae; an invertebrate (e.g. a cnidarian, an echinoderm, a worm, a fly, etc.); a vertebrate (e.g. a fish (e.g. zebrafish, puffer fish, gold fish, etc.), an amphibian (e.g. salamander, frog, etc.), a reptile, a bird, a mammal, etc.); an ungulate (e.g. a goat, a pig, a sheep, a cow, etc.); a rodent (e.g. a mouse, a rat, a hamster, a guinea pig); a lagomorpha (e.g. a rabbit); etc.

In some cases, the SluCas9 polypeptide comprises an amino acid sequence having at least 75%, at least 80%, at least 85%, at least 90%, at least 95%, at least 99%, or 100% amino acid sequence identity to SEQ ID NO: 2.

Transgenic Non-Human Animals

As described above, in some embodiments, a nucleic acid (e.g. a nucleotide sequence encoding a SluCas9 polypeptide, e.g. a naturally occurring SluCas9; a modified, i.e., mutated or variant, SluCas9; a chimeric SluCas9; etc.) or a recombinant expression vector is used as a transgene to generate a transgenic animal that produces a SluCas9 polypeptide. Thus, the present disclosure further provides a transgenic non-human animal, which animal comprises a transgene comprising a nucleic acid comprising a nucleotide sequence encoding a site-directed modifying polypeptide, e.g. a naturally occurring SluCas9; a modified, i.e., mutated or variant, SluCas9; a chimeric SluCas9; etc., as described above. In some embodiments, the genome of the transgenic non-human animal comprises a nucleotide sequence encoding a SluCas9 polypeptide. In some embodiments, the transgenic non-human animal is homozygous for the genetic modification. In some embodiments, the transgenic non-human animal is heterozygous for the genetic modification. In some embodiments, the transgenic non-human animal is a vertebrate, for example, a fish (e.g. zebra fish, gold fish, puffer fish, cave fish, etc.), an amphibian (frog, salamander, etc.), a bird (e.g. chicken, turkey, etc.), a reptile (e.g. snake, lizard, etc.), a mammal (e.g. an ungulate, e.g. a pig, a cow, a goat, a sheep, etc.; a lagomorph (e.g. a rabbit); a rodent (e.g. a rat, a mouse); a nonhuman primate; etc.), etc.

An exogenous nucleic acid comprising a nucleotide sequence encoding a SluCas9 polypeptide (e.g. a naturally occurring SluCas9; a modified, i.e., mutated or variant, SluCas9; a chimeric SluCas9; etc.) can be under the control of (i.e., operably linked to) an unknown promoter (e.g. when the nucleic acid randomly integrates into a host cell genome) or can be under the control of (i.e., operably linked to) a known promoter. Suitable known promoters can be any known promoter and include constitutively active promoters (e.g. CMV promoter), inducible promoters (e.g. heat shock promoter, Tetracycline-regulated promoter, Steroid-regulated promoter, Metal-regulated promoter, estrogen receptor-regulated promoter, etc.), spatially restricted and/or temporally restricted promoters (e.g. a tissue specific promoter, a cell type specific promoter, etc.), etc.

Transgenic Plants

As described above, in some embodiments, a nucleic acid (e.g. a nucleotide sequence encoding a SluCas9 polypeptide, e.g. a naturally occurring SluCas9; a modified, i.e., mutated or variant, SluCas9; a chimeric SluCas9; etc.) or a recombinant expression vector is used as a transgene to generate a transgenic plant that produces a SluCas9 polypeptide. Thus, the present disclosure further provides a transgenic plant, which plant comprises a transgene comprising a nucleic acid comprising a nucleotide sequence encoding SluCas9 polypeptide, e.g. a naturally occurring SluCas9; a modified, i.e., mutated or variant, SluCas9; a chimeric SluCas9; etc., as described above. In some embodiments, the genome of the transgenic plant comprises a nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e., in vitro, ex vivo, or in vivo). Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediatedtransformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See., e.g. Glick and Thompson, (eds.), Methods in Plant Molecular Biology and Biotechnology, Boca Raton, Fla.: CRC Press (1993).

Microprojectile-mediated transformation also can be used to produce a transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid may be introduced into a plant in a manner such that the nucleic acid is able to enter a plant cell(s), e.g. via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Daniell et al. Nat. Biotechnol 16:345-348, 1998; Staub et al. Nat. Biotechnol 18: 333-338, 2000; O'Neill et al. Plant J. 3:729-738, 1993; Knoblauch et al. Nat. Biotechnol 17: 906-909; U.S. Pat. Nos. 5,451,513, 5,545,817, 5,545,818, and 5,576,198; in Inti. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Nati. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants, which can be genetically modified, include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

Also provided by the disclosure are transformed plant cells, tissues, plants and products that contain the transformed plant cells. A feature of the transformed cells, and tissues and products that include the same is the presence of a nucleic acid integrated into the genome, and production by plant cells of a SluCas9 polypeptide, e.g. a naturally occurring SluCas9; a modified, i.e., mutated or variant, SluCas9; a chimeric SluCas9; etc. Recombinant plant cells of the present invention are useful as populations of recombinant cells, or as a tissue, seed, whole plant, stem, fruit, leaf, root, flower, stem, tuber, grain, animal feed, a field of plants, and the like.

A nucleic acid comprising a nucleotide sequence encoding a SluCas9 polypeptide (e.g. a naturally occurring SluCas9; a modified, i.e., mutated or variant, SluCas9; a chimeric SluCas9; etc.) can be under the control of (i.e., operably linked to) an unknown promoter (e.g. when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

The present disclosure provides methods of modulating transcription of a target nucleic acid in a host cell. The methods generally involve contacting the target nucleic acid with an enzymatically inactive SluCas9 polypeptide and a guide RNA. The methods are useful in a variety of applications, which are also provided.

A transcriptional modulation method of the present disclosure overcomes some of the drawbacks of methods involving RNAi. A transcriptional modulation method of the present disclosure finds use in a wide variety of applications, including research applications, drug discovery (e.g. high throughput screening), target validation, industrial applications (e.g. crop engineering; microbial engineering, etc.), diagnostic applications, therapeutic applications, and imaging techniques.

Methods of Modulating Transcription

The present disclosure provides a method of selectively modulating transcription of a target DNA in a host cell. The method generally involves: a) introducing into the host cell: i) a guide RNA, or a nucleic acid comprising a nucleotide sequence encoding the guide RNA; and ii) a variant SluCas9 site-directed polypeptide ("variant SluCas9 polypeptide"), or a nucleic acid comprising a nucleotide sequence encoding the variant SluCas9 polypeptide, where the variant SluCas9 polypeptide exhibits reduced endodeoxyribonuclease activity.

The guide RNA (also referred to herein as "guide RNA"; or "gRNA") comprises: i) a first segment comprising a nucleotide sequence that is complementary to a target sequence in a target DNA; ii) a second segment that interacts with a SluCas9 polypeptide; and iii) a transcriptional terminator. The first segment, comprising a nucleotide sequence that is complementary to a target sequence in a target DNA, is referred to herein as a "targeting segment". The second segment, which interacts with a SluCas9 polypeptide, is also referred to herein as a "protein-binding sequence" or "dSluCas9-binding hairpin," or "dSluCas9 handle." By "segment" it is meant a segment/section/region of a molecule, e.g. a contiguous stretch of nucleotides in an RNA. The definition of "segment," unless otherwise specifically defined in a particular context, is not limited to a specific number of total base pairs, and may include regions of RNA molecules that are of any total length and may or may not include regions with complementarity to other molecules. The variant SluCas9 site-directed polypeptide comprises: i) an RNA-binding portion that interacts with the guide RNA; and an activity portion that exhibits reduced endodeoxyribonuclease activity.

The guide RNA and the variant SluCas9 polypeptide form a complex in the host cell; the complex selectively modulates transcription of a target DNA in the host cell.

In some cases, a transcription modulation method of the present disclosure provides for selective modulation (e.g. reduction or increase) of a target nucleic acid in a host cell. For example, "selective" reduction of transcription of a target nucleic acid reduces transcription of the target nucleic acid by at least 10%, at least 20%, at least 30%, at least 40%, at least 50%, at least 60%, at least 70%, at least 80%, at least 90%, or greater than 90%, compared to the level of transcription of the target nucleic acid in the absence of a guide RNA/variant SluCas9 polypeptide complex. Selective reduction of transcription of a target nucleic acid reduces transcription of the target nucleic acid, but does not substantially reduce transcription of a non-target nucleic acid, e.g. transcription of a non-target nucleic acid is reduced, if at all, by less than 10% compared to the level of transcription of the non-target nucleic acid in the absence of the guide RNA/variant SluCas9 polypeptide complex.

Increased Transcription

"Selective" increased transcription of a target DNA can increase transcription of the target DNA by at least 1.1 fold (e.g. at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20-fold) compared to the level of transcription of the target DNA in the absence of a guide RNA/variant SluCas9 polypeptide complex. Selective increase of transcription of a target DNA increases transcription of the target DNA, but does not substantially increase transcription of a non-target DNA, e.g. transcription of a non-target DNA is increased, if at all, by less than about 5-fold (e.g. less than about 4-fold, less than about 3-fold, less than about 2-fold, less than about 1.8-fold, less than about 1.6-fold, less than about 1.4-fold, less than about 1.2-fold, or less than about 1.1-fold) compared to the level of transcription of the non-targeted DNA in the absence of the guide RNA/variant SluCas9 polypeptide complex.

As a non-limiting example, increased transcription can be achieved by fusing dSluCas9 to a heterologous sequence. Suitable fusion partners indude, but are not limited to, a polypeptide that provides an activity that indirectly increases transcription by acting directly on the target DNA or on a polypeptide (e.g. a histone or other DNA-binding protein) associated with the target DNA. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, crotonylation, decrotonylation, propionylation, depropionylation, myristoylation activity, or demyristoylation activity.

Additional suitable fusion partners include, but are not limited to, a polypeptide that directly provides for increased transcription of the target nucleic acid (e.g. a transcription activator or a fragment thereof, a protein or fragment thereof that recruits a transcription activator, a small molecule/drug-responsive transcription regulator, etc.).

A non-limiting example of a method using a dSluCas9 fusion protein to increase transcription in a prokaryote includes a modification of the bacterial one-hybrid (B1H) or two-hybrid (B2H) system. In the B1H system, a DNA binding domain (BD) is fused to a bacterial transcription activation domain (AD, e.g. the alpha subunit of the *Escherichia coli* RNA polymerase (RNAPa)). Thus, a dSluCas9 can be fused to a heterologous sequence comprising an AD. When the dSluCas9 fusion protein arrives at the upstream region of a promoter (targeted there by the guide RNA) the AD (e.g. RNAPa) of the dSluCas9 fusion protein recruits the RNAP holoenzyme, leading to transcription activation. In the B2H system, the BD is not directly fused to the AD; instead, their interaction is mediated by a protein-protein interaction (e.g. GAL11P-GAL4 interaction). To modify such a system for use in the methods, dSluCas9 can be fused to a first protein sequence that provides for protein-protein interaction (e.g. the yeast GAL11P and/or GAL4 protein) and RNAa can be fused to a second protein sequence that completes the protein-protein interaction (e.g. GAL4 if GAL11Pis fused to dSluCas9, GAL11P if GAL4 is fused to dSluCas9, etc.). The binding affinity between GAL11P and GAL4 increases the efficiency of binding and transcription firing rate.

A non-limiting example of a method using a dSluCas9 fusion protein to increase transcription in eukaryotes includes fusion of dSluCas9 to an activation domain (AD) (e.g. GAL4, herpesvirus activation protein VP16 or VP64, human nuclear factor NF-KB p65 subunit, etc.). To render the system inducible, expression of the dSluCas9 fusion protein can be controlled by an inducible promoter (e.g. Tet-ON, Tet-OFF, etc.). The guide RNA can be design to target known transcription response elements (e.g. promoters, enhancers, etc.), known upstream activating sequences (UAS), sequences of unknown or known function that are suspected of being able to control expression of the target DNA, etc.

Additional Fusion Partners

Non-limiting examples of fusion partners to accomplish increased or decreased transcription include, but are not limited to, transcription activator and transcription repressor domains (e.g. the Kruppel associated box (KRAB or SKD); the Mad mSIN3 interaction domain (SID); the ERF repressor domain (ERD), etc.). In some such cases, the dSluCas9 fusion protein is targeted by the guide RNA to a specific location (i.e., sequence) in the target DNA and exerts locus-specific regulation such as blocking RNA polymerase binding to a promoter (which selectively inhibits transcription activator function), and/or modifying the local chromatin status (e.g. when a fusion sequence is used that modifies the target DNA or modifies a polypeptide associated with the target DNA). In some cases, the changes are transient (e.g. transcription repression or activation). In some cases, the changes are inheritable (e.g. when epigenetic modifications are made to the target DNA or to proteins associated with the target DNA, e.g. nucleosomal histones). In some embodiments, the heterologous sequence can be fused to the C-terminus of the dSluCas9 polypeptide. In some embodiments, the heterologous sequence can be fused to the N-terminus of the dSluCas9 polypeptide. In some embodiments, the heterologous sequence can be fused to an internal portion (i.e., a portion other than the N- or C-terminus) of the dSluCas9 polypeptide. The biological effects of a method using a dSluCas9 fusion protein can be detected by any convenient method (e.g. gene expression assays; chromatin-based assays, e.g. Chromatin ImmunoPrecipitation (ChIP), Chromatin in vivo Assay (CiA), etc.).

In some cases, a method involves use of two or more different guide RNAs. For example, two different guide RNAs can be used in a single host cell, where the two different guide RNAs target two different target sequences in the same target nucleic acid. Thus, for example, a transcriptional modulation method can further comprise introducing into the host cell a second guide RNA, or a nucleic acid comprising a nucleotide sequence encoding the second guide RNA, where the second guide RNA comprises: i) a first segment comprising a nucleotide sequence that is complementary to a second target sequence in the target DNA; ii) a second segment that interacts with the site-directed polypeptide; and iii) a transcriptional terminator. In some cases, use of two different guide RNAs targeting two different targeting sequences in the same target nucleic acid provides for increased modulation (e.g. reduction or increase) in transcription of the target nucleic acid.

As another example, two different guide RNAs can be used in a single host cell, where the two different guide RNAs target two different target nucleic acids. Thus, for example, a transcriptional modulation method can further comprise introducing into the host cell a second guide RNA, or a nucleic acid comprising a nucleotide sequence encoding the second guide RNA, where the second guide RNA comprises: i) a first segment comprising a nucleotide sequence that is complementary to a target sequence in at least a second target DNA; ii) a second segment that interacts with the site-directed polypeptide; and iii) a transcriptional terminator.

In some embodiments, a nucleic acid (e.g. a guide RNA, e.g. a single-molecule guide RNA; a donor polynucleotide; a nucleic acid encoding a SluCas9 polypeptide; etc.) comprises a modification or sequence that provides for an additional desirable feature (e.g. modified or regulated stability; subcellular targeting; tracking, e.g. a fluorescent label; a binding site for a protein or protein complex; etc.). Non-limiting examples include: a 5' cap (e.g. a 7-methylguanylate cap (m 7G)); a 3' polyadenylated tail (i.e., a 3' poly(A) tail); a riboswitch sequence or an aptamer sequence (e.g. to allow for regulated stability and/or regulated accessibility by proteins and/or protein complexes); a terminator sequence; a sequence that forms a dsRNA duplex (i.e., a hairpin)); a modification or sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA, including transcriptional activators, transcriptional repressors, DNA methyltransferases, DNA demethylases, histone acetyltransferases, histone deacetylases, and the like); a modification of RNA that alters the structure of such RNA, consequently the SluCas9 ribonucleoprotein; and combinations thereof.

DNA-Targeting Segment

The DNA-targeting segment (or "DNA-targeting sequence") of a guide RNA comprises a nucleotide sequence that is complementary to a specific sequence within a target DNA (the complementary strand of the target DNA).

In other words, the DNA-targeting segment of a guide RNA interacts with a target DNA in a sequence-specific manner via hybridization (i.e., base pairing). As such, the nucleotide sequence of the DNA-targeting segment may vary and determines the location within the target DNA that the guide RNA and the target DNA will interact. The DNA-targeting segment of a guide RNA can be modified (e.g. by genetic engineering) to hybridize to any desired sequence within a target DNA Stability Control Sequence (e.g. Transcriptional Terminator Segment)

A stability control sequence influences the stability of an RNA (e.g. a guide RNA). One example of a suitable stability control sequence is a transcriptional terminator segment (i.e., a transcription termination sequence). A transcriptional terminator segment of a guide RNA can have a totallength of from about 10 nucleotides to about 100 nucleotides, e.g. from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell. Nucleotide sequences that can be included in a stability control sequence (e.g. transcriptional termination segment, or in any segment of the guide RNA to provide for increased stability) include, for example, a Rho-independent trp termination site.

Additional Sequences

In some embodiments, a guide RNA comprises at least one additional segment at either the 5' or 3' end. For example, a suitable additional segment can comprise a 5' cap (e.g. a 7-methylguanylate cap (m7G)); a 3' polyadenylated tail (i.e., a 3' poly(A) tail); a riboswitch sequence (e.g. to allow for regulated stability and/or regulated accessibility by proteins and protein complexes); a sequence that forms a dsRNA duplex (i.e., a hairpin)); a sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA, including transcriptional activators, transcriptional repressors, DNA methyltransferases, DNA demethylases, histone acetyltransferases, histone deacetylases, and the like) a modification or sequence that provides for increased, decreased, and/or controllable stability; and combinations thereof.

Multiple Simultaneous Guide RNAs

In some embodiments, multiple guide RNAs are used simultaneously in the same cell to simultaneously modulate transcription at different locations on the same target DNA or on different target DNAs. In some embodiments, two or more guide RNAs target the same gene or transcript or locus. In some embodiments, two or more guide RNAs target different unrelated loci. In some embodiments, two or more guide RNAs target different, but related loci.

Because the guide RNAs are small and robust they can be simultaneously present on the same expression vector and can even be under the same transcriptional control if so desired. In some embodiments, two or more (e.g. 3 or more, 4 or more, 5 or more, 10 or more, 15 or more, 20 or more, 25 or more, 30 or more, 35 or more, 40 or more, 45 or more, or 50 or more) guide RNAs are simultaneously expressed in a target cell (from the same or different vectors/from the same or different promoters). In some cases, multiple guide RNAs can be encoded in an array mimicking naturally occurring CRISPR arrays of targeter RNAs. The targeting segments are encoded as approximately 30 nucleotide long sequences (can be about 16 to about 100 nt) and are separated by CRISPR repeat sequences. The array may be introduced into a cell by DNAs encoding the RNAs or as RNAs.

To express multiple guide RNAs, an artificial RNA processing system mediated by the Csy4 endoribonuclease can be used. For example, multiple guide RNAs can be concatenated into a tandem array on a precursor transcript (e.g. expressed from a U6 promoter), and separated by Csy4-specific RNA sequence. Co-expressed Csy4 protein cleaves the precursor transcript into multiple guide RNAs. Advantages for using an RNA processing system include: first, there is no need to use multiple promoters; second, since all guide RNAs are processed from a precursor transcript, their concentrations are normalized for similar dSluCas9-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9%) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

Variant SluCas9 Site-Directed Polypeptide

As noted above, a guide RNA and a variant SluCas9 site-directed polypeptide form a complex. The guide RNA provides target specificity to the complex by comprising a nucleotide sequence that is complementary to a sequence of a target DNA. The variant SluCas9 site-directed polypeptide has reduced endodeoxyribonuclease activity. For example, a variant SluCas9 site-directed polypeptide suitable for use in a transcription modulation method of the present disdosure exhibits less than about 20%, less than about 15%, less than about 10%, less than about 5%, less than about 1%, or less than about 0.1%, of the endodeoxyribonuclease activity of a wild-type SluCas9 polypeptide, e.g. a wild-type SluCas9 polypeptide comprising an amino acid sequence set out in SEQ ID NO: 2. In some embodiments, the variant SluCas9 site-directed polypeptide has substantially no detectable endodeoxyribonuclease activity (dSluCas9). In some embodiments when a variant SluCas9 site-directed polypeptide has reduced catalytic activity, the polypeptide can still bind to target DNA in a site-specific manner (because it is still guided to a target DNA sequence by a guide RNA) as long as it retains the ability to interact with the guide RNA. In some cases, a suitable variant SluCas9 site-directed polypeptide comprises an amino acid sequence having at least 75%, at least 80%, at least 85%, at least 90%, at least 95%, at least 99% or 100% amino acid sequence identity to SEQ ID NO: 2.

In some cases, the variant SluCas9 site-directed polypeptide is a nickase that can cleave the complementary strand of the target DNA but has reduced ability to cleave the non-complementary strand of the target DNA In some cases, the variant SluCas9 site-directed polypeptide in a nickase that can cleave the non-complementary strand of the target DNA but has reduced ability to cleave the complementary strand of the target DNA.

In some cases, the variant SluCas9 site-directed polypeptide has a reduced ability to cleave both the complementary and the non-complementary strands of the target DNA. For example, alanine substitutions are contemplated.

In some cases, the variant SluCas9 site-directed polypeptide is a fusion polypeptide (a "variant SluCas9 fusion polypeptide"), i.e., a fusion polypeptide comprising: i) a variant SluCas9 site-directed polypeptide; and ii) a covalently linked heterologous polypeptide (also referred to as a "fusion partner").

The heterologous polypeptide may exhibit an activity (e.g. enzymatic activity) that will also be exhibited by the variant SluCas9 fusion polypeptide (e.g. methyltransferase activity, acetyltransferase activity, kinase activity, ubiquitinating activity, etc.). A heterologous nucleic acid sequence may be linked to another nucleic acid sequence (e.g. by genetic engineering) to generate a chimeric nucleotide sequence encoding a chimeric polypeptide. In some embodiments, a variant SluCas9 fusion polypeptide is generated by fusing a variant SluCas9 polypeptide with a heterologous sequence that provides for subcellular localization (i.e., the heterologous sequence is a subcellular localization sequence, e.g. a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g. a fluorescent protein, e.g. green fluorescent protein (GFP), YFP, RFP, CFP, mCherry, tdTomato, and the like; a histidine tag, e.g. a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g. a degron, which in some cases is controllable (e.g. a temperature sensitive or drug controllable degron sequence, see below). In some embodiments, the heterologous sequence can provide for increased or decreased transcription from the target DNA (i.e., the heterologous sequence is a transcription modulation sequence, e.g. a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g. to provide the ability of a chimeric dSluCas9 polypeptide to bind to another protein of interest, e.g. a DNA or histone modifying protein, a transcription factor or transcription repressor, a recruiting protein, etc.).

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled at least in part by the degron sequence. In some cases, a suitable degron is constitutive such that the degron exerts its influence on protein stability independent of experimental control (i.e., the degron is not drug inducible, temperature inducible, etc.) In some cases, the degron provides the variant SluCas9 polypeptide with controllable stability such that the variant SluCas9 polypeptide can be turned "on" (i.e., stable) or "off" (i.e., unstable, degraded) depending on the desired conditions. For example, if the degron is a temperature sensitive degron, the variant SluCas9 polypeptide may be functional (i.e., "on", stable) below a threshold temperature (e.g. 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g. Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11:Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1). Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well characterized and tested in both cells and animals. Thus, fusing SluCas9 to a degron sequence produces a "tunable" and "inducible" SluCas9 polypeptide. Any of the fusion partners described herein can be used in any desirable combination. As one non-limiting example to illustrate this point, a SluCas9 fusion protein can comprise a YFP sequence for detection, a degron sequence for stability, and transcription activator sequence to increase transcription of the target DNA Furthermore, the number of fusion partners that can be used in a SluCas9 fusion protein is unlimited. In some cases, a SluCas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, crotonylation activity, decrotonylation activity, propionylation activity, depropionylationa activity, myristoylation activity, or demyristoylation activity, any of which can be directed at modifying the DNA directly (e.g. methylation of DNA) or at modifying a DNA-associated polypeptide (e.g. a histone or DNA binding protein). Further suitable fusion partners include, but are not limited to boundary elements (e.g. CTCF), proteins and fragments thereofthat provide periphery recruitment (e.g. LaminA, Lamin B, etc.), and protein docking elements (e.g. FKBP/FRB, Pil 1/Aby 1, etc.).

In some embodiments, a SluCas9 polypeptide can be codon-optimized. This type of optimization is known in the art and entails the mutation of foreign-derived DNA to mimic the codon preferences of the intended host organism or cell while encoding the same protein. Thus, the codons are changed, but the encoded protein remains unchanged. For example, if the intended target cell were a human cell, a human codon-optimized dSluCas9 (or dSluCas9 variant) would be a suitable site-directed modifying polypeptide. As another non-limiting example, if the intended host cell were a mouse cell, than a mouse codon-optimized SluCas9 (or variant, e.g. enzymatically inactive variant) would be a suitable SluCas9 site-directed polypeptide. While codon optimization is not required, it is acceptable and may be preferable in certain cases.

Polyadenylation signals can also be chosen to optimize expression in the intended host.

Host Cells

A method of the present disclosure to modulate transcription may be employed to induce transcriptional modulation in mitotic or post-mitotic cells in vivo and/or ex vivo and/or in vitro. Because the guide RNA provides specificity by hybridizing to target DNA, a mitotic and/or post-mitotic cell can be any of a variety of host cell, where suitable host cells include, but are not limited to, a bacterial cell; an archaeal cell; a single-celled eukaryotic organism; a plant cell; an algal cell, e.g. *Botryococcus braunii, Chlamydomonas reinhardtii, Nannochloropsis gaditana, Chlorella pyrenoidosa, Sargassum patens*, C. agardh, and the like; a fungal cell; an animal cell; a cell from an invertebrate animal (e.g. an insect, a cnidarian, an echinoderm, a nematode, etc.); a eukaryotic parasite (e.g. a malarial parasite, e.g. *Plasmodium* fakiparum; a helminth; etc.); a cell from a vertebrate animal (e.g. fish, amphibian, reptile, bird, mammal); a mammalian cell, e.g. a rodent cell, a human cell, a non-human primate cell, etc. Suitable host cells include naturally occurring cells; genetically modified cells (e.g. cells genetically modified in a laboratory, e.g. by the "hand of man"); and cells manipulated in vitro in any way. In some cases, a host cell is isolated.

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g. a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e., splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. Target cells are in many embodiments unicellular organisms, or are grown in culture.

If the cells are primary cells, such cells may be harvested from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, e.g. from 5-25 mM.

Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% dimethyl sulfoxide (DMSO), 50% serum, 40% buffered medium, or some other such solution as is commonly used in the art to preserve cells at such freezing temperatures, and thawed in a manner as commonly known in the art for thawing frozen cultured cells.

Introducing Nucleic Acid into a Host Cell

A guide RNA, or a nucleic acid comprising a nucleotide sequence encoding same, can be introduced into a host cell by any of a variety of well-known methods. Similarly, where a method involves introducing into a host cell a nucleic acid comprising a nucleotide sequence encoding a variant SluCas9 site-directed polypeptide, such a nucleic acid can be introduced into a host cell by any of a variety of well-known methods.

Methods of introducing a nucleic acid into a host cell are known in the art, and any known method can be used to introduce a nucleic acid (e.g. an expression construct) into a stem cell or progenitor cell. Suitable methods include, e.g. viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g. Panyam et., al Adv Drug Deliv Rev. 2012 Sep. 13. pii: 50169-409X (12)00283-9. doi: 10.1016/j.addr.2012.09.023), and the like, including but not limiting to exosome delivery.

Nucleic Acids

The present disclosure provides an isolated nucleic acid comprising a nucleotide sequence encoding a guide RNA. In some cases, a nucleic acid also comprises a nucleotide sequence encoding a variant SluCas9 site-directed polypeptide.

In some embodiments, a method involves introducing into a host cell (or a population of host cells) one or more nucleic acids comprising nucleotide sequences encoding a guide RNA and/or a variant SluCas9 site-directed polypeptide. In some embodiments a cell comprising a target DNA is in vitro. In some embodiments a cell comprising a target DNA is in vivo. Suitable nucleic acids comprising nucleotide sequences encoding a guide RNA and/or a variant SluCas9 site-directed polypeptide include expression vectors, where an expression vector comprising a nucleotide sequence encoding a guide Expression Vectors In some embodiments, the recombinant expression vector is a viral construct, e.g. a recombinant adeno-associated virus construct (see, e.g. U.S. Pat. No. 7,078,387), a recombinant adenoviral construct, a recombinant lentiviral construct, a recombinant retroviral construct, etc. Suitable expression vectors include, but are not limited to, viral vectors (e.g. viral vectors based on vaccinia virus; poliovirus; adenovirus (see, e.g. Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:10881097, 1999; WO 94/12649, WO 93/03769; WO 93/19191; WO 94/28938; WO 95/11984 and WO 95/00655); adeno-associated virus (see, e.g. Ali et al., Hum Gene Ther 9:8186,1998, Flannery et al., PNAS 94:6916 6921, 1997; Bennett et al., Invest Opthalmol Vis Sci 38:2857 2863, 1997; Jomary et al., Gene Ther 4:683-690, 1997, Rolling et al., Hum Gene Ther 10:641648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166:154-165; and Flotte et al., PNAS (1993) 90:10613-10617); SV40; herpes simplex virus; human immunodeficiency virus (see, e.g. Miyoshi et al., PNAS 94:10319 23, 1997; Takahashi et al., J Virol 73:7812 7816, 1999); a retroviral vector (e.g. Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g. Bitter et al. (1987) Methods in Enzymology, 153:516-544).

In some embodiments, a nucleotide sequence encoding a guide RNA and/or a variant SluCas9 site-directed polypeptide is operably linked to a control element, e.g. a transcriptional control element, such as a promoter. The transcriptional control element may be functional in either a eukaryotic cell, e.g. a mammalian cell; or a prokaryotic cell (e.g. bacterial or archaeal cell). In some embodiments, a nucleotide sequence encoding a guide RNA and/or a variant SluCas9 site-directed polypeptide is operably linked to multiple control elements that allow expression of the nucleotide sequence encoding a guide RNA and/or a variant SluCas9 site-directed polypeptide in both prokaryotic and eukaryotic cells.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g. the presence of a particular temperature, compound, or protein), it may be a spatially restricted promoter (i.e., transcriptional control element, enhancer, etc.)(e.g. tissue specific promoter, cell type specific promoter, etc.), and it may be a temporally restricted promoter (i.e., the promoter is in the "ON" state or "OFF" state during specific stages of embryonic development or during specific stages of a biological process, e.g. hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g. pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g. Tet-ON, Tet-OFF, etc.), Steroid-regulated promoter, Metal-regulated promoter, estrogen receptor-regulated promoter, etc. Inducible promoters can therefore be regulated by molecules including, but not limited to, doxycycline; RNA polymerase, e.g. T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g. a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a variant SluCas9 site-directed polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g. hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g. EMBL HSENO2, X51956); an aromatic amino acid decarboxylase (AADC) promoter; a neurofilament promoter (see, e.g. GenBank HUMNFL, L04147); a synapsin promoter (see, e.g. GenBank HUMSYNIB, M55301); a thy-1 promoter (see, e.g. Chen et al. (1987) Ce/151:7-19; and Llewellyn, et al. (2010) Nat. Med. 16(10):1161-1166); a serotonin receptor promoter (see, e.g. GenBank S62283); a tyrosine hydroxylase promoter (TH) (see, e.g. Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g. Radovick et al. (1991) Proc. Natl. Acad. Sci. USA 88:3402-3406); an L7 promoter (see, e.g. Oberdick et al. (1990) Science 248:223-226); a DNMT promoter (see, e.g. Bartge et al. (1988) Proc. Natl. Acad. Sci. USA 85:3648-3652); an enkephalin promoter (see, e.g. Comb et al. (1988) EMBO J. 17:3793-3805); a myelin basic protein (MBP) promoter; a Ca2+-calmodulin-dependent protein kinase 11-alpha (CamKlla) promoter (see, e.g. Mayford et al. (1996) Proc. Natl. Acad. Sci. USA 93:13250; and Casanova et al. (2001) Genesis 31:37); a CMV enhancer/platelet-derived growth factor-0 promoter (see, e.g. Liu et al. (2004) Gene Therapy 11:52-60); and the like.

Adipocyte-specific spatially restricted promoters include, but are not limited to aP2 gene promoter/enhancer, e.g. a region from −5.4 kb to +21 bp of a human aP2 gene (see, e.g. Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g. Knight et al. (2003) Proc. Natl. Acad. Sci. USA 100:14725); a fatty acid translocase (FAT/CD36) promoter (see, e.g. Kuriki et al. (2002) Biol. Pharm. Bull. 25:1476; and Sato et al. (2002) J. Biol. Chem. 277:15703); a stearoyi-CoA desaturase-1 (SCD1) promoter (Tabor et al. (1999) J. Biol. Chem. 274:20603); a leptin promoter (see, e.g. Mason et al. (1998) Endocrinol. 139:1013; and Chen et al. (1999) Biochem. Biophys. Res. Comm. 262:187); an adiponectin promoter (see, e.g. Kita et al. (2005) Biochem. Biophys. Res. Comm. 331:484; and Chakrabarti (2010) Endocrinol. 151:2408); an adipsin promoter (see, e.g. Platt et al. (1989) Proc.

Natl. Acad. Sci. USA 86:7490); a resistin promoter (see, e.g. Seo et al. (2003) Malec. Endocrinol. 17:1522); and the like.

Cardiomyocyte-specific spatially restricted promoters include, but are not limited to control sequences derived from the following genes: myosin light chain-2, a-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22a promoter (see, e.g. Akyilrek et al. (2000) Mol. Med. 6:983; and U.S. Pat. No. 7,169,874); a smoothelin promoter (see, e.g. WO 2001/018048); an a-smooth muscle actin promoter; and the like. For example, a 0.4 kb region of the SM22a promoter, within which lie two CArG elements, has been shown to mediate vascular smooth muscle cell-specific expression (see, e.g. Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

Uses

A method for modulating transcription according to the present disclosure finds use in a variety of applications, which are also provided. Applications include research applications; diagnostic applications; industrial applications; and therapeutic applications.

Research applications include, e.g. determining the effect of reducing or increasing transcription of a target nucleic acid on, e.g. development, metabolism, expression of a downstream gene, and the like.

High through-put genomic analysis can be carried out using a transcription modulation method, in which only the DNA-targeting segment of the guide RNA needs to be varied, while the protein-binding segment and the transcription termination segment can (in some cases) be held constant. A library (e.g. a library) comprising a plurality of nucleic acids used in the genomic analysis would include: a promoter operably linked to a guide RNA-encoding nucleotide sequence, where each nucleic acid would include a common protein-binding segment, a different DNA-targeting segment, and a common transcription termination segment. A chip could contain over 5×104 unique guide RNAs. Applications would include large-scale phenotyping, gene-to-function mapping, and meta-genomic analysis.

The methods disclosed herein find use in the field of metabolic engineering. Because transcription levels can be efficiently and predictably controlled by designing an appropriate guide RNA, as disclosed herein, the activity of metabolic pathways (e.g. biosynthetic pathways) can be precisely controlled and tuned by controlling the level of specific enzymes (e.g. via increased or decreased transcription) within a metabolic pathway of interest. Metabolic pathways of interest include those used for chemical (fine chemicals, fuel, antibiotics, toxins, agonists, antagonists, etc.) and/or drug production.

Biosynthetic pathways of interest include but are not limited to (1) the mevalonate pathway (e.g. HMG-CoA reductase pathway) (converts acetyl-GoA to dimethylallyl pyrophosphate (DMAPP) and isopentenyl pyrophosphate (IPP), which are used for the biosynthesis of a wide variety of biomolecules including terpenoids/isoprenoids), (2) the non-mevalonate pathway (i.e., the "2-C-methyl-D-erythritol 4-phosphate/1-deoxy-D-xylulose 5-phosphate pathway" or "MEP/DOXP pathway" or "DXP pathway")(also produces DMAPP and IPP, instead by converting pyruvate and glyceraldehyde 3-phosphate into DMAPP and IPP via an alternative pathway to the mevalonate pathway), (3) the polyketide synthesis pathway (produces a variety of polyketides via a variety of polyketide synthase enzymes. Polyketides include naturally occurring small molecules used for chemotherapy (e. g., tetracyclin, and macrolides) and industrially important polyketides include rapamycin (immunosuppressant), erythromycin (antibiotic), lovastatin (anticholesterol drug), and epothilone B (anticancer drug)), (4) fatty acid synthesis pathways, (5) the DAHP (3-deoxy-D-arabino-heptulosonate ?-phosphate) synthesis pathway, (6) pathways that produce potential biofuels (such as short-chain alcohols and alkane, fatty acid methyl esters and fatty alcohols, isoprenoids, etc.), etc.

Networks and Cascades

The methods disclosed herein can be used to design integrated networks (i.e., a cascade or cascades) of control. For example, a guide RNA I variant SluCas9 site-directed polypeptide may be used to control (i.e., modulate, e.g. increase, decrease) the expression of another DNA-targeting RNA or another variant SluCas9 site-directed polypeptide. For example, a first guide RNA may be designed to target the modulation of transcription of a second chimeric dSluCas9 polypeptide with a function that is different than the first variant SluCas9 site-directed polypeptide (e.g. methyltransferase activity, demethylase activity, acetyltansferase activity, deacetylase activity, etc.). In addition, because different dSluCas9 proteins (e.g. derived from different species) may require a different SluCas9 handle (i.e., protein binding segment), the second chimeric dSluCas9 polypeptide can be derived from a different species than the first dSluCas9 polypeptide above. Thus, in some cases, the second chimeric dSluCas9 polypeptide can be selected such that it may not interact with the first guide RNA. In other cases, the second chimeric dSluCas9 polypeptide can be selected such that it does interact with the first guide RNA. In some such cases, the activities of the two (or more) dSluCas9 proteins may compete (e.g. if the polypeptides have opposing activities) or may synergize (e.g. if the polypeptides have similar or synergistic activities). Likewise, as noted above, any of the complexes (i.e., guide RNA I dSluCas9 polypeptide) in the network can be designed to control other guide RNAs or dSluCas9 polypeptides. Because a guide RNA and variant SluCas9 site-directed polypeptide can be targeted to any desired DNA sequence, the methods described herein can be used to control and regulate the expression of any desired target. The integrated networks (i.e., cascades of interactions) that can be designed range from very simple to very complex, and are without limit.

In a network wherein two or more components (e.g. guide RNAs or dSluCas9 polypeptides) are each under regulatory control of another guide RNA/dSluCas9 polypeptide complex, the level of expression of one component of the network may affect the level of expression (e.g. may increase or decrease the expression) of another component of the network. Through this mechanism, the expression of one component may affect the expression of a different component in the same network, and the network may include a mix of components that increase the expression of other components. as well as components that decrease the expression of other components. As would be readily understood by one of skill in the art, the above examples whereby the level of expression of one component may affect the level of expression of one or more different component(s) are for illustrative purposes, and are not limiting. An additional layer of complexity may be optionally introduced into a network when one or more components are modified (as described above) to be manipulable (i.e., under experimental control, e.g. temperature control; drug control, i.e., drug inducible control; light control; etc.).

As one non-limiting example, a first guide RNA can bind to the promoter of a second guide RNA, which controls the expression of a target therapeutic/metabolic gene. In such a case, conditional expression of the first guide RNA indirectly activates the therapeutic/metabolic gene. RNA cascades of this type are useful, for example, for easily converting a repressor into an activator, and can be used to control the logics or dynamics of expression of a target gene.

A transcription modulation method can also be used for drug discovery and target validation.

Various aspects of the invention make use of the following materials and methods and are illustrated by the following non-limiting examples.

Terminology

All technical and scientific terms used herein have the same meaning as commonly understood by one of ordinary skill in the art to which this invention belongs, unless the technical or scientific term is defined differently herein.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids/triple helices, or a polymer comprising purine and pyrimidine bases or other natural, chemically or biochemically modified, non-natural, or derivatized nucleotide bases.

"Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

"Genomic DNA" refers to the DNA of a genome of an organism including, but not limited to, the DNA of the genome of a bacterium, fungus, archea, protists, viral, plant or animal.

"Manipulating" DNA encompasses binding, nicking one strand, or cleaving (i.e. cutting) both strands of the DNA, or encompasses modifying or editing the DNA or a polypeptide associated with the DNA. Manipulating DNA can silence, activate, or modulate (either increase or decrease) the expression of an RNA or polypeptide encoded by the DNA, or prevent or enhance the binding of a polypeptide to DNA.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, i.e., not include any mismatches.

By "hybridizable" or "complementary" or "substantially complementary" it is meant that a nucleic acid (e.g. RNA) comprises a sequence of nucleotides that enables it to non-covalently bind, i.e., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. In addition, it is also known in the art that for hybridization between two RNA molecules (e.g. dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Generally, the length for a hybridizable nucleic acid is at least 10 nucleotides. Illustrative minimum lengths for a hybridizable nucleic acid are: at least 15 nucleotides; at least 20 nucleotides; at least 22 nucleotides; at least 25 nucleotides; and at least 30 nucleotides). Furthermore, the skilled artisan will recognize that the temperature and wash solution salt concentration maybe adjusted as necessary according to factors such as length of the region of complementation and the degree of complementation.

It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g. a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining non complementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol. 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math. 1981 (2) 482-489).

The terms "peptide", "polypeptide", and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide) refers to a non-covalent interaction between macromolecules (e.g. between a protein and a nucleic acid). While in a state of non-covalent interaction, the macromolecules are said to be "associated" or "interacting" or "binding" (e.g. when a molecule X is said to interact with a molecule Y, it is meant the molecule X binds to molecule Y in a non-covalent manner). Not all components of a binding interaction need be sequence-specific (e.g. contacts with phosphate residues in a DNA backbone), but some portions of a binding interaction may be sequence-specific. Binding interactions are generally characterized by a dissociation constant (Kd) of less than 10-6 M, less than 10-7 M, less than 10-8 M, less than 10-9 M, less than 10-10 M, less than 10-11 M, less than 10-12 M, less than 10-13 M, less than 10-14 M, or less than 10-15 M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein-binding protein). In the case of a protein domain-binding protein, it can bind to itself (to form homo-dimers, homo-trimers, etc.) and/or it can bind to one or more molecules of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g. BLAST, T-COFFEE, MUSCLE, MAFFT, etc.), available over the world wide web at sites including ncbi.nlm.nii.gov/BLAST, ebi.ac.uk/Tools/msa/tcoffee, ebi.Ac.Uk!Tools/msa/muscle, mafft.cbrc/alignment/software. See, e.g. Altschul et al. (1990), J. Mol. Biol. 215:403-10. Sequence alignments standard in the art are used according to the invention to determine amino acid residues in a SluCas9 ortholog that "correspond to" amino acid residues in another SluCas9 ortholog. The amino acid residues of SluCas9 orthologs that correspond to amino acid residues of other SluCas9 orthologs appear at the same position in alignments of the sequences.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, or a guide RNA; also called "non-coding" RNA or "ncRNA"). A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located at 3' of the coding sequence.

As used herein, a "promoter sequence" or "promoter" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAAT" boxes. Various promoters, including inducible promoters, may be used to drive the various vectors of the present invention. A promoter can be a constitutively active promoter (i.e., a promoter that is constitutively in an active "ON" state), it may be an inducible promoter (i.e., a promoter whose state, active/"ON" or inactive/"OFF", is controlled by an external stimulus, e.g. thepresence of a particular temperature, compound, or protein), it may be a spatially restricted promoter (i.e., transcriptional control element, enhancer, etc.)(e.g. tissue specific promoter, cell type specific promoter, etc.), and it may be a temporally restricted promoter (i.e., the promoter is in the "ON" state or "OFF" state during specific stages of embryonic development or during specific stages of a biological process, e.g. hair follicle cycle in mice). Suitable promoters can be derived from viruses and can therefore be referred to as viral promoters, or they can be derived from any organism, including prokaryotic or eukaryotic organisms. Suitable promoters can be used to drive expression by any RNA polymerase (e.g. pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g. Xia et al., Nucleic Acids Res. 2003 Sep. 1; 31(17)), a human H1 promoter (H1), and the like. Examples of inducible promoters include, but are not limited to T7 RNA polymerase promoter, T3 RNApolymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g. T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g. a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a SluCas9 polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g. hair follicle cycle in mice). For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g. EMBL HSENO2, X51956); an aromatic amino acid decarboxylase (AADC) promoter; a neurofilament promoter (see, e.g. GenBank HUMNFL, L04147); a synapsin promoter (see, e.g. GenBank HUMSYNIB, M55301); a thy-1 promoter (see, e.g. Chen et al. (1987) Cell 51:7-19; and Llewellyn, et al. (2010) Nat. Med. 16(10):1161-1166); a serotonin receptor promoter (see, e.g. GenBank S62283); a tyrosine hydroxylase promoter (TH) (see, e.g. Oh et al. (2009) Gene Ther. 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g. Radovick et al. (1991) Proc. Natl. Acad. Sci. USA 88:3402-3406); an L7 promoter (see, e.g. Oberdick et al. (1990) Science 248:223-226); a DNMT promoter (see, e.g. Bartge et al. (1988) Proc. Natl. Acad. Sci. USA 85:3648-3652); an enkephalin promoter (see, e.g. Comb et al. (1988) EMBO J. 17:3793-3805); a myelin basic protein (MBP) promoter; a Ca2+-calmodulin-dependent protein kinase 11-alpha (CamKIM) promoter (see, e.g. Mayford et al. (1996) Proc. Natl. Acad. Sci. USA 93:13250; and Casanova et al. (2001) Genesis 31:37); a CMV enhancer/platelet-derived growth factor-p promoter (see, e.g. Liu et al. (2004) Gene Therapy 11:52-60); and the like.

Adipocyte-specific spatially restricted promoters include, but are not limited to aP2 gene promoter/enhancer, e.g. a region from −5.4 kb to +21 bp of a human aP2 gene (see, e.g. Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g. Knight et al. (2003) Proc. Natl. Acad. Sci. USA 100:14725); a fatty acid translocase (FAT/CD36) promoter (see, e.g. Kuriki et al. (2002) Biol. Pharm. Bull. 25:1476; and Sato et al. (2002) J. Biol. Chem. 277:15703); a stearoyi-CoA desaturase-1 (SCD1) promoter (Tabor et al. (1999) J. Biol. Chem. 274:20603); a leptin promoter (see, e.g. Mason et al. (1998) Endocrinol. 139:1013; and Chen et al. (1999) Biochem. Biophys. Res. Comm. 262:187); an adiponectin promoter (see, e.g. Kita et al. (2005) Biochem. Biophys. Res. Comm. 331:484; and Chakrabarti (2010) Endocrinol. 151:2408); an adipsin promoter (see, e.g. Platt et al. (1989) Proc. Natl. Acad. Sci. USA 86:7490); a resistin promoter (see, e.g. Seo et al. (2003) Molec. Endocrinol. 17:1522); and the like.

Cardiomyocyte-specific spatially restricted promoters include, but are not limited to control sequences derived from the following genes: myosin light chain-2, a-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22a promoter (see, e.g. Akyiirek et al. (2000) Mol. Med. 6:983; and U.S. Pat. No. 7,169,874); a smoothelin promoter (see, e.g. WO 2001/018048); an a-smooth muscle actin promoter; and the like. For example, a 0.4 kb region of the SM22a promoter, within which lie two CArG elements, has been shown to mediate vascular smooth muscle cell-specific expression (see, e.g. Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g. guide RNA) or a coding sequence (e.g. SluCas9 polypeptide) and/or regulate translation of an encoded polypeptide.

The term "naturally-occurring" or "unmodified" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "chimeric" as used herein as applied to a nucleic acid or polypeptide refers to one entity that is composed of structures derived from different sources. For example, where "chimeric" is used in the context of a chimeric polypeptide (e.g. a chimeric SluCas9 protein), the chimeric polypeptide includesamino acid sequences that are derived from different polypeptides. A chimeric polypeptide may comprise either modified or naturally-occurring polypeptide sequences (e.g. a first amino acid sequence from a modified or unmodified SluCas9 protein; and a secondamino acid sequence other than the SluCas9 protein). Similarly, "chimeric" in the context of a polynucleotide encoding a chimeric polypeptide includes nucleotidesequences derived from different coding regions (e.g. a first nucleotide sequence encoding a modified or unmodified SluCas9 protein; and a second nucleotidesequence encoding a polypeptide other than a SluCas9 protein).

The term "chimeric polypeptide" refers to a polypeptide which is not naturally occurring, e.g. is made by the artificial combination (i.e., "fusion") of two or more otherwise separated segments of amino sequence through human intervention. A polypeptide that comprises a chimeric amino acid sequence is a chimeric polypeptide. Some chimeric polypeptides can be referred to as "fusion variants."

"Heterologous," as used herein, means a nucleotide or peptide that is not found in the native nucleic acid or protein, respectively. For example, in a chimeric SluCas9 protein, the RNA-binding domain of a naturally-occurring bacterial SluCas9 polypeptide (or a variant thereof) may be fused to a heterologous polypeptide sequence (i.e., a polypeptide sequence from a protein other than SluCas9 or a polypeptide sequence from another organism). The heterologous polypeptide may exhibit an activity (e.g. enzymatic activity) that will also be exhibited by the chimeric SluCas9 protein (e.g. methyltransferase activity, acetyltransferase activity, kinase activity, ubiquitinating activity, etc.). A heterologous nucleic acid may be linked to a naturally-occurring nucleic acid (or a variant thereof) (e.g. by genetic engineering) to generate a chimeric polynucleotide encoding a chimeric polypeptide. As another example, in a fusion variant SluCas9 site-directed polypeptide, a variant SluCas9 site-directed polypeptide may be fused to a heterologous polypeptide (i.e., a polypeptide other than SluCas9), which exhibits an activity that will also be exhibited by the fusion variant SluCas9 site-directed polypeptide. A heterologous nucleic acid may be linked to a variant SluCas9 site-directed polypeptide (e.g. by genetic engineering) to generate a polynucleotide encoding a fusion variant SluCas9 site-directed polypeptide. "Heterologous," as used herein, additionally means a nucleotide or polypeptide in a cell that is not its native cell.

The term "cognate" refers to two biomolecules that normally interact or co-exist in nature.

"Recombinant," as used herein, means that a particular nucleic acid (DNA or RNA) or vector is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g. guide RNA) that is not translated may also be considered recombinant. Thus, e.g. the term "recombinant" nucleic acid refers to one which is not naturally occurring, e.g. is made by the artificial combination of two otherwise separated segments of sequence through human intervention. This artificial combination is often accomplished by either chemical synthesis means, or by the artificial manipulation of isolated segments of nucleic acids, e.g. by genetic engineering techniques. Such is usually done to replace a codon with a codon encoding the same amino acid, a conservative amino acid, or a non-conservative amino acid. Alternatively, it is performed to join together nuclei acid segments of desired functions to generate a desired combination of functions. This artificial combination is often accomplished by either chemical synthesis means, or by the artificial manipulation of isolated segments of nucleic acids, e.g. by genetic engineering techniques. When a recombinant polynucleotide encodes a polypeptide, the sequence of the encoded polypeptide can be naturally occurring ("wild type") or can be a variant (e.g. a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring("wild type") or non-naturally occurring (e.g. a variant, a mutant, etc.). Thus, a "recombinant" polypeptide is the result of human intervention, but may be a naturally occurring amino acid sequence. The term "non-naturally occurring" includes molecules that are markedly different from their naturally occurring counterparts, including chemically modifiedor mutated molecules.

A "vector" or "expression vector" is a replicon, such as plasmid, phage, virus, or cosmid, to which another DNA segment, i.e., an "insert", may be attached so as to bring about the replication of the attached segment in a cell.

An "expression cassette" comprises a DNA coding sequence operably linked to a promoter. "Operablylinked" refers to a juxtaposition wherein the components so described are in a relationship permitting them to function in their intended manner. For instance, a promoter is operably linked to a coding sequence if the promoter affects its transcription or expression. The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The nucleic acid(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell.

In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include but are not limited to, e.g. viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g. Panyam et al., Adv Drug Deliv Rev. 2012 Sep. 13. pp: 50169-409X(12)00283-9. doi:10.1016/j.addr.2012.09.023), and the like.

The choice of method of genetic modification is generally dependent on the type of cell being transformed and the circumstances under which the transformation is taking place (e.g. in vitro, ex vivo, or in vivo). A general discussion of these methods can be found in Ausubel, et al., Short Protocols in Molecular Biology, 3rd ed., Wiley & Sons, 1995.

A "host cell," as used herein, denotes an in vivo or in vitro eukaryotic cell, a prokaryotic cell (e.g. bacterial or archaeal cell), or a cell from a multicellular organism (e.g. a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g. an expression vector. For example, a bacterial host cell is a genetically modified bacterial host cell by virtue of introduction into a suitable bacterial host cell of an exogenous nucleic acid (e.g. a plasmid or recombinant expression vector) and a eukaryotic host cell is a genetically modified eukaryotic host cell (e.g. a mammalian germ cell), by virtue of introduction into a suitable eukaryotic host cell of an exogenous nucleic acid.

A "target DNA" as used herein is a DNA polynucleotide that comprises a "target site" or "target sequence." The terms "target site," "target sequence," "target protospacer DNA," or "protospacer-like sequence" are used interchangeably herein to refer to a nucleic acid sequence present in a target DNA to which a DNA-targeting segment of a guide RNA will bind, provided sufficient conditions for binding exist. For example, the target site (or target sequence) 5'-GAG-CATATC-3' within a target DNA is targeted by (or is bound by, or hybridizes with, or is complementary to) the RNA sequence 5'-GAUAUGCUC-3'. Suitable DNA/RNA binding conditions include physiological conditions normally present in a cell. Other suitable DNA/RNA binding conditions (e.g. conditions in a cell-free system) are known in the art; see, e.g. Sambrook, supra. The strand of the target DNA that is complementary to and hybridizes with the guide RNA is referred to as the "complementary strand" and the strand of the target DNA that is complementary to the "complementary strand" (and is therefore not complementary to the guide RNA) is referred to as the "non-complementary strand" or "non-complementary strand." By "site-directed modifying polypeptide" or "RNA-binding site-directed polypeptide" or "RNA-binding site-directed modifying polypeptide" or "site-directed polypeptide" it is meant a polypeptide that binds RNA and is targeted to a specific DNA sequence. A site-directed modifying polypeptide as described herein is targeted to a specific DNA sequence by the RNA molecule to which it is bound. The RNA molecule comprises a sequence that binds, hybridizes to, or is complementary to a target sequence within the target DNA, thus targeting the bound polypeptide to a specific location within the target DNA (the target sequence). By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guide RNA and a site-directed modifying polypeptide is used for targeted double-stranded DNA cleavage.

"Nuclease" and "endonuclease" are used interchangeably herein to mean an enzyme which possesses endonucleolytic catalytic activity for polynucleotide cleavage.

By "cleavage domain" or "active domain" or "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

By "site-directed polypeptide" or "RNA-binding site-directed polypeptide" or "RNA-binding site-directed polypeptide" it is meant a polypeptide that binds RNA and is targeted to a specific DNA sequence. A site-directed polypeptide as described herein is targeted to a specific DNA sequence by the RNA molecule to which it is bound. The RNA molecule comprises a sequence that is complementary to a target sequence within the target DNA, thus targeting the bound polypeptide to a specific location within the target DNA (the target sequence).

The "guide sequence" or DNA-targeting segment (or "DNA-targeting sequence") comprises a nucleotide sequence that is complementary to a specific sequence within a target DNA (the complementary strand of the target DNA) designated the "protospacer-like" sequence herein. The protein-binding segment (or "protein-binding sequence") interacts with a site-directed modifying polypeptide. When the site-directed modifying polypeptide is a SluCas9 or SluCas9 related polypeptide (described in more detail below), site-specific cleavage of the target DNA occurs at locations determined by both (i) base-pairing complementarity between the guide RNA and the target DNA; and (ii) a short motif (referred to as the protospacer adjacent motif (PAM)) in the target DNA.

The protein-binding segment of a guide RNA comprises, in part, two complementary stretches of nucleotides that hybridize to one another to form a double stranded RNA duplex (dsRNA duplex).

In some embodiments, a nucleic acid (e.g. a guide RNA, a nucleic acid comprising a nucleotide sequence encoding a guide RNA; a nucleic acid encoding a site-directed polypeptide; etc.) comprises a modification or sequence that provides for an additional desirable feature (e.g. modified or regulated stability; subcellular targeting; tracking, e.g. a fluorescent label; a binding site for a protein or protein complex; etc.). Non-limiting examples include: a 5' cap (e.g. a 7-methylguanylate cap (m7G)); a 3' polyadenylated tail (i.e., a 3' poly(A) tail); a riboswitch sequence (e.g. to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA, including transcriptional activators, transcriptional repressors, DNA methyltransferases, DNA demethylases, histone acetyltransferases, histone deacetylases, and the like); and combinations thereof.

In some embodiments, a guide RNA comprises an additional segment at either the 5' or 3' end that provides for any of the features described above. For example, a suitable third segment can comprise a 5' cap (e.g. a 7-methylguanylate cap (m7G)); a 3' polyadenylated tail (i.e., a 3' poly(A) tail); a riboswitch sequence (e.g. to allow for regulated stability and/or regulated accessibility by proteins and protein complexes); a stability control sequence; a sequence that forms a dsRNA duplex (i.e., a hairpin)); a sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA. including transcriptional activators, transcriptional repressors, DNA methyltransferases, DNA demethylases, histone acetyltransferases, histone deacetylases, and the like); and combinations thereof.

A guide RNA and a SluCas9 polypeptide form a complex (i.e., bind via non-covalent interactions). The guide RNA provides target specificity to the complex by comprising a nucleotide sequence that is complementary to a sequence of a target DNA. The SluCas9 polypeptide of the complex provides the site-specific activity. In other words, the SluCas9 polypeptide is guided to a target DNA sequence (e.g. a target sequence in a chromosomal nucleic acid; a target sequence in an extrachromosomal nucleic acid, e.g. an episomal nucleic acid, a minicircle, etc.; a target sequence in a mitochondrial nucleic acid; a target sequence in a chloroplast nucleic acid; a target sequence in a plasmid; etc.) by virtue of its association with the protein-binding segment of the guide RNA. RNA aptamers are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the RNA molecule of which they are part. RNA aptamers usually comprise a sequence that folds into a particular structure (e.g. a hairpin), which specifically binds a particular drug (e.g. a small molecule). Binding of the drug causes a structural change in the folding of the RNA, which changes a feature of the nucleic acid of which the aptamer is a part. As non-limiting examples: (i) an activator-RNA with an aptamer may not be able to bind to the cognate targeteRNA unless the aptamer is bound by the appropriate drug; (ii) a targeter-RNA with an aptamer may not be able to bind to the cognate activator-RNA unless the aptamer is bound by the appropriate drug; and (iii) a targeter-RNA and an activator-RNA, each comprising a different aptamer that binds a different drug, may not be able to bind to each other unless both drugs are present. As illustrated by these examples, a two-molecule guide RNA can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley Interdiscip Rev RNA. 2012 May-June; 3(3):369-84; all of which are herein incorporated by reference in their entirety.

The term "stem cell" is used herein to refer to a cell (e.g. plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g. mesodermal stem cells), which in turn can differentiate into cells that are further restricted (e.g. neuron progenitors), which can differentiate into end-stage cells (i.e., terminally differentiated cells, e.g. neurons. cardiomyocytes, etc.), which play a characteristic role in a certain tissue type, and may or may not retain the capacity to proliferate further. Stem cells may be characterized by both the presence of specific markers (e.g. proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g. the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g. cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20).

Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, generally from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent. e.g. mice, rats. hamster, primate, etc. (Thomson et al. (1998) Science 282:1145; Thomson et al. (1995) Proc. Natl. Acad. Sci. USA 92:7844; Thomson et al. (1996) Biol. Reprod. 55:254; Shamblott et al., Proc. Natl. Acad. Sci. USA 95:13726, 1998). In culture, ESCs generally grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920. By "embryonic germ stem cell" (EGSC) or "embryonic germ cell" or "EG cell" is meant a PSC that is derived from germ cells and/or germ cell progenitors, e.g. primordial germ cells, i.e., those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, Fox03, GDF3, Cyp26al, TERT, and zfp42.

Examples of methods of generating and characterizing iPSCs may be found in, for example, US Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e., it is no longer undergoing divisions. This quiescent state may be temporary, i.e., reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

By "recombination" it is meant a process of exchange of genetic information between two polynucleotides. As used herein, "homology-directed repair (HDR)" refers to the specialized form DNA repair that takes place, for example, during repair of double-strand breaks in cells. This process requires nucleotide sequence homology, uses a "donor" molecule to template repair of a "target" molecule (i.e., the one that experienced the double-strand break), and leads to the transfer of genetic information from the donor to the target. Homology-directed repair may result in an alteration of the sequence of the target molecule (e.g. insertion, deletion, mutation), if the donor polynucleotide differs from the target molecule and part or all of the sequence of the donor polynucleotide is incorporated into the target DNA In some embodiments, the donor polynucleotide, a portion of the donor polynucleotide, a copy of the donor polynucleotide, or a portion of a copy of the donor polynucleotide integrates into the target DNA.

By "non-homologous end joining (NHEJ) it is meant the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

The terms "treatment", 'treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., Harboor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (1. Lefkovits ed., Academic Press 1997); and Cell and Tissue Culture: Laboratory Procedures in Biotechnology (Doyle & Griffiths, John Wiley & Sons 1998), the disclosures of which are incorporated hereinby reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smalleranges, and are also encompassed within the invention, subject to any specifically excluded limit in the stated range. Where the stated range includes one or both of the limits, ranges excluding either or both of those included limits are also included in the invention.

The phrase "consisting essentially of" is meant herein to exclude anything that is not the specified active component or components of a system, or that is not the specified active portion or portions of a molecule.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Genome Editing

Genome editing generally refers to the process of modifying the nucleotide sequence of a genome, such as in a precise or predetermined manner. Examples of methods of genome editing described herein include methods of using site-directed nucleases to cut DNA at precise target locations in the genome, thereby creating double-strand or single-strand DNA breaks at particular locations within the genome. Such breaks can be and regularly are repaired by natural, endogenous cellular processes such as homology-directed repair (HDR) and non-homologous end-joining (NHEJ), as recently reviewed in Cox et al., Nature Medicine 21(2), 121-31 (2015). NHEJ directly joins the DNA ends resulting from a double-strand break sometimes with the loss or addition of nucleotide sequence which may disrupt or enhance gene expression. HDR utilizes a homologous sequence, or donor sequence, as a template for inserting a defined DNA sequence at the break point. The homologous sequence may be in the endogenous genome, such as a sister chromatid. Alternatively, the donor may be an exogenous nucleic acid such as a plasmid, a single-strand oligonucleotide, a duplex oligonucleotide or a virus, that has regions of high homology with the nuclease-cleaved locus, but which may also contain additional sequence or sequence changes including deletions that can be incorporated into the cleaved target locus. A third repair mechanism is microhomology-mediated end joining (MMEJ), also referred to as "Alternative NHEJ, in which the genetic outcome is similar to NHEJ in that small deletions and insertions can occur at the cleavage site. MMEJ makes use of homologous sequences of a few base pairs flanking the DNA break site to drive a more favored DNA end joining repair outcome, and recent reports have further elucidated the molecular mechanism of this process; see, e.g. Cho and Greenberg, Nature 518, 174-76 (2015); Kent et al., Nature Structural and Molecular Biology, Adv. Online doi:10.1038/nsmb.2961(2015); Mateos-Gomez et al., Nature 518, 254-57 (2015); Ceccaldi et al., Nature 528, 258-62 (2015). In some instances it may be possible to predict likely repair outcomes based on analysis of potential microhomologies at the site of the DNA break.

Each of these genome editing mechanisms can be used to create desired genomic alterations. The first step in the genome editing process is to create generally one or two DNA breaks in the target locus as close as possible to the site of intended mutation. This can achieved via the use of site-directed polypeptides, as described and illustrated herein.

Site-directed polypeptides can introduce double-strand breaks or single-strand breaks in nucleic acid, (e.g. genomic DNA). The double-strand break can stimulate a cell's endogenous DNA-repair pathways (e.g. homology-dependent repair (HDR) and non-homologous end joining (NHEJ) or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage and can lead to disruption or alteration of gene expression. HDR can occur when a homologous repair template, or donor, is available. The homologous donor template comprises sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide or viral nucleic acid. With exogenous donor templates it is common to introduce additional nucleic acid sequence (such as a transgene) or modification (such as a single base change or a deletion) between the flanking regions of homology so additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few basepairs flanking the cleavage site to drive a favored end-joining DNA repair outcome. In some instances it may be possible to predict likely repair outcomes based on analysis of potential microhomologies in the nuclease target regions. Thus, in some cases, homologous recombination is used to insert an exogenous polynucleotide sequence into the target nucleic acid cleavage site. An exogenous polynucleotide sequence is termed a donor polynucleotide herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

EXAMPLES

Example 1: PAM Identification

Depletion Assay: To determine the PAM sequence of SluCas9, a depletion experiment was conducted. Competent cells (BL21DE3 Star harboring pMC7125 (SEQ ID NO: 19)/pMC7204 (SEQ ID NO: 20) were prepared. As control competent cells (BL21DE3 Star harboring pMC7125 (SEQ ID NO: 19) were used. pML2070 (N7-PAM library, according to SEQ ID NO: 34, see FIG. 1A) was transformed into pMC7125/pMC7204 (SEQ ID NO: 20) or pMC7125 competent cells (100 ng pML2070 per 50 µl cell aliquot; 3 aliquots were used) and cells were resuspended in SOC (1 ml per transformation) and shaken at 1000 rpm for 1 h at 37° C. in an Eppendorf Thermomixer. Cell suspensions were plated on LB-Agar (Cm/Kan/Amp/0.2 mM IPTG or w/o kanamycin for the control reactions). Overall 5× plates were used per sample, to ensure multiple coverage of the 16384 cfu complexity of the library (250 µl of rescued SOC was plated per plate. Plates were incubated overnight at 37° C. Cells were harvested and plasmids were extracted. A 271 bp fragment including the VEGFA-target sequence and the PAM motif was amplified via PCR and used for NGS adapter ligation following the manufacturers protocol (Illumina Miseq V2). The NGS libraries were analyzed on an Illumina Miseq sequencer and sequences of depleted and non-depleted controls were compared to assess the successfully cleaved sequences. Additionally, the PAM motif was assessed by cleaving the N7-PAM library (pML2070) in vitro and analyzing the cleaved fragments by NGS. Results are shown in FIG. 1B, wherein the size of the character for a particular base refers to the activity at such position.

Example 2: PAM Characterization

To fully characterize the PAM motif and to assess the influence of single nucleotide substitution (especially A at position N1, as suggested by the PAM motif from in vitro cleavage experiments), fluorescently labeled oligonucleotides (ODNs) were cleaved by SluCas9 (FIG. 2A, top panel) and the cleavage kinetics were determined (FIG. 2A, bottom panel). In addition to that approximately 1000 bp PCR products harboring different PAM motifs were cleaved in vitro. Protocol fluorescence polarization assay:

Oligonucleotide duplexes were prepared in 10 mM Tris (pH=7.8) 50 mM NaCL as 10 µM solutions (from 100 µM stocks) and annealed at 95° C. for 5 minutes and then slowly cooled down in thermo cycler (6° C. per minute). The stocks were subsequently diluted in 10 mM Tris (pH=7.8) 50 mM NaCL+0.05% pluronic. 20 nM oligo (20 µL) were immobilized on streptavidin coated plate, washed twice after 5 minutes and then incubated with a 20 µL sample for a kinetics of 60 minutes (excitation wavelength: 635 nm; emission wavelength: 670 nm). Prior to the cleavage the reaction RNP was formed. To 817.6 µl 1×PBS MgCl2, 4.68 µl SluCas9 (71 µM) and 7.69 µl sgRNA$_{VEGFA}$ (64.8 µM) were added and incubated at 37° C. for 10 minutes. 20 µl RNP was added to each well and the polarization was measured for 60 minutes at 37° C.

```
sgRNA_VEGFA sequence used (SEQ ID NO: 8):
GGACCCCCUCCACCCCGCCUCGUUUUAGUACUCUGGAAA

CAGAAUCUACUGAAACAAGACAAUAUGUCGUGUUUAUCC

CAUCAAUUUAUUGGUGGGAUUUUUUU

Oligonucleotide substrates:
1) With CGGGCGC-PAM
a.
                                    (SEQ ID NO: 9)
ATTO647N-GACCCCCTCCACCCCGCCTCCGGGCGCG b.
                                   (SEQ ID NO: 10)
GCGCGCGCCCGGAGGCGGGGTGGAGGGGGTCGG-Biotin 2) With AGGGCGC-PAM
a.
                                   (SEQ ID NO: 11)
ATTO647N-GACCCCCTCCACCCCGCCTCAGGGCGCG b.
                                   (SEQ ID NO: 12)
GCGCGCGCCCTGAGGCGGGGTGGAGGGGGTCGG-Biotin
```

References: *Methods Enzymol.* 2014; 546:1-20.

Protocol In Vitro PCR Cleavage Assay:

The PCR product for in vitro cleavage (VEGFA-PAM variants) were amplified from plasmids based on pCas595 (or PAM variants) with primers (fwd: tctgatttataatgtgaaaat-tcgcggtgtgaact, SEQ ID NO: 26; rev:agcgccacgcttcccgaagg-gagaaaggcggacagg, SEQ ID NO: 27). PCR product was purified using Qiagen PCR purification Kit™ (following-manufacturer's protocol). Prior to the cleavage reaction, RNPs were formed by adding SluCas9 (10 µM final concentration), sgRNA (15 µM final concentration, 1.3 µl 10×PBS+5 mM MgCl2 and 6.39 µl water (13 µl final volume) and incubated for 10 minutes at 37° C. Subsequently, 400 ng PCR products were digested with 2 µl of RNP solution in 1×PBS 5 mM MgCl2 in 10 µl reaction volume for 30 minutes at 37° C. (followed by heat inactivation by 95° C. for 15 minutes). The cleavage reactions were analyzed on an agarose gel and visualized by ethidium bromide under an UV-table.

sgRNA_{VEGFA} sequence used (SEQ ID NO: 8):
GGACCCCCUCCACCCCGCCUCGUUUUAGUACUCUGGAAAC

AGAAUCUACUGAAACAAGACAAUAUGUCGUGUUUAUCCCA

UCAAUUUAUUGGUGGGAUUUUUUU

Figure 2B:
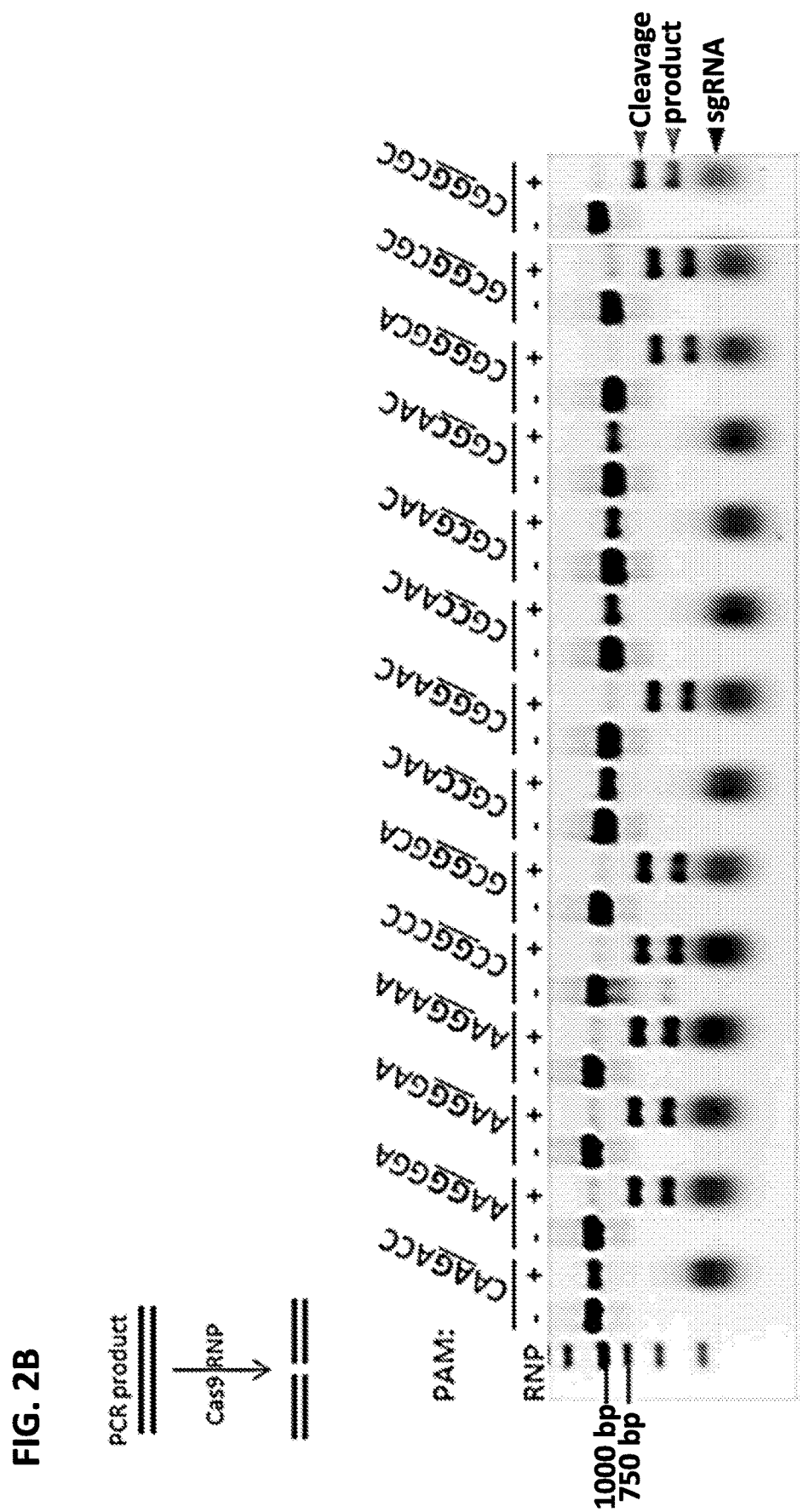
FIG. 2B shows results for the in vitro cleavage of PCR products of approximately 1000 bp in length harboring different PAM motifs by SluCas9. The different PAM sequences are shown with either RNP solution present ("+") or absent ("−"). The arrows on the right of the panel visualizing the agarose gel separation indicate the products obtained via the respective reaction.

The results are visualized in FIG. 2B, bottom panel. Wherein, the different PAM sequences are shown with either RNP solution present ("+") or absent ("-"). The arrows on the right of the panel visualzing the agarose gel separation indicate the products obtained via the respective reaction. The results suggest a PAM sequence of "NNGG".

Example 3: Confirmation of the NNGG PAM Motif by a Live-Dead-Assay

Figure 3A:
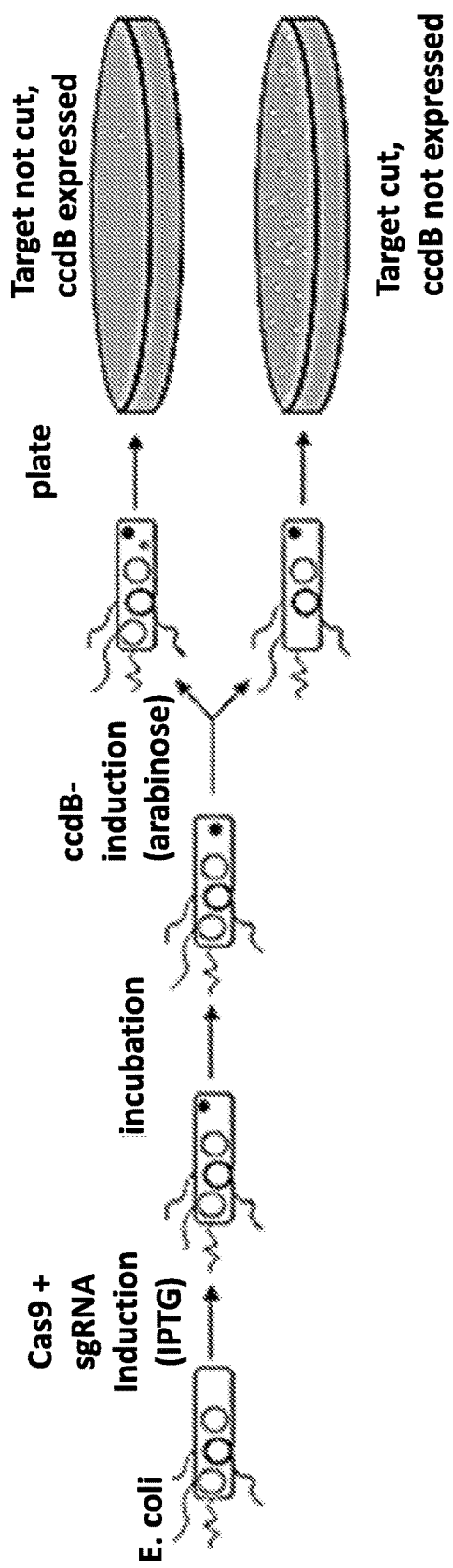
FIGS. 3A-3C show confirmation of the NNGG PAM motif for SluCas9 by a cell survival "live-dead" assay.
Figure 3B:
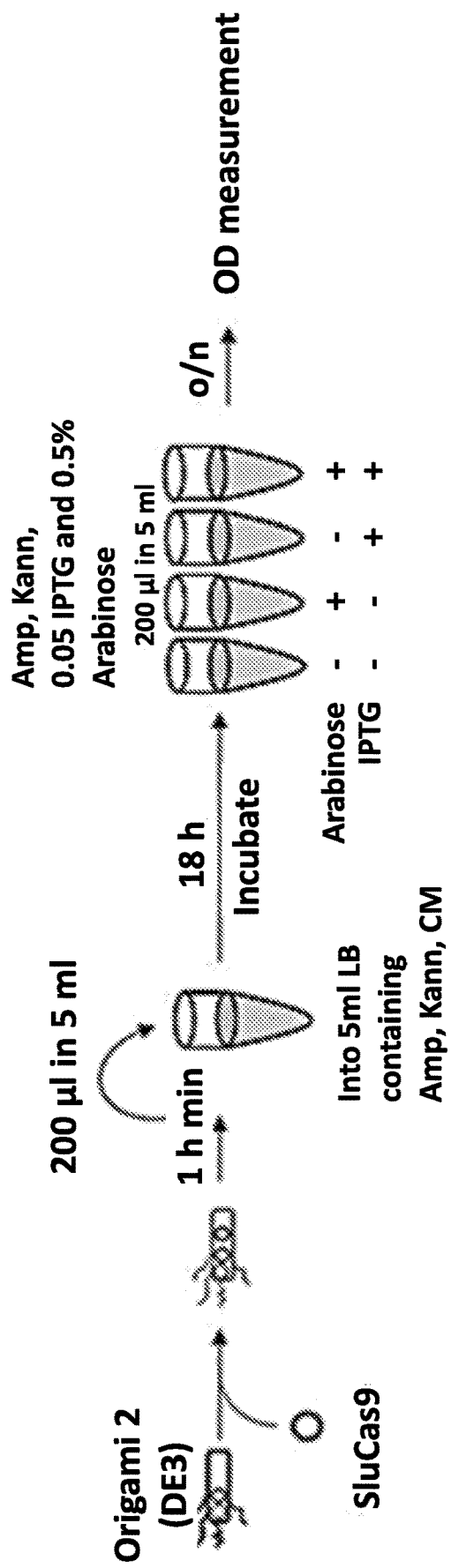
Figure 3C:
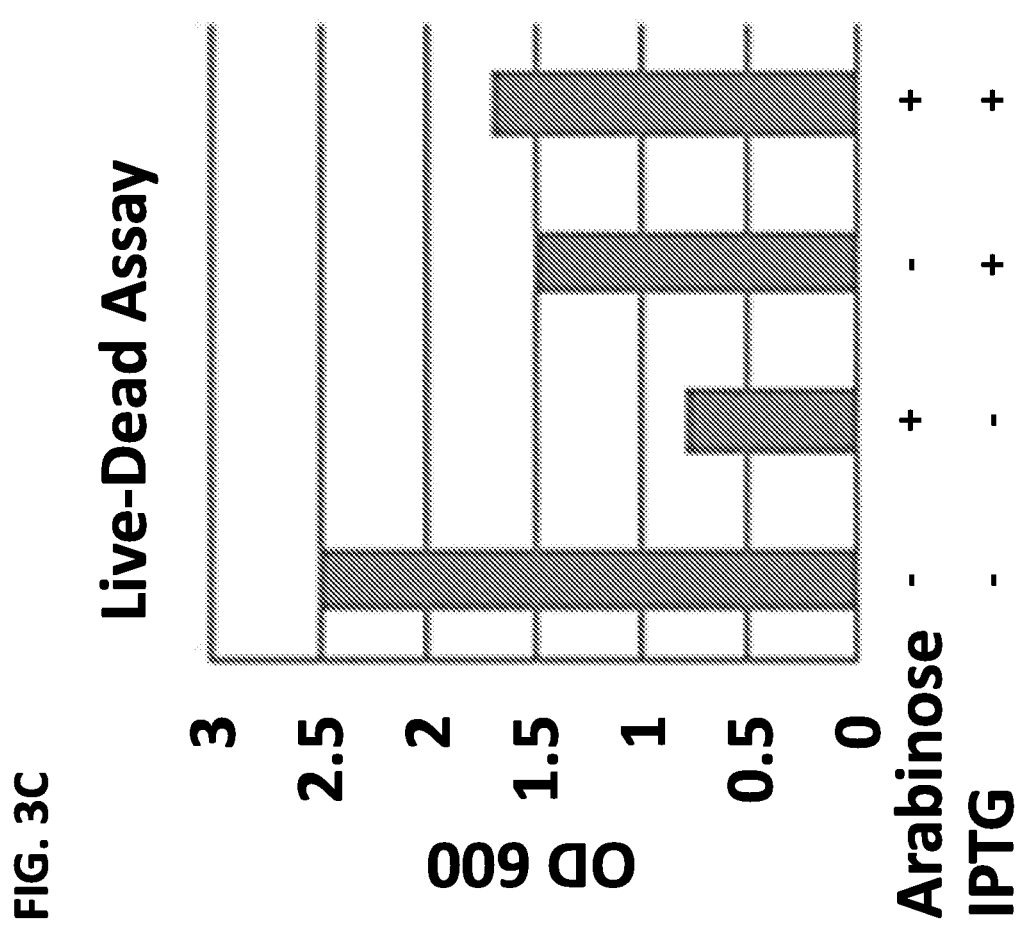

Protocol Live/Dead Assay:
Liquid culture (FIG. 3B): BL21DE3 origami cells harboring a toxic reporter plasmid (pCas634, SEQ ID NO: 25, having an arabinose-inducible ccdB gene with a VEGFA target site and a NNGG PAM) and a plasmid harboring the transcription unit of the sgRNA targeting VEGFA (pCas606, SEQ ID NO: 21) were transformed with a plasmid encoding SluCas9 under an IPTG-inducible Trc promoter (pCas81, SEQ ID NO: 24). After transformation, the cell suspension was rescued with 1 ml SOC and incubated at 37° C. with 1000 rpm shaking (Eppendorf Thermomix). 200 µl were used to inoculate LB medium (supplemented with kanamycin, chloramphenicol and ampicillin) and the liquid culture was incubated overnight at 37° C. with 190 rpm shaking. 200 µl of this overnight culture were used to inoculate 5 ml LB medium supplemented with kanamycin and ampicillin and with/without 0.5% L-arabinose, with/without 0.05 mM IPTG. After incubation at 37° C. overnight (18 h) with 190 rpm shaking, $OD_{600}$ was determined (FIG. 3B).

On Plates (FIG. 3A): BL21DE3 origami cells harboring a toxic reporter plasmid (pCas634, SEQ ID NO: 25, an arabinose-inducible ccdB gene with a VEGFA target site and a "NNGG" PAM) and a plasmid harboring the transcription unit of the sgRNA targeting VEGFA (pCas606, SEQ ID NO: 21) were transformed with a plasmid encoding SluCas9 under an IPTG-inducible Trc promoter (pCas81, SEQ ID NO: 24). After transformation, the cell suspension was rescued with 1 ml SOC medium and incubated at 37° C. with 1000 rpm shaking (Eppendorf Thermomix). 200 µl were plated in LB-Agar plates supplemented with kanamycin, ampicillin, 0.05 mM IPTG and 0.5% L-arabinose. After incubation at 37° C. for 18 h, colonies were counted.

References: Benjamin L. Oakes, Dana C. Nadler, David F. Savage, Protein Engineering of Cas9 for Enhanced Function, Methods in Enzymology, Volume 546, 2014, Pages 491-511, ISSN 0076-6879, Example 4: Activity in Mammalian Cells To determine activity of SluCas9 in mammalian cells following assays were utilized.

HEK293T cells expressing BFP were treated with Ribonucleoprotein complex (RNP) assembled with 1 µg Slu Cas9 protein and 1 µg single guideRNA (sgRNA) (with protein:guide molar ratio between 1:2 to 1:3) targeting the reverse strand of BFP genomic sequence as described. Two different BFP DNA-targeting segments (20 nucleotides each) were used, BFP20 nt_1 (SEQ ID NO: 15), BFP20 nt_2 (SEQ ID NO: 16). See FIG. 4B. An extended, 22 nt version of second guide was also used, BFP22 nt_2 (SEQ ID NO: 17). Transfection was performed as described and cells were analyzed by FACS for loss of BFP disruption 7 days after transfection as described before (Glaser et al., 2016).

Results are visualized in FIG. 4C.

Example 5: ddPCR and T7E1 Assay Using Guide for HBB Gene

Figure 5B:
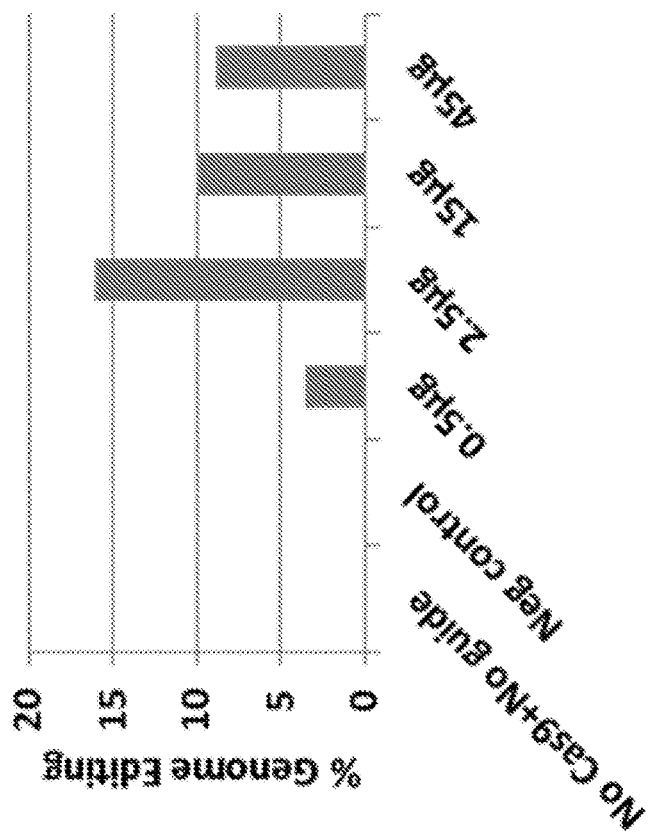
Figure 5C:
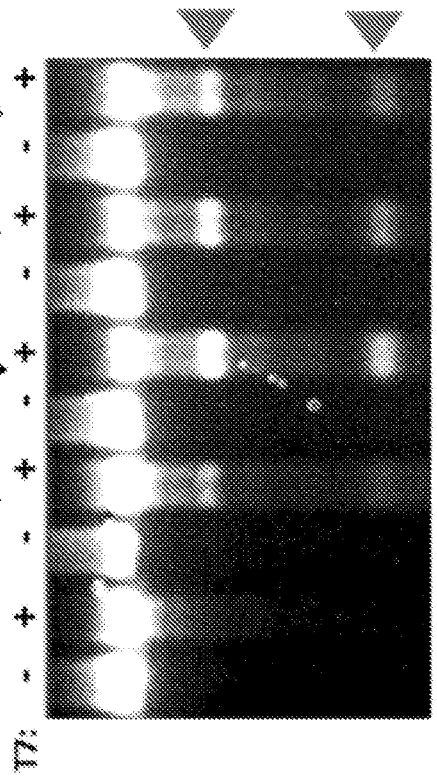

HEK293 cells were treated with RNPs as described below. A guide RNA targeting human gene HBB (ENSENBL gene id: ENSG00000244734) was used (HBB guide 20 nt_1 sequence: ggtgaacgtggatgaagttg (SEQ ID NO: 18), see FIG. 5A). Titration for different Cas9 protein amounts was performed, keeping the molar ratio of protein to guide between 1:2 to 1:3. Cells were harvested, gDNA collected 2 days after transfection and editing was detected by ddPCR (droplet digital PCR). Results are shown in FIG. 5B. Editing on DNA/molecular level was also confirmed by T7E1 endonuclease assay which cleaves DNA only in presence of indels. Results are shown in FIG. 5C.

Droplet digital PCR was performed according to manufacturer's instructions (Bio-Rad) using the following primers, probes and thermocycler profiles.

| Component | VEGFA | HBB (R01) | 1X Final | 20X Assay (25 ul) |
|---|---|---|---|---|
| F primer (100 uM) → | SPRJ1688 | SPRJ1720 | 900 nM | 4.5 |
| R primer (100 uM) → | SPRJ1689 | SPRJ1721 | 900 nM | 4.5 |
| NIP_FAM probe (100 uM) → | SPRJ1695 | SPRJ1725 | 250 nM | 1.25 |
| NSP_HEX probe (100 uM) → | SPRJ1699 | SPRJ1728 | 250 nM | 1.25 |
| HPLC Water | | | | 13.5 |

NHEJ Reaction Setup

| Component | 1 well | 25X |
|---|---|---|
| ddPCR Supermix for probes (no dUTP) | 10 ul | 250 ul |
| 20X assay recipe | 1 ul | 25 ul |
| Sample DNA (50 ng) | 1 ul | — |
| HPLC water | 8 ul | 200 ul |

Thermocycler Profile

| Step | Temp (° C.) | Time | Ramp | # of cycles |
|---|---|---|---|---|
| 1 | 95 | 10 min | 2° C./sec | 1 |
| 2 | 94 | 30 sec | 2° C./sec | 40 |
| 3 | 58.5° C. (HBB); 61.2 (VEGFA) | 1 min | 2° C./sec | |
| 4 | 72° C. | 2 min | 2° C./sec | |
| 5 | 98 | 10 min | 2° C./sec | 1 |
| 6 | 4 | Hold | 2° C./sec | 1 |

Oligonucleotide Primers Used in PCR:

| Name | SEQ ID NO: | Sequence | Modifications | Purity |
|---|---|---|---|---|
| SPRJ1688 | 36 | acggacagacagacagacacc | | desalted |
| SPRJ1689 | 37 | agaacagcccagaagttggac | | desalted |

-continued

| Name | SEQ ID NO: | Sequence | Modifications | Purity |
|---|---|---|---|---|
| SPRJ1695 | 38 | agccccagctacc acctcctcc | 5 6-FAM- 3' BHQ-1 | HPLC |
| SPRJ1699 | 39 | tccaccccgcctc cgggcgc | 5' HEX- 3' BHQ-1 | HPLC |
| SPRJ1720 | 40 | catggtgcatctg actcctg | | desalted |
| SPRJ1721 | 41 | ggtagaccaccag cagccta | | desalted |
| SPRJ1725 | 42 | aggagaagtctgc cgttactgccct | 5' 6-FAM- 3' BHQ-1 | HPLC |
| SPRJ1728 | 43 | tgaagttggtggt gaggccct | 5' HEX- 3' BHQ-1 | HPLC |

Example 6: Determination of Optimal Slu sgRNA Length for Highest Editing

Figure 6:
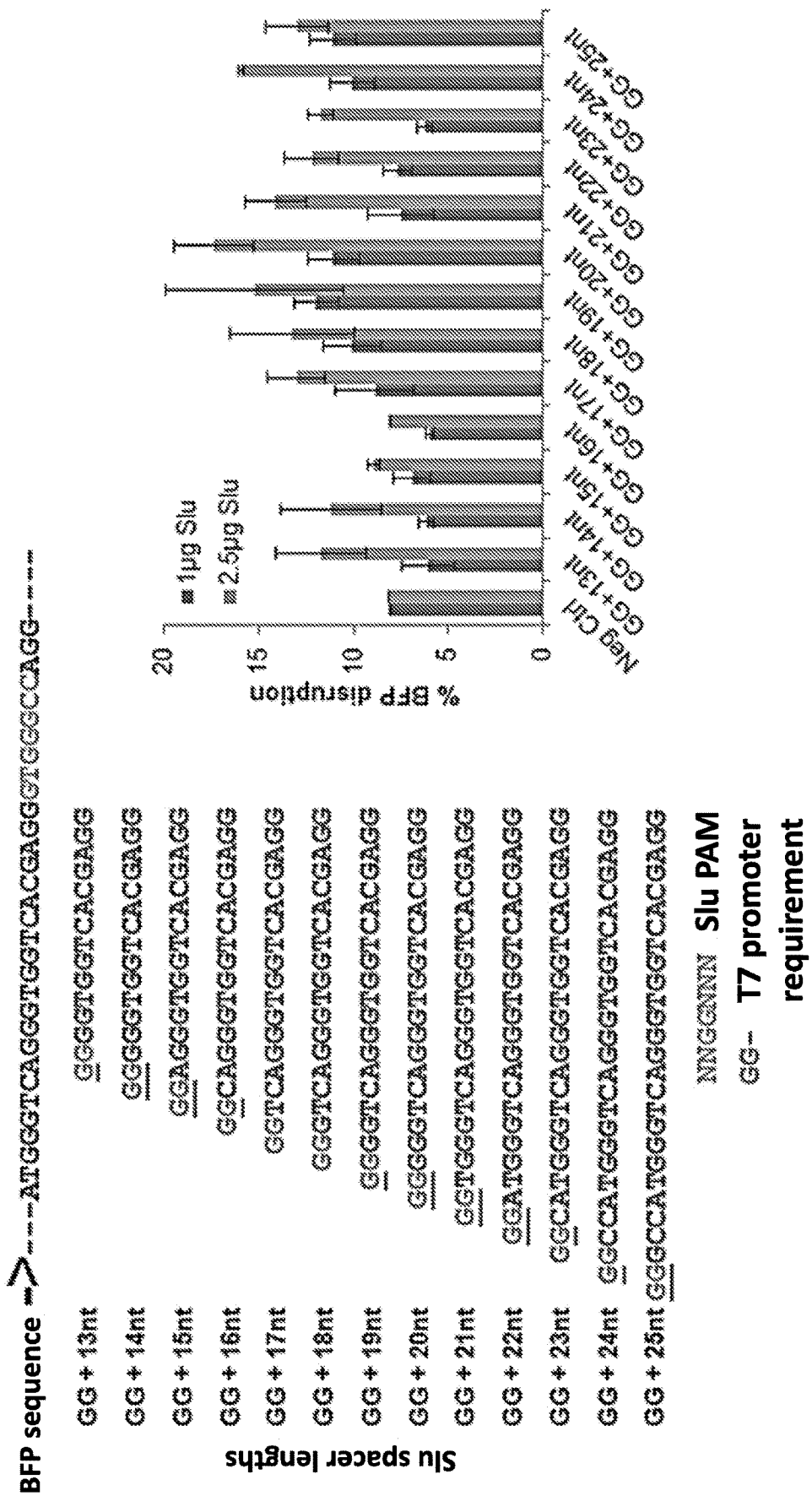
FIG. 6 shows results for the determination of optimal SluCas9 guide RNA length for editing in mammalian cells. Left panel: A part of BFP reverse strand sequence and various DNA-targeting segments (13-25 nucleotides) targeting the BFP gene in HEK cells. Right panel: Quantification of FACS analysis showing guide-dependent loss of BFP signal. Guide not targeting BFP (targeting HBB gene, GG+18 nt, BFP20 nt_1, SEQID NO: 15) was used as a negative control.

A series of different guides varying in length from 13-25 nt were generated by in vitro transcription (IVT). See FIG. 6A (left panel). The guides contain GG at the 5 prime end as required by T7 polymerase for optimal IVT. BFP disruption was performed as described before. Results are visualized in FIG. 6.

Example 7: Activity in Mammalian Cells Using Plasmids a) Bfp Disruption:

HEK293T cells harboring a gene encoding BFP in the AAVS1 locus were transfected with a plasmid comprising SluCas9 (SEQ ID NO: 3), a sgRNA BFP-targeting guide RNA (SEQ ID NO: 15), and SluCas9 tracr RNA (SEQ ID NO: 5) targeting the reverse strand of BFP genomic sequence as described. Transfection of plasmids was performed using Lipofectamine 3000 (Thermo Fischer Scientific, Cat no. L3000015) as described by the supplier. Flow cytometric analyses of BFP signal disruption was carried out 7 days post-transfection. Cells were prepared by washing with 1×PBS, trypsinization, and resuspension in 200 µl FACS buffer (1X PBS supplemented with 2% FCS). BFP signal from 10,000 cells was assayed using the V450 filter set in the BD FACS Canto II. In line with the function of Cas9 proteins, the likely reason for this is Cas9-assisted DNA cleavage followed by insertions/deletions at the BFP open-reading-frame (ORF) and resulting disruption of the BFP ORF. The results are shown in the following table:

| | Percentage of BFP Disruption | Standard deviation |
|---|---|---|
| Negative Control | 4.9 | 0.5 |
| SluCas9 plasmid | 44.7 | 2.2 | b. ddPCR:

HEK293T cells were transfected with plasmid expressing SluCas9 (SEQ ID NO: 3), and a sgRNA (VEGFA targeting guide RNA (SEQ ID NO: 8) and SluCas9 tracr RNA (SEQ ID NO: 15) targeting the reverse strand of VEGFA genomic sequence as described. Transfection of plasmids was performed using Lipofectamine 3000 (Thermo Fischer Scientific, Cat no. L3000015) as described by the supplier. Droplet digital PCR was performed according to manufacturer's instructions using the above mentioned primers, probes and thermocycler profiles.

The results are shown in the following table:

| | Percentage editing by ddPCR | Standard deviation |
|---|---|---|
| Negative Control | 0 | 0 |
| Slu Cas9 plasmid | 66.5 | 0.8 |

Example 8: Characterization of SluCas9 Codon Optimization

The polynucleotide sequence encoding SluCas9 from SEQ ID NO: 3 was compared to two further codon-optimized variants of this sequence (SEQ ID NOs: 44 and 45) using a BFP disruption assay. Reporter cell lines constitutively expressed BFP inserted in-frame into the beta-tubulin gene, and had target sites for SluCas9 upstream of the BFP-encoding sequence. A double strand break generated at the SluCas9 cut site can lead to indel-mediated frame shift, inactivating BFP expression.

The reporter cell line was co-transfected with (1) plasmids carrying one of the SluCas9-encoding polynucleotide sequences driven by a CBh promoter and encoding one of two different BFP-targeting gRNAs (T2 or T3) and (2) a DsRed2-encoding plasmid. The SluCas9-encoding sequences were linked to a GFP-encoding sequence via a sequence encoding self-cleaving peptide T2A, allowing the SluCas9 and GFP to be translated from a single mRNA. DsRed2 expression served as a transfection marker.

Figure 7B:
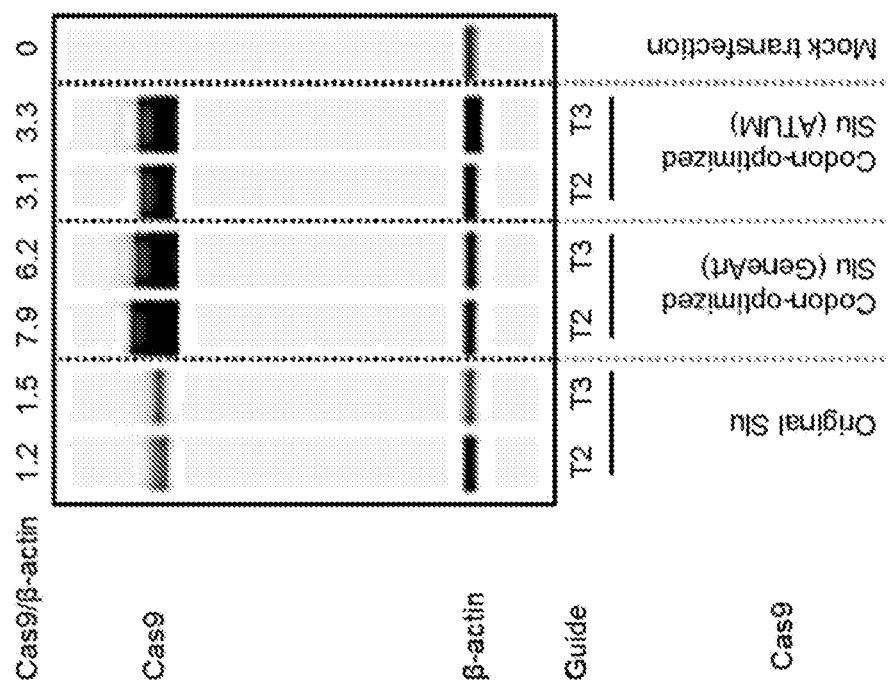
FIGS. 7A-7C show characterization of SluCas9 codon optimization in a BFP disruption assay. A BFP reporter cell line was co-transfected with (1) a plasmid carrying a) the SluCas9-encoding polynucleotide sequence from SEQ ID NO: 3 (Original Slu), b) the polynucleotide sequence of SEQ ID NO: 44 (ATUM), or c) the polynucleotide sequence of SEQ ID NO: 45 (GeneArt) driven by a CBh promoter and encoding either T2 or T3 gRNA targeting BFP, and (2) a DsRed2-encoding plasmid. The SluCas9-encoding sequences were linked to a GFP-encoding sequence via a sequence encoding self-cleaving peptide T2A, allowing the SluCas9 and GFP to be translated from a single mRNA. DsRed2 expression served as a transfection marker.
Figure 7A:
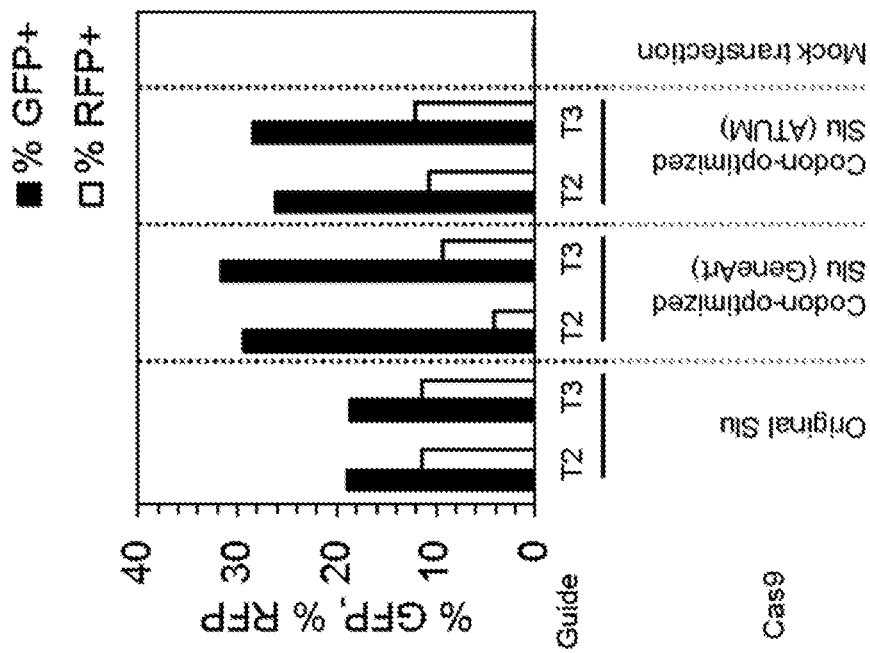
Figure 7C:
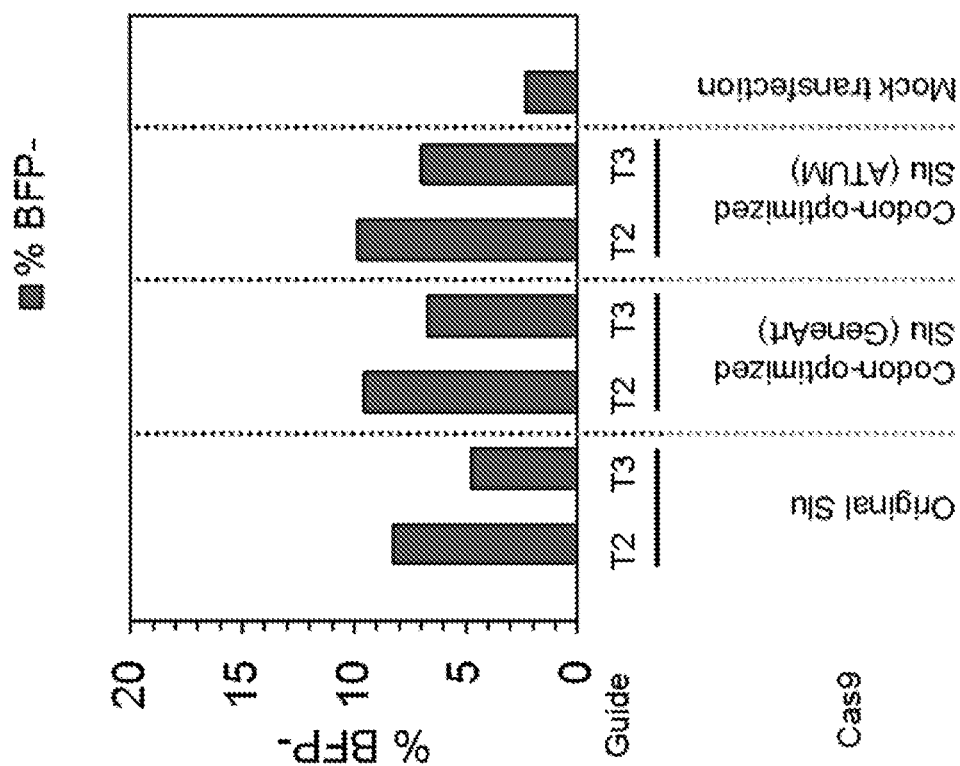

Two days after transfection GFP and RFP (DsRed2) expression was analyzed by flow cytometry (FIG. 7A) and SluCas9 expression was analyzed by Wes™ (ProteinSimple) (FIG. 7B), with beta-actin expression as an internal control. BFP– cells (attributed to frame-shift mutations) were measured by flow cytometry 5 days after transfection (FIG. 7C).

Further Protocols Used in the Above Examples:

RNP Assembly Protocol

After purification Cas9 protein was stored at –80C. IVT (in vitro transcription) guides were stored at –80 C. Once thawed (on ice), IVt guides were stored at –20C. Cas9 protein (for transfection in 24 well plate format) was incubated with in-house IVT transcribed guides in 1:2-1:3 molar ratio of protein:guide. Cas9 and guides were incubated with 1X Cas9 Reaction Buffer from NEB (10X) in a final volume of 5-10 µl (with Nuclease-free water). Incubation was carried out at room temperature (RT) for 10-15 mins.

Lipofection of RNPs Using CRISPR MAX Reagent (Thermo Scientific, Cat no. CMAX00015) (in 24 well plate)

80K-120K HEK293 or HEK293Tces were either plated one day in advance to reach about 70% confluency on the day of transfection, or were reverse transfected. In case of pre-plating, media was changed on the day of transfection and 450 µl of fresh HEK media was added per well.

Tube 1: 25 µl Opti-MEM-1 reagent (Thermo Scientific, cat no. 31985070) was mixed with 1 µl of PLUS reagent and incubated at RT until RNPs are ready. Assembled RNPs+ Tube1 (with PLUS Reagent) incubated for 5 mins at room temperature (RT).

Tube 2: 25 µl Opti-MEM-1 reagent was mixed with 1.5 µl of Lipofectamine CRISPR-MAX reagent and incubated at RT until RNPs are ready.

Tube 1 and 2 were mixed and incubated at RT for 15 mins. Total mix of approx. 50 µl was gently added to cells. One day post transfection, media was changed for each well and 1 ml of fresh HEK293 medium.

ddPCR Assay Protocol:

Cells were harvested 2-4 days post transfection and gDNA extracted with GenElute™ mammalian genomic DNA miniprep kit protocol (Sigma, Cat no. G1N350). ddPCR was performed as described below using the primers (fwd: catggtgcatctgactcctg (SEQ ID NO: 28), rev; ggtagac-caccagcagccta(SEQ ID NO: 29) and fluorescently labelled probes (NHEJ Insensitive Probe, FAM labelled aggagaagtctgccgttactgccct(SEQ ID NO: 30), NHEJ sensitive probe, HEK labelled probe tgaagttggtggtgaggccct(SEQ ID NO: 31). Quantification was performed as described before (Mock et al., 2016).

ddPCR Thermocycler Profile:

| Step | Temp (° C.) | Time | Ramp | # of cycles |
|---|---|---|---|---|
| 1 | 95 | 10 min | 2° C./sec | 1 |
| 2 | 94 | 30 sec | 2° C./sec | 40 |
| 3 | 58.5° C. (HBB) | 1 min | 2° C./sec | |
| 4 | 72° C. | 2 min | 2° C./sec | |
| 5 | 98 | 10 min | 2° C./sec | 1 |
| 6 | 4 | Hold | 2° C./sec | 1 |

T7 Endonuclease Assay:

For detection of Slu Cas9 genome editing activity using T7E assay, cells were harvested 2-4 days post-transfection and gDNA extracted with GenElute™ Mammalian Genomic DNA Miniprep Kit Protocol (Sigma, Cat no. G1N350, PCR performed on HBB locus with primers (fwd: gagacgcag-gaagagatcca, SEQ ID NO: 32; rev; ttagggttgcccataacagc, SEQ ID NO: 33) generating a product of 778 bps. Heteroduplex formation was carried out with 400 ng of PCR product using the following program, 95 C for 5-10 mins, 95 C→85 C Ramp down 1 C/sec, 85 C→25 C Ramp down 0.1 C/sec, Cool to 4 C-Hold, in 9 µl reaction supplemented with NEB Buffer 2. After duplex formation, 1 µl of NEB T7E1 nuclease (NEB, cat no. M03025) was added per reaction to final volume of 10p and incubated at 37 C for 30 mins, loaded on 2% agarose gel and imaged. Cleaved products were 539 and 238 bps.

FACS Analysis for BFP Disruption:

1. 7 days post-transfection, cells were washed with 1×PBS, trypsinized and resuspended in 200 µL PBS+ (2% FCS). Cells were analyzed using BD FACS Conto (10,000 events per well) using the FITC and V450 filters, while gating only singlets.

REFERENCES

2. Glaser, A., McColl, B., and Vadolas, J. (2016). GFP to BFP Conversion: A Versatile Assay for the Quantification of CRISPR/Cas9-mediated Genome Editing. Molecular Therapy Nucleic Acids 5, e334.
3. Mock, U., Hauber, I., and Fehse, B. (2016). Digital PCR to assess gene-editing frequencies (GEF-dPCR) mediated by designer nucleases. Nat Protocols 11, 598-615.

SEQUENCE LISTING

| SEQ ID NO | Sequence | Description |
|---|---|---|
| 1 | ATGAATCAAAAATTTATTTTAGGTTTAGATATTGGTATTACATCTGTTGGATATGG TCTCATAGATTATGAAACTAAAAATATTATAGACGCAGGTGTACGTTTGTTTCCTG AGGCTAATGTAGAAAATAACGAGGGCCGTCGAAGTAAAAGAGGTTCTCGAAGACTT AAGAGAAGAAGGATACATAGATTAGAAAGAGTGAAAAAATTATTAGAAGACTATAA TTTATTAGATCAATCACAAATTCCTCAGTCTACTAATCCTTATGCAATTCGAGTTA AGGGGTTAAGTGAAGCTTTAAGTAAAGATGAATTAGTAATTGCTTTGCTCCATATA GCTAAAAGAAGAGGTATTCATAAAATTGATGTGATTGATTCAAATGATGATGTTGG TAATGAGCTATCGACTAAAGAGCAGCTGAATAAAAATAGTAAATTGTTAAAAGATA AGTTTGTCTGTCAAATACAGCTAGAAAGAATGAATGAAGGTCAAGTTAGAGTGAGA AAAAAATAGATTTAAAACTGCAGACATTATAAAAGAAATTATTCAGCTATTGAATG TTCAAAAAAACTTTCATCAATTAGATGAAAATTTCATAAATAAATATATAGAATTA GTTGAGATGCGTAGAGAGTATTTTGAGGGTCCTGGTAAAGGGAGTCCATATGGATG GGAAGGAGACCCTAAGGCATGGTATGAAACCTTGATGGGACATTGTACTTATTTTC CAGATGAATTAAGAAGCGTTAAATATGCTTATTCTGCGGATTTATTTAATGCATTA AATGATTTAAATAATTTAGTAATTCAAAGAGATGGATTATCAAAATTAGAATATCA TGAAAAGTATCACATTATTGAAAATGTATTTAAACAGAAAAAGAAACCGACTTTGA AACAAATTGCAAATGAAATCAATGTAAATCCAGAAGACATTAAAGGATATAGAATC ACTAAAAGTGGTAAACCACAATTTACTGAGTTTAAACTTTATCATGATTTAAAAAG TGTATTATTTGATCAAAGCATTCTAGAAAATGAAGATGTATTAGACCAAATTGCAG AAATTTTAACTATATATCAAGATAAAGATAGTATTAAAAGTAAACTAACAGAATTA GATATTTTATTGAATGAAGAAGACAAGGAAAATATTGCTCAACTTACTGGTTATAC AGGTACACATAGACTTTCTTTAAAATGTATTCGTCTTGTACTGGAAGAGCAATGGT ATTCTTCTAGAAATCAAATGGAAATATTTACTCATTTAAATATCAAACCAAAGAAA ATTAATTTAACAGCAGCCAATAAAATACCTAAAGCTATGATTGACGAATTTATATT ATCCCCAGTAGTGAAAAGAACCTTTGGACAGGCAATTAATCTTATAAATAAGATTA TTGAAAAATACGGCGTTCCAGAAGATATAATTATCGAATTAGCACGAGAAAATAAT AGTAAAGATAAACAAAAATTTATTAATGAAATGCAAAAGAAAAATGAAAATACACG TAAACGGATTAATGAAATAATAGGGAAGTATGGAAATCAAAATGCTAAAAGATTAG TTGAAAAAATTAGATTACATGATGAACAAGAAGGTAAATGTTTATACTCATTAGAA TCAATACCACTTGAGGACTTATTAAATAATCCGAATCATTATGAAGTAGACCATAT TATACCAAGATCTGTTTCATTTGATAATTCATATCATAACAAAGTATTAGTAAAAC AAAGTGAAAATAGTAAAAAAAGCAATCTAACGCCTTATCAATATTTTAACTCTGGA AAATCAAAACTTTCCTATAATCAATTTAAACAACATATTCTTAATTTAAGTAAATC ACAAGATAGAATTTCAAAGAAAAAGAAAGAATACTTATTAGAAGAACGAGATATTA | ENA\|KXA40553\|KXA40 553.1 *Staphylococcus lugdunensis* CRISPR-associated protein, Csn1 family |

| SEQ ID NO | Sequence | Description |
|---|---|---|
| | AATAAGTTTGAAGTACAAAAAGAATTTATTAATCGTAACTTGGTGATACTAGATAT<br>GCTACAAGAGAGTTAACAAACTATTTAAAAGCCTACTTTAGTGCTAATAACATGAA<br>TGTAAAAGTTAAAACAATTAATGGAAGCTTTACTGACTATTTAAGAAAAGTTTGGA<br>AATTTAAAAAAGAGCGTAATCATGGATATAAACATCATGCTGAAGATGCTCTAATA<br>ATTGCTAACGCTGATTTTCTGTTTAAAGAAAACAAAAAGCTAAAAGCTGTTAATAG<br>TGTATTAGAAAAACCAGAAATTGAAAGTAAACAATTAGATATACAAGTTGATAGTG<br>AAGATAATTATAGTGAAATGTTTATCATTCCTAAACAAGTTCAGGATATTAAAGAC<br>TTTAGAAACTTCAAGTACTCACATAGAGTAGATAAAAAACCGAATAGGCAACTAAT<br>CAATGACACACTTTACTCGACTCGTAAAAAAGATAACAGCACATATATTGTTCAAA<br>CTATAAAGGATATATATGCAAAAGATAATACGACGTTAAAGAAACAATTTGATAAA<br>AGTCCAGAAAAGTTTTTAATGTATCAACATGATCCTCGTACATTTGAAAAGTTAGA<br>AGTTATTATGAAGCAATACGCTAATGAAAAAAATCCTTTGGCTAAATATCATGAAG<br>AAACAGGAGAATATTTAACTAAATATAGTAAAAAAAATAATGGGCCTATCGTAAAA<br>AGCTTAAAATATATTGGCAATAAATTGGGAAGTCATTTAGATGTGACACATCAATT<br>TAAAAGTTCAACTAAAAAATTAGTAAAATTATCAATTAAACCTTATCGCTTTGATG<br>TGTATTTAACAGATAAAGGATATAAATTTATTACCATTTCATATTTAGATGTACTT<br>AAAAAAAGATAATTATTATTATATCCCAGAACAAAAATATGACAAGTTAAAACTAGG<br>AAAAGCGATTGATAAAAATGCTAAATTTATTGCTAGTTTCTATAAAAATGATTTGA<br>TAAAACTTGATGGAGAGATATATAAAATTATTGGAGTAAATAGTGATACTAGAAAT<br>ATGATTGAATTAGATTTACCTGATATTAGATATAAAGAATACTGTGAGTTGAACAA<br>TATTAAAGGAGAACCTCGTATTAAAAAAACTATAGGTAAGAAAGTAAATTCTATAG<br>AAAAATTAACTACGGATGTATTAGGAAATGTCTTTACTAATACTCAATATACAAAA<br>CCACAACTGTTATTTAAGCGAGGCAATTAG | |
| 2 | MNQKFILGLDIGITSVGYGLIDYETKNIIDAGVRLFPEANVENNEGRRSKRGSRRL<br>KRRRIHRLERVKKLLEDYNLLDQSQIPQSTNPYAIRVKGLSEALSKDELVIALLHI<br>AKRRGIHKIDVIDSNDDVGNELSTKEQLNKNSKLLKDKFVCQIQLERMNEGQVRGE<br>KNRFKTADIIKEIIQLLNVQKNFHQLDENFINKYIELVEMRREYFEGPGKGSPYGW<br>EGDPKAWYETLMGHCTYFPDELRSVKYAYSADLFNALNDLNNLVIQRDGLSKLEYH<br>EKYHIIENVFKQKKKPTLKQIANEINVNPEDIKGYRITKSGKPQFTEFKLYHDLKS<br>VLFDQSILENEDVLDQIAEILTIYQDKDSIKSKLTELDILLNEEDKENIAQLTGYT<br>GTHRLSLKCIRLVLEEQWYSSRNQMEIFTHLNIKPKKINLTAANKIPKAMIDEFIL<br>SPVVKRTFGQAINLINKIIEKYGVPEDIIIELARENNSKDKQKFINEMQKKNENTR<br>KRINEIIGKYGNQNAKRLVEKIRLHDEQEGKCLYSLESIPLEDLLNNPNHYEVDHI<br>IPRSVSFDNSYHNKVLVKQSENSKKSNLTPYQYFNSGKSKLSYNQFKQHILNLSKS<br>QDRISKKKEYLLEERDINKFEVQKEFINRNLVDTRYATRELTNYLKAYFSANNMN<br>VKVKTINGSFTDYLRKVWKFKKERNHGYKHHAEDALIIANADFLFKENKKLKAVNS<br>VLEKPEIETKQLDIQVDSEDNYSEMFIIPKQVQDIKDFRNFKYSHRVDKKPNRQLI<br>NDTLYSTRKKDNSTYIVQTIKDIYAKDNTTLKKQFDKSPEKFLMYQHDPRTFEKLE<br>VIMKQYANEKNPLAKYHEETGEYLTKYSKKNNGPIVKSLKYIGNKLGSHLDVTHQF<br>KSSTKKLVKLSIKPYRFDVYLTDKGYKFITISYLDVLKKDNYYIPEQKYDKLKLG<br>KAIDKNAKFIASFYKNDLIKLDGEIYKIIGVNSDTRNMIELDLPDIRYKEYCELNN<br>IKGEPRIKKTIGKKVNSIEKLTTDVLGNVFTNTQYTKPQLLFKRGNGG | amino acid sequence Of SEQ ID NO: 1 |
| 3 | ATGAAACGTCCGGCAGCAACCAAAAAAGCAGGTCAGGCCAAGAAAAAAAAGGTGG<br>TGGTTCAGGTAACCAGAAATTTATCCTGGGTCTGGATATTGGTATTACCAGCGTTG<br>GTTATGGCCTGATTGATTACGAAACCAAAAACATTATTGATGCCGGTGTTCGTCTG<br>TTTCCGGAAGCAAATGTTGAAAATAATGAAGGTCGTCGTAGCAAACGTGGTAGCCG<br>TCGTCTGAAACGTCGTCGTATTCATCGTCTGGAACGTGTTAAAAAACTGCTGGAAG<br>ATTATAACCTGCTGGATCAGAGCCAGATTCCGCAGAGCACCAATCCGTATGCAATT<br>CGTGTTAAAGGTCTGAGCGAAGCACTGAGCAAAGATGAACTGGTTATTGCACTGCT<br>GCATATTGCAAAACGCCGTGGCATTCATAAAATCGATGTGATTGATAGCAATGACG<br>ATGTGGGTAATGAACTGAGCACCAAAGAACAGCTGAACAAAAATAGCAAACTGCTG<br>AAAGACAAATTCGTGTGTCAGATTCAGCTGGAACGTATGAATGAAGGCCAGGTTCG<br>TGGTGAAAAGAATCGCTTTAAAACCGCAGACATCATCAAAGAAATTATCCAGCTGC<br>TGAACGTGCAGAAAAACTTCCATCAGCTGGATGAAAACTTCATCAACAAATACATC<br>GAGCTGGTTGAAATGCGTCGCGAATATTTTGAAGGTCCGGGTAAAGGTAGCCCGTA<br>TGGTTGGGAAGGTGATCCGAAAGCATGGTATGAAACCCTGATGGGTCATTGTACCT<br>ATTTTCCGGATGAACTGCGTAGCGTTAAATATGCCTATAGCGCAGACCTGTTTAAT<br>GCACTGAATGATCTGAATAACCTGGTGATTCAGCGTGATGGTCTGAGCAAACTGGA<br>ATATCATGAGAAATATCACATCATCGAAAACGTGTTCAAACAGAAGAAGAAACCGA<br>CCCTGAAACAAATCGCCAACGAATTAATGTGAACCCGGAAGATATTAAAGGCTAC<br>CGTATTACCAAAAGCGGTAAACCGCAGTTCACCGAATTTAAACTGTATCACGATCT<br>GAAAAGCGTGCTGTTTGATCAGAGCATTCTGGAAAATGAAGATGTGCTGGACCAGA<br>TTGCAGAAATTCTGACCATTTATCAGGACAAAGACAGCATCAAAAGCAAACTGACC<br>GAACTGGATATTCTGCTGAATGAAGAAGATAAAGAGAACATTGCACAGCTGACCGG<br>TTATACCGGCACCCATCGTCTGAGCCTGAAATGTATTCGTCTGGTACTGGAAGAAC<br>AGTGGTATAGCAGCCGTAATCAGATGGAAATCTTTACCCATCTGAACATTAAACCG<br>AAGAAAATCAATCTGACCGCAGCCAACAAAATTCCGAAAGCCATGATTGATGAGTT<br>TATTCTGAGTCCGGTTGTGAAACGTACCTTTGGTCAGGCAATTAACCTGATCAACA<br>AAATCATTGAAAAATATGGCGTGCCTGAGGATATCATTATTGAACTGGCACGTGAA<br>AACAACAGCAAAGATAAACAGAAATTCATCAACGAGATGCAGAAGAAGAACGAAAA<br>TACCCGCAAACGGATTAACGAGATCATTGGCAAATATGGTAATCAGAATGCCAAAC | SluCas9, optimized DNA sequence including nuclear localization signal |

SEQUENCE LISTING

| SEQ ID NO | Sequence | Description |
|---|---|---|
| | GCCTGGTGGAAAAAATTCGTCTGCATGATGAACAAGAGGGCAAATGTCTGTATAGC<br>CTGGAAAGCATTCCTCTGGAAGATCTGCTGAACAATCCGAATCATTATGAAGTGGA<br>TCACATTATTCCGCGTAGCGTGAGCTTTGATAATTCCTATCATAATAAAGTGCTGG<br>TGAAACAGAGCGAAAACTCCAAAAAATCCAACCTGACACCGTATCAGTATTTCAAT<br>AGCGGCAAATCCAACTGAGCTACAACCAGTTTAAACAGCATATTCTGAACCTGAG<br>CAAAAGCCAGGATCGCATCAGCAAGAAGAAGAAGGAGTACCTGCTGGAAGAACGCG<br>ACATCAACAAATTTGAAGTGCAGAAAGAATTTATCAACCGCAACCTGGTTGATACC<br>CGTTATGCAACCCGTGAACTGACCAATTATCTGAAAGCATATTTCAGCGCCAACAA<br>CATGAACGTGAAAGTGAAAACGATTAACGGCAGCTTTACCGATTATCTGCGTAAAG<br>TGTGGAAATTCAAAAAGAACGCAACCACGGCTATAAACATCATGCCGAAGATGCC<br>CTGATTATTGCAAATGCAGATTTCCTGTTTAAAGAAAACAAAAAACTGAAAGCCGT<br>CAACAGCGTGCTGGAAAAACCGGAAATTGAGACAAAACAGCTGGACATTCAGGTTG<br>ATAGCGAAGATAATTACAGCGAAATGTTTATCATCCCGAAACAGGTGCAGGATATC<br>AAAGATTTTCGCAACTTCAAATATAGCCACCGCGTTGACAAAAAACCTAATCGTCA<br>GCTGATTAACGATACCCTGTATAGCACCCGCAAAAAGATAACAGCACCTATATTG<br>TGCAGACCATTAAAGACATCTACGCCAAAGATAATACCACCCTGAAAAAACAGTTC<br>GACAAAAGCCCAGAAAAATTTCTGATGTATCAGCATGATCCGCGTACCTTCGAAAA<br>ACTGGAAGTTATTATGAAACAGTATGCCAACGAGAAAAATCCGCTGGCCAAATATC<br>ACGAAGAAACCGGTGAATATCTGACCAAATATTCCAAGAAGAACAACGGTCCGATC<br>GTTAAATCCCTGAAATATATCGGTAATAAACTGGGCAGCCATCTGGATGTTACCCA<br>TCAGTTTAAAAGCTCCACAAAGAAGCTGGTTAAACTGTCCATCAAACCGTATCGCT<br>TTGATGTGTATCTGACCGACAAAGGCTATAAATTCATTACCATCAGCTATCTGGAC<br>GTGCTGAAAAAGACAACTATTATTATATCCCGGAACAGAAATATGATAAACTGAA<br>ACTGGGTAAAGCCATCGATAAAAACGCCAATTTATCGCCAGCTTCTACAAAAACG<br>ACCTGATTAAACTGGATGGCGAGATCTATAAAATCATCGGTGTTAATAGCGACACC<br>CGCAATATGATTGAGCTGGATCTGCCGGATATTCGCTATAAAGAATATTGCGAACT<br>GAACAACATTAAAGGCGAACCGCGTATCAAAAAGACCATCGGCAAAAAGTGAATA<br>GCATCGAGAAACTGACCACCGATGTTCTGGGTAATGTGTTTACCAATACCCAGTAT<br>ACCAAACCTCAGCTGCTGTTCAAACGCGGTAATGGCGGAGGATCTGGCCCCCCTAA<br>GAAAAAGCGGAAGGTGGGTGGAAGCGGAGGCAGCGGGGGATCAGGCCATCATCATC<br>ACCATCATTAA | |
| 4 | MKRPAATKKAGQAKKKGGGSGNQKFILGLDIGITSVGYGLIDYETKNIIDAGVRL<br>FPEANVENNEGRRSKRGSRRLKRRRIHRLERVKKLLEDYNLLDQSQIPQSTNPYAI<br>RVKGLSEALSKDELVIALLHIAKRRGIHKIDVIDSNDDVGNELSTKEQLNKNSKLL<br>KDKFVCQIQLERMNEGQVRGEKNRFKTADIIKEIIQLLNVQKNFHQLDENFINKYI<br>ELVEMRREYFEGPGKGSPYGWEGDPKAWYETLMGHCTYFPDELRSVKYAYSADLFN<br>ALNDLNNLVIQRDGLSKLEYHEKYHIIENVFKQKKKPTLKQIANEINVNPEDIKGY<br>RITKSGKPQFTEFKLYHDLKSVLFDQSILENEDVLDQIAEILTIYQDKDSIKSKLT<br>ELDILLNEEDKENIAQLTGYTGTHRLSLKCIRLVLEEQWYSSRNQMEIFTHLNIKP<br>KKINLTAANKIPKAMIDEFILSPWKRTFGQAINLINKIIEKYGVPEDIIIELAREN<br>NSKDKQKFINEMQKKNENTRKRINEIIGKYGNQNAKRLVEKIRLHDEQEGKCLYSL<br>ESIPLEDLLNNPNHYEVDHIIPRSVSFDNSYHNKVLVKQSENSKKSNLTPYQYFNS<br>GKSKLSYNQFKQHILNLSKSQDRISKKKKEYLLEERDINKFEVQKEFINRNLVDTR<br>YATRELTNYLKAYFSANNMNVKVKTINGSFTDYLRKVWKFKKERNHGYKHHAEDAL<br>IIANADFLFKENKKLKAVNSVLEKPEIETKQLDIQVDSEDNYSEMFIIPKQVQDIK<br>DFRNFKYSHRVDKKPNRQLINDTLYSTRKKDNSTYIVQTIKDIYAKDNTTLKKQFD<br>KSPEKFLMYQHDPRTFEKLEVIMKQYANEKNPLAKYHEETGEYLTKYSKKNNGPIV<br>KSLKYIGNKLGSHLDVTHQFKSSTKKLVKLSIKPYRFDVYLTDKGYKFITISYLDV<br>LKKDNYYYIPEQKYDKLKLGKAIDKNAKFIASFYKNDLIKLDGEIYKIIGVNSDTR<br>NMIELDLPDIRYKEYCELNNIKGEPRIKKTIGKKVNSIEKLTTDVLGNVFTNTQYT<br>KPQLLFKRGNGGGSGPPKKKRKVGGSGGSGGSGHHHHHH | amino acid sequence of SEQ ID NO: 3 |
| 5 | CTTGTACTTATACCTAAAATTACAGAATCTACTGAAACAAGACAATATGTCGTGTT<br>TATCCCATCAATTTATTGGTGGGATTTTTTTATGTTTTTAGCAAAAAGTAATACCA<br>TACTTTATATTTTTAAATTATAATAAAGATATAAATAAAGGTGG | tracr DNA sequence |
| 6 | NNNNNNNNNNNNNNNNNNNNGTTTTAGTACTCTGGAAACAGAATCTACTGAAACAA<br>GACAATATGTCGTGTTTATCCCATCAATTTATTGGTGGGATTTTTTT<br>"NNNNNNNNNNNNNNNNNNNNcorresponds to the specific target sequence in positions 1 to 20" | sgRNA design DNA sequence |
| 7 | NNNNNNNNNNNNNNNNNNNNGTTTTAGTACTCTGGAAACAGAATCTACTAAAACAA<br>GACTATATGTCGTGTTTATCCCACTAATTTATTAGTGGGAATTTT<br>"NNNNNNNNNNNNNNNNNNNN corresponds to the specific target sequence in positions 1 to 20" | sgRNA design |
| 8 | GGACCCCCUCCACCCCGCCUCGUUUUAGUACUCUGGAAACAGAAUCUACUGAAACA<br>AGACAAUAUGUCGUGUUUAUCCCAUCAAUUUAUUGGUGGGAUUUUUUU | sgRNA VEGFA |
| 9 | GACCCCCTCCACCCCGCCTCCGGGCGCG | oligonucleotide substrate CGGGCGC PAM |

SEQUENCE LISTING

| SEQ ID NO | Sequence | Description |
|---|---|---|
| 10 | GCGCGCGCCCGGAGGCGGGGTGGAGGGGGTCGG | oligonucleotide substrate CGGGCGC PAM |
| 11 | GACCCCCTCCACCCCGCCTCAGGGCGCG | oligonucleotide substrate AGGGCGCPAM |
| 12 | GCGCGCGCCCTGAGGCGGGGTGGAGGGGGTCGG | oligonucleotide substrate AGGGCGC PAM |
| 13 | GGACCCCCUCCACCCCGCCUCGUUUUAGUACUCUGGAAACAGAAUCUACUGAAACA AGACAAUAUGUCGUGUUUAUCCCAUCAAUUUAUUGGUGGGAUUUUUUU | sgRNA VEGFA |
| 14 | ATGGTGAGCAAGGGCGAGGAGCTGTTCACCGGGGTGGTGCCCATCCTGGTCGAGCT GGACGGCGACGTAAACGGCCACAAGTTCAGCGTGTCCGGCGAGGGCGAGGGCGATG CCACCTACGGCAAGCTGACCCTGAAGTTCATCTGCACCACCGGCAAGCTGCCCGTG CCCTGGCCCACCCTCGTGACCACCCTGACCCATGGCGTGCAGTGCTTCAGCCGCTA CCCCGACCACATGAAGCAGCACGACTTCTTCAAGTCCGCCATGCCCGAAGGCTACG TCCAGGAGCGCACCATCTTCTTCAAGGACGACGGCAACTACAAGACCCGCGCCGAG GTGAAGTTCGAGGGCGACACCCTGGTGAACCGCATCGAGCTGAAGGGCATCGACTT CAAGGAGGACGGCAACATCCTGGGGCACAAGCTGGAGTACAACTACAACAGCCACA ACGTCTATATCATGGCCGACAAGCAGAAGAACGGCATCAAGGTGAACTTCAAGATC CGCCACAACATCGAGGACGGCAGCGTGCAGCTCGCCGACCACTACCAGCAGAACAC CCCCATCGGCGACGGCCCCGTGCTGCTGCCCGACAACCACTACCTGAGCACCCAGT CCAAGCTGAGCAAAGACCCCAACGAGAAGCGCGATCACATGGTCCTGCTGGAGTTC GTGACCGCCGCCGGGATCACTCTCGGCATGGACGAGCTGTACAAGTAA | BFP knock in gene sequence HEK293T cells |
| 15 | GGGTCAGGGTGGTCACGAGG | BFP guide 20nt first sequence |
| 16 | CCCTCGAACTTCACCTCGGC | BFP guide 20nt second sequence |
| 17 | CGCCCTCGAACTTCACCTCGGC | BFP guide 22nt second sequence |
| 18 | GGTGAACGTGGATGAAGTTG | HBB guide 20nt first sequence |
| 19 | GGTGGAAGCGGAGGCAGCGGGGGATCAGGCCATCATCATCACCATCATTAATGAAC GGGTCTTGAGGGGTTTTTTGGACTTTTGCGTATTGGGCGCTCTTCCGCTTCCTCGC TCACTGACTCGCTGCGCTCGGTCGTTCGGCTGCGGCGAGCGGTATCAGCTCACTCA AAGGCGGTAATACGGTTATCCACAGAATCAGGGGATAACGCAGGAAAGAACATGTG AGCAAAAGGCCAGCAAAAGGCCAGGAACCGTAAAAAGGCCGCGTTGCTGGCGTTTT TCCATAGGCTCCGCCCCCCTGACGAGCATCACAAAAATCGACGCTCAAGTCAGAGG TGGCGAAACCCGACAGGACTATAAAGATACCAGGCGTTTCCCCCTGGAAGCTCCCT CGTGCGCTCTCCTGTTCCGACCCTGCCGCTTACCGGATACCTGTCCGCCTTTCTCC CTTCGGGAAGCGTGGCGCTTTCTCATAGCTCACGCTGTAGGTATCTCAGTTCGGTG TAGGTCGTTCGCTCCAAGCTGGGCTGTGTGCACGAACCCCCCGTTCAGCCCGACCG CTGCGCCTTATCCGGTAACTATCGTCTTGAGTCCAACCCGGTAAGACACGACTTAT CGCCACTGGCAGCAGCCACTGGTAACAGGATTAGCAGAGCGAGGTATGTAGGCGGT GCTACAGAGTTCTTGAAGTGGTGGCCTAACTACGGCTACACTAGAAGGACAGTATT TGGTATCTGCGCTCTGCTGAAGCCAGTTACCTTCGGAAAAAGAGTTGGTAGCTCTT GATCCGGCAAACAAACCACCGCTGGTAGCGGTGGTTTTTTTGTTTGCAAGCAGCAG ATTACGCGCAGAAAAAAAGGATCTCAAGAAGATCCTTTGATCTTTTCTACGGGGTC TGACGCTCAGTGGAACGAAAACTCACGTTAAGGGATTTTGGTCATGAGATTATCAA AAAGGATCTTCACCTAGATCCTTTTAAATTAAAAATGAAGTTTTAAATCAATCTAA AGTATATATGAGTAAACTTGGTCTGACAGTTACCAATGCTTAATCAGTGAGGCACC TATCTCAGCGATCTGTCTATTTCGTTCATCCATAGTTGCCTGACTCCCCGTCGTGT AGATAACTACGATACGGGAGGGCTTACCATCTGGCCCCAGTGCTGCAATGATACCG CGAGATCCACGCTCACCGGCTCCAGATTTATCAGCAATAAACCAGCCAGCCGGAAG GGCCGAGCGCAGAAGTGGTCCTGCAACTTTATCCGCCTCCATCCAGTCTATTAATT GTTGCCGGGAAGCTAGAGTAAGTAGTTCGCCAGTTAATAGTTTGCGCAACGTTGTT GCCATTGCTGCAGGCATCGTGGTGTCACGCTCGTCGTTTGGTATGGCTTCATTCAG CTCCGGTTCCCAACGATCAAGGCGAGTTACATGATCCCCCATGTTGTGCAAAAAAG CGGTTAGCTCCTTCGGTCCTCCGATCGTTGTCAGAAGTAAGTTGGCCGCAGTGTTA TCACTCATGGTTATGGCAGCACTGCATAATTCTCTTACTGTCATGCCATCCGTAAG ATGCTTTTCTGTGACTGGTGAGTACTCAACCAAGTCATTCTGAGAATAGTGTATGC GGCGACCGAGTTGCTCTTGCCCGGCGTCAATACGGGATAATACCGCGCCACATAGC AGAACTTTAAAAGTGCTCATCATTGGAAAACGTTCTTCGGGGCGAAAACTCTCAAG | DNA sequence PMC7125 |

SEQUENCE LISTING

| SEQ ID NO | Sequence | Description |
|---|---|---|
| | GATCTTACCGCTGTTGAGATCCAGTTCGATGTAACCCACTCGTGCACCCAACTGAT<br>CTTCAGCATCTTTTACTTTCACCAGCGTTTCTGGGTGAGCAAAAACAGGAAGGCAA<br>AATGCCGCAAAAAAGGGAATAAGGGCGACACGGAAATGTTGAATACTCATACTCTT<br>CCTTTTTCAATATTATTGAAGCATTTATCAGGGTTATTGTCTCATGAGCGGATACA<br>TATTTGAATGTATTTAGAAAAATAAACAAATAGGGGTTCCGCGCACATTTCCCCGA<br>AAAGTGCCACTCCTCTTGCTGTGACCGTCTCCGGGAGCTGCATGTGTCAGAGGTTT<br>TCACCGTCATCACCGAAACGCGCGAGGCAGCAGATCAATTCGCGCGCGAAGGCGAA<br>GCGGCATGCATTTACGTTGACACCATCGAATGGTGCAAAACCTTTCGCGGTATGGC<br>ATGATAGCGCCCGGAAGAGAGTCAATTCAGGGTGGTGAATGTGAAACCAGTAACGT<br>TATACGATGTCGCAGAGTATGCCGGTGTCTCTTATCAGACCGTTTCCCGCGTGGTG<br>AACCAGGCCAGCCACGTTTCTGCGAAAACGCGGGAAAAAGTGGAAGCGGCGATGGC<br>GGAGCTGAATTACATTCCCAACCGCGTGGCACAACAACTGGCGGGCAAACAGTCGT<br>TGCTGATTGCGTTGCCCACCTCCAGTCTGGCCCTGACGCGCCGTCGCAAATTGTCG<br>CGGCGATTAAATCTCGCGCCGATCAACTGGGTGCCAGCGTGGTGGTGTCGATGGTA<br>GAACGAAGCGGCGTCGAAGCCTGTAAAGCGGCGGTGCACAATCTTCTCGCGCAACG<br>CGTCAGTGGGCTGATCATTAACTATCCGCTGGATGACCAGGATGCGCATTGCTGTGG<br>AAGCTGCCTGCACTAATGTTCCGGCGTTATTTCTTGATGTCTCTGACCAGACACCC<br>ATCAACAGTATTATTTTCTCCCATGAAGATGGTACGCGACTGGGCGTGGAGCATCT<br>GGTCGCATTGGGTCACCAGCAAATCGCGCTGTTAGCGGGCCCATTAAGTTCTGTCT<br>CGGCGCGTCTGCGTCTGGCTGGCTGGCATAAATATCTCACTCGCAATCAAATTCAG<br>CCGATAGCGGAACGGGAAGGCGACTGGAGTGCCATGTCCGGTTTTCAACAAACCAT<br>GCAAATGCTGAATGAGGGCATCGTTCCCACTGCGATGCTGGTTGCCAACGATCAGA<br>TGGCGCTGGGCGCAATGCGCGCCATTACCGAGTCCGGGCTGCGCGTTGGTGCGGAT<br>ATCTCGGTAGTGGGATACGACGATACCGAAGATAGCTCATGTTTATATCCCGCCGTT<br>AACCACCATCAAACAGGATTTTCGCCTGCTGGGGCAAACCAGCGTGGACCGCTTGC<br>TGCAACTCTCTCAGGGCCAGGCGGTGAAGGGCAATCAGCTGTTGCCCGTCTCACTG<br>GTGAAAAGAAAAACCACCCTGGCGCCCAATACGCAAACCGCCTCTCCCCGCGCGTT<br>GGCCGATTCATTAATGCAGCTGGCACGACAGGTTTCCCGACTGGAAAGCGGGCAGT<br>GAGCGCAATATTCTGAAATGAGCTGTTGACAATTAATCATCCGGCTCGTATAATGT<br>GTGGAATTGTGAGCGGATAACAATTTTCACACAGGAAACAGAATTCTAGCATTGTG<br>AGCGGATAACAATTCCCCTCTAGAAATAATTTTGTTTAACTTTAAGAAGGAGATAT<br>ACCATGCATCATCATCACCATCATGGTGGTGGTAGCGGTAAAGTCCGGCAGCAAC<br>CAAAAAAGCAGGTCAGGCCAAGAAAAAAAAAGGTGGTGGTTCAGGTAACCAGAAAT<br>TTATCCTGGGTCTGGATATTGGTATTACCAGCGTTGGTTATGGCCTGATTGATTAC<br>GAAACCAAAAACATTATTGATGCCGGTGTTCGTCTGTTTCCGGAAGCAAATGTTGA<br>AAATAATGAAGGTCGTCGTAGCAAACGTGGTAGCCGTCGTCTGAAACGTCGTCGTA<br>TTCATCGTCTGGAACGTGTTAAAAAACTGCTGGAAGATTATAACCTGCTGGATCAG<br>AGCCAGATTCCGCAGAGCACCAATCCGTATGCAATTCGTGTTAAAGGTCTGAGCGA<br>AGCACTGAGCAAAGATGAACTGGTTATTGCACTGCTGCATATTGCAAAACGCCGTG<br>GCATTCATAAAATCGATGTGATTGATAGCAATGACGATGTGGGTAATGAACTGAGC<br>ACCAAAGAACAGCTGAACAAAAATAGCAAACTGCTGAAAGACAAATTCGTGTGTCA<br>GATTCAGCTGGAACGTATGAATGAAGGCCAGGTTCGTGGTGAAAAGAATCGCTTTA<br>AAACCGCAGACATCATCAAAGAAATTATCCAGCTGCTGAACGTGCAGAAAAACTTC<br>CATCAGCTGGATGAAAACTTCATCAACAAATACATCGAGCTGGTTGAAATGCGTCG<br>CGAATATTTTGAAGGTCCGGGTAAAGGTAGCCCGTATGGTTGGGAAGGTGATCCGA<br>AAGCATGGTATGAAACCCTGATGGGTCATTGTACCTATTTTCCGGATGAACTGCGT<br>AGCGTTAAATATGCCTATAGCGCAGACCTGTTTAATGCACTGAATGATCTGAATAA<br>CCTGGTGATTCAGCGTGATGGTCTGAGCAAACTGGAATATCATGAGAAATATCACA<br>TCATCGAAACGTGTTCAAACAGAAGAAGAAACCGACCCTGAAACAAATCGCCAAC<br>GAAATTAATGTGAACCCGGAAGATATTAAAGGCTACCGTATTACCAAAAGCGGTAA<br>ACCGCAGTTCACCGAATTTAAACTGTATCACGATCTGAAAAGCGTGCTGTTTGATC<br>AGAGCATTCTGGAAAATGAAGATGTGCTGGACCAGATTGCAGAAATTCTGACCATT<br>TATCAGGACAAAGACAGCATCAAAAGCAAACTGACCGAACTGGATATTCTGCTGAA<br>TGAAGAAGATAAAGAGAACATTGCACAGCTGACCGGTTATACCGGCACCCATCGTC<br>TGAGCCTGAAATGTATTCGTCTGGTACTGGAAGAACAGTGGTATAGCAGCCGTAAT<br>CAGATGGAAATCTTTACCCATCTGAACATTAAACCGAAGAAAATCAATCTGACCGC<br>AGCCAACAAATTCCGAAAGCCATGATTGATGAGTTTATTCTGAGTCCGGTTGTGA<br>AACGTACCTTTGGTCAGGCAATTAACCTGATCAACAAAATCATTGAAAAATATGGC<br>GTGCCTGAGGATATCATTATTGAACTGGCACGTGAAAACAACAGCAAAGATAAACA<br>GAAATTCATCAACGAGATGCAGAAGAAGAACGAAAATACCCGCAAACGGATTAACG<br>AGATCATTGGCAAATATGGTAATCAGAATGCCAAACGCCTGGTGGAAAAAATTCGT<br>CTGCATGATGAACAAGAGGGCAAATGTCTGTATAGCCTGGAAAGCATTCCTCTGGA<br>AGATCTGCTGAACAATCCGAATCATTATGAAGTGGATCACATTATTCCGCGTAGCG<br>TGAGCTTTGATAATTCCTATCATAATAAAGTGCTGGTGAAACAGAGCGAAAACTCC<br>AAAAAATCCAACCTGACACCGTATCAGTATTTCAATAGCGGCAAATCCAACTGAG<br>CTACAACCAGTTTAAACAGCATATTCTGAACCTGAGCAAAAGCCAGGATCGCATCA<br>GCAAGAAGAAGAAGGAGTACCTGCTGGAAGAACGCGACATCAACAAATTTGAAGTG<br>CAGAAAGAATTTATCAACCGCAACCTGGTTGATACCCGTTATGCAACCCGTGAACT<br>AGACCAATTATCTGAAGCATATTTCAGCGCCAACAACATGAACGTGAAAGTGAAAA<br>CGATTAACGGCAGCTTTACCGATTATCTGCGTAAAGTGTGGAAATTCAAAAAAGAA<br>CGCAACCACGGCTATAAACATCATGCCGAAGATGCCCTGATTATTGCAAATGCAGA<br>TTTCCTGTTTAAAGAAAACAAAAAACTGAAAGCCGTCAACAGCGTGCTGGAAAAAC<br>CGGAAATTGAGACAAAACAGCTGGACATTCAGGTTGATAGCGAAGATAATTACGC | |

SEQUENCE LISTING

| SEQ ID NO | Sequence | Description |
|---|---|---|
| | GAAATGTTTATCATCCCGAAACAGGTGCAGGATATCAAAGATTTTCGCAACTTCAA<br>ATATAGCCACCGCGTTGACAAAAAACCTAATCGTCAGCTGATTAACGATACCCTGT<br>ATAGCACCCGCAAAAAGATAACAGCACCTATATTGTGCAGACCATTAAAGACATC<br>TACGCCAAAGATAATACCACCCTGAAAAAACAGTTCGACAAAAGCCCAGAAAAATT<br>TCTGATGTATCAGCATGATCCGCGTACCTTCGAAAAACTGGAAGTTATTATGAAAC<br>AGTATGCCAACGAGAAAAATCCGCTGGCCAAATATCACGAAGAAACCGGTGAATAT<br>CTGACCAAATATTCCAAGAAGAACAACGGTCCGATCGTTAAATCCCTGAAATATAT<br>CGGTAATAAACTGGGCAGCCATCTGGATGTTACCCATCAGTTTAAAAGCTCCACAA<br>AGAAGCTGGTTAAACTGTCCATCAAACCGTATCGCTTTGATGTGTATCTGACCGAC<br>AAAGGCTATAAATTCATTACCATCAGCTATCTGGACGTGCTGAAAAAAGACAACTA<br>TTATTATATCCCGGAACAGAAATATGATAAACTGAAACTGGGTAAAGCCATCGATA<br>AAAACGCCAAATTTATCGCCAGCTTCTACAAAAACGACCTGATTAAACTGGATGGC<br>GAGATCTATAAAATCATCGGTGTTAATAGCGACACCCGCAATATGATTGAGCTGGA<br>TCTGCCGGATATTCGCTATAAAGAATATTGCGAACTGAACAACATTAAAGGCGAAC<br>CGCGTATCAAAAAGACCATCGGCAAAAAGTGAATAGCATCGAGAAACTGACCACC<br>GATGTTCTGGGTAATGTGTTTACCAATACCCAGTATACCAAACCTCAGCTGCTGTT<br>CAAACGCGGTAATGGCGGAGGATCTGGCCCCCCTAAGAAAAAGCGGAAGGTG | |
| 20 | CCACTGTAGAAGAGCAAATGCCACCTGACGTCTAAGAAATTCGCGTTAAATTTTTG<br>TTAAATCAGCTCATTTTTTAACCAATAGGCCGAAATCGGCAAAATCCCTTATAAAT<br>CAAAAGAATAGACCGAGATAGGGTTGAGTGGCCGCTACACTAGGGCGCGTCTAATA<br>CGACTCACTATAGGACCCCTCCACCCCGCCTCGTTTTAGTACTCTGGAAACAGAA<br>TCTACTAAAACAAGACTATATGTCGTGTTTATCCCACTAATTTATTAGTGGGAATT<br>TTTTGTTTTAGCATAACCCCTTGGGGCCTCTAAACGGGTCTTGAGGGGTTTTTTG<br>TCACTGCCCGCTTTCCAGTCGGGAAACCTGTCGTGCCAGCTGCATTAATGAATCGT<br>TCGTCAGAACTGCTTACGCGGTTTGTCACTCGGTCGCTACGCTCCGGGCGTGAGAC<br>TGCGGCGGGCGCTGCGGACACATACAAAGTTACCCACAGATTCCGTGGATAAGCAG<br>GGGACTAACATGTGAGGCAAAACAGCAGGGCCGCGCCGGTGGCGTTTTTCCATAGG<br>CTCCGCCCTCCTGCCAGAGTTCACATAAACAGACGCTTTTCCGGTGCATCTGTGGG<br>AGCCGTGAGGCTCAACCATGAATCTGACAGTACGGGCGAAACCCGACAGGACTTAA<br>AGATCCCCACCGTTTCCGGCGGGTCGCTCCCTCTTGCGCTCTCCTGTTCCGACCCT<br>GCCGTTTACCGGATACCTGTTCCGCCTTTCTCCCTTACGGGAAGTGTGGCGCTTTC<br>TCATAGCTCACACACTGGTATCTCGGCTCGGTGTAGGTCGTTCGCTCCAAGCTGGG<br>CTGTAAGCAAGAACTCCCCGTTCAGCCCGACTGCTGCGCCTTATCCGGTAACTGTT<br>CACTTGAGTCCAACCCGGAAAAGCACGGTAAAACGCCACTGGCAGCAGCCATTGGT<br>AACTGGGAGTTCGCAGAGGATTTGTTTAGCTAAACACGCGGTTGCTCTTGAAGTGT<br>GCGCCAAAGTCCGGCTACACTGGAAGGACAGATTTGGTTGCTGTGCTCTGCGAAAG<br>CCAGTTACCACGGTTAAGCAGTTCCCCAACTGACTTAACCTTCGATCAAACCACCT<br>CCCCAGGTGGTTTTTTCGTTTACAGGGCAAAAGATTACGCGCAGAAAAAAAGGATC<br>TCAAGAAGATCCTTTGATCTTTTCTACTGAACCGCTCAATCTAAAGTATATATGAG<br>TAAACTTGGTCTGACAGTTATTAGAAAAACTCATCGAGCATCAAATGAAACTGCAA<br>ATTTATTCATTCAGGATTATCAATACCATATTTTTGAAAAAGCCGTTTCTGTAATG<br>AAGGAGAAAACTCACCGAGGCAGTTCCATAGGATGGCAAGATCCTGGTATCGGTCT<br>GCGATTCCGACTCGTCCAACATCAATACAACCTATTAATTTCCCCTCGTCAAAAAT<br>AAGGTTATCAAGTGAGAAATCACCATGAGTGACGACTGAATCCGGTGAGAATGGCA<br>AAAGTTTATGCATTTCTTTCCAGACTTGTTCAACAGGCCAGCCATTACGCTCGTCA<br>TCAAAATCACTCGCATCAACCAAACCGTTATTCATTCGTGATTGCGCCTGAGCGAG<br>ACGAAATACGCGATCGCTGTTAAAAGGACAATTACAAACAGGAATCGAATGCAACC<br>GGCGCAGGAACACTGCCAGCGCATCAACAATATTTTCACCTGAATCAGGATATTCT<br>TCTAATACCTGGAATGCTGTTTTCCCGGGGATCGCAGTGGTGAGTAACCATGCATC<br>ATCAGGAGTACGGATAAAATGCTTGATGGTCGGAAGAGGCATAAATTCCGTCAGCC<br>AGTTTAGTCTGACCATCTCATCTGTAACATCATTGGCAACGCTACCTTTGCCATGT<br>TTCAGAAACAACTCTGGCGCATCGGGCTTCCCATACAATCGATAGATTGTCGCACC<br>TGATTGCCCGACATTATCGCGAGCCCATTTATACCCATATAAATCAGCATCCATGT<br>TGGAATTTAATCGCGGCCTAGAGCAAGACGTTTCCCGTTGAATATGGCTCATACTC<br>TTCCTTTTTCAATATTATTGAAGCATTTATCAGGGTTATTGTCTCATGAGCGGATA<br>CATATTTGAATGTATTTAGAAAAATAAACAAATAGGGGTTCCGCGCACATTTCCCC<br>GAAAAGTG | DNA sequence pMC7204 |
| 21 | CCACTGTAGAAGAGCAAATGCCACCTGACGTCTAAGAAATTCGCGTTAAATTTTTG<br>TTAAATCAGCTCATTTTTTAACCAATAGGCCGAAATCGGCAAAATCCCTTATAAAT<br>CAAAAGAATAGACCGAGATAGGGTTGAGTGGCCGCTACACTAGGGCGCGTCTAATA<br>CGACTCACTATAGGACCCCTCCACCCCGCCTCGTTTTAGTACTCTGGAAACAGAA<br>TCTACTGAAACAAGACAATATGTCGTGTTTATCCCATCAATTTATTGTGGGATTT<br>TTTTCTAGCATAACCCCTTGGGGCCTCTAAACGGGTCTTGAGGGGTTTTTTGTCAC<br>TGCCCGCTTTCCAGTCGGGAAACCTGTCGTGCCAGCTGCATTAATGAATCGTTCGT<br>CAGAACTGCTTACGCGGTTTGTCACTCGGTCGCTACGCTCCGGGCGTGAGACTGCG<br>GCGGGCGCTGCGGACACATACAAAGTTACCCACAGATTCCGTGGATAAGCAGGGGA<br>CTAACATGTGAGGCAAAACAGCAGGGCCGCGCCGGTGGCGTTTTTCCATAGGCTCC<br>GCCCTCCTGCCAGAGTTCACATAAACAGACGCTTTTCCGGTGCATCTGTGGGAGCC<br>GTGAGGCTCAACCATGAATCTGACAGTACGGGCGAAACCCGACAGGACTTAAAGAT<br>CCCCACCGTTTCCGGCGGGTCGCTCCCTCTTGCGCTCTCCTGTTCCGACCCTGCCG<br>TTTACCGGATACCTGTTCCGCCTTTCTCCCTTACGGGAAGTGTGGCGCTTTCTCAT | DNA sequence pCas606 |

SEQUENCE LISTING

| SEQ ID NO | Sequence | Description |
|---|---|---|
| | AGCTCACACACTGGTATCTCGGCTCGGTGTAGGTCGTTCGCTCCAAGCTGGGCTGT<br>AAGCAAGAACTCCCCGTTCAGCCCGACTGCTGCGCCTTATCCGGTAACTGTTCACT<br>TGAGTCCAACCCGGAAAAGCACGGTAAAACGCCACTGGCAGCAGCCATTGGTAACT<br>GGGAGTTCGCAGAGGATTTGTTTAGCTAAACACGCGGTTGCTCTTGAAGTGTGCGC<br>CAAAGTCCGGCTACACTGGAAGGACAGATTTGGTTGCTGTGCTCTGCGAAAGCCAG<br>TTACCACGGTTAAGCAGTTCCCCAACTGACTTAACCTTCGATCAAACCACCTCCCC<br>AGGTGGTTNTTCGTTTACAGGGCAAAAGATTACGCGCAGAAAAAAAGGATCTCAAG<br>AAGATCCTTTGATCTTTTCTACTGAACCGCTCAATCTAAAGTATATATGAGTAAAC<br>TTGGTCTGACAGTTATTAGAAAAACTCATCGAGCATCAAATGAAACTGCAATTTAT<br>TCATATCAGGATTATCAATACCATA!TTTTGAAAAAGCCGTTTCTGTAATGAAGGA<br>GAAAACTCACCGAGGCAGTTCCATAGGATGGCAAGATCCTGGTATCGGTCTGCGAT<br>TCCGACTCGTCCAACATCAATACAACCTATTAATTTCCCCTCGTCAAAAATAAGGT<br>TATCAAGTGAGAAATCACCATGAGTGACGACTGAATCCGGTGAGAATGGCAAAAGT<br>TTATGCATTTCTTTCCAGACTTGTTCAACAGGCCAGCCATTACGCTCGTCATCAAA<br>ATCACTCGCATCAACCAAACCGTTATTCATTCGTGATTGCGCCTGAGCGAGACGAA<br>ATACGCGATCGCTGTTAAAGGACAATTACAAACAGGAATCGAATGCAACCGGCGC<br>AGGAACACTGCCAGCGCATCAACAATATTTTCACCTGAATCAGGATATTCTTCTAA<br>TACCTGGAATGCTGTTTTCCCGGGGATCGCAGTGGTGAGTAACCATGCATCATCAG<br>GAGTACGGATAAAATGCTTGATGGTCGGAAGAGGCATAAATTCCGTCAGCCAGTTT<br>AGTCTGACCATCTCATCTGTAACATCATTGGCAACGCTACCTTTGCCATGTTTCAG<br>AAACAACTCTGGCGCATCGGGCTTCCCATACAATCGATAGATTGTCGCACCTGATT<br>GCCCGACATTATCGCGAGCCCATTTATACCCATATAAATCAGCATCCATGTTGGAA<br>TTTAATCGCGGCCTAGAGCAAGACGTTTCCCGTTGAATATGGCTCATACTCTTCCT<br>TTTTCAATATTATTGAAGCATTTATCAGGGTTATTGTCTCATGAGCGGATACATAT<br>TTGAATGTATTTAGAAAAATAAACAAATAGGGGTTCCGCGCACATTTCCCCGAAAA<br>GTG | |
| 22 | TCAATCTAAAGTATATATGAGTAAACTTGGTCTGACAGTTATTACGCCCCGCCCTG<br>CCACTCATCGCAGTACTGTTGTAATTCATTAAGCATTCTGCCGACATGGAAGCCAT<br>CACAAACGGCATGATGAACCTGAATCGCCAGCGGCATCAGCACCTTGTCGCCTTGC<br>GTATAATATTTGCCCAAGGTGAAAACGGGGGCGAAGAAGTTGTCCATATTGGCCAC<br>GTTTAAATCAAAACTGGTGAAACTCACCCAGGGATTGGCTGAGACGAAAAACATAT<br>TCTCAATAAACCCTTTAGGGAAATAGGCCAGGTTTTCACCGTAACACGCCACATCT<br>TGCGAATATATGTGTAGAAACTGCCGGAAATCGTCGTGGTATTCACTCCAGAGCGA<br>TGAAAACGTTTCAGTTTGCTCATGGAAAACGGTGTAACAAGGGTGAACACTATCCC<br>ATATCACCAGCTCACCGTCTTTCATTGCCATACGTAATTCCGGATGAGCATTCATC<br>AGGCGGGCAAGAATGTGAATAAAGGCCGGATAAAACTTGGTGCTTATTTTTCTTTAC<br>GGTCTTTAAAAAGGCCGTAATATCCAGCTGAACGGTCTGGTTATAGGTACATTGAG<br>CAACTGACTGAAATGCCTCAAAATGTTCTTTACGATGCCATTGGGATATATCAACG<br>GTGGTATATCCAGTGATTTTTTCTCCATACTCTTCCTTTTTCAATATTATTGAAG<br>CATTTATCAGGGTTATTGTCTCATGAGCGGATACATATTTGAATGTATTTAGAAAA<br>ATAAACAAATAGGGGTTCCGCGCACATTTCCCCGAAAAGTGCCACCTTATGACAACT<br>TGACGGCTACATCATTCACTTTTTCTTCACAACCGGCACGGAACTCGCTCGGGCTG<br>GCCCCGGTGCATTTTTAAATACCCGCGAGAAATAGAGTTGATCGTCAAAACCAAC<br>ATTGCGACCGACGGTGGCGATAGGCATCCGGGTGGTGCTCAAAAGCAGCTTCGCCT<br>GGCTGATACGTTGGTCCTCGCGCCAGCTTAAGACGCTAATCCCTAACTGCTGGCGG<br>AAAAGATGTGACAGACGCGACGGCGACAAGCAAACATGCTGTGCGACGCTGGCGAT<br>ATCAAAATTGCTGTCTGCCAGGTGATCGCTGATGTACTGACAAGCCTCGCGTACCC<br>GATTATCCATCGGTGGATGGAGCGACTCGTTAATCGCTTCCATGCGCCGCAGTAAC<br>AATTGCTCAAGCAGATTTATCGCCAGCAGCTCCGAATAGCGCCCTTCCCCTTGCCC<br>AGGCGTTAATGTTTGCCCAAACAGGTCGCTGAAATGCGGCTGGTGCGCTTCATCCG<br>GGCGAAAGAACCCCGTATTGGCAAATATTGACGGCCAGTTAAGCCATTCATGCCAG<br>TAGGCGCGCGGACGAAAGTAAACCCACTGGTGATACCATTCGCGAGCCTCCGGATG<br>ACGACCGTAGTGATGAATCTCTCCTGGCGGGAACAGCAAAATATCACCCGGTCGGC<br>AAACAAATTCTCGTCCCTGATTTTTCACCACCCCTGACCGCGAATGGTGAGATTG<br>AGAATATAACCTTTCATTCCCAGCGGTCGGTCGATAAAAAAATCGAGATAACCGTT<br>GGCCTCAATCGGCGTTAAACCCGCCACCAGATGGGCATTAAACGAGTATCCCGGCA<br>GCAGGGGATCATTTTGCGCTTCAGCCATACTTTTCATACTCCCGCCATTCAGAGAA<br>GAAACCAATTGTCCATATTGCATCAGACATTGCCGTCACTGCGTCTTTTACTGGCT<br>CTTCTCGCTAACCAAACCGGTAACCCCGCTTATTAAAAGCATTCTGTAACAAAGCG<br>GGACCAAAGCCATGACAAAAACGCGTAACAAAAGTGTCTATAATCACGGCAGAAAA<br>GTCCACATTGATTATTTGCACGGCGTCACACTTTGCTATGCCATAGCATTTTTATC<br>CATAAGATTAGCGGATCCTACCTGACGCTTTTTATCGCAACTCTCTACTGTTTCTC<br>CATACCCGTTTTTTGGGCTAACAGGAGGAATTAAATGGTGAGCAAAGGTGAGGAAC<br>TGATCAAAGAAAACATGCATATGAAACTGTACATGGAAGGCACCGTGAATAACCAT<br>CACTTTAAATGTACCAGCGAAGGTGAAGGTAAACCGTATGAAGGCACCCAGACCAT<br>GCGTATTAAAGTTGTTGAAGGTGGTCCGCTGCCGTTTGCATTTGATATTCTGGCAA<br>CCAGCTTTATGTATGGTAGCCGTACCTTTATTAACCATACCCAGGGTATTCCGGAT<br>TTCTTTAAACAGAGCTTTCCGGAAGGTTTTACCTGGGAACGTGTTACCACCTATGA<br>AGATGGTGGTGTTCTGACCGCAACCCAGGATACCAGTCTGCAGGATGGTTGTCTGA<br>TTTATAATGTGAAATTCGCGGTGTGAACTTTCCGAGCAATGGTCCGGTTATGCAG<br>AAAAAAACCCTGGGTTGGGAAGCAAATACCGAAATGCTGTATCCGGCAGATGGTGG<br>CCTGGAAGGTCGTAGCGATATGGCACTGAAACTGGTTGGTGGTGGTCATCTGATTT | DNA sequence PML2017 |

| SEQ ID NO | Sequence | Description |
|---|---|---|
| | GTAACTTTAAAACCACCTATCGCAGCAAAAAACCTGCCAAAAATCTGAAAATGCCT<br>GGCGTGTATTATGTGGATCATCGTCTGGAACGCATTAAAGAAGCAGATAAAGAAAC<br>CTATGTGGAACAGCATGAAGTTGCAGTTGCACGTTATTGTGATCTGCCGAGCAAAC<br>TGGGTCATAAACTGAATAGCGGTCTGCGTAGCCGTGCACAGGCAAGCAATAGCGCA<br>GGTTGATGGCACCGCAGGTCCGGTAGCACCGGTAGTCGCGGTGGTGGTAGCGGTGC<br>AGCAAATGATGAAAATTATGCACTGGCAGCCTGATAATGCCTGGCGGCAGTAGCGC<br>GGTGGTCCCACCTGACCCCATGCCGAACTCAGAAGTGAAACGCCGTAGCGCCGATG<br>GTAGTGTGGGCTCTCCCCATGCGAGAGTAGGGAACTGCCAGGCATCAAATAAAACG<br>AAAGGCTCAGTCGAAAGACTGGGCCTTATAGGACCCCCTCCACCCCGCCTCNNNNN<br>NNCAACGATCGTTTAATTTGTTTTTGTCACTCGGTCGCTACGCTCCGGGCGTGAGA<br>CTGCGGCGGGCTCTTCCGCTTCCTCGCTCACTGACTCGCTACGCTCGGTCGTTCGA<br>CTGCGGCGAGCGGTGTCAGCTCACTCAAAAGCGGTAATACGGTTATCCACAGAATC<br>AGGGGATAAAGCCGGAAAGAACATGTGAGCAAAAAGCAAAGCACCGGAAGAAGCCA<br>ACGCCGCAGGCGTTTTTCCATAGGCTCCGCCCCCTGACGAGCATCACAAAAATCG<br>ACGCTCAAGCCAGAGGTGGCGAAACCCGACAGGACTATAAAGATACCAGGCGTTTC<br>CCCCTGGAAGCTCCCTCGTGCGCTCTCCTGTTCCGACCCTGCCGCTTACCGGATAC<br>CTGTCCGCCTTTCTCCCTTCGGGAAGCGTGGCGCTTTCTCATAGCTCACGCTGTTG<br>GTATCTCAGTTCGGTGTAGGTCGTTCGCTCCAAGCTGGGCTGTGTGCACGAACCCC<br>CCGTTCAGCCCGACCGCTGCGCCTTATCCGGTAACTATCGTCTTGAGTCCAACCCG<br>GTAAGACACGACTTATCGCCACTGGCAGCAGCCATTGGTAACTGATTTAGAGGACT<br>TTGTCTTGAAGTTATGCACCTGTTAAGGCTAAACTGAAAGAACAGATTTTGGTGAG<br>TGCGGTCCTCCAACCCACTTACCTTGGTTCAAAGAGTTGGTAGCTCAGCGAACCTT<br>GAGAAAACCACCGTTGGTAGCGGTGGTTTTTCTTTATTTATGAGATGATGAATCAA<br>TCGGTCTATCAAGTCAACGAACAGCTATTCCGTTACTCTAGATTTTCTACTGAACC<br>GC | |
| 23 | TCAATCTAAAGTATATATGAGTAAACTTGGTCTGACAGTTATTACGCCCCGCCCTG<br>CCACTCATCGCAGTACTGTTGTAATTCATTAAGCATTCTGCCGACATGGAAGCCAT<br>CACAAACGGCATGATGAACCTGAATCGCCAGCGGCATCAGCACCTTGTCGCCTTGC<br>GTATAATATTTGCCCAAGGTGAAAACGGGGGCGAAGAAGTTGTCCATATTGGCCAC<br>GTTTAAATCAAAACTGGTGAAACTCACCCAGGGATTGGCTGAGACGAAAACATAT<br>TCTCAATAAACCCTTTAGGGAAATAGGCCAGGTTTTCACCGTAACACGCCACATCT<br>TGCGAATATATGTGTAGAAACTGCCGGAAATCGTCGTGGTATTCACTCCAGAGCGA<br>TGAAAACGTTTCAGTTTGCTCATGGAAAACGGTGTAACAAGGGTGAACACTATCCC<br>ATATCACCAGCTCACCGTCTTTCATTGCCATACGTAATTCCGGATGAGCATTCATC<br>AGGCGGGCAAGAATGTGAATAAAGGCCGGATAAAACTTGTGCTTATTTTTCTTTAC<br>GGTCTTTAAAAAGGCCGTAATATCCAGCTGAACGGTCTGGTTATAGGTACATTGAG<br>CAACTGACTGAAATGCCTCAAAATGTTCTTTACGATGCCATTGGGATATATCAACG<br>GTGGTATATCCAGTGATTTTTTCTCCATACTCTTCCTTTTTCAATATTATTGAAG<br>CATTTATCAGGGTTATTGTCTCATGAGCGGATACATATTTGAATGTATTTAGAAAA<br>ATAAACAAATAGGGGTTCCGCGCACATTTCCCCGAAAAGTGCCACTTATGACAACT<br>TGACGGCTACATCATTCACTTTTTCTTCACAACCGGCACGGAACTCGCTCGGGCTG<br>GCCCCGGTGCATTTTTAAATACCCGCGAGAATAGAGTTGATCGTCAAAACCAAC<br>ATTGCGACCGACGGTGGCGATAGGCATCCGGGTGGTGCTCAAAAGCAGCTTCGCCT<br>GGCTGATACGTTGGTCCTCGCGCCAGCTTAAGACGCTAATCCCTAACTGCTGGCGG<br>AAAAGATGTGACAGACGCGACGGCGACAAGCAAACATGCTGTGCGACGCTGGCGAT<br>ATCAAAATTGCTGTCTGCCAGGTGATCGCTGATGTACTGACAAGCCTCGCGTACCC<br>GATTATCCATCGGTGGATGGAGCGACTCGTTAATCGCTTCCATGCGCCGCAGTAAC<br>AATTGCTCAAGCAGATTTATCGCCAGCAGCTCCGAATAGCGCCCTTCCCCTTGCCC<br>GGCGTTAATGATTTGCCCAAACAGGTCGCTGAAATGCGGCTGGTGCGCTTCATCCG<br>GGCGAAAGAACCCCGTATTGGCAAATATTGACGGCCAGTTAAGCCATTCATGCCAG<br>TAGGCGCGCGGACGAAAGTAAACCCACTGGTGATACCATTCGCGAGCCTCCGGATG<br>ACGACCGTAGTGATGAATCTCTCCTGGCGGGAACAGCAAAATATCACCCGGTCGGC<br>AAAACAAATTCTCGTCCCTGATTTTTCACCACCCCTGACCGCGAATGGTGAGATTG<br>AGAATATAACCTTTCATTCCCAGCGGTCGGTCGATAAAAAAATCGAGATAACCGTT<br>GGCCTCAATCGGCGTTAAACCCGCCACCAGATGGGCATTAAACGAGTATCCCGGCA<br>GCAGGGGATCATTTTGCGCTTCAGCCATACTTTTCATACTCCCGCCATTCAGAGAA<br>GAAACCAATTGTCCATATTGCATCAGACATTGCCGTCACTGCGTCTTTTACTGGCT<br>CTTCTCGCTAACCAAACCGGTAACCCCGCTTATTAAAAGCATTCTGTAACAAAGCG<br>GGACCAAAGCCATGACAAAAACGCGTAACAAAAGTGTCTATAATCACGGCAGAAAA<br>GTCCACATTGATTATTTGCACGGCGTCACACTTTGCTATGCCATAGCATTTTTATC<br>CATAAGATTAGCGGATCCTACCTGACGCTTTTTATCGCAACTCTCTACTGTTTCTC<br>CATACCCGTTTTTTGGGCTAACAGGAGGAATTAAATGGTGAGCAAAGGTGAGGAAC<br>TGATCAAAGAAAACATGCATATGAAACTGTACATGGAAGGCACCGTGAATAACCAT<br>CACTTTAAATGTACCAGCGAAGGTGAAGGTAAACCGTATGAAGGCACCCAGACCAT<br>GCGTATTAAAGTTGTTGAAGGTGGTCCGCTGCCGTTTGCATTTGATATTCTGGCAA<br>CCAGCTTTATGTATGGTAGCCGTACCTTTATTAACCATACCCAGGGTATTCCGGAT<br>TTCTTTAAACAGAGCTTTCCGGAAGGTTTTACCTGGGAACGTGTTACCACCTATGA<br>AGATGGTGGTGTTCTGACCGCAACCCAGGATACCAGTCTGCAGGATGGTTGTCTGA<br>TTTATAATGTGAAATTCGCGGTGTGAACTTTCCGAGCAATGGTCCGGTTATGCAG<br>AAAAAAACCCTGGGTTGGGAAGCAAATACCGAAATGCTGTATCCGGCAGATGGTGG<br>CCTGGAAGGTCGTAGCGATATGGCACTGAAACTGGTTGGTGGTGGTCATCTGATTT<br>GTAACTTTAAAACCACCTATCGCAGCAAAAAACCTGCCAAAAATCTGAAAATGCCT | DNA sequence pCas595 |

| SEQ ID NO | Sequence | Description |
|---|---|---|
| | GGCGTGTATTATGTGGATCATCGTCTGGAACGCATTAAAGAAGCAGATAAAGAAAC<br>CTATGTGGAACAGCATGAAGTTGCAGTTGCACGTTATTGTGATCTGCCGAGCAAAC<br>TGGGTCATAAACTGAATAGCGGTCTGCGTAGCCGTGCACAGGCAAGCAATAGCGCA<br>GTTGATGGCACCGCAGGTCCGGGTAGCACCGGTAGTCGCGGTGGTGGTAGCGGTGC<br>AGCAAATGATGAAAATTATGCACTGGCAGCCTGATAATGCCTGGCGGCAGTAGCGC<br>GGTGGTCCCACCTGACCCCATGCCGAACTCAGAAGTGAAACGCCGTAGCGCCGATG<br>GTAGTGTGGGCTCTCCCCATGCGAGAGTAGGGAACTGCCAGGCATCAAATAAAACG<br>AAAGGCTCAGTCGAAAGACTGGGCCTTATAGGACCCCCTCCACCCCGCCTCCCGGC<br>CCGTTTAATTTGTTTTTGTCACTCGGTCGCTACGCTCCGGGCGTGAGACTGCGGCG<br>GGCTCTTCCGCTTCCTCGCTCACTGACTCGCTACGCTCGGTCGTTCGACTGCGGCG<br>AGCGGTGTCAGCTCACTCAAAAGCGGTAATACGGTTATCCACAGAATCAGGGGATA<br>AAGCCGGAAAGAACATGTGAGCAAAAAGCAAAGCACCGGAAGAAGCCAACGCCGCA<br>GGCGTTTTTCCATAGGCTCCGCCCCCCTGACGAGCATCACAAAAATCGACGCTCAA<br>GCCAGAGGTGGCGAAACCCGACAGGACTATAAAGATACCAGGGTTTCCCCCTGGAA<br>GCTCCCTCGTGCGCTCTCCTGTTCCGACCCTGCCGCTTACCGGCATACCTGTCCGC<br>CTTTCTCCCTTCGGGAAGCGTGGCGCTTTCTCATAGCTCACGCTGTTGGTATCTCA<br>GTTCGGTGTAGGTCGTTCGCTCCAAGCTGGGCTGTGTGCACGAACCCCCCGTTCAG<br>CCCGACCGCTGCGCCTTATCCGGTAACTATCGTCTTGAGTCCAACCCGGTAAGACA<br>CGACTTATCGCCACTGGCAGCAGCCATTGGTAACTGATTTAGAGGACTTTGTCTTG<br>AAGTTATGCACCTGTTAAGGCTAAACTGAAAGAACAGATTTTGGTGAGTGCGGTCC<br>TCCAACCCACTTACCTTGGTTCAAAGAGTTGGTAGCTCAGCGAACCTTGAGAAAAC<br>CACCGTTGGTAGCGGTGGTTTTTCTTTATTTATGAGATGATGAATCAATCGGTCTA<br>TCAAGTCAACGAACAGCTATTCCGTTACTCTAGATTTTCTACTGAACCGC | |
| 24 | GGTGGAAGCGGAGGCAGCGGGGGATCAGGCCATCATCATCACCATCATTAATGAAC<br>GGGTCTTGAGGGGTTTTTTGGACTTTTGCGTATTGGGCGCTCTTCCGCTTCCTCGC<br>TCACTGACTCGCTGCGCTCGGTCGTTCGGCTGCGGCGAGCGGTATCAGCTCACTCA<br>AAGGCGGTAATACGGTTATCCACAGAATCAGGGGATAACGCAGGAAAGAACATGTG<br>AGCAAAAGGCCAGCAAAAGGCCAGGAACCGTAAAAAGGCCGCGTTGCTGGCGTTTT<br>TCCATAGGCTCCGCCCCCCTGACGAGCATCACAAAAATCGACGCTCAAGTCAGAGG<br>TGGCGAAACCCGACAGGACTATAAAGATACCAGGCGTTTCCCCCTGGAAGCTCCCT<br>CGTGCGCTCTCCTGTTCCGACCCTGCCGCTTACCGGATACCTGTCCGCCTTTCTCC<br>CTTCGGGAAGCGTGGCGCTTTCTCATAGCTCACGCTGTAGGTATCTCAGTTCGGTG<br>TAGGTCGTTCGCTCCAAGCTGGGCTGTGTGCACGAACCCCCCGTTCAGCCCGACCG<br>CTGCGCCTTATCCGGTAACTATCGTCTTGAGTCCAACCCGGTAAGACACGACTTAT<br>CGCCACTGGCAGCAGCCACTGGTAACAGGATTAGCAGAGCGAGGTATGTAGGCGGT<br>GCTACAGAGTTCTTGAAGTGGTGGCCTAACTACGGCTACACTAGAAGGACAGTATT<br>TGGTATCTGCGCTCTGCTGAAGCCAGTTACCTTCGGAAAAAGAGTTGGTAGCTCTT<br>GATCCGGCAAACAAACCACCGCTGGTAGCGGTGGTTTTTTTGTTTGCAAGCAGCAG<br>ATTACGCGCAGAAAAAAAGGATCTCAAGAAGATCCTTTGATCTTTTCTACGGGGTC<br>TGACGCTCAGTGGAACGAAAACTCACGTTAAGGGATTTTGGTCATGAGATTATCAA<br>AAAGGATCTTCACCTAGATCCTTTTAAATTAAAAATGAAGTTTTAAATCAATCTAA<br>AGTATATATGAGTAAACTTGGTCTGACAGTTACCAATGCTTAATCAGTGAGGCACC<br>TATCTCAGCGATCTGTCTATTTCGTTCATCCATAGTTGCCTGACTCCCCGTCGTGT<br>AGATAACTACGATACGGGAGGGCTTACCATCTGGCCCCAGTGCTGCAATGATACCG<br>CGAGATCCACGCTCACCGGCTCCAGATTTATCAGCAATAAACCAGCCAGCCGGAAG<br>GGCCGAGCGCAGAAGTGGTCCTGCAACTTTATCCGCCTCCATCCAGTCTATTAATT<br>GTTGCCGGGAAGCTAGAGTAAGTAGTTCGCCAGTTAATAGTTTGCGCAACGTTGTT<br>GCCATTGCTGCAGGCATCGTGGTGTCACGCTCGTCGTTTGGTATGGCTTCATTCAG<br>CTCCGGTTCCCAACGATCAAGGCGAGTTACATGATCCCCCATGTTGTGCAAAAAAG<br>CGGTTAGCTCCTTCGGTCCTCCGATCGTTGTCAGAAGTAAGTTGGCCGCAGTGTTA<br>TCACTCATGGTTATGGCAGCACTGCATAATTCTCTTACTGTCATGCCATCCGTAAG<br>ATGCTTTTCTGTGACTGGTGAGTACTCAACCAAGTCATTCTGAGAATAGTGTATGC<br>GGCGACCGAGTTGCTCTTGCCCGGCGTCAATACGGGATAATACCGCGCCACATAGC<br>AGAACTTTAAAAGTGCTCATCATTGGAAAACGTTCTTCGGGGCGAAAACTCTCAAG<br>GATCTTACCGCTGTTGAGATCCAGTTCGATGTAACCCACTCGTGCACCCAACTGAT<br>CTTCAGCATCTTTTACTTTCACCAGCGTTTCTGGGTGAGCAAAAACAGGAAGGCAA<br>AATGCCGCAAAAAAGGGAATAAGGGCGACACGGAAATGTTGAATACTCATACTCTT<br>CCTTTTTCAATATTATTGAAGCATTTATCAGGGTTATTGTCTCATGAGCGGATACA<br>TATTTGAATGTATTTAGAAAAATAAACAAATAGGGGTTCCGCGCACATTTCCCCGA<br>AAAGTGCCACTCCTCTTGCTGTGACCGTCTCCGGGAGCTGCATGTGTCAGAGGTTT<br>TCACCGTCATCACCGAAACGCGCGAGGCAGCAGATCAATTCGCGCGCGAAGGCGAA<br>GCGGCATGCATTTACGTTGACACCATCGAATGGTGCAAAACCTTTCGCGGTATGGC<br>ATGATAGCGCCCGGAAGAGAGTCAATTCAGGGTGGTGAATGTGAAACCAGTAACGT<br>TATACGATGTCGCAGAGTATGCCGGTGTCTCTTATCAGACCGTTTCCCGCGTGGTG<br>AACCAGGCCAGCCACGTTTCTGCGAAAACGCGGGAAAAGTGGAAGCGGCGATGGC<br>GGAGCTGAATTACATTCCCAACCGCGTGGCACAACAACTGGCGGGCAAACAGTCGT<br>TGCTGATTGGCGTTGCCACCTCCAGTCTGGCCCTGCACGCGCCGTCGCAAATTGTC<br>GCGGCGATTAAATCTCGCGCCGATCAACTGGGTGCCAGCGTGGTGGTGTCGATGGT<br>AGAACGAAGCGGCGTCGAAGCCTGTAAAGCGGCGGTGCACAATCTTCTCGCGCAAC<br>GCGTCAGTGGGCTGATCATTAACTATCCGCTGGATGACCAGGATGCCATTGCTGTG<br>GAAGCTGCCTGCACTAATGTTCCGGCGTTATTTCTTGATGTCTCTGACCAGACACC<br>GCATCAACATATTATTTTCTCCCATGAAGATGGTACGCGACTGGGCGTGGAGCATC | DNA sequence pCas81 |

SEQUENCE LISTING

| SEQ ID NO | Sequence | Description |
|---|---|---|
| | TGGTCGCATTGGGTCACCAGCAAATCGCGCTGTTAGCGGGCCCATTAAGTTCTGTC<br>TCGGCGCGTCTGCGTCTGGCTGGCTGGCATAAATATCTCACTCGCAATCAAATTCA<br>GCCGATAGCGGAACGGGAAGGCGACTGGAGTGCCATGTCCGGTTTTCAACAAACCA<br>TGCAAATGCTGAATGAGGGCATCGTTCCCACTGCGATGCTGGTTGCCAACGATCAG<br>ATGGCGCTGGGCGCAATGCGCGCCATTACCGAGTCCGGGCTGCGCGTTGGTGCGGA<br>TATCTCGGTAGTGGGATACGACGATACCGAAGATAGCTCATGTTATATCCCGCCGT<br>TAACCACCATCAAACAGGATTTTCGCCTGCTGGGGCAAACCAGCGTGGACCGCTTG<br>CTGCAACTCTCTCAGGGCCAGGCGGTGAAGGGCAATCAGCTGTTGCCCGTCTCACT<br>GGTGAAAAGAAAAACCACCCTGGCGCCCAATACGCAAACCGCCTCTCCCCGCGCGT<br>TGGCCGATTCATTAATGCAGCTGGCACGACAGGTTTCCCGACTGGAAAGCGGGCAG<br>TGAGCGCAATATTCTGAAATGAGCTGTTGACAATTAATCATCCGGCTCGTATAATG<br>TGTGGAATTGTGAGCGGATAACAATTTTCACACAGGAAACAGAATTCTAGCATTGT<br>GAGCGGATAACAATTCCCCTCTAGAAATAATTTTGTTTAACTTTAAGAAGGAGATA<br>TACCATGAAACGTCCGGCAGCAACCAAAAAAGCAGGTCAGGCCAAGAAAAAAAAG<br>GTGGTGGTTCAGGTAACCAGAAATTTATCCTGGGTCTGGATATTGGTATTACCAGC<br>GTTGGTTATGGCCTGATTGATTACGAAACCAAAAACATTATTGATGCCGGTGTTCG<br>TCTGTTTCCGGAAGCAAATGTTGAAAATAATGAAGGTCGTCGTAGCAAACGTGGTA<br>GCCGTCGTCTGAAACGTCGTCGTATTCATCGTCTGGAACGTGTTAAAAAACTGCTG<br>GAAGATTATAACCTGCTGGATCAGAGCCAGATTCCGCAGAGCACCAATCCGTATGC<br>AATTCGTGTTAAAGGTCTGAGCGAAGCACTGAGCAAAGATGAACTGGTTATTGCAC<br>TGCTGCATATTGCAAAACGCCGTGGCATTCATAAAATCGATGTGATTGATAGCAAT<br>GACGATGTGGGTAATGAACTGAGCACCAAAGAACAGCTGAACAAAATAGCAAACT<br>GCTGAAAGACAAATTCGTGTGTCAGATTCAGCTGGAACGTATGAATGAAGGCCAGG<br>TTCGTGGTGAAAAGAATCGCTTTAAAACCGCAGACATCATCAAAGAAATTATCCAG<br>CTGCTGAACGTGCAGAAAAACTTCCATCAGCTGGATGAAAACTTCATCAACAAATA<br>CATCGAGCTGGTTGAAATGCGTCGCGAATATTTTGAAGGTCCGGGTAAAGGTAGCC<br>CGTATGGTTGGGAAGGTGATCCGAAAGCATGGTATGAAACCCTGATGGGTCATTGT<br>ACCTATTTTCCGGATGAACTGCGTAGCGTTAAATATGCCTATAGCGCAGACCTGTT<br>TAATGCACTGAATGATCTGAATAACCTGGTGATTCAGCGTGATGGTCTGAGCAAAC<br>TGGAATATCATGAGAAATATCACATCATCGAAAACGTGTTCAAACAGAAGAAGAAA<br>CCGACCCTGAAACAAATCGCCAACGAAATTAATGTGAACCCGGAAGATATTAAAGG<br>CTACCGTATTACCAAAAGCGGTAAACCGCAGTTCACCGAATTTAAACTGTATCACG<br>ATCTGAAAAGCGTGCTGTTTGATCAGAGCATTCTGGAAAATGAAGATGTGCTGGAC<br>CAGATTGCAGAAATTCTGACCATTTATCAGGACAAAGACAGCATCAAAGCAAACT<br>GACCGAACTGGATATTCTGCTGAATGAAGAAGATAAAGAGAACATTGCACAGCTGA<br>CCGGTTATACCGGCACCCATCGTCTGAGCCTGAAATGTATTCGTCTGGTACTGGAA<br>GAACAGTGGTATAGCAGCCGTAATCAGATGGAAATCTTTACCCATCTGAACATTAA<br>ACCGAAGAAAATCAATCTGACCGCAGCCAACAAAATTCCGAAAGCCATGATTGATG<br>AGTTTATTCTGAGTCCGGTTGTGAAACGTACCTTTGGTCAGGCAATTAACCTGATC<br>AACAAAATCATTGAAAAATATGGCGTGCCTGAGGATATCATTATTGAACTGGCACG<br>TGAAAACAACAGCAAAGATAAACAGAAATTCATCAACGAGATGCAGAAGAAGAACG<br>AAAATACCCGCAAACGGATTAACGAGATCATTGGCAAATATGGTAATCAGAATGCC<br>AAACGCCTGGTGGAAAAAATTCGTCTGCATGATGAACAAGAGGGCAAATGTCTGTA<br>TAGCCTGGAAAGCATTCCTCTGGAAGATCTGCTGAACAATCCGAATCATTATGAAG<br>TGGATCACATTATTCCGCGTAGCGTGAGCTTTGATAATTCCTATCATAATAAAGTG<br>CTGGTGAAACAGAGCGAAAACTCCAAAAAATCCAACCTGACACCGTATCAGTATTT<br>CAATAGCGGCAAATCCAAACTGAGCTACAACCAGTTTAAACAGCATATTCTGAACC<br>TGAGCAAAAGCCAGGATCGCATCAGCAAGAAGAAGAAGGAGTACCTGCTGGAAGAA<br>CGCGACATCAACAAATTTGAAGTGCAGAAAGAATTTATCAACCGCAACCTGGTTGA<br>TACCCGTTATGCAACCCGTGAACTGACCAATTATCTGAAAGCATATTTCAGCGCCA<br>ACAACATGAACGTGAAAGTGAAAACGATTAACGGCAGCTTTACCGATTATCTGCGT<br>AAAGTGTGGAAATTCAAAAAAGAACGCAACCACGGCTATAAACATCATGCCGAAGA<br>CTGCCCTGATTATTGCAAATGAGATTTCCTGTTTAAAGAAAACAAAAACTGAAAG<br>CCGTCAACAGCGTGCTGGAAAAACCGGAAATTGAGACAAAACAGCTGGACATTCAG<br>GTTGATAGCGAAGATAATTACAGCGAAATGTTTATCATCCCGAAACAGGTGCAGGA<br>TATCAAAGATTTTCGCAACTTCAAATATAGCCACCGCGTTGACAAAAAACCTAATC<br>GTCAGCTGATTAACGATACCCTGTATAGCACCCGCAAAAAAGATAACAGCACCTAT<br>ATTGTGCAGACCATTAAAGACATCTACGCCAAAGATAATACCACCCTGAAAAAACA<br>GTTCGACAAAAGCCCAGAAAAATTTCTGATGTATCAGCATGATCCGCGTACCTTCG<br>AAAAACTGGAAGTTATTATGAAACAGTATGCCAACGAGAAAAATCCGCTGGCCAAA<br>TATCACGAAGAAACCGGTGAATATCTGACCAAATATTCCAAGAAGAACAACGGTCC<br>GATCGTTAAATCCCTGAAATATATCGGTAATAAACTGGGCAGCCATCTGGATGTTA<br>CCCATCAGTTTAAAAGCTCCACAAAGAAGCTGGTTAAACTGTCCATCAAACCGTAT<br>CGCTTTGATGTGTATCTGACCGACAAAGGCTATAAATTCATTACCATCAGCTATCT<br>GGACGTGCTGAAAAAAGACAACTATTATTATATCCCGGAACAGAAATATGATAAAC<br>TGAAACTGGGTAAAGCCATCGATAAAAACGCCAAATTTATCGCCAGCTTCTACAAA<br>AACGACCTGATTAAACTGGATGGCGAGATCTATAAAATCATCGGTGTTAATAGCGA<br>CACCCGCAATATGATTGAGCTGGATCTGCCGGATATTCGCTATAAAGAATATTGCG<br>AACTGAACAACATTAAAGGCGAACGCGTATCAAAAAGACCATCGGCAAAAAGTG<br>AATAGCATCGAGAAACTGACCACCGATGTTCTGGGTAATGTGTTTACCAATACCCA<br>GTATACCAAACCTCAGCTGCTGTTCAAACGCGGTAATGGCGGAGGATCTGGCCCCC<br>CTAAGAAAAAGCGGAAGGTG | |

SEQUENCE LISTING

| SEQ ID NO | Sequence | Description |
|---|---|---|
| 25 | CCGGTGATACCACGATACTATGACTGAGAGTCAACGCCATGAGCGGCCTCATTTCT<br>TATTCTGAGTTACAACAGTCCGCACCGCTGCCGGTAGCTATTGACTATCCGGCTGC<br>ACTAGCCCTGCGTCAGATGGCTCTGATCCAAGGCAAACTGCCAAAATATCTGCTGG<br>CACCGGAAGTCAGCGCCCTGCACCATTATGTTCCGGATCTGCATCGCAGGATGCTG<br>CTGGCTACCCTGTGGAACACCTACATCTGTATTAACGAAGCGCTGGCATTGACCCT<br>GAGTGATTTTCTCTGGTGCCGCCCTATCCCTTTGTGCAGCTTGCCACGCTCAAAG<br>GGGTTTGAGGTCCAACCGTACGAAAACGTACGGTAAGAGGAAAATTATCGTCTGAA<br>AAATCGATTAGTAGACAAGAAAGTCCGTTAAGTGCCAATTTTCGATTAAAAAGACA<br>CCGTTTTGATGGCGTTTTCCAATGTACATTATGTTTCGATATATCAGACAGTTACT<br>TCACTAACGTACGTTTTCGTTCTATTGGCCTTCAGACCCCATATCCTTAATGTCCT<br>TTATTTGCTGGGGTTATCAGATCCCCCGACACGTTTAATTAATGCTTTCTCCGCC<br>GGAGATCGACGCACAGCGTTCTGTGCTCTATGATGTTATTTCTTAATAATCATCCA<br>GGTATTCTCTTTATCACCATACGTAGTGCGAGTGTCCACCTTAACGCAGGGCTTTC<br>CGTCACAGCGCGATATGTCAGCCAGCGGGGCTTTCTTTTGCCAGACCGCTTCCATC<br>CTCTGCATTTCAGCAATCTGGCTATACCCGTCATTCATAAACCACGTAAATGCCGT<br>CACGCAGGAAGCCAGGACGAAGAATATCGTCAGTACAAGATAAATCGCGGATTTCC<br>ACGTATAGCGTGACATCTCACGACGCATTTCATGGATCATCGCTTTCGCCGTATCG<br>GCAGCCTGATTCAGCGCTTCTGTCGCCGGTTTCTGCTGTGCTAATCCGGCTTGTTT<br>CAGTTCTTTCTCAACCTGAGTGAGCGCGGAACTCACCGATTTCCTGACGGTGTCAG<br>TCATATTACCGGACGCGCTGTCCAGCTCACGAATGACCCTGCTCAGCGTTTCACTT<br>TGCTGCTGTAATTGTGATGAGGCGGCCTGAAACTGTTCTGTCAGAGAAGTAACACG<br>CTTTTCCAGCGCCTGATGATGCCCGATAAGGGCGGCAATTTGTTTAATTTCGTCGC<br>TCATACAAAATCCTGCCTATCGTGAGAATGACCAGCCTTTATCCGGCTTCTGTCGT<br>ATCTGTTCGGCGAGTCGCTGTCGTTCTTTCTCCTGCTGACGCTGTTTTTCCGCCAG<br>ACGTTCGCGCTCTCTCTGCCTTTCCATCTCCTGATGTATCCCCTGGAACTCCGCCA<br>TCGCATCGTTAACAAGGGACTGAAGATCGATTTCTTCCTGTATATCCTTCATGGCA<br>TCACTGACCAGTGCGTTCAGCTTGTCAGGCTCTTTTTCAAAATCAAACGTTCTGCC<br>GGAATGGGATTCCTGCTCAGGCTCTGACTTCAGCTCCTGTTTTAGCGTCAGAGTAT<br>CCCTCTCGCTGAGGGCTTCCCGTAACGAGGTAGTCACGTCAATTACGCTGTCACGT<br>TCATCACGGGACTGCTGCACCTGCCTTTCAGCCTCCCTGCGCTCAAGAATGGCCTG<br>TAGCTGCTCAGTATCGAATCGCTGAACCTGACCCGCGCCCAGATGCCGCTCAGGCT<br>CACGGTCAATGCCCTGCGCCTTCAGGGAACGGGAATCAACCCGGTCAGCGTGCTGA<br>TACCGTTCAAGGTGCTTATTCTGGAGGTCAGCCCAGCGTTCCCTCTGGGCAACAAG<br>GTATTCTTTGCGTTCGGTCGGTGTTTCCCCGAAACGTGCCTTTTTTGCGCCACCGC<br>GCTCCGGCTCTTTGGTGTTAGCCCGTTTAAAATACTGCTCAGGGTCACGGTGAATA<br>CCGTCATTAATGCGTTCAGAGAACATGATATGGGCGTGGGGCTGCTCGCCACCGGC<br>TATCGCTGCTTTCGGATTATGGATAGCGAACTGATAGGCATGGCGGTCGCCAATTT<br>CCTGTTGGACAAAATCGCGGACAAGCTCAAGACGTTGTTCGGGTTTTAACTCACGC<br>GGCAGGGCAATCTCGATTTCACGGTAGGTACAGCCGTTGGCACGTTCAGACGTGTC<br>AGCGGCTTTCCAGAACTCGGACGGTTTATGCGCTGCCCACGCCGGCATATTGCCGG<br>ACTCCTTGTGCTCAAGGTCGGAGTCTTTTTCACGGGCATACTTTCCCTCACGCGCA<br>ATATAATCGGCATGAGGAGAGGCACTGCCTTTTCCGCCGGTTTTTACGCTGAGATG<br>ATAGGATGCCATCGTGTTTTATCCCGCTGAAGGCGCGCACCGTTTCTGAACGAAGT<br>GAAGAAACGTCTAAGTGCGCCCTGATAAATAAAGAGTTATCAGGGATTGTAGTGG<br>GATTTGACCTCCTCTGCCATCACTGAGCATAATCATTCCGTTAGCATTCAGGAGGT<br>AAACAGCATGAATAAAAGCGAAAAACAGGAACAATGGGCAGCAGAAAGAGTGCAGT<br>ATATTCGCGGCTTAAAGTCGCCGAATGAGCAACAGAAACTTATGCTGATACTGACG<br>GATAAAGCAGATAAAACAGCACAGGATATCAAAACGCTGTCCCTGCTGATGAAGGC<br>TGAACAGGCAGCAGAGAAAGCGCAGGAAGCCAGAGCGAAAGTCATGAACCTGATAC<br>AGGCAGAAAAGCGAGCCGAAGCCAGAGCCGCCCGTAAAGCCCGTGACCATGCTCTG<br>TACCAGTCTGCCGGATTGCTTATCCTGGCGGGTCTGGTTGACAGTAAGACGGGTAA<br>GCCTGTTGATGATACCGCTGCCTTACTGGGTGCATTAGCCAGTCTGAATGACCTGT<br>CACGGGATAATCCGAAGTGGTCAGACTGGAAAATCAGAGGGCAGGAACTGCTGAAC<br>AGCAAAAAGTCAGATAGCACCACATAGCAGACCCGCCATAAAACGCCCTGAGAAGC<br>CCGTGACGGGCTTTTCTTGTATTATGGGTAGTTTCCTTGCATGAATCCATAAAAGG<br>CGCCTGTAGTGCCATTTACCCCCATTCACTGCCAGAGCCGTGAGCGCAGCGAACTG<br>AATGTCACGAAAAAGACAGCGACTCAGGTGCCTGATGGTCGGAGACAAAAGGAATA<br>TTCAGCGATTTGCCCGAGCTTGCGAGGGTGCTACTTAAGCCTTTAGGGTTTTAAGG<br>TCTGTTTTGTAGAGGAGCAAACAGCGTTTGCGACATCCTTTTGTAATACTGCGGAA<br>CTGACTAAAGTAGTGAGTTATACACAGGGCTGGGATCTATTCTTTTTATCTTTTTT<br>TATTCTTTCTTTATTCTATAAATTATAACCACTTGAATATAAACAAAAAAAACACA<br>CAAAGGTCTAGCGGAATTTACAGAGGGTCTAGCAGAATTTACAAGTTTTCCAGCAA<br>AGGTCTAGCAGAATTTACAGATACCCACAACTCAAAGGAAAAGGACTAGTAATTAT<br>CATTGACTAGCCCATCTCAATTGGTATAGTGATTAAAATCACCTAGACCAATTGAG<br>ATGTATGTCTGAATTAGTTGTTTTCAAAGCAAATGAACTAGCGATTAGTCGCTATG<br>ACTTAACGGAGCATGAAACCAAGCTAATTTTATGCTGTGTGGCACTACTCAACCCC<br>ACGATTGAAAACCCTACAAGGAAAGAACGGACGGTATCGTTCACTTATAACCAATA<br>CGCTCAGATGATGAACATCAGTAGGGAAAATGCTTATGGTGTATTAGCTAAAGCAA<br>CCAGAGAGCTGATGACGAGAACTGTGGAAATCAGGAATCCTTTGGTTAAAGGCTTT<br>GAGATTTTCCAGTGGACAAACTATGCCAAGTTCTCAAGCGAAAATTAGAATTAGT<br>TTTTAGTGAAGAGATATTGCCTTATCTTTTCCAGTTAAAAAAATTCATAAAATATA<br>ATCTGGAACATGTTAAGTCTTTTGAAAACAAATACTCTATGAGGATTTATGAGTGG<br>TTATTAAAAGAACTAACACAAAAGAAAACTCACAAGGCAAATATAGAGATTAGCCT | DNA sequence pCas634 |

SEQUENCE LISTING

| SEQ ID NO | Sequence | Description |
|---|---|---|
| | TGATGAATTTAAGTTCATGTTAATGCTTGAAAATAACTACCATGAGTTTAAAAGGC | |
| | TTAACCAATGGGTTTTGAAACCAATAAGTAAAGATTTAAACACTTACAGCAATATG | |
| | AAATTGGTGGTTGATAAGCGAGGCCGCCCGACTGATACGTTGATTTTCCAAGTTGA | |
| | ACTAGATAGACAAATGGATCTCGTAACCGAACTTGAGAACAACCAGATAAAAATGA | |
| | ATGGTGACAAAATACCAACAACCATTACATCAGATTCCTACCTACATAACGGACTA | |
| | AGAAAAACACTACACGATGCTTTAACTGCAAAAATTCAGCTCACCAGTTTTGAGGC | |
| | AAAATTTTTGAGTGACATGCAAAGTAAGTATGATCTCAATGGTTCGTTCTCATGGC | |
| | TCACGCAAAAACAACGAACCACACTAGAGAACATACTGGCTAAATACGGAAGGATC | |
| | TGAGGTTCTTATGGCTCTTGTATCTATCAGTGAAGCATCAAGACTAACAAACAAAA | |
| | GTAGAACAACTGTTCACCGTTACATATCAAAGGGAAAACTGTCCATATGCACAGAT | |
| | GAAAACGGTGTAAAAAAGATAGATACATCAGAGCTTTTACGAGTTTTTGGTGCATT | |
| | CAAAGCTGTTCACCATGAACAGATCGACAATGTAACAGATGAACAGCATGTAACAC | |
| | CTAATAGAACAGGTGAAACCAGTAAAACAAAGCAACTAGAACATGAAATTGAACAC | |
| | CTGAGACAACTTGTTACAGCTCAACAGTCACACATAGACAGCCTGAAACAGGCGAT | |
| | TGCTGCTTACGAATCAAAGCTGCCGACAACACGGGAGCCAGTGACGCCTCCCGTGG | |
| | GGAAAAAATCATGGCAATTCTGGAAGAAATAGCGCTTTCAGCCGGCAAACCGGCTG | |
| | AAGCCGGATCTGCGATTCTGATAACAAACTAGCAACACCAGAACAGCCCGTTTGCG | |
| | GGCAGCAAAACCCGTACTTTTGGACGTTCCGGCGGTTTTTTGTGGCGAGTGGTGTT | |
| | CGGGCGGTGCGCGCAAGATCCATTATGTTAAACGGGCGAGTTTACATCTCAAAACC | |
| | GCCCGCTTAACACCATCAGAAATCCTCAGCGCGATTTTAAGCACCAACCCCCCCCC | |
| | GTAACACCCAAATCCATACTGAAAGTGGCTTTGTTGAATAAATCGAACTTTTGCTG | |
| | AGTTGAAGGATCAGATCACGCATCCTCCCGACAACACAGACCATTCCGTGGCAAAG | |
| | CAAAAGTTCAGAATCACCAACTGGTCCACCTACAACAAAGCTCTCATCAACCGTGG | |
| | CTCCCTCACTTTCTGGCTGGATGATGAGGCGATTCAGGCCTGGTATGAGTCGGCAA | |
| | CACCTTCATCACGAGGAAGGCCCCAGCGCTATTCTGATCTCGCCATCACCACCGTT | |
| | CTGGTGATTAAACGCGTATTCCGGCTGACCCTGCGGGCTGCGCAGGGTTTTATTGA | |
| | TTCCATTTTTGCCCTGATGAACGTTCCGTTGCGCTGCCCGGATTACACCAGTGTCA | |
| | GTAAGCGGGCAAAGTCGGTTAATGTCAGTTTCAAAACGTCCACCCGGGGTGAAATC | |
| | GCACACCTGGTGATTGATTCCACCGGGCTGAAGGTCTTTGGTCAAGGCGAATGGAA | |
| | AGTCAGAAAGCACGGCAAAGAGCGCCGTCGTATCTGGCGAAAGTTGCATCTTGCTG | |
| | TTGACAGCAACACACATGAAGTTGTCTGTGCAGACCTGTCGCTGAATAACGTCACG | |
| | GACTCAGAAGCCTTCCCGGGCCTTATCCGGCAGACTCACAGAAAAATCAGGGCAGC | |
| | CGCGGCAGACGGGGCTTACGATACCCGGCTCTGTCACGATGAACTGCGCCGCAAAA | |
| | AAATCAGCGCGCTTATTCCTCCCCGAAAAGGTGCGGGTTACTGGCCCGGTGAATAT | |
| | GCAGACCGTAACCGTGCAGTGGCTAATCAGCGAATGACCGGGAGTAATGCGCGGTG | |
| | GAAATGGACAACAGATTACAACCGTCGCTCGATAGCGGAACGGCGATGTACCGGG | |
| | TAAAACAGCTGTTCGGGGGTTCACTGACGCTGCGTGACTACGATGGTCAGGTTGCG | |
| | GAGGCTATGGCCCTGGTACGAGCGCTGAACAAAATGACGAAAGCAGGTATGCCTGA | |
| | AAGCGTGCGTATTGCCTGAAAACACAACCCGCTACGGGGGAGACTTACCCGAAATC | |
| | TGATTTATTCAACAAAGCCGGGTGTGGTGAACTACAAAGCAGACCCGTTGAGGTTA | |
| | TCAGTTCGATGCACAATCAGCAGCGCATAAAATATGCACAAGACAGGAGCACCCT | |
| | TCGCATTAAGCTGTGGTGGTAACAAGTAGTGCCGGGCTACCATCAGCGAGCATGAT | |
| | GCGCTCCCACAGCATTCGCCTTGGCAGTATGGAAGTTCCTCGCTCCAGTTCGGGCC | |
| | GGTATCCACCTCGAGCTTTCTACGGGGTCTGACGCTCAGTGGAACGAAAACTCACG | |
| | TTAAGGGATTTTGGTCATGAGATTATCAAAAAGGATCTTCACCTAGATCCTTTTCG | |
| | ACCGAATAAATACCTGTGACGGAAGATCACTTCGCAGAATAAATAAATCCTGGTGT | |
| | CCCTGTTGATACCGGGAAGCCCTGGGCCAACTTTTGGCGAAAATGAGACGTTGATC | |
| | GGCACGTAAGAGGTTCCAACTTTCACCATAATGAAATAAGATCACTACCGGGCGTA | |
| | TTTTTTGAGTTGTCGAGATTTTCAGGAGCTAAGGAAGCTAAAATGGAGAAAAAAAT | |
| | CACTGGATATACCACCGTTGATATATCCCAATGGCATCGTAAAGAACATTTTGAGG | |
| | CATTTCAGTCAGTTGCTCAATGTACCTATAACCAGACCGTTCAGCTGGATATTACG | |
| | GCCTTTTTAAAGACCGTAAAGAAAAATAAGCACAAGTTTTATCCGGCCTTTATTCA | |
| | CATTCTTGCCCGCCTGATGAATGCTCATCCGGAATTACGTATGGCAATGAAAGACG | |
| | GTGAGCTGGTGATATGGGATAGTGTTCACCCTTGTTACACCGTTTTCCATGAGCAA | |
| | ACTGAAACGTTTTCATCGCTCTGGAGTGAATACCACGACGATTTCCGGCAGTTTCT | |
| | ACACATATATTCGCAAGATGTGGCGTGTTACGGTGAAAACCTGGCCTATTTCCCTA | |
| | AAGGGTTTATTGAGAATATGTTTTTCGTCTCAGCCAATCCCTGGGTGAGTTTCACC | |
| | AGTTTTGATTTAAACGTGGCCAATATGGACAACTTCTTCGCCCCCGTTTTCACCTT | |
| | GGGCAAATATTATACGCAAGGCGACAAGGTGCTGATGCCGCTGGCGATTCAGGTTC | |
| | ATCATGCCGTTTGTGATGGCTTCCATGTCGGCAGAATGCTTAATGAATTACAACAG | |
| | TACTGCGATGAGTGGCAGGGCGGGGCGTAATTTTTTTAAGGCAGTTATTGGTGCCC | |
| | TTAAACGCCTGGTTGCTACGCCTGAATAAGTGATAATAAGCGGATGAATGGCAGAA | |
| | ATTCGAAAGCAAATTCGACCCGGTCGTCGGTTCAGGGCAGGGTCGTTAAATAGCCG | |
| | CTTATGTCTATTGCTGGTTTACCGGATTATTGACTACCGGAAGCAGTGTGACCGTG | |
| | TGCTTCTCAAATGCCTGAGGATCAAAAGTGCTCCATGGAATTATGACAACTTGACG | |
| | GCTACATCATTCACTTTTTCTTCACAACCGGCACGGAACTCGCTCGGGCTGGCCCC | |
| | GGTGCATTTTTAAATACCCGCGAGAAATAGAGTTGATCGTCAAAACCAACATTGC | |
| | GACCGACGGTGGCGATAGGCATCGGGTGGTGCTCAAAAGCAGCTTCGCCTGGCTG | |
| | ATACGTTGGTCCTCGCGCCAGCTTAAGACGCTAATCCCTAACTGCTGGCGGAAAAG | |
| | ATGTGACAGACGCGACGGCGACAAGCAAACATGCTGTGCGACGCTGGCGATATCAA | |
| | AATTGCTGTCTGCCAGGTGATCGCTGATGTACTGACAAGCCTCGCGTACCCGATTA | |
| | TCCATCGGTGGATGGAGCGACTCGTTAATCGCTTCCATGCGCCGCAGTAACAATTG | |
| | CTCAAGCAGATTTATCGCCAGCAGCTCCGAATAGCGCCCTTCCCCTTGCCCGGCGT | |

| SEQ ID NO | Sequence | Description |
|---|---|---|
| | TAATGATTTGCCCAAACAGGTCGCTGAAATGCGGCTGGTGCGCTTCATCCGGGCGA<br>AAGAACCCCGTATTGGCAAATATTGACGGCCAGTTAAGCCATTCATGCCAGTAGGC<br>GCGCGGACGAAAGTAAACCCACTGGTGATACCATTCGCGAGCCTCCGGATGACGAC<br>CGTAGTGATGAATCTCTCCTGGCGGGAACAGCAAAATATCACCCGGTCGGCAAACA<br>AATTCTCGTCCCTGATTTTTCACCACCCCTGACCGCGAATGGTGAGATTGAGAAT<br>ATAACCTTTCATTCCCAGCGGTCGGTCGATAAAAAAATCGAGATAACCGTTGGCCT<br>CAATCGGCGTTAAACCCGCCACCAGATGGGCATTAAACGAGTATCCCGGCAGCAGG<br>GGATCATTTTGCGCTTCAGCCATACTTTTCATACTCCCGCCATTCAGAGAAGAAAC<br>CAATTGTCCATATTGCATCAGACATTGCCGTCACTGCGTCTTTTACTGGCTCTTCT<br>CGCTAACCAAACCGGAAACCCCGCTTATTAAAAGCATTCGTAACAAAGCGGGACC<br>AAAGCCATGACAAAAACGCGTAACAAAAGTGTCTATAATCACGGCAGAAAAGTCCA<br>CATTGATTATTTGCACGGCGTCACACTTTGCTATGCCATAGCATTTTTATCCATAA<br>GATTAGCGGATCCTACCTGACGCTTTTTATCGCAACTCTCTACTGTCGTGCGCAAC<br>GCGTGACATCGACTAGGAGGCCTTTCTATGCAGTTCAAAGTGTATACCTATAAACG<br>CGAAAGCCGTTATCGTCTGTTTGTTGATGTTCAGAGCGATATTATTGATACACCGG<br>GTCGTCGTATGGTTATTCCGCTGGCAAGCGCACGTCTGCTGAGCGATAAAGTTAGC<br>CGTGAACTGTATCCGGTTGTTCATATTGGTGATGAAAGCTGGCGTATGATGACCAC<br>CGATATGGCAAGCGTTCCGGTTAGCGTTATTGGTGAAGAAGTTGCAGATCTGAGCC<br>ATCGTGAAAACGATATCAAAAATGCCATCAACCTGATGTTTGGGGCATCTTATAG<br>GACCCCCTCCACCCCGCCTCGCGGGCAGTTTGCCTGGCGGCAGTAGCGCGGTGGTC<br>CCACCTGACCCCATGCCGAACTCAGAAGTGAAACGCCGTAGCGCCGATGGTAGTGT<br>GGGCTCTCCCCATGCCGAGAGTAGGGAACTGCCAGGCATCAAATAAAACGAAAGGCT<br>CAGTCGAAAGACTGGGCCTTA | |
| 26 | TCTGATTTATAATGTGAAAATTCGCGGTGTGAACT | VEGFA-PAMS-forward primer |
| 27 | AGCGCCACGCTTCCCGAAGGGAGAAAGGCGGACAGG | VEGFA-PAMS-reverse primer |
| 28 | CATGGTGCATCTGACTCCTG | ddCPR R01 forward primer |
| 29 | GGTAGACCACCAGCAGCCTA | ddCPR R01 reverse primer |
| 30 | AGGAGAAGTCTGCCGTTACTGCCCT | ddPCR NHEJ Insensitive Probe FAM labelled |
| 31 | TGAAGTTGGTGGTGAGGCCCT | ddPCR NHEJ sensitive Probe HEX labelled |
| 32 | GAGACGCAGGAAGAGATCCA | HBB PCR forward primer for T7E1 assay |
| 33 | TTAGGGTTGCCCATAACAGC | HBB PCR reverse primer for T7E1 assay |
| 34 | GACCCCCTCCACCCCGCCTCNNNNNNN<br>"PAM-Library Variable element for PAM identification Sequence, "n" in positions 21 . . 27 represent the variable (randomized) region in the sequence" | PAM-Library Variable element for PAM identification |
| 35 | MNQKFILGLDIGITSVGYGLIDYETKNIIDAGVRLFPEANVENNEGRRSKRGSRRL<br>KRRRIHRLERVKKLLEDYNLLDQSQIPQSTNPYAIRVKGLSEALSKDELVIALLHI<br>AKRRGIHKIDVIDSNDDVGNELSTKEQLNKNSKLLKDKFVCQIQLERMNEGQVRGE<br>KNRFKTADIIKEIIQLLNVQKNFHQLDENFINKYIELVEMRREYFEGPGKGSPYGW<br>EGDPKAWYETLMGHCTYFPDELRSVKYAYSADLFNALNDLNNLVIQRDGLSKLEYH<br>EKYHIIENVFKQKKKPTLKQIANEINVNPEDIKGYRITKSGKPQFTEFKLYHDLKS<br>VLFDQSILENEDVLDQIAEILTIYQDKDSIKSKLTELDILLNEEDKENIAQLTGYT<br>GTHRLSLKCIRLVLEEQWYSSRNQMEIFTHLNIKPKKINLTAANKIPKAMIDEFIL<br>SPWKRTFGQAINLINKIIEKYGVPEDIIIELARENNSKDKQKFINEMQKKNENTRK<br>RINEIIGKYGNQNAKRLVEKIRLHDEQEGKCLYSLESIPLEDLLNNPNHYEVDHII<br>PRSVSFDNSYHNKVLVKQSENSKKSNLTPYQYFNSGKSKLSYNQFKQHILNLSKSQ<br>DRISKKKKEYLLEERDINKFEVQKEFINRNLVDTRYATRELTNYLKAYFSANNMNV<br>KVKTINGSFTDYLRKVWKFKKERNHGYKHHAEDALIIANADFLFKENKKLKAVNSV<br>LEKPEIESKQLDIQVDSEDNYSEMFIIPKQVQDIKDFRNFKYSHRVDKKPNRQLIN<br>DTLYSTRKKDNSTYIVQTIKDIYAKDNTTLKKQFDKSPEKFLMYQHDPRTFEKLEV<br>IMKQYANEKNPLAKYHEETGEYLTKYSKKNNGPIVKSLKYIGNKLGSHLDVTHQFK<br>SSTKKLVKLSIKPYRFDVYLTDKGYKFITISYLDVLKKDNYYYIPEQKYDKLKLGK | *Staphylococcus lugdunensis* CRISPR Cas9 protein sequence according to https://www.ncbi.nlm.nih.gov/protein/WP_002460848.1?report=genbank&log$=protalign&blast_rank=1&RID=0Z7T5FGN015, accessed on 2018-12-11 |

SEQUENCE LISTING

| SEQ ID NO | Sequence | Description |
|---|---|---|
| | AIDKNAKFIASFYKNDLIKLDGEIYKIIGVNSDTRNMIELDLPDIRYKEYCELNNI KGEPRIKKTIGKKVNSIEKLTTDVLGNVFTNTQYTKPQLLFKRGNGG | |
| 36 | ACGGACAGACAGACAGACACC | SPRJ1688 |
| 37 | AGAACAGCCCAGAAGTTGGAC | SPRJ1689 |
| 38 | AGCCCCAGCTACCACCTCCTCC | SPRJ1695 |
| 39 | TCCACCCCGCCTCCGGGCGC | SPRJ1699 |
| 40 | CATGGTGCATCTGACTCCTG | SPRJ1720 |
| 41 | GGTAGACCACCAGCAGCCTA | SPRJ1721 |
| 42 | AGGAGAAGTCTGCCGTTACTGCCCT | SPRJ1725 |
| 43 | TGAAGTTGGTGGTGAGGCCCT | SPRJ1728 |
| 44 | ATGAACCAAAAGTTCATTCTGGGGCTCGATATCGGCATCACCTCCGTGGGATATGG TCTGATCGACTACGAGACTAAGAACATCATCGACGCTGGAGTGCGACTGTTCCCGG AAGCGAACGTGGAGAACAACGAAGGCCGCAGATCCAAGCGCGGGTCCAGAAGGCTC AAGAGGCGGAGGATCCATAGACTCGAAAGAGTGAAGAAGCTCCTTGAAGATTACAA TCTGTTGGACCAGAGCCAGATTCCCCAAAGCACCAACCCGTACGCCATCAGAGTGA AGGGCCTGTCCGAAGCCCTGTCGAAAGATGAACTGGTCATTGCCCTGCTGCATATT GCCAAACGGCGCGGAATCCATAAGATCGACGTGATAGACTCCAACGATGACGTGGG CAACGAACTGTCAACCAAGGAGCAGCTGAACAAGAACTCGAAACTGCTGAAGGACA AGTTCGTCTGCCAAATTCAACTGGAACGGATGAACGAGGGACAAGTCAGGGGAGAG AAAAAACCGGTTCAAGACCGCGGACATCATCAAGGAGATCATCCAACTCCTGAATGT GCAGAAGAACTTTCACCAGCTGGATGAAAACTTCATTAACAAGTACATTGAACTGG TGGAAATGCGGAGGGAGTACTTCGAGGGACCTGGAAAGGGATCCCCTTACGGCTGG GAAGGGGACCCCAAGGCTTGGTACGAAACGCTCATGGGCCATTGCACTTACTTTCC GGACGAACTCCGGTCCGTGAAGTACGCATACTCTGCCGATCTGTTCAATGCACTCA ACGACCTTAACAACTTGGTGATCCAGCGCGATGGCCTGTCCAAGTTGGAATACCAC GAAAAGTATCACATCATCGAGAACGTGTTCAAGCAGAAAAAGAAGCCAACTCTGAA GCAGATTGCCAACGAAATTAACGTGAACCCCGAGGATATCAAGGGATACCGGATCA CTAAGTCCGGCAAACCACAGTTCACCGAGTTCAAGCTGTACCACGATCTGAAGTCG GTGCTCTTTGACCAGTCCATCCTGGAAAACGAAGATGTGCTGGACCAGATTGCTGA GATCCTGACCATCTACCAGGACAAGGACTCGATTAAGAGCAAGCTCACGGAGCTGG ACATTCTGCTGAACGAAGAGGATAAGGAGAACATCGCGCAGCTCACTGGTTACACC GGTACCCACCGCTTGTCCCTTAAGTGCATCCGGCTGGTCCTCGAGGAACAATGGTA CTCCAGCCGGAACCAGATGGAGATCTTCACGCACTTGAACATCAAGCCGAAGAAGA TTAACCTGACCGCTGCGAACAAGATACCCAAGGCCATGATCGACGAGTTTATCCTC TCACCGGTGGTCAAGCGCACCTTCGGACAAGCCATCAACCTCATCAACAAGATTAT CGAGAAGTACGGCGTGCCTGAGGATATCATCATCGAGCTGGCTCGGGAGAACAACT CAAAGGATAAGCAGAAGTTCATTAACGAGATGCAGAAAAAGAACGAGAACACTCGC AAGCGGATTAATGAGATCATCGGTAAATACGGGAACCAGAACGCCAAGCGGCTTGT GGAAAAGATTCGGCTCCACGACGAGCAGGAGGGAAAGTGTCTGTACTCGCTGGAGA GCATTCCCCTGGAGGACCTCCTGAACAACCCAAACCACTACGAAGTGGATCACATA ATCCCCCGCAGCGTGTCATTCGACAATTCCTACCATAACAAGGTCCTCGTGAAGCA GTCCGAGAATAGCAAGAAGTCCAACCTGACTCCGTACCAGTACTTCAACTCCGGCA AATCCAAGCTGTCCTACAACCAGTTCAAACAGCACATCCTCAACCTGTCAAAGAGC CAGGACAGGATCTCGAAGAAGAAGAAGGAATACCTTCTCGAGGAACGGGATATCAA TAAGTTCGAGGTGCAGAAGGAGTTTATCAATAGAAACCTGGTGGACACTCGCTATG CCACCCGCGAACTGACCAACTACCTGAAGGCGTACTTCTCCGCCAACAACATGAAC GTGAAGGTCAAAACTATTAACGGCAGCTTCACCGACTATCTGCGCAAGGTCTGGAA GTTCAAGAAGGAACGCAACCACGGTTACAAGCACCACGCGGAAGATGCGCTGATTA TCGCCAACGCTGACTTCCTGTTCAAGGAAAACAAGAAGCTCAAGGCCGTGAACTCA GTGCTCGAGAAGCCTGAAATCGAGACTAAGCAGCTGGACATCCAGGTCGATTCGGA AGATAACTACTCCGAAATGTTCATCATCCCTAAGCAAGTGCAGGACATCAAGGACT TCAGGAATTTCAAGTACAGCCATCGCGTGGACAAGAAGCCAAACAGACAGCTGATC AACGATACACTGTATTCCACCCGGAAGAAGGACAACTCCACCTACATCGTCCAAAC CATTAAGGACATCTACGCAAAGGACAACACCACGCTTAAGAAGCAGTTCGACAAGA GCCCCGAAAAGTTCCTCATGTACCAGCACGACCCCAGAACCTTCGAGAAGCTTGAA GTGATCATGAAGCAGTACGCCAACGAAAAGAACCCACTGGCTAAGTACCACGAGGA AACCGGCGAATACCTGACCAAGTACTCCAAAAAGAACAACGGACCGATCGTCAAGT CCCTGAAGTACATTGGGAACAAGCTCGGCTCGCACCTCGATGTGACCCACCAGTTC AAGTCCTCGACCAAAAAGCTCGTGAAGCTGTCCATCAAGCCGTACCGGTTCGACGT GTACCTGACTGACAAGGGATATAAGTTCATCACCATTTCCTACCTCGACGTGTTGA AGAAGGATAACTACTACTACATTCCGGAACAGAAGTACGACAAGCTCAAGCTCGGA AAGGCCATCGACAAAAATGCGAAGTTCATCGCGAGCTTCTACAAGAATGACTTGAT CAAGCTGGATGGCGAAATCTACAAGATCATCGGGGTCAACTCCGATACCCGCAACA TGATTGAGCTGGATCTGCCCGACATTCGGTACAAGGAATACTGCGAGCTGAACAAC | Codon-optimized SluCas9 polynucleotide 1 |

| SEQ ID NO | Sequence | Description |
|---|---|---|
| | ATCAAGGGAGAACCGCGGATCAAGAAAACCATCGGAAAGAAAGTGAACAGCATCGA GAAACTGACTACTGACGTCCTGGGAAACGTGTTCACCAACACACAATACACCAAAC CCCAGCTGCTGTTTAAGCGCGGGAAC | |
| 45 | ATGAACCAGAAGTTCATCCTGGGCCTCGACATCGGCATCACCTCTGTTGGCTACGG CCTGATCGACTACGAGACAAAGAACATCATCGATGCCGGCGTGCGGCTGTTCCCTG AGGCCAACGTGGAAAACAACGAGGGCCGCAGAAGCAAGAGAGGCAGCAGAAGGCTG AAGCGGCGGAGAATCCACCGGCTGGAAAGAGTGAAGAAGCTGCTCGAGGACTACAA CCTGCTGGACCAGTCTCAGATCCCTCAGAGCACAAACCCCTACGCCATCAGAGTGA AGGGCCTGTCTGAGGCCCTGAGCAAGGACGAGCTGGTTATCGCCCTGCTGCACATT GCCAAGCGGAGAGGCATCCACAAGATCGACGTGATCGACAGCAACGACGACGTGGG CAATGAGCTGAGCACCAAAGAGCAGCTGAACAAGAACAGCAGCGTGCTGAAGGACA AGTTCGTGTGCCAGATTCAGCTGGAACGGATGAATGAGGGCCAAGTGCGGGGCGAG AAGAACAGATTCAAGACCGCCGACATCATCAAAGAGATCATCCAGCTGCTCAACGT GCAGAAGAACTTCCACCAGCTGGACGAGAACTTCATCAACAAGTACATCGAGCTGG TCGAGATGCGGCGCGAGTACTTTGAAGGCCCTGGAAAGGGCAGCCCTTATGGCTGG GAAGGCGATCCCAAGGCTTGGTACGAGACACTGATGGGCCACTGCACCTACTTTCC CGACGAGCTGAGAAGCGTGAAGTACGCCTACAGCGCCGACCTGTTCAACGCCCTGA ACGACCTGAACAACCTCGTGATCCAGAGAGATGGCCTGTCCAAGCTGGAATACCAC GAGAAGTACCACATCATTGAGAACGTGTTCAAGCAGAAGAAGAAGCCCACACTGAA GCAGATCGCCAACGAGATCAACGTGAACCCCGAGGACATCAAGGGCTACAGAATCA CCAAGAGCGGCAAGCCCCAGTTCACCGAGTTCAAGCTGTACCACGATCTGAAGTCC GGTGCTGTTCGACCAGAGCATCCTGGAAAACGAGACGTGCTGGATCAGATCGCCGA GATCCTGACCATCTACCAGGACAAGGACAGCATCAAGAGCAAGCTGACCGAGCTGG ACATCCTGCTGAACGAAGAGGACAAAGAGAATATCGCCCAGCTGACCGGCTACACC GGCACACATAGACTGAGCCTGAAGTGCATCCGGCTGGTGCTGGAAGAACAGTGGTA CTCCAGCCGGAACCAGATGGAAATCTTCACCCACCTGAACATCAAGCCCAAGAAGA TCAACCTGACCGCCGCCAACAAGATCCCCAAGGCCATGATCGACGAGTTCATTCTG AGCCCCGTGGTCAAGAGAACCTTCGGCCAGGCCATCAATCTGATCAACAAGATTAT CGAGAAGTATGGCGTGCCCGAGGATATCATCATCGAACTGGCCAGAGAGAACAACA GCAAGGACAAGCAAAAGTTCATCAACGAGATGCAGAAAAAGAACGAGAACACCCGG AAGCGGATCAACGAAATCATCGGGAAGTACGGCAACCAGAACGCCAAGAGACTGGT GGAAAAGATCCGGCTGCACGACGAGCAAGAGGGCAAGTGTCTGTACAGCCTGGAAT CTATCCCTCTCGAGGATCTGCTGAACAATCCCAACCACTACGAGGTGGACCACATT ATCCCCAGAAGCGTGTCCTTCGACAACAGCTACCACAACAAGGTGCTGGTCAAGCA GAGCGAGAACTCCAAGAAGTCCAATCTGACCCCTTACCAGTACTTCAACAGCGGCA AGTCTAAGCTGAGCTACAACCAGTTTAAGCAGCACATCCTGAACCTCAGCAAGAGC CAGGACCGGATCAGCAAGAAGAAGAAAGAGTACCTGCTCGAAGAGAGGGACATTAA CAAGTTCGAGGTGCAGAAAGAGTTTATCAACCGGAACCTGGTGGACACCAGATACG CCACCAGAGAGCTGACCAACTACCTGAAGGCCTACTTCAGCGCCAACAACATGAAC GTGAAAGTCAAGACCATCAACGGCAGCTTCACCGACTACCTGCGGAAAGTGTGGAA GTTTAAGAAAGAGCGGAACCACGGCTACAAGCACCACGCCGAAGATGCCCTGATTA TCGCCAATGCCGACTTCCTGTTCAAAGAGAACAAGAAACTGAAGGCCGTGAACAGC GTGCTGGAAAAGCCCGAGATCGAGACAAAACAGCTCGACATCCAGGTGGACAGCGA GGACAACTACAGCGAGATGTTCATCATCCCCAAACAGGTGCAGGATATCAAGGACT TCCGGAACTTCAAGTACAGCCACCGCGTGGACAAGAAGCCTAACCGGCAGCTGATC AATGACACCCTGTACAGCACCCGCAAGAAGGACAACAGCACCTACATCGTGCAGAC GATCAAGGACATCTACGCCAAGGACAATACGACCCTGAAGAAGCAGTTCGACAAGA GCCCCGAGAAGTTCCTGATGTACCAGCACGACCCCAGGACCTTCGAGAAGCTGGAA GTGATCATGAAGCAGTACGCTAATGAGAAGAACCCGCTGGCCAAGTACCACGAGGA AACCGGCGAGTACCTGACCAAGTACTCTAAGAAGAACAACGGCCCCATCGTGAAGT CCCTGAAGTATATCGGCAACAAGCTGGGCAGCCACCTGGACGTGACACACCAGTTC AAGAGCAGCACCAAGAAGCTGGTCAAACTGTCCATCAAGCCaTACCGCTTCGACGT GTACCTGACAGACAAGGGGTACAAGTTTATCACCATCAGCTACCTCGACGTGCTGA AGAAGGATAACTACTACTACATCCCCGAGCAGAAGTACGACAAGCTGAAGCTGGGA AAAGCCATCGACAAGAATGCCAAGTTCATTGCCAGCTTCTACAAGAACGACCTCAT CAAGCTGGACGGCGAGATCTACAAGATCATCGGCGTGAACTCCGACACACGGAACA TGATTGAGCTGGACCTGCCTGACATCCGGTACAAAGAGTACTGCGAACTGAACAAT ATCAAGGGCGAGCCCCGGATCAAAAAGACGATCGGCAAGAAAGTGAACAGCATTGA GAAGCTGACCACCGATGTGCTGGGCAATGTGTTCACCAACACACAGTACACCAAGC CTCAGCTGCTGTTCAAGCGGGGCAAT | Codon-optimized SluCas9 polynucleotide 2 |

The invention claimed is:

1. A composition comprising:
   (i) a SluCas9 polypeptide comprising amino acids 1-1056 of SEQ ID NO: 2, and
   (ii) a single-guide RNA (sgRNA) molecule comprising SEQ ID NO: 6 or 7,
   wherein the sgRNA molecule combines with the SluCas9 polypeptide to induce a single-stranded or double-stranded break in the genomic DNA molecule.

2. The composition of claim 1, wherein the SluCas9 polypeptide further comprises one or more nuclear localization signals (NLSs).

3. The composition of claim 1, wherein the SluCas9 polypeptide further comprises a C- or N-terminally attached polypeptide with a nucleobase editing activity or deaminase activity.

4. The composition of claim 1, wherein the SluCas9 polypeptide and the sgRNA molecule form a ribonucleoprotein (RNP).

5. The composition of claim 1, wherein the composition is a lipid nanoparticle composition.

\* \* \* \* \*

SEQUENCE LISTING

<160> NUMBER OF SEQ ID NOS: 45

<210> SEQ ID NO 1
<211> LENGTH: 3165
<212> TYPE: DNA

<213> ORGANISM: Staphylococcus lugdunensis
<220> FEATURE:
<221> NAME/KEY: misc_feature
<223> OTHER INFORMATION: ENAA40553A40553.1 Staphylococcus
    lugdunensis CRISPR-associated protein, Csn1 family

<400> SEQUENCE: 1

| | | | | | |
|---|---|---|---|---|---|
| atgaatcaaa | aatttatttt | aggtttagat | attggtatta | catctgttgg | atatggtctc | 60 |
| atagattatg | aaactaaaaa | tattatagac | gcaggtgtac | gtttgtttcc | tgaggctaat | 120 |
| gtagaaaata | acgagggccg | tcgaagtaaa | agaggttctc | gaagacttaa | gagaagaagg | 180 |
| atacatagat | tagaaagagt | gaaaaaatta | ttagaagact | ataatttatt | agatcaatca | 240 |
| caaattcctc | agtctactaa | tccttatgca | attcgagtta | aggggttaag | tgaagcttta | 300 |
| agtaaagatg | aattagtaat | tgctttgctc | catatagcta | aaagaagagg | tattcataaa | 360 |
| attgatgtga | ttgattcaaa | tgatgatgtt | ggtaatgagc | tatcgactaa | agagcagctg | 420 |
| aataaaaata | gtaaattgtt | aaagataag | tttgtctgtc | aaatacagct | agaaagaatg | 480 |
| aatgaaggtc | aagttagagg | agaaaaaaat | agatttaaaa | ctgcagacat | tataaaagaa | 540 |
| attattcagc | tattgaatgt | tcaaaaaaac | tttcatcaat | tagatgaaaa | tttcataaat | 600 |
| aaatatatag | aattagttga | gatgcgtaga | gagtattttg | agggtcctgg | taagggagt | 660 |
| ccatatggat | gggaaggaga | ccctaaggca | tggtatgaaa | ccttgatggg | acattgtact | 720 |
| tattttccag | atgaattaag | aagcgttaaa | tatgcttatt | ctgcggattt | atttaatgca | 780 |
| ttaaatgatt | taaataattt | agtaattcaa | agagatggat | tatcaaaatt | agaatatcat | 840 |
| gaaaagtatc | acattattga | aaatgtattt | aaacagaaaa | agaaaccgac | tttgaaacaa | 900 |
| attgcaaatg | aaatcaatgt | aaatccagaa | gacattaaag | gatatagaat | cactaaaagt | 960 |
| ggtaaaccac | aatttactga | gtttaaactt | tatcatgatt | taaaaagtgt | attatttgat | 1020 |
| caaagcattc | tagaaaatga | agatgtatta | gaccaaattg | cagaaatttt | aactatatat | 1080 |
| caagataaag | atagtattaa | aagtaaacta | acagaattag | atattttatt | gaatgaagaa | 1140 |
| gacaaggaaa | atattgctca | acttactggt | tatacaggta | cacatagact | ttctttaaaa | 1200 |
| tgtattcgtc | ttgtactgga | agagcaatgg | tattcttcta | gaaatcaaat | ggaaatattt | 1260 |
| actcatttaa | atatcaaacc | aaagaaaatt | aatttaacag | cagccaataa | aatacctaaa | 1320 |
| gctatgattg | acgaatttat | attatcccca | gtagtgaaaa | gaacctttgg | acaggcaatt | 1380 |
| aatcttataa | ataagattat | tgaaaaatac | ggcgttccag | aagatataat | tatcgaatta | 1440 |
| gcacgagaaa | ataatagtaa | agataaacaa | aaatttatta | tgaaatgca | aaagaaaaat | 1500 |
| gaaaatacac | gtaaacggat | taatgaaata | atagggaagt | atggaaatca | aaatgctaaa | 1560 |
| agattagttg | aaaaaattag | attacatgat | gaacaagaag | gtaaatgtttt | atactcatta | 1620 |
| gaatcaatac | cacttgagga | cttattaaat | aatccgaatc | attatgaagt | agaccatatt | 1680 |
| ataccaagat | ctgtttcatt | tgataattca | tatcataaca | agtattagt | aaaacaaagt | 1740 |
| gaaaatagta | aaaaaagcaa | tctaacgcct | tatcaatatt | ttaactctgg | aaaatcaaaa | 1800 |
| ctttcctata | atcaatttaa | acaacatatt | cttaatttaa | gtaaatcaca | agatagaatt | 1860 |
| tcaagaaaaa | agaagaata | cttattagaa | gaacgagata | ttaataagtt | tgaagtacaa | 1920 |
| aaagaattta | ttaatcgtaa | cttggtagat | actagatatg | ctacaagaga | gttaacaaac | 1980 |
| tatttaaaag | cctactttag | tgctaataac | atgaatgtaa | aagttaaaac | aattaatgga | 2040 |
| agctttactg | actatttaag | aaaagttttgg | aaatttaaaa | aagagcgtaa | tcatggatat | 2100 |
| aaacatcatg | ctgaagatgc | tctaataatt | gctaacgctg | attttctgtt | taagaaaaac | 2160 |

```
aaaaagctaa aagctgttaa tagtgtatta gaaaaaccag aaattgaaag taaacaatta      2220
gatatacaag ttgatagtga agataattat agtgaaatgt ttatcattcc taaacaagtt      2280
caggatatta aagactttag aaacttcaag tactcacata gagtagataa aaaaccgaat      2340
aggcaactaa tcaatgacac actttactcg actcgtaaaa aagataacag cacatatatt      2400
gttcaaacta taaaggatat atatgcaaaa gataatacga cgttaaagaa acaatttgat      2460 aaagtccag aaaagtttt aatgtatcaa catgatcctc gtacatttga aaagttagaa        2520
gttattatga agcaatacgc taatgaaaaa aatcctttgg ctaaatatca tgaagaaaca      2580
ggagaatatt taactaaata tagtaaaaaa aataatgggc ctatcgtaaa aagcttaaaa      2640
tatattggca ataaattggg aagtcattta gatgtgacac atcaatttaa aagttcaact      2700
aaaaaattag taaaattatc aattaaacct tatcgctttg atgtgtattt aacagataaa      2760
ggatataaat ttattaccat ttcatattta gatgtactta aaaaagataa ttattattat      2820
atcccagaac aaaatatga caagttaaaa ctaggaaaag cgattgataa aaatgctaaa      2880
tttattgcta gtttctataa aaatgatttg ataaaacttg atggagagat atataaaatt      2940
attggagtaa atagtgatac tagaaatatg attgaattag atttacctga tattagatat      3000
aaagaatact gtgagttgaa caatattaaa ggagaacctc gtattaaaaa aactataggt      3060
aagaaagtaa attctataga aaaattaact acgatgtat taggaaatgt ctttactaat       3120
actcaatata caaaaccaca actgttattt aagcgaggca attag                      3165
```

<210> SEQ ID NO 2
<211> LENGTH: 1056
<212> TYPE: PRT
<213> ORGANISM: Staphylococcus lugdunensis
<220> FEATURE:
<221> NAME/KEY: misc_feature
<223> OTHER INFORMATION: amino acid sequence of SEQ ID NO: 1

<400> SEQUENCE: 2

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
                20                  25                  30

Val Arg Leu Phe Pro Glu Ala Asn Val Glu Asn Asn Glu Gly Arg Arg
            35                  40                  45

Ser Lys Arg Gly Ser Arg Arg Leu Lys Arg Arg Ile His Arg Leu
        50                  55                  60

Glu Arg Val Lys Lys Leu Leu Glu Asp Tyr Asn Leu Leu Asp Gln Ser
65                  70                  75                  80

Gln Ile Pro Gln Ser Thr Asn Pro Tyr Ala Ile Arg Val Lys Gly Leu
                85                  90                  95

Ser Glu Ala Leu Ser Lys Asp Glu Leu Val Ile Ala Leu Leu His Ile
                100                 105                 110

Ala Lys Arg Arg Gly Ile His Lys Ile Asp Val Ile Asp Ser Asn Asp
            115                 120                 125

Asp Val Gly Asn Glu Leu Ser Thr Lys Glu Gln Leu Asn Lys Asn Ser
        130                 135                 140

Lys Leu Leu Lys Asp Lys Phe Val Cys Gln Ile Gln Leu Glu Arg Met
145                 150                 155                 160

Asn Glu Gly Gln Val Arg Gly Glu Lys Asn Arg Phe Lys Thr Ala Asp
                165                 170                 175

```
Ile Ile Lys Glu Ile Ile Gln Leu Leu Asn Val Gln Lys Asn Phe His
            180                 185                 190

Gln Leu Asp Glu Asn Phe Ile Asn Lys Tyr Ile Glu Leu Val Glu Met
            195                 200                 205

Arg Arg Glu Tyr Phe Glu Gly Pro Gly Lys Gly Ser Pro Tyr Gly Trp
            210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
            245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
            275                 280                 285

Val Phe Lys Gln Lys Lys Lys Pro Thr Leu Lys Gln Ile Ala Asn Glu
            290                 295                 300

Ile Asn Val Asn Pro Glu Asp Ile Lys Gly Tyr Arg Ile Thr Lys Ser
305                 310                 315                 320

Gly Lys Pro Gln Phe Thr Glu Phe Lys Leu Tyr His Asp Leu Lys Ser
            325                 330                 335

Val Leu Phe Asp Gln Ser Ile Leu Glu Asn Glu Asp Val Leu Asp Gln
            340                 345                 350

Ile Ala Glu Ile Leu Thr Ile Tyr Gln Asp Lys Asp Ser Ile Lys Ser
            355                 360                 365

Lys Leu Thr Glu Leu Asp Ile Leu Leu Asn Glu Glu Asp Lys Glu Asn
            370                 375                 380

Ile Ala Gln Leu Thr Gly Tyr Thr Gly Thr His Arg Leu Ser Leu Lys
385                 390                 395                 400

Cys Ile Arg Leu Val Leu Glu Glu Gln Trp Tyr Ser Ser Arg Asn Gln
            405                 410                 415

Met Glu Ile Phe Thr His Leu Asn Ile Lys Pro Lys Lys Ile Asn Leu
            420                 425                 430

Thr Ala Ala Asn Lys Ile Pro Lys Ala Met Ile Asp Glu Phe Ile Leu
            435                 440                 445

Ser Pro Val Val Lys Arg Thr Phe Gly Gln Ala Ile Asn Leu Ile Asn
450                 455                 460

Lys Ile Ile Glu Lys Tyr Gly Val Pro Glu Asp Ile Ile Ile Glu Leu
465                 470                 475                 480

Ala Arg Glu Asn Asn Ser Lys Asp Lys Gln Lys Phe Ile Asn Glu Met
            485                 490                 495

Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
            515                 520                 525

His Asp Glu Gln Glu Gly Lys Cys Leu Tyr Ser Leu Glu Ser Ile Pro
            530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
            565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
```

```
                595                 600                 605
    His Ile Leu Asn Leu Ser Lys Ser Gln Asp Arg Ile Ser Lys Lys Lys
        610                 615                 620
    Lys Glu Tyr Leu Leu Glu Glu Arg Asp Ile Asn Lys Phe Glu Val Gln
    625                 630                 635                 640
    Lys Glu Phe Ile Asn Arg Asn Leu Val Asp Thr Arg Tyr Ala Thr Arg
                    645                 650                 655
    Glu Leu Thr Asn Tyr Leu Lys Ala Tyr Phe Ser Ala Asn Asn Met Asn
                660                 665                 670
    Val Lys Val Lys Thr Ile Asn Gly Ser Phe Thr Asp Tyr Leu Arg Lys
            675                 680                 685
    Val Trp Lys Phe Lys Lys Glu Arg Asn His Gly Tyr Lys His His Ala
        690                 695                 700
    Glu Asp Ala Leu Ile Ile Ala Asn Ala Asp Phe Leu Phe Lys Glu Asn
    705                 710                 715                 720
    Lys Lys Leu Lys Ala Val Asn Ser Val Leu Glu Lys Pro Glu Ile Glu
                    725                 730                 735
    Ser Lys Gln Leu Asp Ile Gln Val Asp Ser Glu Asp Asn Tyr Ser Glu
                740                 745                 750
    Met Phe Ile Ile Pro Lys Gln Val Gln Asp Ile Lys Asp Phe Arg Asn
            755                 760                 765
    Phe Lys Tyr Ser His Arg Val Asp Lys Lys Pro Asn Arg Gln Leu Ile
        770                 775                 780
    Asn Asp Thr Leu Tyr Ser Thr Arg Lys Lys Asp Asn Ser Thr Tyr Ile
    785                 790                 795                 800
    Val Gln Thr Ile Lys Asp Ile Tyr Ala Lys Asp Asn Thr Thr Leu Lys
                    805                 810                 815
    Lys Gln Phe Asp Lys Ser Pro Glu Lys Phe Leu Met Tyr Gln His Asp
                820                 825                 830
    Pro Arg Thr Phe Glu Lys Leu Glu Val Ile Met Lys Gln Tyr Ala Asn
            835                 840                 845
    Glu Lys Asn Pro Leu Ala Lys Tyr His Glu Glu Thr Gly Glu Tyr Leu
        850                 855                 860
    Thr Lys Tyr Ser Lys Lys Asn Asn Gly Pro Ile Val Lys Ser Leu Lys
    865                 870                 875                 880
    Tyr Ile Gly Asn Lys Leu Gly Ser His Leu Asp Val Thr His Gln Phe
                    885                 890                 895
    Lys Ser Ser Thr Lys Lys Leu Val Lys Leu Ser Ile Lys Pro Tyr Arg
                900                 905                 910
    Phe Asp Val Tyr Leu Thr Asp Lys Gly Tyr Lys Phe Ile Thr Ile Ser
            915                 920                 925
    Tyr Leu Asp Val Leu Lys Lys Asp Asn Tyr Tyr Ile Pro Glu Gln
        930                 935                 940
    Lys Tyr Asp Lys Leu Lys Leu Gly Lys Ala Ile Asp Lys Asn Ala Lys
    945                 950                 955                 960
    Phe Ile Ala Ser Phe Tyr Lys Asn Asp Leu Ile Lys Leu Asp Gly Glu
                    965                 970                 975
    Ile Tyr Lys Ile Ile Gly Val Asn Ser Asp Thr Arg Asn Met Ile Glu
                980                 985                 990
    Leu Asp Leu Pro Asp Ile Arg Tyr  Lys Glu Tyr Cys Glu  Leu Asn Asn
            995                1000               1005
    Ile Lys  Gly Glu Pro Arg Ile  Lys Lys Thr Ile Gly  Lys Lys Val
        1010               1015               1020
```

```
Asn Ser Ile Glu Lys Leu Thr Thr Asp Val Leu Gly Asn Val Phe
    1025                1030                1035

Thr Asn Thr Gln Tyr Thr Lys Pro Gln Leu Leu Phe Lys Arg Gly
    1040                1045                1050

Asn Gly Gly
    1055

<210> SEQ ID NO 3
<211> LENGTH: 3315
<212> TYPE: DNA
<213> ORGANISM: artificial sequence
<220> FEATURE:
<223> OTHER INFORMATION: Synthetic polynucleotide
<220> FEATURE:
<221> NAME/KEY: misc_feature
<223> OTHER INFORMATION: SluCas9, optimized DNA sequence including
      nuclear localization signal

<400> SEQUENCE: 3
```

| | |
|---|---|
| atgaaacgtc cggcagcaac caaaaaagca ggtcaggcca agaaaaaaaa aggtggtggt | 60 |
| tcaggtaacc agaaatttat cctgggtctg gatattggta ttaccagcgt tggttatggc | 120 |
| ctgattgatt acgaaaccaa aaacattatt gatgccggtt tcgtctgtt tccggaagca | 180 |
| aatgttgaaa ataatgaagg tcgtcgtagc aaacgtggta ccgtcgtct gaaacgtcgt | 240 |
| cgtattcatc gtctgaaacg tgttaaaaaa ctgctggaag attataacct gctggatcag | 300 |
| agccagattc gcagagcac caatccgtat gcaattcgtg ttaaaggtct gagcgaagca | 360 |
| ctgagcaaag atgaactggt tattgcactg ctgcatattg caaaacgccg tggcattcat | 420 |
| aaaatcgatg tgattgatag caatgacgat gtgggtaatg aactgagcac caagaacag | 480 |
| ctgaacaaaa atagcaaact gctgaaagac aaattcgtgt gtcagattca gctggaacgt | 540 |
| atgaatgaag gccaggttcg tggtgaaaag aatcgcttta aaccgcaga catcatcaaa | 600 |
| gaaattatcc agctgctgaa cgtgcagaaa aacttccatc agctggatga aaacttcatc | 660 |
| aacaaataca tcgagctggt tgaaatgcgt cgcgaatatt ttgaaggtcc gggtaaaggt | 720 |
| agcccgtatg ttgggaagg tgatccgaaa gcatggtatg aaaccctgat gggtcattgt | 780 |
| acctattttc cggatgaact gcgtagcgtt aaatatgcct atagcgcaga cctgtttaat | 840 |
| gcactgaatg atctgaataa cctggtgatt cagcgtgatg gtctgagcaa actgaatat | 900 |
| catgagaaat atcacatcat cgaaaacgtg ttcaaacaga gaagaaacc gaccctgaaa | 960 |
| caaatcgcca cgaaattaa tgtgaacccg gaagatatta aggctaccg tattaccaaa | 1020 |
| agcggtaaac cgcagttcac cgaatttaaa ctgtatcacg atctgaaaag cgtgctgttt | 1080 |
| gatcagagca ttctggaaaa tgaagatgtg ctggaccaga ttgcagaaat tctgaccatt | 1140 |
| tatcaggaca agacagcat caaaagcaaa ctgaccgaac tggatattct gctgaatgaa | 1200 |
| gaagataaag agaacattgc acagctgacc ggttataccg caccatcg tctgagcctg | 1260 |
| aaatgtattc gtctggtact ggaagaacag tggtatagca ccgtaatca gatggaaatc | 1320 |
| tttacccatc tgaacattaa accgaagaaa atcaatctga ccgcagccaa caaaattccg | 1380 |
| aaagccatga ttgatgagtt tattctgagt ccggttgtga acgtaccctt tggtcaggca | 1440 |
| attaacctga tcaacaaaat cattgaaaaa tatggcgtgc ctgaggatat cattattgaa | 1500 |
| ctggcacgtg aaaacaacag caagataaa cagaaattca tcaacgagat gcagaagaag | 1560 |
| aacgaaaata cccgcaaacg gattaacgag atcattggca aatatggtaa tcagaatgcc | 1620 |
| aaacgcctgg tggaaaaaat tcgtctgcat gatgaacaag agggcaaatg tctgtatagc | 1680 |

```
ctggaaagca ttcctctgga agatctgctg aacaatccga atcattatga agtggatcac    1740
attattccgc gtagcgtgag ctttgataat tcctatcata ataaagtgct ggtgaaacag    1800
agcgaaaact ccaaaaaatc caacctgaca ccgtatcagt atttcaatag cggcaaatcc    1860
aaactgagct acaaccagtt taaacagcat attctgaacc tgagcaaaag ccaggatcgc    1920
atcagcaaga agaagaagga gtacctgctg aagaacgcg acatcaacaa atttgaagtg    1980
cagaaagaat ttatcaaccg caacctggtt gatacccgtt atgcacccg tgaactgacc     2040 aattatctga agcatattt cagcgccaac aacatgaacg tgaaagtgaa aacgattaac    2100
ggcagcttta ccgattatct gcgtaaagtg tggaaattca aaaagaacg caaccacggc     2160 tataaacatc atgccgaaga tgccctgatt attgcaaatg cagatttcct gtttaaagaa    2220
aacaaaaaac tgaaagccgt caacagcgtg ctggaaaaac cggaaattga caaaaacag     2280 ctggacattc aggttgatag cgaagataat tacagcgaaa tgtttatcat cccgaaacag    2340
gtgcaggata tcaaagattt tcgcaacttc aaatatagcc accgcgttga caaaaaacct    2400
aatcgtcagc tgattaacga taccctgtat agcacccgca aaaagataa cagcacctat     2460 attgtgcaga ccattaaaga catctacgcc aaagataata ccaccctgaa aaacagttc     2520 gacaaaagcc cagaaaaatt tctgatgtat cagcatgatc cgcgtacctt cgaaaaactg    2580
gaagttatta tgaaacagta tgccaacgag aaaaatccgc tggccaaata tcacgaagaa    2640
accggtgaat atctgaccaa atattccaag aagaacaacg gtccgatcgt taaatccctg    2700
aaatatatcg gtaataaact gggcagccat ctggatgtta cccatcagtt taaaagctcc    2760
acaaagaagc tggttaaact gtccatcaaa ccgtatcgct ttgatgtgta tctgaccgac    2820
aaaggctata aattcattac catcagctat ctggacgtgc tgaaaaaaga caactattat    2880
tatatcccgg aacagaaata tgataaactg aaactgggta agccatcga taaaaacgcc    2940 aaatttatcg ccagcttcta caaaaacgac ctgattaaac tggatggcga gatctataaa    3000
atcatcggtg ttaatagcga cacccgcaat atgattgagc tggatctgcc ggatattcgc    3060 tataagaat attgcgaact gaacaacatt aaaggcgaac gcgtatcaa aaagaccatc     3120 ggcaaaaaag tgaatagcat cgagaaactg accaccgatg ttctgggtaa tgtgtttacc    3180
aatacccagt ataccaaacc tcagctgctg ttcaaacgcg gtaatggcgg aggatctggc    3240 cccctaaga aaagcggaa ggtgggtgga agcggaggca gcggggatc aggccatcat     3300 catcaccatc attaa                                                     3315
```

<210> SEQ ID NO 4
<211> LENGTH: 1104
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: amino acid sequence of SEQ ID NO: 3

<400> SEQUENCE: 4

Met Lys Arg Pro Ala Ala Thr Lys Lys Ala Gly Gln Ala Lys Lys Lys
1               5                   10                  15

Lys Gly Gly Gly Ser Gly Asn Gln Lys Phe Ile Leu Gly Leu Asp Ile
                20                  25                  30

Gly Ile Thr Ser Val Gly Tyr Gly Leu Ile Asp Tyr Glu Thr Lys Asn
            35                  40                  45

```
Ile Ile Asp Ala Gly Val Arg Leu Phe Pro Glu Ala Asn Val Glu Asn
 50                  55                  60

Asn Glu Gly Arg Arg Ser Lys Arg Gly Ser Arg Arg Leu Lys Arg Arg
 65                  70                  75                  80

Arg Ile His Arg Leu Glu Arg Val Lys Lys Leu Leu Glu Asp Tyr Asn
                 85                  90                  95

Leu Leu Asp Gln Ser Gln Ile Pro Gln Ser Thr Asn Pro Tyr Ala Ile
                100                 105                 110

Arg Val Lys Gly Leu Ser Glu Ala Leu Ser Lys Asp Glu Leu Val Ile
                115                 120                 125

Ala Leu Leu His Ile Ala Lys Arg Arg Gly Ile His Lys Ile Asp Val
130                 135                 140

Ile Asp Ser Asn Asp Asp Val Gly Asn Glu Leu Ser Thr Lys Glu Gln
145                 150                 155                 160

Leu Asn Lys Asn Ser Lys Leu Leu Lys Asp Lys Phe Val Cys Gln Ile
                165                 170                 175

Gln Leu Glu Arg Met Asn Glu Gly Gln Val Arg Gly Glu Lys Asn Arg
                180                 185                 190

Phe Lys Thr Ala Asp Ile Ile Lys Glu Ile Gln Leu Leu Asn Val
                195                 200                 205

Gln Lys Asn Phe His Gln Leu Asp Glu Asn Phe Ile Asn Lys Tyr Ile
210                 215                 220

Glu Leu Val Glu Met Arg Arg Glu Tyr Phe Glu Gly Pro Gly Lys Gly
225                 230                 235                 240

Ser Pro Tyr Gly Trp Glu Gly Asp Pro Lys Ala Trp Tyr Glu Thr Leu
                245                 250                 255

Met Gly His Cys Thr Tyr Phe Pro Asp Glu Leu Arg Ser Val Lys Tyr
                260                 265                 270

Ala Tyr Ser Ala Asp Leu Phe Asn Ala Leu Asn Asp Leu Asn Asn Leu
                275                 280                 285

Val Ile Gln Arg Asp Gly Leu Ser Lys Leu Glu Tyr His Glu Lys Tyr
290                 295                 300

His Ile Ile Glu Asn Val Phe Lys Gln Lys Lys Lys Pro Thr Leu Lys
305                 310                 315                 320

Gln Ile Ala Asn Glu Ile Asn Val Asn Pro Glu Asp Ile Lys Gly Tyr
                325                 330                 335

Arg Ile Thr Lys Ser Gly Lys Pro Gln Phe Thr Glu Phe Lys Leu Tyr
                340                 345                 350

His Asp Leu Lys Ser Val Leu Phe Asp Gln Ser Ile Leu Glu Asn Glu
                355                 360                 365

Asp Val Leu Asp Gln Ile Ala Glu Ile Leu Thr Ile Tyr Gln Asp Lys
370                 375                 380

Asp Ser Ile Lys Ser Lys Leu Thr Glu Leu Asp Ile Leu Leu Asn Glu
385                 390                 395                 400

Glu Asp Lys Glu Asn Ile Ala Gln Leu Thr Gly Tyr Thr Gly Thr His
                405                 410                 415

Arg Leu Ser Leu Lys Cys Ile Arg Leu Val Leu Glu Glu Gln Trp Tyr
                420                 425                 430

Ser Ser Arg Asn Gln Met Glu Ile Phe Thr His Leu Asn Ile Lys Pro
                435                 440                 445

Lys Lys Ile Asn Leu Thr Ala Ala Asn Lys Ile Pro Lys Ala Met Ile
450                 455                 460

Asp Glu Phe Ile Leu Ser Pro Val Val Lys Arg Thr Phe Gly Gln Ala
```

-continued

```
            465                 470                 475                 480
        Ile Asn Leu Ile Asn Lys Ile Ile Glu Lys Tyr Gly Val Pro Glu Asp
                        485                 490                 495
        Ile Ile Ile Glu Leu Ala Arg Glu Asn Asn Ser Lys Asp Lys Gln Lys
                        500                 505                 510
        Phe Ile Asn Glu Met Gln Lys Lys Asn Glu Asn Thr Arg Lys Arg Ile
                        515                 520                 525
        Asn Glu Ile Ile Gly Lys Tyr Gly Asn Gln Asn Ala Lys Arg Leu Val
                        530                 535                 540
        Glu Lys Ile Arg Leu His Asp Glu Gln Glu Gly Lys Cys Leu Tyr Ser
        545                 550                 555                 560
        Leu Glu Ser Ile Pro Leu Glu Asp Leu Leu Asn Asn Pro Asn His Tyr
                        565                 570                 575
        Glu Val Asp His Ile Ile Pro Arg Ser Val Ser Phe Asp Asn Ser Tyr
                        580                 585                 590
        His Asn Lys Val Leu Val Lys Gln Ser Glu Asn Ser Lys Lys Ser Asn
                        595                 600                 605
        Leu Thr Pro Tyr Gln Tyr Phe Asn Ser Gly Lys Ser Lys Leu Ser Tyr
                        610                 615                 620
        Asn Gln Phe Lys Gln His Ile Leu Asn Leu Ser Lys Ser Gln Asp Arg
        625                 630                 635                 640
        Ile Ser Lys Lys Lys Lys Glu Tyr Leu Leu Glu Glu Arg Asp Ile Asn
                        645                 650                 655
        Lys Phe Glu Val Gln Lys Glu Phe Ile Asn Arg Asn Leu Val Asp Thr
                        660                 665                 670
        Arg Tyr Ala Thr Arg Glu Leu Thr Asn Tyr Leu Lys Ala Tyr Phe Ser
                        675                 680                 685
        Ala Asn Asn Met Asn Val Lys Val Lys Thr Ile Asn Gly Ser Phe Thr
                        690                 695                 700
        Asp Tyr Leu Arg Lys Val Trp Lys Phe Lys Lys Glu Arg Asn His Gly
        705                 710                 715                 720
        Tyr Lys His His Ala Glu Asp Ala Leu Ile Ile Ala Asn Ala Asp Phe
                        725                 730                 735
        Leu Phe Lys Glu Asn Lys Lys Leu Lys Ala Val Asn Ser Val Leu Glu
                        740                 745                 750
        Lys Pro Glu Ile Glu Thr Lys Gln Leu Asp Ile Gln Val Asp Ser Glu
                        755                 760                 765
        Asp Asn Tyr Ser Glu Met Phe Ile Ile Pro Lys Gln Val Gln Asp Ile
                        770                 775                 780
        Lys Asp Phe Arg Asn Phe Lys Tyr Ser His Arg Val Asp Lys Lys Pro
        785                 790                 795                 800
        Asn Arg Gln Leu Ile Asn Asp Thr Leu Tyr Ser Thr Arg Lys Lys Asp
                        805                 810                 815
        Asn Ser Thr Tyr Ile Val Gln Thr Ile Lys Asp Ile Tyr Ala Lys Asp
                        820                 825                 830
        Asn Thr Thr Leu Lys Lys Gln Phe Asp Lys Ser Pro Glu Lys Phe Leu
                        835                 840                 845
        Met Tyr Gln His Asp Pro Arg Thr Phe Glu Lys Leu Glu Val Ile Met
        850                 855                 860
        Lys Gln Tyr Ala Asn Glu Lys Asn Pro Leu Ala Lys Tyr His Glu Glu
        865                 870                 875                 880
        Thr Gly Glu Tyr Leu Thr Lys Tyr Ser Lys Lys Asn Asn Gly Pro Ile
                        885                 890                 895
```

```
Val Lys Ser Leu Lys Tyr Ile Gly Asn Lys Leu Gly Ser His Leu Asp
            900                 905                 910

Val Thr His Gln Phe Lys Ser Ser Thr Lys Lys Leu Val Lys Leu Ser
            915                 920                 925

Ile Lys Pro Tyr Arg Phe Asp Val Tyr Leu Thr Asp Lys Gly Tyr Lys
            930                 935                 940

Phe Ile Thr Ile Ser Tyr Leu Asp Val Leu Lys Lys Asp Asn Tyr Tyr
945                 950                 955                 960

Tyr Ile Pro Glu Gln Lys Tyr Asp Lys Leu Lys Leu Gly Lys Ala Ile
                965                 970                 975

Asp Lys Asn Ala Lys Phe Ile Ala Ser Phe Tyr Lys Asn Asp Leu Ile
            980                 985                 990

Lys Leu Asp Gly Glu Ile Tyr Lys Ile Ile Gly Val Asn Ser Asp Thr
            995                 1000                1005

Arg Asn Met Ile Glu Leu Asp Leu Pro Asp Ile Arg Tyr Lys Glu
            1010                1015                1020

Tyr Cys Glu Leu Asn Asn Ile Lys Gly Glu Pro Arg Ile Lys Lys
            1025                1030                1035

Thr Ile Gly Lys Lys Val Asn Ser Ile Glu Lys Leu Thr Thr Asp
            1040                1045                1050

Val Leu Gly Asn Val Phe Thr Asn Thr Gln Tyr Thr Lys Pro Gln
            1055                1060                1065

Leu Leu Phe Lys Arg Gly Asn Gly Gly Gly Ser Gly Pro Pro Lys
            1070                1075                1080

Lys Lys Arg Lys Val Gly Gly Ser Gly Gly Ser Gly Gly Ser Gly
            1085                1090                1095

His His His His His His
            1100

<210> SEQ ID NO 5
<211> LENGTH: 156
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: tracr DNA sequence

<400> SEQUENCE: 5
cttgtactta tacctaaaat tacagaatct actgaaacaa gacaatatgt cgtgtttatc      60
ccatcaattt attggtggga tttttttatg tttttagcaa aaagtaatac catactttat    120
atttttaaat tataataaag atataaataa aggtgg                              156

<210> SEQ ID NO 6
<211> LENGTH: 103
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA design DNA sequence
<220> FEATURE:
<221> NAME/KEY: misc_feature
<222> LOCATION: (1)..(20)
<223> OTHER INFORMATION: n is any nucleotide

<400> SEQUENCE: 6
```
nnnnnnnnnn nnnnnnnnnn gttttagtac tctggaaaca gaatctactg aaacaagaca    60
atatgtcgtg tttatcccat caatttattg gtgggatttt ttt    103

<210> SEQ ID NO 7
<211> LENGTH: 101
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA design
<220> FEATURE:
<221> NAME/KEY: misc_feature
<222> LOCATION: (1)..(20)
<223> OTHER INFORMATION: n is any nucleotide

<400> SEQUENCE: 7
nnnnnnnnnn nnnnnnnnnn gttttagtac tctggaaaca gaatctacta aacaagact    60 atatgtcgtg tttatcccac taatttatta gtgggaattt t    101

<210> SEQ ID NO 8
<211> LENGTH: 104
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA VEGFA

<400> SEQUENCE: 8 ggaccccuc caccccgccu cguuuuagua cucuggaaac agaaucuacu gaaacaagac    60
aauaugucgu guuuauccca ucaauuuauu ggugggauuu uuuu    104

<210> SEQ ID NO 9
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: oligonucleotide substrate CGGGCGC PAM

<400> SEQUENCE: 9
gaccccctcc accccgcctc cgggcgcg    28

<210> SEQ ID NO 10
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: oligonucleotide substrate CGGGCGC PAM

<400> SEQUENCE: 10
gcgcgcgccc ggaggcgggg tggaggggggt cgg    33

<210> SEQ ID NO 11
<211> LENGTH: 28
<212> TYPE: DNA
<213> ORGANISM: Artificial sequence
<220> FEATURE:
<223> OTHER INFORMATION: Synthetic polynucleotide

```
<220> FEATURE:
<221> NAME/KEY: misc_feature
<223> OTHER INFORMATION: oligonucleotide substrate AGGGCGCPAM

<400> SEQUENCE: 11
gaccccctcc accccgcctc agggcgcg                                      28

<210> SEQ ID NO 12
<211> LENGTH: 33
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: oligonucleotide substrate AGGGCGC PAM

<400> SEQUENCE: 12
gcgcgcgccc tgaggcgggg tggaggggt cgg                                 33

<210> SEQ ID NO 13
<211> LENGTH: 104
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: sgRNA VEGFA

<400> SEQUENCE: 13
ggacccccuc caccccgccu cguuuuagua cucuggaaac agaaucuacu gaaacaagac   60
aauaugucgu guuuaucccca ucaauuuauu ggugggauuu uuuu                  104

<210> SEQ ID NO 14
<211> LENGTH: 720
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: BFP knock in gene sequence HEK293T cells

<400> SEQUENCE: 14
atggtgagca agggcgagga gctgttcacc ggggtggtgc ccatcctggt cgagctggac   60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccca tggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctgggcac   420 aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccaa gctgagcaaa gaccccaacg agaagcgcga tcacatggtc  660
ctgctggagt tcgtgaccgc cgccgggatc actctcggca tggacgagct gtacaagtaa  720

<210> SEQ ID NO 15
```

```
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: BFP guide 20nt first sequence

<400> SEQUENCE: 15
gggtcagggt ggtcacgagg                                               20

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: BFP guide 20nt second sequence

<400> SEQUENCE: 16
ccctcgaact tcacctcggc                                               20

<210> SEQ ID NO 17
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: BFP guide 22nt second sequence

<400> SEQUENCE: 17
cgccctcgaa cttcacctcg gc                                            22

<210> SEQ ID NO 18
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HBB guide 20nt first sequence

<400> SEQUENCE: 18
ggtgaacgtg gatgaagttg                                               20

<210> SEQ ID NO 19
<211> LENGTH: 6772
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence pMC7125

<400> SEQUENCE: 19
ggtggaagcg gaggcagcgg gggatcaggc catcatcatc accatcatta atgaacgggt    60
cttgaggggt tttttggact tttgcgtatt gggcgctctt ccgcttcctc gctcactgac   120
tcgctgcgct cggtcgttcg gctgcggcga gcggtatcag ctcactcaaa ggcggtaata   180
cggttatcca cagaatcagg ggataacgca ggaaagaaca tgtgagcaaa aggccagcaa   240
```

```
aaggccagga accgtaaaaa ggccgcgttg ctggcgtttt tccataggct ccgcccccct    300
gacgagcatc acaaaaatcg acgctcaagt cagaggtggc gaaacccgac aggactataa    360
agataccagg cgtttccccc tggaagctcc ctcgtgcgct ctcctgttcc gaccctgccg    420
cttaccggat acctgtccgc ctttctccct cgggaagcg tggcgctttc tcatagctca     480
cgctgtaggt atctcagttc ggtgtaggtc gttcgctcca agctgggctg tgtgcacgaa    540
ccccccgttc agcccgaccg ctgcgcctta tccggtaact atcgtcttga gtccaacccg    600
gtaagacacg acttatcgcc actggcagca gccactggta acaggattag cagagcgagg    660
tatgtaggcg gtgctacaga gttcttgaag tggtggccta actacggcta cactagaagg    720
acagtatttg gtatctgcgc tctgctgaag ccagttacct tcggaaaaag agttggtagc    780
tcttgatccg gcaaacaaac caccgctggt agcggtggtt ttttgtttg caagcagcag      840
attacgcgca gaaaaaaagg atctcaagaa gatcctttga tcttttctac ggggtctgac    900
gctcagtgga acgaaaactc acgttaaggg attttggtca tgagattatc aaaaaggatc    960
ttcacctaga tccttttaaa ttaaaaatga agttttaaat caatctaaag tatatatgag    1020
taaacttggt ctgacagtta ccaatgctta atcagtgagg cacctatctc agcgatctgt    1080
ctatttcgtt catccatagt tgcctgactc cccgtcgtgt agataactac gatacgggag    1140
ggcttaccat ctggccccag tgctgcaatg ataccgcgag atccacgctc accggctcca    1200
gatttatcag caataaacca gccagccgga agggccgagc gcagaagtgg tcctgcaact    1260
ttatccgcct ccatccagtc tattaattgt tgccgggaag ctagagtaag tagttcgcca    1320
gttaatagtt tgcgcaacgt tgttgccatt gctgcaggca tcgtggtgtc acgctcgtcg    1380
tttggtatgg cttcattcag ctccggttcc caacgatcaa ggcgagttac atgatccccc    1440
atgttgtgca aaaagcggt tagctccttc ggtcctccga tcgttgtcag aagtaagttg      1500
gccgcagtgt tatcactcat ggttatggca gcactgcata attctcttac tgtcatgcca    1560
tccgtaagat gcttttctgt gactggtgag tactcaacca agtcattctg agaatagtgt    1620
atgcggcgac cgagttgctc ttgcccggcg tcaatacggg ataataccgc gccacatagc    1680
agaactttaa aagtgctcat cattggaaaa cgttcttcgg ggcgaaaact ctcaaggatc    1740
ttaccgctgt tgagatccag ttcgatgtaa cccactcgtg cacccaactg atcttcagca    1800
tcttttactt tcaccagcgt ttctgggtga gcaaaaacag gaaggcaaaa tgccgcaaaa    1860
aagggaataa gggcgacacg gaaatgttga atactcatac tcttcctttt tcaatattat    1920
tgaagcattt atcagggtta ttgtctcatg agcggataca tatttgaatg tatttagaaa    1980
aataaacaaa tagggggttcc gcgcacattt ccccgaaaag tgccactcct cttgctgtga   2040
ccgtctccgg gagctgcatg tgtcagaggt tttcaccgtc atcaccgaaa cgcgcgaggc    2100
agcagatcaa ttcgcgcgcg aaggcgaagc ggcatgcatt tacgttgaca ccatcgaatg    2160
gtgcaaaacc tttcgcggta tggcatgata gcgcccggaa gagagtcaat tcagggtggt    2220
gaatgtgaaa ccagtaacgt tatacgatgt cgcagagtat gccggtgtct cttatcagac    2280
cgtttcccgc gtggtgaacc aggccagcca cgtttctgcg aaaacgcggg aaaaagtgga    2340
agcggcgatg gcggagctga attacattcc caaccgcgtg gcacaacaac tggcgggcaa    2400
acagtcgttg ctgattgcgt tgccacctcc agtctggccc tgcacgcgcc gtcgcaaatt    2460
gtcgcggcga ttaaatctcg cgccgatcaa ctgggtgcca gcgtggtggt gtcgatggta    2520
gaacgaagcg gcgtcgaagc ctgtaaagcg gcggtgcaca atcttctcgc gcaacgcgtc    2580
agtgggctga tcattaacta tccgctggat gaccaggatg ccattgctgt ggaagctgcc    2640
```

```
tgcactaatg ttccggcgtt atttcttgat gtctctgacc agacacccat caacagtatt    2700
attttctccc atgaagatgg tacgcgactg ggcgtggagc atctggtcgc attgggtcac    2760
cagcaaatcg cgctgttagc gggcccatta agttctgtct cggcgcgtct gcgtctggct    2820
ggctggcata aatatctcac tcgcaatcaa attcagccga tagcggaacg ggaaggcgac    2880
tggagtgcca tgtccggttt tcaacaaacc atgcaaatgc tgaatgaggg catcgttccc    2940
actgcgatgc tggttgccaa cgatcagatg gcgctgggcg caatgcgcgc cattaccgag    3000
tccgggctgc gcgttggtgc ggatatctcg gtagtgggat acgacgatac cgaagatagc    3060
tcatgttata tcccgccgtt aaccaccatc aaacaggatt ttcgcctgct ggggcaaacc    3120
agcgtggacc gcttgctgca actctctcag ggccaggcgg tgaagggcaa tcagctgttg    3180
cccgtctcac tggtgaaaag aaaaaccacc ctggcgccca atacgcaaac cgcctctccc    3240
cgcgcgttgg ccgattcatt aatgcagctg gcacgacagg tttcccgact ggaaagcggg    3300
cagtgagcgc aatattctga atgagctgt tgacaattaa tcatccggct cgtataatgt    3360
gtggaattgt gagcggataa caattttcac acaggaaaca gaattctagc attgtgagcg    3420
gataacaatt cccctctaga ataattttg tttaacttta agaaggagat ataccatgca    3480
tcatcatcac catcatggtg gtggtagcgg taaacgtccg gcagcaacca aaaaagcagg    3540
tcaggccaag aaaaaaaaag gtggtggttc aggtaaccag aaatttatcc tgggtctgga    3600
tattggtatt accagcgttg gttatggcct gattgattac gaaaccaaaa acattattga    3660
tgccggtgtt cgtctgtttc cggaagcaaa tgttgaaaat aatgaaggtc gtcgtagcaa    3720
acgtggtagc cgtcgtctga aacgtcgtcg tattcatcgt ctggaacgtg ttaaaaaact    3780
gctggaagat tataacctgc tggatcagag ccagattccg cagagcacca atccgtatgc    3840
aattcgtgtt aaaggtctga gcgaagcact gagcaaagat gaactggtta ttgcactgct    3900
gcatattgca aaacgccgtg gcattcataa aatcgatgtg attgatagca atgacgatgt    3960
gggtaatgaa ctgagcacca agaacagct gaacaaaaat agcaaactgc tgaaagacaa    4020
attcgtgtgt cagattcagc tggaacgtat gaatgaaggc caggttcgtg gtgaaaagaa    4080
tcgctttaaa accgcagaca tcatcaaaga aattatccag ctgctgaacg tgcagaaaaa    4140
cttccatcag ctggatgaaa acttcatcaa caaatacatc gagctggttg aaatgcgtcg    4200
cgaatatttt gaaggtccgg gtaaaggtag cccgtatggt tgggaaggtg atccgaaagc    4260
atggtatgaa accctgatgg gtcattgtac ctatttccg gatgaactgc gtagcgttaa    4320
atatgcctat agcgcagacc tgtttaatgc actgaatgat ctgaataacc tggtgattca    4380
gcgtgatggt ctgagcaaac tggaatatca tgagaaatat cacatcatcg aaaacgtgtt    4440
caaacagaag aagaaaccga ccctgaaaca aatcgccaac gaaattaatg tgaacccgga    4500
agatattaaa ggctaccgta ttaccaaaag cggtaaaccg cagttcaccg aatttaaact    4560
gtatcacgat ctgaaaagcg tgctgtttga tcagagcatt ctggaaaatg aagatgtgct    4620
ggaccagatt gcagaaattc tgaccatta tcaggacaaa gacagcatca aaagcaaact    4680
gaccgaactg gatattctgc tgaatgaaga agataaagag aacattgcac agctgaccgg    4740
ttataccggc acccatcgtc tgagcctgaa atgtattcgt ctggtactgg aagaacagtg    4800
gtatagcagc cgtaatcaga tggaaatctt tacccatctg aacattaaac cgaagaaaat    4860
caatctgacc gcagccaaca aaattccgaa agccatgatt gatgagttta ttctgagtcc    4920
ggttgtgaaa cgtacctttg gtcaggcaat taacctgatc aacaaaatca ttgaaaaata    4980
```

| | | | |
|---|---|---|---|
| tggcgtgcct | gaggatatca | ttattgaact | ggcacgtgaa | aacaacagca | aagataaaca | 5040 |
| gaaattcatc | aacgagatgc | agaagaagaa | cgaaaatacc | cgcaaacgga | ttaacgagat | 5100 |
| cattggcaaa | tatggtaatc | agaatgccaa | acgcctggtg | gaaaaaattc | gtctgcatga | 5160 |
| tgaacaagag | ggcaaatgtc | tgtatagcct | ggaaagcatt | cctctggaag | atctgctgaa | 5220 |
| caatccgaat | cattatgaag | tggatcacat | tattccgcgt | agcgtgagct | ttgataattc | 5280 |
| ctatcataat | aaagtgctgg | tgaaacagag | cgaaaactcc | aaaaaatcca | acctgacacc | 5340 |
| gtatcagtat | ttcaatagcg | gcaaatccaa | actgagctac | aaccagttta | aacagcatat | 5400 |
| tctgaacctg | agcaaaagcc | aggatcgcat | cagcaagaag | aagaaggagt | acctgctgga | 5460 |
| agaacgcgac | atcaacaaat | tgaagtgca | gaaagaattt | atcaaccgca | acctggttga | 5520 |
| tacccgttat | gcaacccgtg | aactgaccaa | ttatctgaaa | gcatatttca | gcgccaacaa | 5580 |
| catgaacgtg | aaagtgaaaa | cgattaacgg | cagctttacc | gattatctgc | gtaaagtgtg | 5640 |
| gaaattcaaa | aaagaacgca | accacggcta | taaacatcat | gccgaagatg | ccctgattat | 5700 |
| tgcaaatgca | gatttcctgt | ttaaagaaaa | caaaaaactg | aaagccgtca | acagcgtgct | 5760 |
| ggaaaaaccg | gaaattgaga | caaaacagct | ggacattcag | gttgatagcg | aagataatta | 5820 |
| cagcgaaatg | tttatcatcc | cgaaacaggt | gcaggatatc | aaagattttc | gcaacttcaa | 5880 |
| atatagccac | cgcgttgaca | aaaaacctaa | tcgtcagctg | attaacgata | ccctgtatag | 5940 |
| cacccgcaaa | aaagataaca | gcacctatat | tgtgcagacc | attaaagaca | tctacgccaa | 6000 |
| agataatacc | accctgaaaa | aacagttcga | caaaagccca | gaaaaatttc | tgatgtatca | 6060 |
| gcatgatccg | cgtaccttcg | aaaaactgga | agttattatg | aaacagtatg | ccaacgagaa | 6120 |
| aaatccgctg | gccaaatatc | acgaagaaac | cggtgaatat | ctgaccaaat | attccaagaa | 6180 |
| gaacaacggt | ccgatcgtta | aatccctgaa | atatatcggt | aataaactgg | gcagccatct | 6240 |
| ggatgttacc | catcagttta | aaagctccac | aaagaagctg | gttaaactgt | ccatcaaacc | 6300 |
| gtatcgcttt | gatgtgtatc | tgaccgacaa | aggctataaa | ttcattacca | tcagctatct | 6360 |
| ggacgtgctg | aaaaaagaca | actattatta | tatcccggaa | cagaaatatg | ataaactgaa | 6420 |
| actgggtaaa | gccatcgata | aaacgccaa | atttatcgcc | agcttctaca | aaaacgacct | 6480 |
| gattaaactg | gatggcgaga | tctataaaat | catcggtgtt | aatagcgaca | cccgcaatat | 6540 |
| gattgagctg | gatctgccgg | atattcgcta | taagaatat | tgcgaactga | acaacattaa | 6600 |
| aggcgaaccg | cgtatcaaaa | agaccatcgg | caaaaagtg | aatagcatcg | agaaactgac | 6660 |
| caccgatgtt | ctgggtaatg | tgtttaccaa | tacccagtat | accaaacctc | agctgctgtt | 6720 |
| caaacgcggt | aatggcggag | gatctggccc | ccctaagaaa | aagcggaagg | tg | 6772 |

<210> SEQ ID NO 20
<211> LENGTH: 2192
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence pMC7204

<400> SEQUENCE: 20

| | | | | | |
|---|---|---|---|---|---|
| ccactgtaga | agagcaaatg | ccacctgacg | tctaagaaat | tcgcgttaaa | ttttgttaa | 60 |
| atcagctcat | tttttaacca | ataggccgaa | atcggcaaaa | tcccttataa | atcaaaagaa | 120 |
| tagaccgaga | tagggttgag | tggccgctac | actagggcgc | gtctaatacg | actcactata | 180 |

| | |
|---|---|
| ggaccccctc caccccgcct cgttttagta ctctggaaac agaatctact aaaacaagac | 240 |
| tatatgtcgt gtttatccca ctaatttatt agtgggaatt tttttgtttt agcataaccc | 300 |
| cttgggcct ctaaacgggt cttgagggt tttttgtcac tgcccgcttt ccagtcggga | 360 |
| aacctgtcgt gccagctgca ttaatgaatc gttcgtcaga actgcttacg cggtttgtca | 420 |
| ctcggtcgct acgctccggg cgtgagactg cggcgggcgc tgcggacaca tacaaagtta | 480 |
| cccacagatt ccgtggataa gcaggggact aacatgtgag gcaaaacagc agggccgcgc | 540 |
| cggtggcgtt tttccatagg ctccgccctc ctgccagagt tcacataaac agacgctttt | 600 |
| ccggtgcatc tgtgggagcc gtgaggctca accatgaatc tgacagtacg ggcgaaaccc | 660 |
| gacaggactt aaagatcccc accgtttccg gcgggtcgct ccctcttgcg ctctcctgtt | 720 |
| ccgaccctgc cgtttaccgg atacctgttc cgcctttctc ccttacggga agtgtggcgc | 780 |
| tttctcatag ctcacacact ggtatctcgg ctcggtgtag gtcgttcgct ccaagctggg | 840 |
| ctgtaagcaa gaactcccg ttcagcccga ctgctgcgcc ttatccggta actgttcact | 900 |
| tgagtccaac ccggaaaagc acggtaaaac gccactggca gcagccattg gtaactggga | 960 |
| gttcgcagag gatttgttta gctaaacacg cggttgctct tgaagtgtgc gccaaagtcc | 1020 |
| ggctacactg gaaggacaga tttggttgct gtgctctgcg aaagccagtt accacggtta | 1080 |
| agcagttccc caactgactt aaccttcgat caaaccacct ccccaggtgg tttttcgtt | 1140 |
| tacagggcaa aagattacgc gcagaaaaaa aggatctcaa gaagatcctt tgatcttttc | 1200 |
| tactgaaccg ctcaatctaa agtatatatg agtaaacttg gtctgacagt tattagaaaa | 1260 |
| actcatcgag catcaaatga aactgcaatt tattcatatc aggattatca ataccatatt | 1320 |
| tttgaaaaag ccgtttctgt aatgaaggag aaaactcacc gaggcagttc cataggatgg | 1380 |
| caagatcctg gtatcggtct gcgattccga ctcgtccaac atcaatacaa cctattaatt | 1440 |
| tcccctcgtc aaaaataagg ttatcaagtg agaaatcacc atgagtgacg actgaatccg | 1500 |
| gtgagaatgg caaaagttta tgcatttctt tccagacttg ttcaacaggc cagccattac | 1560 |
| gctcgtcatc aaaatcactc gcatcaacca accgttatt cattcgtgat tgcgcctgag | 1620 |
| cgagacgaaa tacgcgatcg ctgttaaaag gacaattaca acaggaatc gaatgcaacc | 1680 |
| ggcgcaggaa cactgccagc gcatcaacaa tattttcacc tgaatcagga tattcttcta | 1740 |
| atacctggaa tgctgttttc ccggggatcg cagtggtgag taaccatgca tcatcaggag | 1800 |
| tacggataaa atgcttgatg gtcggaagag gcataaattc cgtcagccag tttagtctga | 1860 |
| ccatctcatc tgtaacatca ttggcaacgc tacctttgcc atgtttcaga acaactctg | 1920 |
| gcgcatcggg cttcccatac aatcgataga ttgtcgcacc tgattgcccg acattatcgc | 1980 |
| gagcccattt ataccatat aaatcagcat ccatgttgga atttaatcgc ggcctagagc | 2040 |
| aagacgtttc ccgttgaata tggctcatac tcttcctttt tcaatattat tgaagcattt | 2100 |
| atcagggtta ttgtctcatg agcggataca tatttgaatg tatttagaaa aataaacaaa | 2160 |
| tagggggttcc gcgcacattt ccccgaaaag tg | 2192 |

```
<210> SEQ ID NO 21
<211> LENGTH: 2188
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence pCas606
```

<400> SEQUENCE: 21

```
ccactgtaga agagcaaatg ccacctgacg tctaagaaat tcgcgttaaa ttttttgttaa       60
atcagctcat ttttttaacca ataggccgaa atcggcaaaa tcccttataa atcaaaagaa      120
tagaccgaga tagggttgag tggccgctac actagggcgc gtctaatacg actcactata      180
ggaccccctc caccccgcct cgttttagta ctctggaaac agaatctact gaaacaagac      240
aatatgtcgt gtttatccca tcaatttatt ggtgggattt ttttctagca taaccccttg      300
gggcctctaa acgggtcttg aggggttttt tgtcactgcc cgctttccag tcgggaaacc      360
tgtcgtgcca gctgcattaa tgaatcgttc gtcagaactg cttacgcggt tgtcactcg       420
gtcgctacgc tccgggcgtg agactgcggc gggcgctgcg gacacataca aagttaccca      480
cagattccgt ggataagcag gggactaaca tgtgaggcaa acagcaggg ccgcgccggt       540
ggcgttttttc cataggctcc gccctcctgc cagagttcac ataaacagac gcttttccgg     600
tgcatctgtg ggagccgtga ggctcaacca tgaatctgac agtacgggcg aaacccgaca      660
ggacttaaag atccccaccg tttccggcgg gtcgctccct cttgcgctct cctgttccga      720
ccctgccgtt taccggatac ctgttccgcc tttctccctt acgggaagtg tggcgctttc      780
tcatagctca cacactggta tctcggctcg gtgtaggtcg ttcgctccaa gctgggctgt      840
aagcaagaac tccccgttca gcccgactgc tgcgccttat ccggtaactg ttcacttgag      900
tccaacccgg aaaagcacgg taaaacgcca ctggcagcag ccattggtaa ctgggagttc      960
gcagaggatt tgtttagcta aacacgcggt tgctcttgaa gtgtgcgcca aagtccggct     1020
acactggaag gacagatttg gttgctgtgc tctgcgaaag ccagttacca cggttaagca     1080
gttccccaac tgacttaacc ttcgatcaaa ccacctcccc aggtggtttt ttcgtttaca     1140
gggcaaaaga ttacgcgcag aaaaaaagga tctcaagaag atcctttgat ctttttctact    1200
gaaccgctca atctaaagta tatatgagta aacttggtct gacagttatt agaaaaactc     1260
atcgagcatc aaatgaaact gcaatttatt catatcagga ttatcaatac catatttttg     1320
aaaaagccgt ttctgtaatg aaggagaaaa ctcaccgagg cagttccata ggatggcaag     1380
atcctggtat cggtctgcga ttccgactcg tccaacatca atacaaccta ttaatttccc     1440
ctcgtcaaaa ataaggttat caagtgagaa atcaccatga gtgacgactg aatccggtga     1500
gaatggcaaa agtttatgca tttctttcca gacttgttca acaggccagc cattacgctc     1560
gtcatcaaaa tcactcgcat caaccaaacc gttattcatt cgtgattgcg cctgagcgag     1620
acgaaatacg cgatcgctgt taaaaggaca attacaaaca ggaatcgaat gcaaccggcg     1680
caggaacact gccagcgcat caacaatatt ttcacctgaa tcaggatatt cttctaatac     1740
ctggaatgct gttttcccgg ggatcgcagt ggtgagtaac catgcatcat caggagtacg     1800
gataaaatgc ttgatggtcg gaagaggcat aaattccgtc agccagttta gtctgaccat     1860
ctcatctgta acatcattgg caacgctacc tttgccatgt ttcagaaaca actctggcgc     1920
atcgggcttc ccatacaatc gatagattgt cgcacctgat tgcccgacat atcgcgagc     1980
ccatttatac ccatataaat cagcatccat gttggaattt aatcgcggcc tagagcaaga    2040
cgtttcccgt tgaatatggc tcatactctt ccttttttcaa tattattgaa gcatttatca    2100
gggttattgt ctcatgagcg gatacatatt tgaatgtatt tagaaaaata aacaaatagg    2160
ggttccgcgc acatttcccc gaaaagtg                                        2188
```

<210> SEQ ID NO 22
<211> LENGTH: 3922

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence pML2017
<220> FEATURE:
<221> NAME/KEY: misc_feature
<222> LOCATION: (3076)..(3082)
<223> OTHER INFORMATION: n is any nucleotide

<400> SEQUENCE: 22
tcaatctaaa gtatatatga gtaaacttgg tctgacagtt attacgcccc gccctgccac      60
tcatcgcagt actgttgtaa ttcattaagc attctgccga catggaagcc atcacaaacg     120
gcatgatgaa cctgaatcgc cagcggcatc agcaccttgt cgccttgcgt ataatatttg     180
cccaaggtga aaacgggggc gaagaagttg tccatattgg ccacgtttaa atcaaaactg     240
gtgaaactca cccagggatt ggctgagacg aaaaacatat tctcaataaa ccctttaggg     300
aaataggcca ggttttcacc gtaacacgcc acatcttgcg aatatatgtg tagaaactgc     360
cggaaatcgt cgtggtattc actccagagc gatgaaaacg tttcagtttg ctcatggaaa     420
acggtgtaac aagggtgaac actatcccat atcaccagct caccgtcttt cattgccata     480
cgtaattccg gatgagcatt catcaggcgg gcaagaatgt gaataaaggc cggataaaac     540
ttgtgcttat ttttctttac ggtctttaaa aaggccgtaa tatccagctg aacggtctgg     600
ttataggtac attgagcaac tgactgaaat gcctcaaaat gttctttacg atgccattgg     660
gatatatcaa cggtggtata tccagtgatt ttttctcca tactcttcct ttttcaatat     720
tattgaagca tttatcaggg ttattgtctc atgagcggat acatatttga atgtatttag     780
aaaaataaac aaatagggt tccgcgcaca tttccccgaa aagtgccact tatgacaact     840
tgacggctac atcattcact ttttcttcac aaccggcacg gaactcgctc gggctggccc     900
cggtgcattt tttaaatacc cgcgagaaat agagttgatc gtcaaaacca acattgcgac     960
cgacggtggc gataggcatc cgggtggtgc tcaaaagcag cttcgcctgg ctgatacgtt    1020
ggtcctcgcg ccagcttaag acgctaatcc ctaactgctg gcggaaaaga tgtgacagac    1080
gcgacggcga caagcaaaca tgctgtgcga cgctggcgat atcaaaattg ctgtctgcca    1140
ggtgatcgct gatgtactga caagcctcgc gtacccgatt atccatcggt ggatggagcg    1200
actcgttaat cgcttccatg cgccgcagta acaattgctc aagcagattt atcgccagca    1260
gctccgaata gcgcccttcc ccttgcccgg cgttaatgat ttgcccaaac aggtcgctga    1320
aatgcggctg gtgcgcttca tccgggcgaa agaacccgt attggcaaat attgacggcc    1380
agttaagcca ttcatgccag taggcgcgcg gacgaaagta aacccactgg tgataccatt    1440
cgcgagcctc cggatgacga ccgtagtgat gaatctctcc tggcgggaac agcaaaatat    1500
cacccggtcg gcaaacaaat tctcgtccct gatttttcac caccccctga ccgcgaatgg    1560
tgagattgag aatataacct ttcattccca gcggtcggtc gataaaaaaa tcgagataac    1620
cgttggcctc aatcggcgtt aaacccgcca ccagatgggc attaaacgag tatcccggca    1680 gcagggggatc attttgcgct tcagccatac ttttcatact cccgccattc agagaagaaa    1740
ccaattgtcc atattgcatc agacattgcc gtcactgcgt cttttactgg ctcttctcgc    1800
taaccaaacc ggtaacccg cttattaaaa gcattctgta acaaagcggg accaaagcca    1860
tgacaaaaac gcgtaacaaa agtgtctata atcacggcag aaaagtccac attgattatt    1920
tgcacggcgt cacactttgc tatgccatag catttttatc cataagatta gcggatccta    1980
```

```
cctgacgctt tttatcgcaa ctctctactg tttctccata cccgtttttt gggctaacag    2040
gaggaattaa atggtgagca aaggtgagga actgatcaaa gaaaacatgc atatgaaact    2100
gtacatggaa ggcaccgtga ataaccatca ctttaaatgt accagcgaag gtgaaggtaa    2160
accgtatgaa ggcacccaga ccatgcgtat taaagttgtt gaaggtggtc cgctgccgtt    2220
tgcatttgat attctggcaa ccagctttat gtatggtagc cgtacccttta ttaaccatac    2280 ccagggtatt ccggatttct ttaaacagag cttttccggaa ggttttacct gggaacgtgt    2340
taccacctat gaagatggtg gtgttctgac cgcaacccag gataccagtc tgcaggatgg    2400
ttgtctgatt tataatgtga aaattcgcgg tgtgaacttt ccgagcaatg gtccggttat    2460
gcagaaaaaa accctgggtt gggaagcaaa taccgaaatg ctgtatccgg cagatggtgg    2520
cctggaaggt cgtagcgata tggcactgaa actggttggt ggtggtcatc tgatttgtaa    2580 cttttaaaacc acctatcgca gcaaaaaacc tgccaaaaat ctgaaaatgc ctggcgtgta    2640
ttatgtggat catcgtctgg aacgcattaa agaagcagat aaagaaacct atgtggaaca    2700
gcatgaagtt gcagttgcac gttattgtga tctgccgagc aaactgggtc ataaactgaa    2760
tagcggtctg cgtagccgtg cacaggcaag caatagcgca gttgatggca ccgcaggtcc    2820
gggtagcacc ggtagtcgcg gtggtggtag cggtgcagca aatgatgaaa attatgcact    2880
ggcagcctga taatgcctgg cggcagtagc gcggtggtcc cacctgaccc catgccgaac    2940
tcagaagtga aacgccgtag cgccgatggt agtgtgggct ctccccatgc gagagtaggg    3000
aactgccagg catcaaataa aacgaaaggc tcagtcgaaa gactgggcct tataggaccc    3060
cctccacccc gcctcnnnnn nncaacgatc gtttaatttg ttttttgtcac tcggtcgcta    3120 cgctccgggc gtgagactgc ggcgggctct tccgcttcct cgctcactga ctcgctacgc    3180
tcggtcgttc gactgcggcg agcggtgtca gctcactcaa aagcggtaat acggttatcc    3240
acagaatcag gggataaagc cggaaagaac atgtgagcaa aaagcaaagc accggaagaa    3300
gccaacgccg caggcgtttt tccataggct ccgcccccct gacgagcatc acaaaaatcg    3360
acgctcaagc cagaggtggc gaaacccgac aggactataa agataccagg cgtttccccc    3420
tggaagctcc ctcgtgcgct ctcctgttcc gaccctgccg cttaccggat acctgtccgc    3480
ctttctccct cgggaagcg tggcgctttc tcatagctca cgctgttggt atctcagttc    3540
ggtgtaggtc gttcgctcca agctgggctg tgtgcacgaa ccccccgttc agcccgaccg    3600
ctgcgcctta tccggtaact atcgtcttga gtccaacccg gtaagacacg acttatcgcc    3660
actggcagca gccattggta actgatttag aggactttgt cttgaagtta tgcacctgtt    3720
aaggctaaac tgaaagaaca gattttggtg agtgcggtcc tccaacccac ttaccttggt    3780
tcaaagagtt ggtagctcag cgaaccttga gaaaaccacc gttggtagcg gtggtttttc    3840
tttatttatg agatgatgaa tcaatcggtc tatcaagtca acgaacagct attccgttac    3900
tctagatttt ctactgaacc gc                                              3922
```

<210> SEQ ID NO 23
<211> LENGTH: 3914
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence pCas595

<400> SEQUENCE: 23

```
tcaatctaaa gtatatatga gtaaacttgg tctgacagtt attacgcccc gccctgccac    60
tcatcgcagt actgttgtaa ttcattaagc attctgccga catggaagcc atcacaaacg   120
gcatgatgaa cctgaatcgc cagcggcatc agcaccttgt cgccttgcgt ataatatttg   180
cccaaggtga aaacgggggc gaagaagttg tccatattgg ccacgtttaa atcaaaactg   240
gtgaaactca cccagggatt ggctgagacg aaaaacatat tctcaataaa ccctttaggg   300
aaataggcca ggttttcacc gtaacacgcc acatcttgcg aatatatgtg tagaaactgc   360
cggaaatcgt cgtggtattc actccagagc gatgaaaacg tttcagtttg ctcatggaaa   420
acggtgtaac aagggtgaac actatcccat atcaccagct caccgtcttt cattgccata   480
cgtaattccg gatgagcatt catcaggcgg gcaagaatgt gaataaaggc cggataaaac   540
ttgtgcttat ttttctttac ggtctttaaa aaggccgtaa tatccagctg aacggtctgg   600
ttataggtac attgagcaac tgactgaaat gcctcaaaat gttctttacg atgccattgg   660
gatatatcaa cggtggtata tccagtgatt ttttctcca tactcttcct ttttcaatat   720
tattgaagca tttatcaggg ttattgtctc atgagcggat acatatttga atgtatttag   780
aaaaataaac aaataggggt tccgcgcaca tttccccgaa aagtgccact tatgacaact   840
tgacggctac atcattcact ttttcttcac aaccggcacg gaactcgctc gggctggccc   900
cggtgcattt tttaaatacc cgcgagaaat agagttgatc gtcaaaacca cattgcgac   960 cgacggtggc gataggcatc cgggtggtgc tcaaaagcag cttcgcctgg ctgatacgtt  1020
ggtcctcgcg ccagcttaag acgctaatcc ctaactgctg gcggaaaaga tgtgacagac  1080
gcgacggcga caagcaaaca tgctgtgcga cgctggcgat atcaaaattg ctgtctgcca  1140
ggtgatcgct gatgtactga caagcctcgc gtacccgatt atccatcggt ggatggagcg  1200
actcgttaat cgcttccatg cgccgcagta acaattgctc aagcagattt atcgccagca  1260
gctccgaata gcgcccttcc ccttgcccgg cgttaatgat ttgcccaaac aggtcgctga  1320
aatgcggctg gtgcgcttca tccgggcgaa agaacccgt attggcaaat attgacggcc  1380
agttaagcca ttcatgccag taggcgcgcg gacgaaagta aacccactgg tgataccatt  1440
cgcgagcctc cggatgacga ccgtagtgat gaatctctcc tggcgggaac agcaaaatat  1500
cacccggtcg gcaaacaaat tctcgtccct gatttttcac cacccccctga ccgcgaatgg  1560 tgagattgag aatataacct ttcattccca gcggtcggtc gataaaaaaa tcgagataac  1620
cgttggcctc aatcggcgtt aaacccgcca ccagatgggc attaaacgag tatcccggca  1680 gcagggggatc attttgcgct tcagccatac ttttcatact cccgccattc agagaagaaa  1740
ccaattgtcc atattgcatc agacattgcc gtcactgcgt cttttactgg ctcttctcgc  1800
taaccaaacc ggtaacccg cttattaaaa gcattctgta acaaagcggg accaaagcca  1860
tgacaaaaac gcgtaacaaa agtgtctata atcacggcag aaaagtccac attgattatt  1920
tgcacggcgt cacactttgc tatgccatag cattttatc cataagatta gcggatccta  1980
cctgacgctt tttatcgcaa ctctctactg tttctccata cccgttttt gggctaacag  2040 gaggaattaa atggtgagca aaggtgagga actgatcaaa gaaaacatgc atatgaaact  2100
gtacatggaa ggcaccgtga ataaccatca ctttaaatgt accagcgaag gtgaaggtaa  2160
accgtatgaa ggcacccaga ccatgcgtat taaagttgtt gaaggtggtc cgctgccgtt  2220
tgcatttgat attctggcaa ccagctttat gtatggtagc cgtacccttta ttaaccatac  2280 ccagggtatt ccggatttct ttaaacagag ctttccggaa ggttttacct gggaacgtgt  2340
```

```
taccacctat gaagatggtg gtgttctgac cgcaacccag gataccagtc tgcaggatgg    2400
ttgtctgatt tataatgtga aaattcgcgg tgtgaacttt ccgagcaatg gtccggttat    2460
gcagaaaaaa accctgggtt gggaagcaaa taccgaaatg ctgtatccgg cagatggtgg    2520
cctggaaggt cgtagcgata tggcactgaa actggttggt ggtggtcatc tgatttgtaa    2580
ctttaaaacc acctatcgca gcaaaaaacc tgccaaaaat ctgaaaatgc ctggcgtgta    2640
ttatgtggat catcgtctgg aacgcattaa agaagcagat aaagaaacct atgtggaaca    2700
gcatgaagtt gcagttgcac gttattgtga tctgccgagc aaactgggtc ataaactgaa    2760
tagcggtctg cgtagccgtg cacaggcaag caatagcgca gttgatggca ccgcaggtcc    2820
gggtagcacc ggtagtcgcg gtggtggtag cggtgcagca aatgatgaaa attatgcact    2880
ggcagcctga taatgcctgg cggcagtagc gcggtggtcc cacctgaccc catgccgaac    2940
tcagaagtga aacgccgtag cgccgatggt agtgtgggct ctccccatgc gagagtaggg    3000
aactgccagg catcaaataa acgaaaggc tcagtcgaaa gactgggcct tataggaccc    3060
cctccacccc gcctcccggc ccgtttaatt tgttttttgtc actcggtcgc tacgctccgg    3120
gcgtgagact gcggcgggct cttccgcttc ctcgctcact gactcgctac gctcggtcgt    3180
tcgactgcgg cgagcggtgt cagctcactc aaaagcggta atacgttat ccacagaatc    3240 aggggataaa gccggaaaga acatgtgagc aaaaagcaaa gcaccggaag aagccaacgc    3300
cgcaggcgtt tttccatagg ctccgccccc ctgacgagca tcacaaaaat cgacgctcaa    3360
gccagaggtg gcgaaacccg acaggactat aaagatacca ggcgtttccc cctggaagct    3420
ccctcgtgcg ctctcctgtt ccgaccctgc cgcttaccgg atacctgtcc gcctttctcc    3480
cttcgggaag cgtggcgctt tctcatagct cacgctgttg gtatctcagt tcggtgtagg    3540
tcgttcgctc caagctgggc tgtgtgcacg aaccccccgt tcagcccgac cgctgcgcct    3600
tatccggtaa ctatcgtctt gagtccaacc cggtaagaca cgacttatcg ccactggcag    3660
cagccattgg taactgattt agaggacttt gtcttgaagt tatgcacctg ttaaggctaa    3720
actgaaagaa cagattttgg tgagtgcggt cctccaaccc acttaccttg gttcaaagag    3780
ttggtagctc agcgaacctt gagaaaacca ccgttggtag cggtggtttt tctttattta    3840
tgagatgatg aatcaatcgg tctatcaagt caacgaacag ctattccgtt actctagatt    3900
ttctactgaa ccgc    3914
```

<210> SEQ ID NO 24
<211> LENGTH: 6740
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence pCas81

<400> SEQUENCE: 24

```
ggtggaagcg gaggcagcgg gggatcaggc catcatcatc accatcatta atgaacgggt     60
cttgaggggt tttttggact tttgcgtatt gggcgctctt ccgcttcctc gctcactgac    120
tcgctgcgct cggtcgttcg gctgcggcga gcggtatcag ctcactcaaa ggcggtaata    180
cggttatcca cagaatcagg ggataacgca ggaaagaaca tgtgagcaaa aggccagcaa    240
aaggccagga accgtaaaaa ggccgcgttg ctggcgtttt tccataggct ccgcccccct    300
gacgagcatc acaaaaatcg acgctcaagt cagaggtggc gaaacccgac aggactataa    360
```

-continued

```
agataccagg cgtttccccc tggaagctcc ctcgtgcgct ctcctgttcc gaccctgccg    420
cttaccggat acctgtccgc ctttctccct tcgggaagcg tggcgctttc tcatagctca    480
cgctgtaggt atctcagttc ggtgtaggtc gttcgctcca agctgggctg tgtgcacgaa    540
ccccccgttc agcccgaccg ctgcgcctta tccgtaact atcgtcttga gtccaacccg     600
gtaagacacg acttatcgcc actggcagca gccactggta acaggattag cagagcgagg    660
tatgtaggcg gtgctacaga gttcttgaag tggtggccta actacggcta cactagaagg    720
acagtatttg gtatctgcgc tctgctgaag ccagttacct tcggaaaaag agttggtagc    780
tcttgatccg gcaaacaaac caccgctggt agcggtggtt ttttttgtttg caagcagcag    840 attacgcgca gaaaaaaagg atctcaagaa gatcctttga tcttttctac ggggtctgac    900
gctcagtgga acgaaaactc acgttaaggg attttggtca tgagattatc aaaaaggatc    960
ttcacctaga tccttttaaa ttaaaaatga agttttaaat caatctaaag tatatatgag   1020
taaacttggt ctgacagtta ccaatgctta atcagtgagg cacctatctc agcgatctgt   1080
ctatttcgtt catccatagt tgcctgactc cccgtcgtgt ataactac gatacggaga    1140 ggcttaccat ctggccccag tgctgcaatg ataccgcgag atccacgctc accggctcca   1200
gatttatcag caataaacca gccagccgga agggccgagc gcagaagtgg tcctgcaact   1260
ttatccgcct ccatccagtc tattaattgt tgccgggaag ctagagtaag tagttcgcca   1320
gttaatagtt tgcgcaacgt tgttgccatt gctgcaggca tcgtggtgtc acgctcgtcg   1380
tttggtatgg cttcattcag ctccggttcc caacgatcaa ggcgagttac atgatccccc   1440
atgttgtgca aaaaagcggt tagctccttc ggtcctccga tcgttgtcag aagtaagttg   1500
gccgcagtgt tatcactcat ggttatggca gcactgcata attctcttac tgtcatgcca   1560
tccgtaagat gcttttctgt gactggtgag tactcaacca agtcattctg agaatagtgt   1620
atgcggcgac cgagttgctc ttgcccggcg tcaatacggg ataataccgc gccacatagc   1680
agaactttaa aagtgctcat cattggaaaa cgttcttcgg ggcgaaaact ctcaaggatc   1740
ttaccgctgt tgagatccag ttcgatgtaa cccactcgtg cacccaactg atcttcagca   1800
tcttttactt tcaccagcgt ttctgggtga gcaaaaacag gaaggcaaaa tgccgcaaaa   1860
aagggaataa gggcgacacg gaaatgttga atactcatac tcttcctttt tcaatattat   1920
tgaagcattt atcagggtta ttgtctcatg agcggataca tatttgaatg tatttagaaa   1980
aataaacaaa taggggttcc gcgcacattt ccccgaaaag tgccactcct cttgctgtga   2040
ccgtctccgg gagctgcatg tgtcagaggt tttcaccgtc atcaccgaaa cgcgcgaggc   2100
agcagatcaa ttcgcgcgcg aaggcgaagc ggcatgcatt tacgttgaca ccatcgaatg   2160
gtgcaaaacc tttcgcggta tggcatgata gcgcccggaa gagagtcaat tcagggtggt   2220
gaatgtgaaa ccagtaacgt tatacgatgt cgcagagtat gccggtgtct cttatcagac   2280
cgtttcccgc gtggtgaacc aggccagcca cgtttctgcg aaaacgcggg aaaaagtgga   2340
agcggcgatg gcggagctga attacattcc caaccgcgtg gcacaacaac tggcgggcaa   2400
acagtcgttg ctgattggcg ttgccacctc cagtctggcc ctgcacgcgc cgtcgcaaat   2460
tgtcgcggcg attaaatctc gcgccgatca actgggtgcc agcgtggtgg tgtcgatggt   2520
agaacgaagc ggcgtcgaag cctgtaaagc ggcggtgcac aatcttctcg cgcaacgcgt   2580
cagtgggctg atcattaact atccgctgga tgaccaggat gccattgctg tggaagctgc   2640
ctgcactaat gttccggcgt tatttcttga tgtctctgac cagacaccca tcaacagtat   2700
tatttctctc catgaagatg gtacgcgact gggcgtggag catctggtcg cattgggtca   2760
```

```
ccagcaaatc gcgctgttag cgggcccatt aagttctgtc tcggcgcgtc tgcgtctggc    2820
tggctggcat aaatatctca ctcgcaatca aattcagccg atagcggaac gggaaggcga    2880
ctggagtgcc atgtccggtt ttcaacaaac catgcaaatg ctgaatgagg catcgttcc     2940 cactgcgatg ctggttgcca acgatcagat ggcgctgggc gcaatgcgcg ccattaccga    3000
gtccgggctg cgcgttggtg cggatatctc ggtagtggga tacgacgata ccgaagatag    3060
ctcatgttat atcccgccgt taaccaccat caaacaggat tttcgcctgc tggggcaaac    3120
cagcgtggac cgcttgctgc aactctctca gggccaggcg gtgaagggca atcagctgtt    3180
gcccgtctca ctggtgaaaa gaaaaaccac cctggcgccc aatacgcaaa ccgcctctcc    3240
ccgcgcgttg gccgattcat taatgcagct ggcacgacag gtttcccgac tggaaagcgg    3300
gcagtgagcg caatattctg aaatgagctg ttgacaatta atcatccggc tcgtataatg    3360
tgtggaattg tgagcggata caatttttca cacaggaaac agaattctag cattgtgagc    3420
ggataacaat tcccctctag aaataatttt gtttaacttt aagaaggaga tataccatga    3480
aacgtccggc agcaaccaaa aaagcaggtc aggccaagaa aaaaaaggt ggtggttcag     3540 gtaaccagaa atttatcctg ggtctggata ttggtattac cagcgttggt tatggcctga    3600
ttgattacga aaccaaaaac attattgatg ccggtgttcg tctgtttccg gaagcaaatg    3660
ttgaaaataa tgaaggtcgt cgtagcaaac gtggtagccg tcgtctgaaa cgtcgtcgta    3720
ttcatcgtct ggaacgtgtt aaaaaactgc tggaagatta aacctgctg gatcagagcc     3780 agattccgca gagcaccaat ccgtatgcaa ttcgtgttaa aggtctgagc gaagcactga    3840
gcaaagatga actggttatt gcactgctgc atattgcaaa acgccgtggc attcataaaa    3900
tcgatgtgat tgatagcaat gacgatgtgg gtaatgaact gagcaccaaa gaacagctga    3960
acaaaaatag caaactgctg aaagacaaat tcgtgtgtca gattcagctg gaacgtatga    4020
atgaaggcca ggttcgtggt gaaaagaatc gctttaaaac cgcagacatc atcaaagaaa    4080
ttatccagct gctgaacgtg cagaaaaact tccatcagct ggatgaaaac ttcatcaaca    4140
aatacatcga gctggttgaa atgcgtcgcg aatattttga aggtccgggt aaaggtagcc    4200
cgtatggttg ggaaggtgat ccgaaagcat ggtatgaaac cctgatgggt cattgtacct    4260
attttccgga tgaactgcgt agcgttaaat atgcctatag cgcagacctg tttaatgcac    4320
tgaatgatct gaataacctg gtgattcagc gtgatggtct gagcaaactg gaatatcatg    4380
agaaatatca catcatcgaa aacgtgttca acagaagaa gaaaccgacc ctgaaacaaa     4440
tcgccaacga aattaatgtg aacccggaag atattaaagg ctaccgtatt accaaaagcg    4500
gtaaaccgca gttcaccgaa tttaaactgt atcacgatct gaaaagcgtg ctgtttgatc    4560
agagcattct ggaaaatgaa gatgtgctgg accagattgc agaaattctg accatttatc    4620
aggacaaaga cagcatcaaa agcaaactga ccgaactgga tattctgctg aatgaagaag    4680
ataaagagaa cattgcacag ctgaccggtt ataccggcac ccatcgtctg agcctgaaat    4740
gtattcgtct ggtactggaa gaacagtggt atagcagccg taatcagatg gaaatctta     4800 cccatctgaa cattaaaccg aagaaaatca atctgaccgc agccaacaaa attccgaaag    4860
ccatgattga tgagtttatt ctgagtccgg ttgtgaaacg tacctttggt caggcaatta    4920
acctgatcaa caaaatcatt gaaaatatg gcgtgcctga ggatatcatt attgaactgg     4980
cacgtgaaaa caacagcaaa gataaacaga aattcatcaa cgagatgcag aagaagaacg    5040
aaaatacccg caaacggatt aacgagatca ttggcaaata tggtaatcag aatgccaaac    5100
```

```
gcctggtgga aaaaattcgt ctgcatgatg aacaagaggg caaatgtctg tatagcctgg    5160
aaagcattcc tctggaagat ctgctgaaca atccgaatca ttatgaagtg gatcacatta    5220
ttccgcgtag cgtgagcttt gataattcct atcataataa agtgctggtg aaacagagcg    5280
aaaactccaa aaaatccaac ctgacaccgt atcagtattt caatagcggc aaatccaaac    5340
tgagctacaa ccagtttaaa cagcatattc tgaacctgag caaaagccag gatcgcatca    5400
gcaagaagaa gaaggagtac ctgctggaag aacgcgacat caacaaattt gaagtgcaga    5460
aagaatttat caaccgcaac ctggttgata cccgttatgc aacccgtgaa ctgaccaatt    5520
atctgaaagc atatttcagc gccaacaaca tgaacgtgaa agtgaaaacg attaacggca    5580
gctttaccga ttatctgcgt aaagtgtgga aattcaaaaa agaacgcaac cacggctata    5640
aacatcatgc cgaagatgcc ctgattattg caaatgcaga tttcctgttt aaagaaaaca    5700
aaaaactgaa agccgtcaac agcgtgctgg aaaaaccgga aattgagaca aaacagctgg    5760
acattcaggt tgatagcgaa gataattaca gcgaaatgtt tatcatcccg aaacaggtgc    5820
aggatatcaa agattttcgc aacttcaaat atagccaccg cgttgacaaa aaacctaatc    5880
gtcagctgat taacgatacc ctgtatagca cccgcaaaaa agataacagc acctatattg    5940
tgcagaccat taaagacatc tacgccaaag ataataccac cctgaaaaaa cagttcgaca    6000
aaagcccaga aaatttctg atgtatcagc atgatccgcg taccttcgaa aaactggaag    6060
ttattatgaa acagtatgcc aacgagaaaa atccgctggc caaatatcac gaagaaaccg    6120
gtgaatatct gaccaaatat tccaagaaga caacggtcc gatcgttaaa tccctgaaat    6180
atatcggtaa taaactgggc agccatctgg atgttaccca tcagtttaaa agctccacaa    6240
agaagctggt taaactgtcc atcaaaccgt atcgctttga tgtgtatctg accgacaaag    6300
gctataaatt cattaccatc agctatctgg acgtgctgaa aaaagacaac tattattata    6360
tcccggaaca gaaatatgat aaactgaaac tgggtaaagc catcgataaa aacgccaaat    6420
ttatcgccag cttctacaaa aacgacctga ttaaactgga tggcgagatc tataaaatca    6480
tcggtgttaa tagcgacacc cgcaatatga ttgagctgga tctgccggat attcgctata    6540 agaatattg cgaactgaac aacattaaag gcgaaccgcg tatcaaaaag accatcggca    6600 aaaagtgaa tagcatcgag aaactgacca ccgatgttct gggtaatgtg tttaccaata    6660
cccagtatac caaacctcag ctgctgttca acgcggtaa tggcggagga tctggccccc    6720
ctaagaaaaa gcggaaggtg                                                6740
```

<210> SEQ ID NO 25
<211> LENGTH: 9489
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DNA sequence pCas634

<400> SEQUENCE: 25

```
ccggtgatac cacgatacta tgactgagag tcaacgccat gagcggcctc atttcttatt      60
ctgagttaca acagtccgca ccgctgccgg tagctattga ctatccggct gcactagccc    120
tgcgtcagat ggctctgatc caaggcaaac tgccaaaata tctgctggca ccggaagtca    180
gcgccctgca ccattatgtt ccggatctgc atcgcaggat gctgctggct accctgtgga    240
acacctacat ctgtattaac gaagcgctgg cattgaccct gagtgatttt tctctggtgc    300
```

```
cgccctatcc ctttgtgcag cttgccacgc tcaaaggggt ttgaggtcca accgtacgaa    360
aacgtacggt aagaggaaaa ttatcgtctg aaaaatcgat tagtagacaa gaaagtccgt    420
taagtgccaa ttttcgatta aaaagacacc gttttgatgg cgttttccaa tgtacattat    480
gtttcgatat atcagacagt tacttcacta acgtacgttt tcgttctatt ggccttcaga    540
ccccatatcc ttaatgtcct ttatttgctg gggttatcag atcccccga cacgtttaat     600 taatgctttc tccgccggag atcgacgcac agcgttctgt gctctatgat gttatttctt    660
aataatcatc caggtattct ctttatcacc atacgtagtg cgagtgtcca ccttaacgca    720
gggctttccg tcacagcgcg atatgtcagc cagcggggct ttcttttgcc agaccgcttc    780
catcctctgc atttcagcaa tctggctata cccgtcattc ataaaccacg taaatgccgt    840
cacgcaggaa gccaggacga agaatatcgt cagtacaaga taaatcgcgg atttccacgt    900
atagcgtgac atctcacgac gcatttcatg gatcatcgct ttcgccgtat cggcagcctg    960
attcagcgct tctgtcgccg gtttctgctg tgctaatccg gcttgtttca gttctttctc   1020
aacctgagtg agcgcggaac tcaccgattt cctgacggtg tcagtcatat taccggacgc   1080
gctgtccagc tcacgaatga ccctgctcag cgtttcactt tgctgctgta attgtgatga   1140
ggcggcctga aactgttctg tcagagaagt aacacgcttt tccagcgcct gatgatgccc   1200
gataagggcg gcaatttgtt taatttcgtc gctcatacaa aatcctgcct atcgtgagaa   1260
tgaccagcct ttatccggct tctgtcgtat ctgttcggcg agtcgctgtc gttctttctc   1320
ctgctgacgc tgttttttccg ccagacgttc gcgctctctc tgcctttcca tctcctgatg   1380
tatcccctgg aactccgcca tcgcatcgtt aacaagggac tgaagatcga tttcttcctg   1440
tatatccttc atggcatcac tgaccagtgc gttcagcttg tcaggctctt tttcaaaatc   1500
aaacgttctg ccggaatggg attcctgctc aggctctgac ttcagctcct gttttagcgt   1560
cagagtatcc ctctcgctga gggcttcccg taacgaggta gtcacgtcaa ttacgctgtc   1620
acgttcatca cggggactgct gcacctgcct ttcagcctcc ctgcgctcaa gaatggcctg   1680
tagctgctca gtatcgaatc gctgaacctg accgcgcccc agatgccgct caggctcacg   1740
gtcaatgccc tgcgccttca gggaacggga atcaacccgg tcagcgtgct gataccgttc   1800
aaggtgctta ttctggaggt cagcccagcg ttccctctgg gcaacaaggt attctttgcg   1860
ttcggtcggt gtttccccga aacgtgcctt ttttgcgcca ccgcgctccg gctctttggt   1920
gttagcccgt ttaaaatact gctcagggtc acggtgaata ccgtcattaa tgcgttcaga   1980
gaacatgata tgggcgtggg gctgctcgcc accggctatc gctgctttcg gattatggat   2040
agcgaactga taggcatggc ggtcgccaat ttcctgttgg acaaaatcgc ggacaagctc   2100
aagacgttgt tcgggtttta actcacgcgg cagggcaatc tcgatttcac ggtaggtaca   2160
gccgttggca cgttcagacg tgtcagcggc tttccagaac tcggacggtt tatgcgctgc   2220
ccacgccggc atattgccgg actccttgtg ctcaaggtcg gagtcttttt cacgggcata   2280 ctttcccctca cgcgcaatat aatcggcatg aggagaggca ctgccttttc cgccggtttt   2340
tacgctgaga tgataggatg ccatcgtgtt ttatcccgct gaaggcgcgc accgtttctg   2400
aacgaagtga agaaacgtct aagtgcgccc tgataaataa aagagttatc agggattgta   2460
gtgggatttg acctcctctg ccatcactga gcataatcat tccgttagca ttcaggaggt   2520
aaacagcatg aataaaagcg aaaaacagga acaatgggca gcagaaagag tgcagtatat   2580
tcgcggctta aagtcgccga atgagcaaca gaaacttatg ctgatactga cggataaagc   2640
agataaaaca gcacaggata tcaaaacgct gtccctgctg atgaaggctg aacaggcagc   2700
```

```
agagaaagcg caggaagcca gagcgaaagt catgaacctg atacaggcag aaaagcgagc    2760
cgaagccaga gccgcccgta aagcccgtga ccatgctctg taccagtctg ccggattgct    2820
tatcctggcg ggtctggttg acagtaagac gggtaagcct gttgatgata ccgctgcctt    2880
actgggtgca ttagccagtc tgaatgacct gtcacgggat aatccgaagt ggtcagactg    2940
gaaaatcaga gggcaggaac tgctgaacag caaaaagtca gatagcacca catagcagac    3000
ccgccataaa acgccctgag aagcccgtga cgggcttttc ttgtattatg ggtagtttcc    3060
ttgcatgaat ccataaaagg cgcctgtagt gccatttacc cccattcact gccagagccg    3120
tgagcgcagc gaactgaatg tcacgaaaaa gacagcgact caggtgcctg atggtcggag    3180
acaaaaggaa tattcagcga tttgcccgag cttgcgaggg tgctacttaa gcctttaggg    3240
ttttaaggtc tgttttgtag aggagcaaac agcgtttgcg acatcctttt gtaatactgc    3300
ggaactgact aaagtagtga gttatacaca gggctgggat ctattctttt tatctttttt    3360
tattctttct ttattctata aattataacc acttgaatat aaacaaaaaa aacacacaaa    3420
ggtctagcgg aatttacaga gggtctagca gaatttacaa gttttccagc aaaggtctag    3480
cagaatttac agatacccac aactcaaagg aaaaggacta gtaattatca ttgactagcc    3540
catctcaatt ggtatagtga ttaaaatcac ctagaccaat tgagatgtat gtctgaatta    3600
gttgttttca aagcaaatga actagcgatt agtcgctatg acttaacgga gcatgaaacc    3660
aagctaattt tatgctgtgt ggcactactc aaccccacga ttgaaaaccc tacaaggaaa    3720
gaacggacgg tatcgttcac ttataaccaa tacgctcaga tgatgaacat cagtagggaa    3780
aatgcttatg gtgtattagc taaagcaacc agagagctga tgacgagaac tgtggaaatc    3840
aggaatcctt tggttaaagg ctttgagatt ttccagtgga caaactatgc caagttctca    3900
agcgaaaaat tagaattagt ttttagtgaa gagatattgc cttatctttt ccagttaaaa    3960
aaattcataa aatataatct ggaacatgtt aagtcttttg aaaacaaata ctctatgagg    4020
atttatgagt ggttattaaa agaactaaca caaagaaaa ctcacaaggc aaatatagag    4080
attagccttg atgaatttaa gttcatgtta atgcttgaaa ataactacca tgagtttaaa    4140
aggcttaacc aatgggtttt gaaaccaata agtaaagatt taaacactta cagcaatatg    4200
aaattggtgg ttgataagcg aggccgcccg actgatacgt tgattttcca agttgaacta    4260
gatagacaaa tggatctcgt aaccgaactt gagaacaacc agataaaaat gaatggtgac    4320
aaaataccaa caaccattac atcagattcc tacctacata acggactaag aaaaacacta    4380
cacgatgctt taactgcaaa aattcagctc accagttttg aggcaaaatt tttgagtgac    4440
atgcaaagta agtatgatct caatggttcg ttctcatggc tcacgcaaaa caacgaacc     4500 acactagaga acatactggc taaatacgga aggatctgag gttcttatgg ctcttgtatc    4560
tatcagtgaa gcatcaagac taacaaacaa agtagaaca actgttcacc gttacatatc     4620
aaagggaaaa ctgtccatat gcacagatga aaacggtgta aaaagatag atacatcaga    4680 gcttttacga gttttggtg cattcaaagc tgttcaccat gaacagatcg acaatgtaac     4740
agatgaacag catgtaacac ctaatagaac aggtgaaacc agtaaaacaa agcaactaga    4800
acatgaaatt gaacacctga gacaacttgt tacagctcaa cagtcacaca tagacagcct    4860
gaaacaggcg atgctgctta tcgaatcaaa gctgccgaca acacgggagc cagtgacgcc    4920
tcccgtgggg aaaaaatcat ggcaattctg gaagaaatag cgctttcagc cggcaaaccg    4980
gctgaagccg gatctgcgat tctgataaca aactagcaac accagaacag cccgtttgcg    5040
```

```
ggcagcaaaa cccgtacttt tggacgttcc ggcggttttt tgtggcgagt ggtgttcggg    5100
cggtgcgcgc aagatccatt atgttaaacg ggcgagttta catctcaaaa ccgcccgctt    5160
aacaccatca gaaatcctca gcgcgatttt aagcaccaac ccccccccgt aacacccaaa    5220
tccatactga aagtggcttt gttgaataaa tcgaacttttt gctgagttga aggatcagat    5280
cacgcatcct cccgacaaca cagaccattc cgtggcaaag caaaagttca gaatcaccaa    5340
ctggtccacc tacaacaaag ctctcatcaa ccgtggctcc ctcactttct ggctggatga    5400
tgaggcgatt caggcctggt atgagtcggc aacaccttca tcacgaggaa ggccccagcg    5460
ctattctgat ctcgccatca ccaccgttct ggtgattaaa cgcgtattcc ggctgaccct    5520
gcgggctgcg cagggtttta ttgattccat ttttgccctg atgaacgttc cgttgcgctg    5580
cccggattac accagtgtca gtaagcgggc aaagtcggtt aatgtcagtt tcaaaacgtc    5640
cacccggggt gaaatcgcac acctggtgat tgattccacc gggctgaagg tctttggtga    5700
aggcgaatgg aaagtcagaa agcacggcaa agagcgccgt cgtatctggc gaaagttgca    5760
tcttgctgtt gacagcaaca cacatgaagt tgtctgtgca gacctgtcgc tgaataacgt    5820
cacggactca gaagccttcc cgggccttat ccggcagact cacagaaaaa tcagggcagc    5880
cgcggcagac ggggcttacg atacccggct ctgtcacgat gaactgcgcc gcaaaaaaat    5940
cagcgcgctt attcctcccc gaaaaggtgc gggttactgg cccggtgaat atgcagaccg    6000
taaccgtgca gtggctaatc agcgaatgac cgggagtaat gcgcggtgga aatgacaac    6060 agattacaac cgtcgctcga tagcggaaac ggcgatgtac cgggtaaaac agctgttcgg    6120
gggttcactg acgctgcgtg actacgatgg tcaggttgcg gaggctatgg ccctggtacg    6180
agcgctgaac aaaatgacga aagcaggtat gcctgaaagc gtgcgtattg cctgaaaaca    6240
caacccgcta cggggagac ttacccgaaa tctgatttat tcaacaaagc cgggtgtggt    6300
gaactacaaa gcagacccgt tgaggttatc agttcgatgc acaatcagca gcgcataaaa    6360
tatgcacaag aacaggagca ccccttcgcat taagctgtgg tggtaacaag tagtgccggg    6420
ctaccatcag cgagcatgat gcgctcccac agcattcgcc ttggcagtat ggaagttcct    6480
cgctccagtt cgggccggta tccacctcga gcttttctacg gggtctgacg ctcagtggaa    6540
cgaaaactca cgttaaggga ttttggtcat gagattatca aaaaggatct tcacctagat    6600
ccttttcgac cgaataaata cctgtgacgg aagatcactt cgcagaataa ataaatcctg    6660
gtgtccctgt tgataccggg aagccctggg ccaacttttg gcgaaaatga cgcgttgatc    6720
ggcacgtaag aggttccaac tttcaccata atgaaataag atcactaccg ggcgtatttt    6780
ttgagttgtc gagattttca ggagctaagg aagctaaaat ggagaaaaaa atcactggat    6840
ataccaccgt tgatatatcc caatggcatc gtaaagaaca ttttgaggca tttcagtcag    6900
ttgctcaatg tacctataac cagaccgttc agctggatat tacggccttt ttaaagaccg    6960
taaagaaaaa taagcacaag ttttatccgg cctttattca cattcttgcc cgcctgatga    7020
atgctcatcc ggaattacgt atggcaatga aagacggtga gctggtgata tgggatagtg    7080
ttcacccttg ttacaccgtt ttccatgagc aaactgaaac gttttcatcg ctctggagtg    7140
aataccacga cgatttccgg cagtttctac acatatattc gcaagatgtg gcgtgttacg    7200
gtgaaaacct ggcctatttc cctaaagggt ttattgagaa tatgttttc gtctcagcca    7260 atccctgggt gagtttcacc agttttgatt taaacgtggc caatatggac aacttcttcg    7320
cccccgtttt caccttgggc aaatattata cgcaaggcga caaggtgctg atgccgctgg    7380
cgattcaggt tcatcatgcc gtttgtgatg gcttccatgt cggcagaatg cttaatgaat    7440
```

```
tacaacagta ctgcgatgag tggcagggcg gggcgtaatt tttttaaggc agttattggt    7500
gcccttaaac gcctggttgc tacgcctgaa taagtgataa taagcggatg aatggcagaa    7560
attcgaaagc aaattcgacc cggtcgtcgg ttcagggcag ggtcgttaaa tagccgctta    7620
tgtctattgc tggtttaccg gattattgac taccggaagc agtgtgaccg tgtgcttctc    7680
aaatgcctga ggccagtttg ctcaggctct ccccgtggag gtaataattg acgatatgat    7740 ccttttttc tgatcaaaag tgctccatgg aattatgaca acttgacggc tacatcattc    7800 acttttctt cacaaccggc acggaactcg ctcgggctgg ccccggtgca ttttttaaat    7860
acccgcgaga aatagagttg atcgtcaaaa ccaacattgc gaccgacggt ggcgataggc    7920
atccgggtgg tgctcaaaag cagcttcgcc tggctgatac gttggtcctc gcgccagctt    7980
aagacgctaa tccctaactg ctggcggaaa agatgtgaca gacgcgacgg cgacaagcaa    8040
acatgctgtg cgacgctggc gatatcaaaa ttgctgtctg ccaggtgatc gctgatgtac    8100
tgacaagcct cgcgtacccg attatccatc ggtggatgga gcgactcgtt aatcgcttcc    8160
atgcgccgca gtaacaattg ctcaagcaga tttatcgcca gcagctccga atagcgccct    8220
tccccttgcc cggcgttaat gatttgccca acaggtcgc tgaaatgcgg ctggtgcgct     8280
tcatccgggc gaaagaaccc cgtattggca aatattgacg gccagttaag ccattcatgc    8340
cagtaggcgc gcggacgaaa gtaaacccac tggtgatacc attcgcgagc tccggatga    8400 cgaccgtagt gatgaatctc tcctggcggg aacagcaaaa tatcacccgg tcggcaaaca   8460
aattctcgtc cctgatttt caccacccc tgaccgcgaa tggtgagatt gagaatataa    8520
cctttcattc ccagcggtcg gtcgataaaa aaatcgagat aaccgttggc ctcaatcggc    8580
gttaaacccg ccaccagatg ggcattaaac gagtatcccg gcagcagggg atcattttgc    8640
gcttcagcca tactttcat actcccgcca ttcagagaag aaaccaattg tccatattgc     8700
atcagacatt gccgtcactg cgtcttttac tggctcttct cgctaaccaa accggaaacc    8760
ccgcttatta aaagcattct gtaacaaagc gggaccaaag ccatgacaaa acgcgtaac    8820 aaaagtgtct ataatcacgg cagaaaagtc cacattgatt atttgcacgg cgtcacactt    8880
tgctatgcca tagcattttt atccataaga ttagcggatc ctacctgacg ctttttatcg    8940
caactctcta ctgtcgtgcg caacgcgtga catcgactag gaggcctttc tatgcagttc    9000
aaagtgtata cctataaacg cgaaagccgt tatcgtctgt tgttgatgt tcagagcgat    9060 attattgata caccgggtcg tcgtatggtt attccgctgg caagcgcacg tctgctgagc    9120
gataaagtta gccgtgaact gtatccggtt gttcatattg gtgatgaaag ctggcgtatg    9180
atgaccaccg atatggcaag cgttccggtt agcgttattg gtgaagaagt tgcagatctg    9240
agccatcgta aaaacgatat caaaaatgcc atcaacctga tgttttgggg catcttatag    9300 gacccctcc acccgcctc gcgggcagtt tgcctggcgg cagtagcgcg gtggtcccac    9360
ctgaccccat gccgaactca gaagtgaaac gccgtagcgc cgatggtagt gtgggctctc    9420
cccatgcgag agtagggaac tgccaggcat caaataaac gaaaggctca gtcgaaagac    9480
tgggcctta                                                            9489
```

<210> SEQ ID NO 26
<211> LENGTH: 35
<212> TYPE: DNA
<213> ORGANISM: Artificial sequence
<220> FEATURE:
<223> OTHER INFORMATION: Synthetic polynucleotide
<220> FEATURE:

```
<221> NAME/KEY: misc_feature
<223> OTHER INFORMATION: VEGFA-PAMS-forward primer

<400> SEQUENCE: 26
tctgatttat aatgtgaaaa ttcgcggtgt gaact                               35

<210> SEQ ID NO 27
<211> LENGTH: 36
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: VEGFA-PAMS-reverse primer

<400> SEQUENCE: 27
agcgccacgc ttcccgaagg gagaaaggcg gacagg                              36

<210> SEQ ID NO 28
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: ddCPR RO1 forward primer

<400> SEQUENCE: 28
catggtgcat ctgactcctg                                                20

<210> SEQ ID NO 29
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: ddCPR RO1 reverse primer

<400> SEQUENCE: 29
ggtagaccac cagcagccta                                                20

<210> SEQ ID NO 30
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: ddPCR NHEJ Insensitive Probe FAM labelled

<400> SEQUENCE: 30
aggagaagtc tgccgttact gccct                                          25

<210> SEQ ID NO 31
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: ddPCR NHEJ sensitive Probe HEX labelled

<400> SEQUENCE: 31
```

```
tgaagttggt ggtgaggccc t                                              21
```

<210> SEQ ID NO 32
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HBB PCR forward primer for T7E1 assay

<400> SEQUENCE: 32

```
gagacgcagg aagagatcca                                                20
```

<210> SEQ ID NO 33
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: HBB PCR reverse primer for T7E1 assay

<400> SEQUENCE: 33

```
ttagggttgc ccataacagc                                                20
```

<210> SEQ ID NO 34
<211> LENGTH: 27
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: PAM-Library Variable element for PAM
      identification
<220> FEATURE:
<221> NAME/KEY: misc_feature
<222> LOCATION: (21)..(27)
<223> OTHER INFORMATION: n is any nucleotide

<400> SEQUENCE: 34

```
gacccctcc accccgcctc nnnnnnn                                         27
```

<210> SEQ ID NO 35
<211> LENGTH: 1056
<212> TYPE: PRT
<213> ORGANISM: Staphylococcus lugdunensis
<220> FEATURE:
<221> NAME/KEY: misc_feature
<223> OTHER INFORMATION: Staphylococcus lugdunensis CRISPR Cas9 sequence
      according to https://www.ncbi.nlm.nih.gov/protein/
      WP_002460848.1?report=genbank&log$=protalign&blast_rank=1&RID=
      0Z7T5FGN015, accessed on 2018-12-11

<400> SEQUENCE: 35

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

-continued

```
Glu Arg Val Lys Lys Leu Leu Glu Asp Tyr Asn Leu Leu Asp Gln Ser
 65                  70                  75                  80

Gln Ile Pro Gln Ser Thr Asn Pro Tyr Ala Ile Arg Val Lys Gly Leu
                 85                  90                  95

Ser Glu Ala Leu Ser Lys Asp Glu Leu Val Ile Ala Leu Leu His Ile
            100                 105                 110

Ala Lys Arg Arg Gly Ile His Lys Ile Asp Val Ile Asp Ser Asn Asp
        115                 120                 125

Asp Val Gly Asn Glu Leu Ser Thr Lys Glu Gln Leu Asn Lys Asn Ser
    130                 135                 140

Lys Leu Leu Lys Asp Lys Phe Val Cys Gln Ile Gln Leu Glu Arg Met
145                 150                 155                 160

Asn Glu Gly Gln Val Arg Gly Glu Lys Asn Arg Phe Lys Thr Ala Asp
                165                 170                 175

Ile Ile Lys Glu Ile Ile Gln Leu Leu Asn Val Gln Lys Asn Phe His
            180                 185                 190

Gln Leu Asp Glu Asn Phe Ile Asn Lys Tyr Ile Glu Leu Val Glu Met
        195                 200                 205

Arg Arg Glu Tyr Phe Glu Gly Pro Gly Lys Gly Ser Pro Tyr Gly Trp
210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
        275                 280                 285

Val Phe Lys Gln Lys Lys Lys Pro Thr Leu Lys Gln Ile Ala Asn Glu
    290                 295                 300

Ile Asn Val Asn Pro Glu Asp Ile Lys Gly Tyr Arg Ile Thr Lys Ser
305                 310                 315                 320

Gly Lys Pro Gln Phe Thr Glu Phe Lys Leu Tyr His Asp Leu Lys Ser
                325                 330                 335

Val Leu Phe Asp Gln Ser Ile Leu Glu Asn Glu Asp Val Leu Asp Gln
            340                 345                 350

Ile Ala Glu Ile Leu Thr Ile Tyr Gln Asp Lys Asp Ser Ile Lys Ser
        355                 360                 365

Lys Leu Thr Glu Leu Asp Ile Leu Leu Asn Glu Asp Lys Glu Asn
    370                 375                 380

Ile Ala Gln Leu Thr Gly Tyr Thr Gly Thr His Arg Leu Ser Leu Lys
385                 390                 395                 400

Cys Ile Arg Leu Val Leu Glu Glu Gln Trp Tyr Ser Ser Arg Asn Gln
                405                 410                 415

Met Glu Ile Phe Thr His Leu Asn Ile Lys Pro Lys Lys Ile Asn Leu
            420                 425                 430

Thr Ala Ala Asn Lys Ile Pro Lys Ala Met Ile Asp Glu Phe Ile Leu
        435                 440                 445

Ser Pro Val Val Lys Arg Thr Phe Gly Gln Ala Ile Asn Leu Ile Asn
    450                 455                 460

Lys Ile Ile Glu Lys Tyr Gly Val Pro Glu Asp Ile Ile Glu Leu
465                 470                 475                 480

Ala Arg Glu Asn Asn Ser Lys Asp Lys Gln Lys Phe Ile Asn Glu Met
```

```
                485                 490                 495
Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
            515                 520                 525

His Asp Glu Gln Glu Gly Lys Cys Leu Tyr Ser Leu Glu Ser Ile Pro
            530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
                565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
            595                 600                 605

His Ile Leu Asn Leu Ser Lys Ser Gln Asp Arg Ile Ser Lys Lys Lys
            610                 615                 620

Lys Glu Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
            675                 680                 685

Val Trp Lys Phe Lys Lys Glu Arg Asn His Gly Tyr Lys His His Ala
            690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
            755                 760                 765

Phe Lys Tyr Ser His Arg Val Asp Lys Lys Pro Asn Arg Gln Leu Ile
            770                 775                 780

Asn Asp Thr Leu Tyr Ser Thr Arg Lys Lys Asp Asn Ser Thr Tyr Ile
785                 790                 795                 800

Val Gln Thr Ile Lys Asp Ile Tyr Ala Lys Asp Asn Thr Thr Leu Lys
                805                 810                 815

Lys Gln Phe Asp Lys Ser Pro Glu Lys Phe Leu Met Tyr Gln His Asp
            820                 825                 830

Pro Arg Thr Phe Glu Lys Leu Glu Val Ile Met Lys Gln Tyr Ala Asn
            835                 840                 845

Glu Lys Asn Pro Leu Ala Lys Tyr His Glu Glu Thr Gly Glu Tyr Leu
850                 855                 860

Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
                885                 890                 895

Lys Ser Ser Thr Lys Lys Leu Val Lys Leu Ser Ile Lys Pro Tyr Arg
            900                 905                 910
```

-continued

```
Phe Asp Val Tyr Leu Thr Asp Lys Gly Tyr Lys Phe Ile Thr Ile Ser
        915                 920                 925

Tyr Leu Asp Val Leu Lys Lys Asp Asn Tyr Tyr Ile Pro Glu Gln
    930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                965                 970                 975

Ile Tyr Lys Ile Ile Gly Val Asn Ser Asp Thr Arg Asn Met Ile Glu
            980                 985                 990

Leu Asp Leu Pro Asp Ile Arg Tyr  Lys Glu Tyr Cys Glu  Leu Asn Asn
        995                 1000                1005

Ile Lys  Gly Glu Pro Arg Ile  Lys Lys Thr Ile Gly  Lys Lys Val
    1010                1015                1020

Asn Ser  Ile Glu Lys Leu Thr  Thr Asp Val Leu Gly  Asn Val Phe
    1025                1030                1035

Thr Asn  Thr Gln Tyr Thr Lys  Pro Gln Leu Leu Phe  Lys Arg Gly
    1040                1045                1050

Asn Gly  Gly
    1055

<210> SEQ ID NO 36
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1688

<400> SEQUENCE: 36
acggacagac agacagacac c                                              21

<210> SEQ ID NO 37
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1689

<400> SEQUENCE: 37
agaacagccc agaagttgga c                                              21

<210> SEQ ID NO 38
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1695

<400> SEQUENCE: 38
agccccagct accacctcct cc                                             22

<210> SEQ ID NO 39
<211> LENGTH: 20
```

```
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1699

<400> SEQUENCE: 39
tccaccccgc ctccgggcgc                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1720

<400> SEQUENCE: 40
catggtgcat ctgactcctg                                              20

<210> SEQ ID NO 41
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1721

<400> SEQUENCE: 41
ggtagaccac cagcagccta                                              20

<210> SEQ ID NO 42
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1725

<400> SEQUENCE: 42
aggagaagtc tgccgttact gccct                                        25

<210> SEQ ID NO 43
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: SPRJ1728

<400> SEQUENCE: 43
tgaagttggt ggtgaggccc t                                            21

<210> SEQ ID NO 44
<211> LENGTH: 3162
<212> TYPE: DNA
<213> ORGANISM: Artificial sequence
<220> FEATURE:
<223> OTHER INFORMATION: Synthetic polynucleotide
```

<220> FEATURE:
<221> NAME/KEY: misc_feature
<223> OTHER INFORMATION: Codon-optimized SluCas9 polynucleotide 1

<400> SEQUENCE: 44

| | | | | | |
|---|---|---|---|---|---|
| atgaaccaaa | agttcattct | ggggctcgat | atcggcatca | cctccgtggg | atatggtctg | 60 |
| atcgactacg | agactaagaa | catcatcgac | gctggagtgc | gactgttccc | ggaagcgaac | 120 |
| gtggagaaca | acgaaggccg | cagatccaag | cgcgggtcca | aaggctcaa | gaggcggagg | 180 |
| atccatagac | tcgaaagagt | gaagaagctc | cttgaagatt | acaatctgtt | ggaccagagc | 240 |
| cagattcccc | aaagcaccaa | cccgtacgcc | atcagagtga | agggcctgtc | cgaagccctg | 300 |
| tcgaaagatg | aactggtcat | tgccctgctg | catattgcca | acggcgcgg | aatccataag | 360 |
| atcgacgtga | tagactccaa | cgatgacgtg | ggcaacgaac | tgtcaaccaa | ggagcagctg | 420 |
| aacaagaact | cgaaactgct | gaaggacaag | ttcgtctgcc | aaattcaact | ggaacggatg | 480 |
| aacgagggac | aagtcagggg | agagaaaaac | cggttcaaga | ccgcggacat | catcaaggag | 540 |
| atcatccaac | tcctgaatgt | gcagaagaac | tttcaccagc | tggatgaaaa | cttcattaac | 600 |
| aagtacattg | aactggtgga | aatgcggagg | gagtacttcg | agggacctgg | aaagggatcc | 660 |
| ccttacggct | gggaaggga | ccccaaggct | tggtacgaaa | cgctcatggg | ccattgcact | 720 |
| tactttccgg | acgaactccg | gtccgtgaag | tacgcatact | ctgccgatct | gttcaatgca | 780 |
| ctcaacgacc | ttaacaactt | ggtgatccag | cgcgatggcc | tgtccaagtt | ggaataccac | 840 |
| gaaaagtatc | acatcatcga | aacgtgttc | aagcagaaaa | agaagccaac | tctgaagcag | 900 |
| attgccaacg | aaattaacgt | gaaccccgag | gatatcaagg | ataccggat | cactaagtcc | 960 |
| ggcaaaccac | agttcaccga | gttcaagctg | taccacgatc | tgaagtcggt | gctcttgac | 1020 |
| cagtccatcc | tggaaaacga | agatgtgctg | gaccagattg | ctgagatcct | gaccatctac | 1080 |
| caggacaagg | actcgattaa | gagcaagctc | acggagctgg | acattctgct | gaacgaagag | 1140 |
| gataaggaga | catcgcgca | gctcactggt | tacaccggta | cccaccgctt | gtcccttaag | 1200 |
| tgcatccggc | tggtcctcga | ggaacaatgg | tactccagcc | ggaaccagat | ggagatcttc | 1260 |
| acgcacttga | acatcaagcc | gaagaagatt | aacctgaccg | ctgcgaacaa | gatacccaag | 1320 |
| gccatgatcg | acgagtttat | cctctcaccg | gtggtcaagc | gcaccttcgg | acaagccatc | 1380 |
| aacctcatca | caagattat | cgagaagtac | ggcgtgcctg | aggatatcat | catcgagctg | 1440 |
| gctcgggaga | caactcaaa | ggataagcag | aagttcatta | cgagatgca | gaaaagaac | 1500 |
| gagaacactc | gcaagcggat | taatgagatc | atcggtaaat | acgggaacca | gaacgccaag | 1560 |
| cggcttgtgg | aaaagattcg | gctccacgac | gagcaggagg | gaaagtgtct | gtactcgctg | 1620 |
| gagagcattc | ccctggagga | cctcctgaac | aacccaaacc | actacgaagt | ggatcacata | 1680 |
| atcccccgca | gcgtgtcatt | cgacaattcc | taccataaca | aggtcctcgt | gaagcagtcc | 1740 |
| gagaatagca | agaagtccaa | cctgactccg | taccagtact | tcaactccgg | caaatccaag | 1800 |
| ctgtcctaca | accagttcaa | acagcacatc | ctcaacctgt | caaagagcca | ggacaggatc | 1860 |
| tcgaagaaga | agaaggaata | ccttctcgag | gaacgggata | tcaataagtt | cgaggtgcag | 1920 |
| aaggagttta | tcaatagaaa | cctggtggac | actcgctatg | ccacccgcga | actgaccaac | 1980 |
| tacctgaagg | cgtacttctc | cgccaacaac | atgaacgtga | aggtcaaaac | tattaacggc | 2040 |
| agcttcaccg | actatctgcg | caaggtctgg | aagttcaaga | aggaacgcaa | ccacggttac | 2100 |
| aagcaccacg | cggaagatgc | gctgattatc | gccaacgctc | acttcctgtt | caaggaaaac | 2160 |
| aagaagctca | aggccgtgaa | ctcagtgctc | gagaagcctg | aaatcgagac | taagcagctg | 2220 |

```
gacatccagg tcgattcgga agataactac tccgaaatgt tcatcatccc taagcaagtg    2280
caggacatca aggacttcag gaatttcaag tacagccatc gcgtggacaa gaagccaaac    2340
agacagctga tcaacgatac actgtattcc acccggaaga aggacaactc cacctacatc    2400
gtccaaacca ttaaggacat ctacgcaaag gacaacacca cgcttaagaa gcagttcgac    2460
aagagccccg aaaagttcct catgtaccag cacgacccca gaaccttcga gaagcttgaa    2520
gtgatcatga agcagtacgc caacgaaaag aacccactgg ctaagtacca cgaggaaacc    2580
ggcgaatacc tgaccaagta ctccaaaaag aacaacggac cgatcgtcaa gtccctgaag    2640
tacattggga caagctcgg ctcgcacctc gatgtgaccc accagttcaa gtcctcgacc    2700
aaaaagctcg tgaagctgtc catcaagccg taccggttcg acgtgtacct gactgacaag    2760
ggatataagt tcatcaccat ttcctacctc gacgtgttga agaaggataa ctactactac    2820
attccggaac agaagtacga caagctcaag ctcggaaagg ccatcgacaa aaatgcgaag    2880
ttcatcgcga gcttctacaa gaatgacttg atcaagctgg atggcgaaat ctacaagatc    2940
atcggggtca actccgatac ccgcaacatg attgagctgg atctgcccga cattcggtac    3000
aaggaatact gcgagctgaa caacatcaag ggagaaccgc ggatcaagaa aaccatcgga    3060
aagaaagtga acagcatcga gaaactgact actgacgtcc tgggaaacgt gttcaccaac    3120
acacaataca ccaaaccca gctgctgttt aagcgcggga ac                       3162

<210> SEQ ID NO 45
<211> LENGTH: 3162
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Codon-optimized SluCas9 polynucleotide 2

<400> SEQUENCE: 45
atgaaccaga agttcatcct gggcctcgac atcggcatca cctctgttgg ctacggcctg      60
atcgactacg agacaaagaa catcatcgat gccggcgtgc ggctgttccc tgaggccaac     120
gtggaaaaca cgagggccg cagaagcaag agaggcagca gaaggctgaa gcggcggaga     180
atccaccggc tggaaagagt gaagaagctg ctcgaggact acaacctgct ggaccagtct     240
cagatccctc agagcacaaa ccctacgcc atcagagtga agggcctgtc tgaggccctg     300
agcaaggacg agctggttat cgccctgctg cacattgcca gcggagaggg catccacaag     360
atcgacgtga tcgacagcaa cgacgacgtg ggcaatgagc tgagcaccaa agagcagctg     420
aacaagaaca gcaagctgct gaaggacaag ttcgtgtgcc agattcagct ggaacggatg     480
aatgagggcc aagtgcgggg cgagaagaac agattcaaga ccgccgacat catcaaagag     540
atcatccagc tgctcaacgt gcagaagaac ttccaccagc tggacgagaa cttcatcaac     600
aagtacatcg gctggtcga gatgcggcgc gagtactttg aaggccctgg aaagggcagc     660
ccttatggct gggaaggcga tcccaaggct tggtacgaga cactgatggg ccactgcacc     720
tactttcccg acgagctgag aagcgtgaag tacgcctaca cgccgacct gttcaacgcc     780 ctgaacgacc tgaacaacct cgtgatccag agagatggcc tgtccaagct ggaataccac     840
gagaagtacc acatcattga gaacgtgttc aagcagaaga agaagccac actgaagcag     900 atcgccaacg agatcaacgt gaaccccgag gacatcaagg gctacagaat caccaagagc     960
ggcaagcccc agttcaccga gttcaagctg taccacgatc tgaagtccgt gctgttcgac    1020
```

```
cagagcatcc tggaaaacga ggacgtgctg gatcagatcg ccgagatcct gaccatctac    1080
caggacaagg acagcatcaa gagcaagctg accgagctgg acatcctgct gaacgaagag    1140
gacaaagaga atatcgccca gctgaccggc tacaccggca cacatagact gagcctgaag    1200
tgcatccggc tggtgctgga agaacagtgg tactccagcc ggaaccagat ggaaatcttc    1260
acccacctga acatcaagcc caagaagatc aacctgaccg ccgccaacaa gatccccaag    1320
gccatgatcg acgagttcat tctgagcccc gtggtcaaga gaaccttcgg ccaggccatc    1380
aatctgatca caagattat cgagaagtat ggcgtgcccg aggatatcat catcgaactg    1440
gccagagaga acaacagcaa ggacaagcaa aagttcatca cgagatgca gaaaaagaac    1500 gagaacaccc ggaagcggat caacgaaatc atcgggaagt acggcaacca gaacgccaag    1560
agactggtgg aaaagatccg gctgcacgac gagcaagagg gcaagtgtct gtacagcctg    1620
gaatctatcc ctctcgagga tctgctgaac aatcccaacc actacgaggt ggaccacatt    1680
atccccagaa gcgtgtcctt cgacaacagc taccacaaca aggtgctggt caagcagagc    1740
gagaactcca agaagtccaa tctgaccccct taccagtact tcaacagcgg caagtctaag    1800
ctgagctaca accagtttaa gcagcacatc ctgaacctca gcaagagcca ggaccggatc    1860
agcaagaaga gaaagagta cctgctcgaa gagagggaca ttaacaagtt cgaggtgcag    1920
aaagagttta tcaaccggaa cctggtggac accagatacg ccaccagaga gctgaccaac    1980
tacctgaagg cctacttcag cgccaacaac atgaacgtga agtcaagac catcaacggc    2040 agcttcaccg actacctgcg gaaagtgtgg aagtttaaga agagcggaa ccacggctac    2100 aagcaccacg ccgaagatgc cctgattatc gccaatgccg acttcctgtt caaagagaac    2160
aagaaactga aggccgtgaa cagcgtgctg gaaaagcccg agatcgagac aaaacagctc    2220
gacatccagg tggacagcga ggacaactac agcgagatgt tcatcatccc caaacaggtg    2280
caggatatca aggacttccg gaacttcaag tacagccacc gcgtggacaa gaagcctaac    2340
cggcagctga tcaatgacac cctgtacagc acccgcaaga ggacaacag cacctacatc    2400 gtgcagacga tcaaggacat ctacgccaag gacaatacga ccctgaagaa gcagttcgac    2460
aagagccccg agaagttcct gatgtaccag cacgacccca ggaccttcga gaagctggaa    2520
gtgatcatga agcagtacgc taatgagaag aacccgctgg ccaagtacca cgaggaaacc    2580
ggcgagtacc tgaccaagta ctctaagaag aacaacggcc ccatcgtgaa gtccctgaag    2640
tatatcggca acaagctggg cagccacctg gacgtgacac accagttcaa gagcagcacc    2700
aagaagctgg tcaaactgtc catcaagcca taccgcttcg acgtgtacct gacagacaag    2760
gggtacaagt ttatcaccat cagctacctc gacgtgctga agaaggataa ctactactac    2820
atccccgagc agaagtacga caagctgaag ctgggaaaag ccatcgacaa gaatgccaag    2880
ttcattgcca gcttctacaa gaacgacctc atcaagctgg acggcgagat ctacaagatc    2940
atcggcgtga actccgacac acggaacatg attgagctgg acctgcctga catccggtac    3000
aaagagtact gcgaactgaa caatatcaag ggcgagcccc ggatcaaaaa gacgatcggc    3060
aagaaagtga acagcattga gaagctgacc accgatgtgc tggcaatgt gttcaccaac    3120 acacagtaca ccaagcctca gctgctgttc aagcggggca at                       3162
```